(12) United States Patent
Klosin et al.

(10) Patent No.: US 6,268,444 B1
(45) Date of Patent: Jul. 31, 2001

(54) 3-HETEROATOM SUBSTITUTED CYCLOPENTADIENYL-CONTAINING METAL COMPLEXES AND OLEFIN POLYMERIZATION PROCESS

(75) Inventors: Jerzy Klosin, Midland; William J. Kruper, Jr., Sanford; Peter N. Nickias, Midland; Jasson T. Patton, Midland; David R. Wilson, Midland, all of MI (US)

(73) Assignee: Dow Chemical Company, Midland, MI (US)

( * ) Notice: Subject to any disclaimer, the term of this patent is extended or adjusted under 35 U.S.C. 154(b) by 0 days.

(21) Appl. No.: 09/230,185

(22) PCT Filed: Jul. 28, 1997

(86) PCT No.: PCT/US97/13170

§ 371 Date: Jan. 15, 1999

§ 102(e) Date: Jan. 15, 1999

(87) PCT Pub. No.: WO98/06727

PCT Pub. Date: Feb. 19, 1998

Related U.S. Application Data

(60) Provisional application No. 60/034,819, filed on Dec. 19, 1996, and provisional application No. 60/023,768, filed on Aug. 8, 1996.

(51) Int. Cl.[7] .............................. C08F 4/16; C07F 17/00; B10J 31/38

(52) U.S. Cl. ...................... 526/127; 526/134; 526/161; 526/943; 526/348.6; 502/104; 502/152; 502/155; 556/7; 556/11; 556/12; 556/13; 556/53

(58) Field of Search .................................. 526/127, 134, 526/161, 943, 348.6; 502/104, 152, 155; 556/7, 11, 12, 13, 53

(56) References Cited

U.S. PATENT DOCUMENTS

| 5,055,438 | 10/1991 | Canich ..................... 502/117 |
| 5,057,475 | 10/1991 | Canich et al. ............ 502/104 |
| 5,064,802 | 11/1991 | Stevens et al. ........... 502/155 |
| 5,096,867 | 3/1992 | Canich ..................... 502/103 |
| 5,132,380 | 7/1992 | Stevens et al. ........... 526/126 |
| 5,304,614 | 4/1994 | Winter et al. ............. 526/127 |
| 5,350,817 | 9/1994 | Winter et al. ............. 526/119 |
| 5,621,126 | 4/1997 | Canich et al. .............. 556/9 |

FOREIGN PATENT DOCUMENTS

| 416815 | 8/1990 | (EP) . |
| 468651 | 7/1991 | (EP) . |
| 514828 | 5/1992 | (EP) . |
| 520732 | 6/1992 | (EP) . |
| 577581 | 6/1993 | (EP) . |

(List continued on next page.)

OTHER PUBLICATIONS

I. M. Lee, et al., "Organometallics" 1992, 11, 2115–2122.
N. Piccolravazzi, et al., "Organometallics" 1990, 9, 3098–3105.
H. Plenio, et al., "J. Organometallic Chem." 1996, 519, 269–272.
E. Barsties, et al., "J. Organometallic Chem." 1996, 520, 63–68.
R. Leino, et al., "Macromolecules" 1997, 30, 3477–3483.

*Primary Examiner*—David W. Wu
*Assistant Examiner*—R. Harlan

(57) ABSTRACT

This invention relates to heteroatom substituted cyclopentadienyl-containing ligands, metal complexes containing these ligands, catalyst systems prepared from catalyst components comprising these metal complexes. The metal complexes contain a "a" heteroatom-Cp bond or a ring heteroatom-Cp bond in the 3-position of the Cp. In preferred metal complexes the ligand is a 3-heteroatom substituted indenyl group. The catalyst systems for olefin polymerization may be used at high temperatures, are highly active and produce high molecular weight polymer.

17 Claims, 3 Drawing Sheets

FOREIGN PATENT DOCUMENTS

| | | |
|---|---|---|
| 0 670 325 A2 * | 2/1995 | (EP) . |
| WO 93/19104 | 9/1993 | (WO) . |
| WO 95/00526 | 1/1995 | (WO) . |
| WO 95/07942 | 3/1995 | (WO) . |
| WO 95/14024 | 5/1995 | (WO) . |
| WO 96/13529 | 5/1996 | (WO) . |

* cited by examiner

3-HETEROATOM SUBSTITUTED CYCLOPENTADIENYL-CONTAINING METAL COMPLEXES AND OLEFIN POLYMERIZATION PROCESS

CROSS REFERENCE TO RELATED APPLICATION

This application claims benefit of priority under 35 U.S.C. §371 of PCT/US97/13170, filed Jul. 28, 1997, which was published under PCT Article 21 (2) in English, and which claims benefit of priority of U.S. Provisional Application No. 60/034,819 filed Dec. 19, 1996, and Application No. 60/023,768 filed Aug. 8, 1996.

FIELD OF THE INVENTION

This invention relates to a class of metal complexes, the ligands used to prepare these metal complexes and to olefin polymerization catalysts derived therefrom that are particularly suitable for use in a polymerization process for preparing polymers by polymerization of α-olefins and mixtures of α-olefins.

BACKGROUND

Constrained geometry metal complexes and methods for their preparation are disclosed in U.S. application Ser. No. 545,403. filed Jul. 3, 1990 (EP-A-416,815); U.S. application Ser. No. 547,718, filed Jul. 3, 1990 (EP-A-468,651); U.S. application Ser. No. 702,475, filed May 20, 1991 (EP-A-514,828); U.S. application Ser. No. 876,268, filed May 1, 1992. (EP-A-520,732) and U.S. application Ser. No. 8,003, filed Jan. 21, 1993 (WO 93/19104), as well as U.S. Pat. Nos. 5,055,438, 5,057,475, 5,096,867, 5,064,802, 5,132,380, and WO 95/00526. The teachings of all of the foregoing patents or the corresponding U.S. patent applications are hereby incorporated by reference.

U.S. Pat. Nos. 5,350,817 and 5,304,614 disclose zirconium complexes with bridged-metallocene ligands, wherein two indenyl groups are covalently linked together by a bridge containing carbon or silicon, which are useful for the polymerization of propylene.

EP-A-577,581 discloses unsymmetrical bis-Cp metallocenes containing a fluorene ligand with heteroatom substituents.

E. Barsties, S. Schaible; M.-H. Prosenc; U. Rief; W. Roll; O. Weyland; B. Dorerer; H.-H. Brintzinger *J. Organometallic Chem.* 1996, 520, 63–68, and H. Plenio; D. Birth *J. Organometallic Chem.* 1996, 519, 269–272 disclose systems in which the cyclopentadienyl ring of the indenyl is substituted with a dimethylamino group in non-bridged and Si-bridged bis-indenyl useful for the formation of isotactic polypropylene and polyethylene.

R. Leino; H. J. K. Luttikhedde; P. Lehmus; C.-E. Wilen; R. Sjoholm; A. Lehtonen; J. Seppala; J. H. Nasman *Macromolecules,* 1997, 30, 3477–3488 disclose $C_2$-bridged bis-indenyl metallocenes with oxygen in the 2-position of the indenyl group, and I. M. Lee; W. J. Gauthier; J. M. Ball; B. Iyengar: S. Collins *Organometallics,* 1992, 11, 2115–2122 discloses $C_2$-bridged bis-indenyl metallocenes with oxygen in the 5,6-positions of the indenyl group, while N. Piccolravazzi; P. Pino; G. Consiglio; A. Sironi; M. Moret *Organometallics,* 1990, 9, 3098–3105 discloses non-bridged bis-indenyl metallocenes with oxygen in the 4 and 7 positions of the indenyl group.

It has been thought that heteroatom-substitution, as opposed to carbon or H-substitution, on any position of the indenyl system of a metallocene complex, when used in an olefin polymerization catalyst, renders the catalyst less active, that is, there is lower catalyst productivity for polymerizations with α-olefins, and the polymer produced has lower molecular weight with lower tacticity. It has been suggested that the diminished activity of this broad class of catalysts is due to interaction of the heteroatom lone pair electrons with the Lewis acid cocatalyst polymerization activator, resulting in a more electronically deactivated Cp ring which is also more sterically hindered. SEE P. Foster; M. D. Rausch; J. C. W. Chien. J. *Organometallic Chem.* 1996, 519, 269–272.

Disclosure of random heteroatom substitution in mono-Cp metallocenes is found in EP-A-416,815, WO 95107942, WO 96/13529. U.S. Patent Nos. 5,096,867 and 5,621,126 and related cases.

Up to now it has been thought that heteroatom substitution in metallocene complexes for use as olefin polymerization catalysts would have disadvantages due to unwanted interactions of the lone pair electrons of the heteroatom either with the transition metal atom of the same or a different metallocene molecule, or with other components of the catalyst system.

Numerous improvements in various metallocene complexes used as olefin polymerization catalysts have been made. However, problems still remain with catalyst efficiency and deactivation of the catalyst under high temperature polymerization conditions. It would be advantageous to be able to produce polyolefins with higher molecular weights. It would also be advantageous to be able to improve other physical characteristics of the polymers produced by altering the substitution around the cyclopentadienyl group of the metallocene complexes used in olefin polymerization catalyst systems.

SUMMARY OF THE INVENTION

According to the present invention there are provided metal complexes corresponding to the formula:

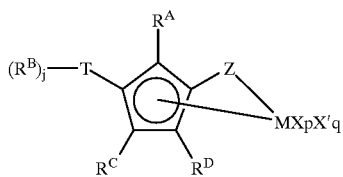

where

M is a metal from one of Groups 3 to 13 of the Periodic Table of the Elements, the lanthanides or actinides, which is in the +2, +3 or +4 formal oxidation state and which is π-bonded to one cyclopentadienyl group (Cp) which is a cyclic, delocalized. π-bound ligand group having 5 substituents: $R^A$; $(R^B)_j$-T where j is zero, 1 or 2: $R^C$; $R^D$ and Z; where $R^A$, $R^B$, $R^C$ and $R^D$ are R groups; and where T is a heteroatom which is covalently bonded to the Cp ring, and to $R^B$ when j is 1 or 2,and when j is 0, T is F, Cl, Br, or I; when j is 1, T is 0 or S, or N or P and $R^B$ has a double bond to T; when j is 2, T is N or P; and where $R^B$ independently each occurrence is hydrogen, or, is a group having from 1 to 80 nonhydrogen atoms which is hydrocarbyl, hydrocarbylsilyl, halo-substituted hydrocarbyl, hydrocarbyloxy-substituted hydrocarbyl, hydrocarbylamino-substituted hydrocarbyl, hydrocarbylsilylhydrocarbyl, hydrocarbylamino, di(hydrocarbyl)amino, hydrocarbyloxy, each $R^B$ optionally being substituted with one or more groups which independently each occurrence is hydrocarbyloxy, hydrocarbylsiloxy, hydrocarbylsilylamino, di(hydrocarbylsilyl)amino, hydrocarbyl amino, di(hydrocarbyl)amino, di(hydrocarbyl)phosphino, hydrocarbylsulfido, hydrocarbyl, halo-substituted hydrocarbyl, hydrocarbyloxy-substituted hydrocarbyl, hydrocarbylamino-substituted hydrocarbyl, hydrocarbylsilyl or hydrocarbylsilylhydrocarbyl having from 1 to 20 nonhydrogen atoms, or a noninterfering group having from 1 to 20 nonhydrogen atoms, and each of $R^A$, $R^C$ and $R^D$ is hydrogen, or is a group having from 1 to 80 nonhydrogen atoms which is hydrocarbyl, halo-substituted hydrocarbyl, hydrocarbyloxy-substituted hydrocarbyl, hydrocarbylamino-substituted hydrocarbyl, hydrocarbylsilyl, hydrocarbylsilylhydrocarbyl, each $R^A$, $R^C$ or $R^D$ optionally being substituted with one or more groups which independently each occurrence is hydrocarbyloxy, hydrocarbylsiloxy, hydrocarbylsilylamino, di(hydrocarbylsilyl)amino, hydrocarbylamino, di(hydrocarbyl)amino, di(hydrocarbyl,)phosphino, hydrocarbylsulfido, hydrocarbyl, halo-substituted hydrocarbyl, hydrocarbyloxy-substituted hydrocarbyl, hydrocarbylamino-substituted hydrocarbyl, hydrocarbylsilyl or hydrocarbylsilylhydrocarbyl having from 1 to 20 nonhydrogen atoms, or a noninterfering group having from 1 to 20 nonhydrogen atoms; or, optionally, two or more of $R^A$, $R^B$, $R^C$ and $R^D$ are covalently linked with each other to form one or more fused rings or ring systems having from 1 to 80 nonhydrogen atoms for each R group, the one or more fused rings or ring systems being unsubstituted or substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, hydrocarbylsulfido, hydrocarbyl, halo-substituted hydrocarbyl, hydrocarbyloxy-substituted hydrocarbyl, hydrocarbylamino-substituted hydrocarbyl, hydrocarbylsilyl or hydrocarbylsilylhydrocarbyl having from 1 to 20 nonhydrogen atoms, or a noninterfering group having from 1 to 20 nonhydrogen atoms;

Z is a divalent moiety bound to both Cp and M via σ-bonds, where Z comprises boron, or a member of Group 14 of the Periodic Table of the Elements, and also comprises nitrogen, phosphorus, sulfur or oxygen;

X is an anionic or dianionic ligand group having tip to 60 atoms exclusive of the class of ligands that are cyclic, delocalized, π-bound ligand groups;

X' independently each occurrence is a neutral Lewis base ligating compound having up to 20 atoms;

p is zero, 1 or 2, and is two less than the formal oxidation state of M, when X is an anionic ligand; when X is a dianionic ligand group, p is 1; and q is zero, 1 or 2.

The above complexes may exist as isolated crystals optionally in pure form or as a mixture with other complexes, in the form of a solvated adduct, optionally in a solvent, especially an organic liquid, as well as in the form of a dimer or chelated derivative thereof, wherein the chelating agent is an organic material, preferably a neutral Lewis base, especially a trihydrocarbylamine, trihydrocarbylphosphine, or halogenated derivative thereof.

Also, according to the present invention, there is provided a catalyst system for olefin polymerization prepared from catalyst system components comprising:

(A) a catalyst component comprising a metal complex of one of the aforementioned complexes; and (B) a cocatalyst component comprising an activating cocatalyst wherein the molar ratio of (A) to (B) is from 1:10,000 to 100:1; or activation of (A) by use of an activating technique.

Another embodiment of this invention is a catalyst system for olefin polymerization prepared front catalyst system components comprising:

(A) a catalyst component comprising a metal complex of one of the aforementioned metal complexes; and (B) a cocatalyst component comprising an activating cocatalyst wherein the molar ratio of (A) to (B) is from 1:10,000 to 100:1.

wherein the metal complex is in the form of a radical cation.

Further according to the present invention there is provided a process for the polymerization of olefins comprising contacting one or more $C_{2-20}$ α-olefins under polymerization conditions with one of the aforementioned catalyst systems.

A preferred process of this invention is a high temperature solution polymerization process for the polymerization of olefins comprising contacting one or more $C_{2-20}$ α-olefins under polymerization conditions with one of the aforementioned catalyst systems at a temperature from about 100° C. to about 250° C.

Within the scope of this invention are the polyolefin products produced by the aforementioned processes. Preferred products have long chain branching and reverse molecular architecture.

This invention also provides a cyclopentadienyl-containing ligand of one of the aforementioned metal complexes where the ligand is in the form of:

(A) a free base with 2 protons capable of being deprotonated;

(B) a dilithium salt;

(C) a magnesium salt: or (D) a mono or disilylated dianion.

Within the scope of this aspect of the invention is the use of one of these ligands for synthesis to produce a metal complex of this invention, or for synthesis to produce a metal complex comprising a metal from one of Groups 3 to 13 of the Periodic Table of the Elements, the lanthanides or actinides, and from 1 to 4 of the ligands.

The present catalysts and processes result in the highly efficient production of high molecular weight olefin polymers over a wide range of polymerization conditions, and especially at elevated temperatures. They are especially useful for the solution or bulk polymerization of ethylene/propylene (EP polymers), ethylene/octene (EO polymers), ethylene/styrene (ES polymers), propylene and ethylene/propylene/diene (EPDM polymers) wherein the diene is ethylidenenorbornene, 1,4-hexadiene or similar nonconjugated diene. The use of elevated temperatures dramatically increases the productivity of such processes due to the fact that increased polymer solubility at elevated temperatures allows the use of increased conversions (higher concentration of polymer product) without exceeding solution viscosity limitations of the polymerization equipment as well as reduced energy costs needed to devolatilize the reaction product.

The catalysts of this invention may also be supported on a support material and used in olefin polymerization processes in a slurry or in the gas phase. The catalyst may be prepolymerized with one or more olefin monomers in situ in a polymerization reactor or in a separate process with intermediate recovery of the prepolymerized catalyst prior to the primary polymerization process.

Up to now it has been thought that heteroatom substitution directly on a cyclopentadienyl (Cp) group which is a cyclic, delocalized, π-bound ligand group of a metallocene complex would not have a beneficial effect upon the usefulness of the complex in an olefin polymerization catalyst system. However, it has now been found that the preferred metallocene complexes of this invention with heteroatom substitution directly on a single π-bonded Cp group have extraordinary properties as olefin catalysts, allowing the production) of high molecular weight polymers with desirable characteristics at high catalyst activities. Metallocene complexes with heteroatom substitution in the 3-position are highly preferred.

DETAILED DESCRIPTION

Figure 1:
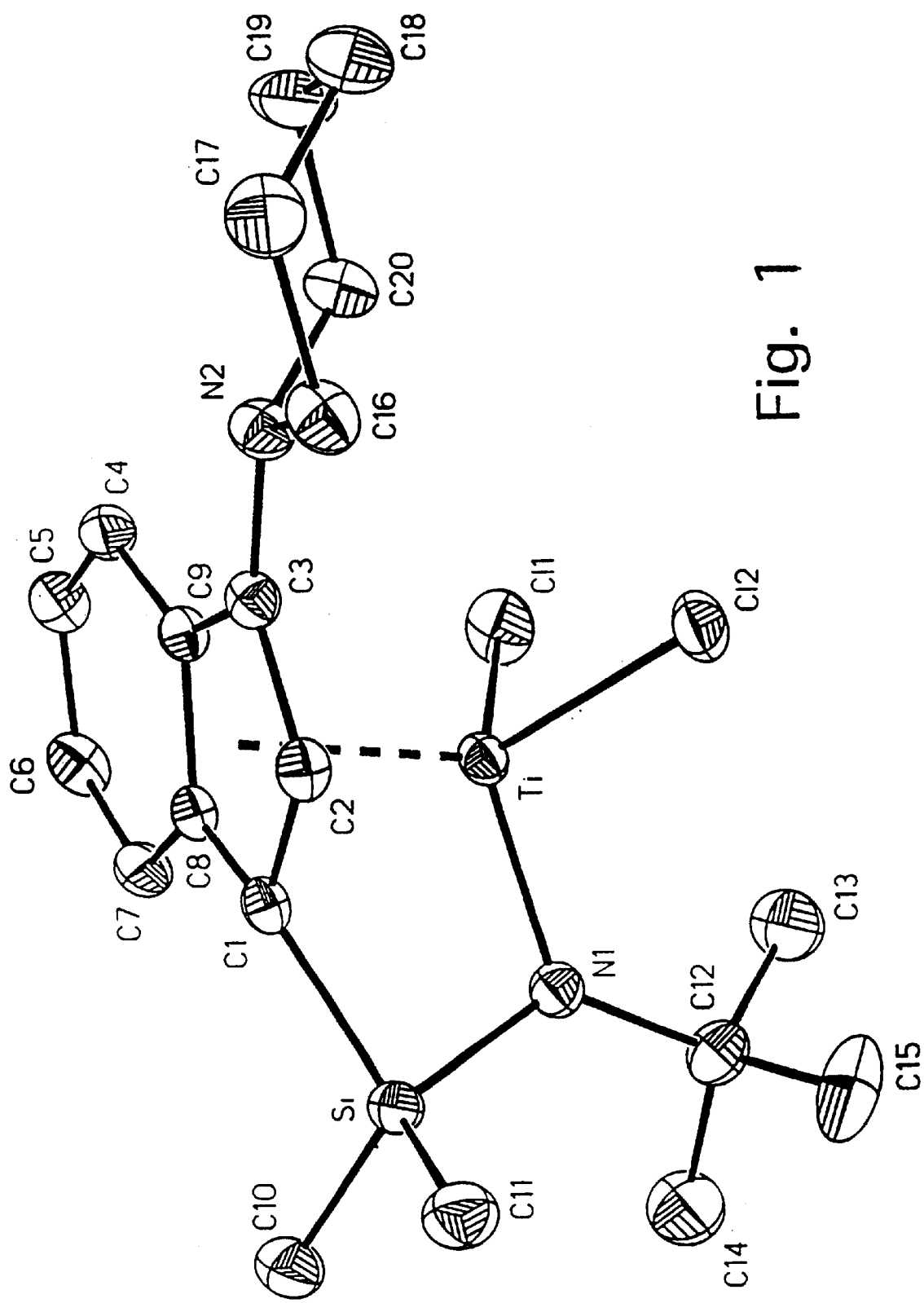
FIG. 1 shows the crystal structure of dichloro(N-(1,1-dimethylethyl)-1,1-dimethyl-1-((1,2,3,3a,7a-η)-3-(1-piperidinyl)-1H-inden-1-yl)silanaminato-(2-)-N-)-titanium.

All reference to the Periodic Table of the Elements herein shall refer to the Periodic Table of the Elements, published and copyrighted by CRC Press, Inc. 1989. Also, any reference to a Group or Groups shall be to the Group or Groups as reflected in this Periodic Table of the Elements using the IUPAC system for numbering groups.

Olefins as used herein are $C_{2-20}$ aliphatic or aromatic compounds containing vinylic unsaturation, as well as cyclic compounds such as cyclobutene, cyclopentene, and norbornene, including norbornene substituted in the 5- and 6-positions with $C_{1-20}$ hydrocarbyl groups. Also included are mixtures of such olefins as well as mixtures of such olefins with $C_{4-40}$ diolefin compounds. Examples of the latter compounds include ethylidene norbornene, 1,4-hexadiene, norbornadiene, and the like. The catalysts and processes herein are especially suited for use in preparation of ethylene/ 1-butene, ethylene/1-hexene, ethylene/styrene, ethylene/propylene, ethylene/1-pentene, ethylene/4-methyl-1-pentene and ethylene/1-octene copolymers as well as terpolymers of ethylene, propylene and a nonconjugated diene, such as, for example, EPDM terpolymers.

Preferred X' groups are carbon monoxide; phosphines, especially trimethylphosphine, triethylphosphine, triphenylphosphine and bis(1,2-dimethylphosphino)ethane; $P(OR^i)_3$, wherein $R^i$ is hydrocarbyl, silyl or a combination thereof; ethers, especially tetrahydrofuran; amines, especially pyridine, bipyridine, tetramethylethylenediamine (TMEDA), and triethylamine; olefins; and conjugated dienes having from 4 to 40 carbon atoms. Complexes including the latter X' groups include those wherein the metal is in the +2 formal oxidation state.

Preferred coordination complexes according to the present invention are complexes corresponding to the formula:

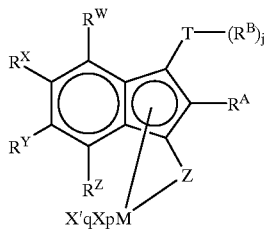

where $R^W$, $R^X$, $R^Y$ and $R^Z$ are R groups, each of which independently is hydrogen, or is a group having from 1 to 80 nonhydrogen atoms which is hydrocarbyl, halo-substituted hydrocarbyl, hydrocarbyloxy-substituted hydrocarbyl, hydrocarbylamino-substituted hydrocarbyl, hydrocarbylsilyl, hydrocarbylsilylhydrocarbyl, each of $R^W$, $R^X$, $R^Y$ and $R^Z$ optionally being substituted with one or more groups which independently each occurrence is hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, hydrocarbylsulfido, hydrocarbyl, halo-substituted hydrocarbyl, hydrocarbyloxy-substituted hydrocarbyl, hydrocarbylamino-substituted hydrocarbyl, hydrocarbylsilyl or hydrocarbylsilylhydrocarbyl having from 1 to 20 nonhydrogen atoms, or a noninterfering group having from 1 to 20 nonhydrogen atoms; or, optionally, two or more of $R^W$, $R^X$, $R^Y$, $R^Z$, $R^A$ and $R^B$ are covalently linked with each other to form one or more fused rings or ring systems having from 1 to 80 nonhydrogen atoms for each R group, the one or more fused rings or ring systems being unsubstituted or substituted with one or more groups which are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, hydrocarbylsulfido, hydrocarbyl, halo-substituted hydrocarbyl, hydrocarbyloxy-substituted hydrocarbyl, hydrocarbylamino-substituted hydrocarbyl, hydrocarbylsilyl or hydrocarbylsilylhydrocarbyl having from 1 to 20 nonhydrogen atoms, or a noninterfering group having from 1 to 20 nonhydrogen atoms.

Preferred $R^B$ groups are those wherein $R^B$ is hydrocarbyl, hydrocarbylsilyl, hydrocarbyloxy-substituted hydrocarbyl, hydrocarbylamino-substituted hydrocarbyl and T is O or N, more preferred are those wherein $R^B$ is hydrocarbyl or hydrocarbylsilyl and T is O or N, and still more preferred are wherein $R^B$ is hydrocarbyl or hydrocarbylsilyl and T is N.

Preferred heteroatom-containing substituents at the 3-position of the Cp are those wherein the $(R^B)_j$-T group is methoxy, ethoxy, propoxy, methylethyloxy, 1,1-dimethyethyloxy, trimethylsiloxy, 1,1-dimethylethyl (dimethylsilyl)oxy, dimethylamino, diethylamino, methylethylamino, methylphenylamino, dipropylamino, dibutylamino, piperidinyl, morpholinyl, pyrrolidinyl, hexahydro-1H-azepin-1-yl, hexahydro-1(2H)-azocinyl, octahydro-1H-azonin-1-yl or octahydro-1(2H)-azecinyl. More preferred are those wherein the $(R^B)_j$-T group is dimethylamino, methylphenylamino, piperidinyl or pyrrolidinyl.

In another aspect of this invention either the ligand or metal complex has one or more fused rings or ring systems in addition to the Cp or indenyl wherein the one or more fused rings or ring systems contain one or more ring heteroatoms which are N, O, S, or P. Preferred ring heteroatoms are N or O, with N being more highly preferred.

Other highly preferred complexes correspond to the formula:

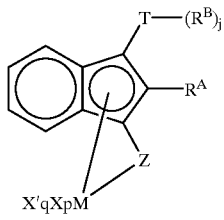

where the symbols are as previously defined, or, more preferred, correspond to the formula:

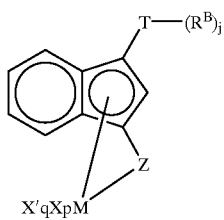

where the symbols are as previously defined.

Highly preferred are the metal complexes and the heteroatom-containing ligands thereof where —Z— is —Z*—Y—, with Z* bonded to Cp and Y bonded to M, and Y is —O—, —S—, —NR*—, —PR*—;

Z* is $SiR^*_2$, $CR^*_2$, $SiR^*_2SiR^*_2$, $CR^*_2CR^*_2$, $CR^*=CR^*$, $CR^*_2SiR^*_2$, $CR^*_2SiR^*_2CR^*_2$, $SiR^*_2CR^*_2SiR^*_2$, $CR^*_2CR^*_2SiR^*_2$, $CR^*_2CR^*_2CR^*_2$, or $GeR^*_2$; and R* independently each occurrence is hydrogen, or a member selected from hydrocarbyl, hydrocarbyloxy, silyl, halogenated alkyl, halogenated aryl, and combinations thereof, said R* having up to 20 nonhydrogen atoms, and optionally, two R* groups from Z (when R* is not hydrogen), or an R* group from Z and an R* group from Y form a ring system;

where p is 2, q is zero, M is in the +4 formal oxidation state, and X is independently each occurrence methyl, benzyl, trimethylsilylmethyl, allyl, pyrollyl or two X groups together are 1,4-butane-diyl, 2-butene-1,4-diyl, 2,3-dimethyl-2-butene-1,4-diyl, 2-methyl-2-butene-1, 4-diyl, or xylyldiyl.

Also highly preferred are the metal complexes and the hetcroatom-containing ligands thereof where —Z— is —Z*—Y—, with Z* bonded to Cp and Y bonded to M, and Y is —O—, —S—, —NR*—, —PR*—, Z* is $SiR^*_2$, $CR^*_2$, $SiR^*_2SiR^*_2$, $CR^*_2CR^*_2$, $CR^*=CR^*$, $CR^*_2SiR^*_2$, $CR^*_2SiR^*_2CR^*_2$, $SiR^*_2CR^*_2SiR^*_2$, $CR^*_2CR^*_2SiR^*_2$. $CR^*_2CR^*_2CR^*_2$, $GeR^*_2$; and R* independently each occurrence is hydrogen, or a member selected from hydrocarbyl, hydrocarbyloxy, silyl, halogenated alkyl, halogenated aryl, and combinations thereof, said R* having up to 20 nonhydrogen atoms, and optionally, two R* groups from Z (when R* is not hydrogen), or an R* group from Z and an R* group from Y form a ring system;

where p is 1, q is zero, M is in the +3 formal oxidation state, and X is 2-(N,N-dimethyl)aminobenzyl, 2-(N,N-dimethylaminomethyl)phenyl, allyl, methallyl, trimethylsilylallyl.

Also highly preferred are the metal complexes and the heteroatom-containing ligands thereof where —Z— is —Z*—Y—, with Z* bonded to Cp and Y bonded to M, and Y is —O—, —S—, —NR*—, —PR*—;

Z* is $SiR^*_2$, $CR^*_2$, $SiR^*_2SiR^*_2$, $CR^*_2CR^*_2$, $CR^*=CR^*$, $CR^*_2SiR^*_2$, $CR^*_2SiR^*_2CR^*_2$, $SiR^*_2CR^*_2SiR^*_2$, $CR^*_2CR^*_2SiR^*_2$, $CR^*_2CR^*_2CR^*_2$, or $GeR^*_2$; and R* independently each occurrence is hydrogen, or a member selected from hydrocarbyl, hydrocarbyloxy, silyl, halogenated alkyl, halogenated aryl, and combinations thereof, said R* having up to 20 nonhydrogen atoms, and optionally, two R* groups from Z (when R* is not hydrogen), or an R* group from Z and an R* group from Y form a ring system;

when p is 0, q is 1, M is in the +2 formal oxidation state, and X' is 1,4-diphenyl-1,3-butadiene, 1,3-pentadiene or 2,4-hexadiene.

A variety of metals can be used in the preparation of the metal complexes of this invention, desirably a metal from one of Groups 3 to 13 of the Periodic Table of the Elements, the lanthanides or actinides, which is in the +2, +3 or +4 formal oxidation state, more desirably a metal from one of Groups 3 to 13. Metal complexes of this invention having somewhat different characteristics are those where M is a metal from one of Groups 3–6, one of Groups 7–9 or one of Groups 10–12. Preferred are those where M is a metal from Group 4, desirably Ti, Zr or Hf, with Ti and Zr being more preferred. Ti is the most highly preferred metal, especially for use in complexes which contain only one Cp-containing ligand which is the heteratom-containing ligand of this invention, while Zr is highly preferred for use in complexes which contain two Cp-containing ligands, at least one of which is a heteratom-containing ligand.

In one embodiment it is preferred that Ti is in the +4 formal oxidation state, while, alternatively it is preferred that Ti is in the +3 formal oxidation state, and more preferred is that Ti is in the +2 formal oxidation state.

In another embodiment it is preferred that Zr is in the +4 formal oxidation state, or, alternatively, in the +2 formal oxidation state.

In another aspect of this invention it is preferred that Y is —NR*, with the more preferred —NR* being those where R* is a group having a primary or secondary carbon atom bonded to N. Highly preferred are where R* is cyclohexyl or isopropyl.

A preferred coordination complex is that corresponding to the formula:

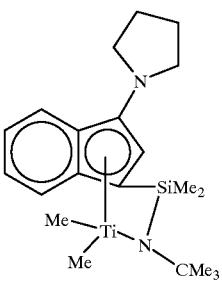

Illustrative derivatives of metals that may be employed in the practice of the present invention include:
(N-(1,1-dimethylethyl)-1,1-dimethyl-1-((1,2,3,3a,7a-η)-3-(1-pyrrolidinyl)-1H-inden-1-yl)silanaminato(2-)-N) dimethyltitanium (N-(1,1-dimethylethyl)-1,1-dimethyl-1-((1,2,3,3a,7a-η)-2-methyl-3-(1-pyrrolidinyl)-1H-inden-1-yl)silanaminato(2-)-N)dimethyltitanium (N-(1,1-dimethylethyl)-1,1-dimethyl-1-((1,2,3,3a,7a-η)-2ethyl-3-(1-pyrrolidinyl)-1H-inden-1-yl)silanaminato(2-)-N)dimethyltitanium (N-(1,1-dimethylethyl)-1,1-dimethyl-1-((1,2,3,3a,7a-η)-2-ethyl-6-methyl-3-(1-pyrrolidinyl)-1H-inden-1-yl)silanaminato(2-)-N)dimethyltitanium (N-(1,1-dimethylethyl)-1,1-dimethyl-1-((1,2,3,3a,7a-η)-4-methyl-3-(1-pyrrolidinyl)-1H-inden-1-yl)silanaminato(2-)-N)dimethyltitanium (N-(1,1-dimethylethyl)-1,1-dimethyl-1-((1,2,3,3a,7a-η)-5-ethyl-3-(1-pyrrolidinyl)-1H-inden-1-yl)silanaminato(2-)-N)dimethyltitanium (N-(1,1-dimethylethyl)-1,1-dimethyl-1-((1,2,3,3a,7a-η)-6-(1-methylethyl)-3-(1-pyrrolidinyl)-1H-inden-1-yl)silanaminato(2-)-N)dimethyltitanium (N-(1,1-dimethylethyl)-1,1-dimethyl-1-((1,2,3,3a,7a-η)-5-ethyl-6-methyl-3-(1-pyrrolidinyl)-1H-inden-1-yl)silanaminato(2-)-N)dimethyltitanium (N-(1,1-dimethylethyl)-1,1-dimethyl-1-((1,2,3,3a,7a-η)-5-butyl-3-(1-pyrrolidinyl)-1H-inden-1-yl)silanaminato(2-)-N)dimethyltitanium (N-(1,1-dimethylethyl)-1,1-dimethyl-1-((1,2,3,3a,7a-η)-5-(1,1-dimethylethyl)-3-(1-pyrrolidinyl)-1H-inden-1-yl)silanaminato(2-)-N)dimethyltitanium (N-(1,1-dimethylethyl)-1,1-dimethyl-1-((1,2,3,3a,7a-η)-5-phenyl-3-(1-pyrrolidinyl)-1H-inden-1-yl)silanaminato(2-)-N)dimethyltitanium (N-(1,1-dimethylethyl)-1,1-dimethyl-1-((1,2,3,3a,7a-η)-3-(1-pyrrolidinyl)-1H-inden-1-yl)silanaminato(2-)-N)((1,2,3,4-η)-1,3-pentadiene)titanium (N-(1,1-dimethylethyl)-1,1-dimethyl-1-((1,2,3,3a,7a-η)-2-methyl-3-(1-pyrrolidinyl)-1H-inden-1-yl)silanaminato(2-)-N)((1,2,3,4-η)-1,3-pentadiene)titanium (N-(1,1-dimethylethyl)-1,1-dimethyl-1-((1,2,3,3a,7a-η)-2-ethyl-3-(1-pyrrolidinyl)-1H-inden-1-yl)silanaminato(2-)-N)((1,2,3,4-η)-1,3-pentadiene)titanium (N-(1,1-dimethylethyl)-1,1-dimethyl-1-((1,2,3,3a,7a-η)-4-methyl-3-(1-pyrrolidinyl)-1H-inden-1-yl)silanaminato(2-)-N)((1,2,3,4-η)-1,3-pentadiene)titanium (N-(1,1-dimethylethyl)-1,1-dimethyl-1-((1 2,3,3a,7a-r)-5-ethyl-3-(1-pyrrolidinyl)-1H-inden-1-yl)silanaminato(2-)-N)((1,2,3,4-η)-1,3-pentadiene)titanium (N-(1,1-dimethylethyl)-1,1-dimethyl-1-((1,2,3,3a,7a-η)-6-(1-methylethyl)-3-(1-pyrrolidinyl)-1H-inden-1-yl)silanaminato(2-)-N)((1,2,3,4-η)-1,3-pentadiene)titanium (N-(1,1-dimethylethyl)-1,1-dimethyl-1-((1,2,3,3a,7a-η)-5-ethyl-6-methyl-3-(1-pyrrolidinyl)-1H-inden-1-yl)silanaminato(2-)-N)((1,2,3,4-η)-1,3-pentadiene)titanium (N-(1,1 -dimethylethyl)-1,1-dimethyl-1-((1,2,3,3a,7a-η)-5-butyl-3-(1-pyrrolidinyl)-1H-inden-1-yl)silanaminato(2-)-N)((1,2,3,4-η)-1,3-pentadiene)titanium (N-(1,1-dimethylethyl)-1,1-dimethyl-1-((1,2,3,3a,7a-η)-5-(1,1-dimethylethyl)-3-(1-pyrrolidinyl)-1H-inden-1-yl)silanaminato(2-)-N)((1,2,3,4-η)-1,3-pentadiene)titanium (N-(1,1-dimethylethyl)-1,1-dimethyl-1-((1,2,3,3a,7a-η)-5-phenyl-3-(1-pyrrolidinyl)-1H-inden-1-yl)silanaminato(2-)-N)((1,2,3,4-η)-1,3-pentadiene)titanium ((2-(dimethylamino)phenyl)methyl)(N-(1,1-dimethylethyl)-1,1-dimethyl-1-((1,2,3,3a,7a-η)-3-(1-pyrrolidinyl)-1H-inden-1-yl)silanaminato(2-)-N)titanium ((2-(dimethylamino)phenyl)methyl)(N-(1,1-dimethylethyl)-1,1-dimethyl-1-((1,2,3,3a,7a-η)-2-methyl-3-(1-pyrrolidinyl)-1H-inden-1-yl)silanaminato(2-)-N)titanium ((2-(dimethylamino)phenyl)methyl)(N-(1,1-dimethylethyl)-1,1-dimethyl-1-((1,2,3,3a,7a-η)-2-ethyl-3-(1-pyrrolidinyl)-1H-inden-1-yl)silanaminato(2-)-N)titanium ((2-(dimethylamino)phenyl)methyl)(N-(1,1-dimethylethyl)-1,1-dimethyl-1-((1,2,3,3a,7a-η)-2-ethyl-6-methyl-3-(1-pyrrolidinyl)-1H-inden-1-yl)silanaminato(2-)-N)titanium ((2-(dimethylamino)phenyl)methyl)(N-(1,1-dimethylethyl)-1,1-di methyl-1-((1,2,3,3a,7a-η)-4-methyl-3-(1-pyrrolidinyl)-1,1-inden-1-yl)silanaminato(2-)-N)dimethyltitanium ((2-(dimethylamino)phenyl)methyl)(N-(1,1-dimethylethyl)-1,1-dimethyl-1-((1,2,3,3a,7a-η)-5ethyl-3-(1-pyrrolidinyl)-1H-inden-1-yl)silanaminato(2-)-N)titanium ((2-(dimethylamino)phenyl)methyl)(N-(1,1-dimethylethyl)-1,1-dimethyl-1-((1,2,3,3a,7-η)-6-(1-methylethyl)-3-(1-pyrrolidinyl)-1H-inden-1-yl)silanaminato(2-)-N)titanium ((2-(dimethylamino)phenyl)methyl)(N-(1,1-dimethylethyl)-1,1-dimethyl-1-(1,2,3,3a,7a-η)-5-ethyl-6-methyl-3-(1-pyrrolidinyl)-1H-inden-1-yl)silanaminato(2-)-N)titanium ((2-(dimethylamino)phenyl)methyl)(N-(1,1-dimethylethyl)-1,1-dimethyl-1-((1,2,3,3a,7a-η)-5-butyl-3-(1-pyrrolidinyl)-1H-inden-1-yl)silanaminato(2-)-N)titanium ((2-(dimethylamino)phenyl)methyl)(N-(1,1-dimethylethyl)-1,1-dimethyl-1-((1,2,3,3a,7a-η)-5-(1,1-dimethylethyl)-3-(1-pyrrolidinyl)-1H-inden-1-yl)silanaminato(2-)-N)titanium ((2-(dimethylamino)phenyl)methyl)(N-(1,1-dimethylethyl)-1,1-dimethyl-1-((1,2,3,3a,7a-η)-5-phenyl-3-(1-pyrrolidinyl)-1H-inden-1-yl)silanaminato(2-)-N)titanium (N-cyclohexyl-1,1-dimethyl-1-((1,2,3,3a,7a-η)-2-methyl-3-(1-pyrrolidinyl)-1H-inden-1-yl)silanaminato(2-)-N)dimethyltitanium (N-cyclohexyl-1,1-dimethyl-1-((1,2,3,3a,7a-η)-2-ethyl-3-(1-pyrrolidinyl)-1H-inden-1-yl)silanaminato(2-)-N)dimethyltitanium (N-cyclohexyl-1,1-dimethyl-1-((1,2,3,3a,7a-η)-2-ethyl-6-methyl-3-(1-pyrrolidinyl)-1H-inden-1-yl)silanaminato(2-)-N)dimethyltitanium (N-cyclohexyl-1,1-dimethyl-1-((1,2,3,3a,7a-η)-4-methyl-3-(1-pyrrolidinyl)-1H-inden-1-yl)silanaminato(2-)-N)dimethyltitanium (N-cyclohexyl-1,1-dimethyl-1-((1,2,3,3a,7a-η)-5-ethyl-3-(1-pyrrolidinyl)-1H-inden-1-yl)silanaminato(2-)-N)dimethyltitanium (N-cyclohexyl-1,1-dimethyl-1-((1.2,3,3a,7a-η)-6-(1-methylethyl)-3-(1-pyrrolidinyl)-1H-inden-1-yl)silanaminato(2-)-N)dimethyltitanium (N-cyclohexyl-1,1-dimethyl-1-((1,2,3,3a,7a-η)-5-ethyl-6-methyl-3-(1-pyrrolidinyl)-1H-inden-1-yl)silanaminato(2-)-N)dimethyltitanium (N-cyclohexyl-1,1-dimethyl-1-((1,2,3,3a,7a-η)-5-butyl-3-(1-pyrrolidinyl)-1H-inden-1-yl)silanaminato(2-)-N)dimethyltitanium (N-cyclohexyl-1,1-dimethyl-1-((1,2,3,3a,7a-η)-5-(1,1-dimethylethyl)-3-(1-pyrrolidinyl)-1H-inden-1-yl)silanaminato(2-)-N)dimethyltitanium (N-cyclohexyl-1,1-dimethyl-1-((1,2,3,3a,7a-η)-5-phenyl-3-(1-pyrrolidinyl)-1H-inden-1-yl)silanaminato(2-)-N)dimethyltitanium (1,1-dimethyl-N-(1-methylethyl)-1-((1,2,3,3a,7a-η)-3-(1-pyrrolidinyl)-1H-inden-1-yl)silanaminato(2-)-N)dimethyltitanium (1,1-dimethyl-N-(1-methylethyl)-1-((1,2,3,3a,7a-η)-2-methyl-3-(1-pyrrolidinyl)-1H-inden-1-yl)silanaminato(2-)-N)di methyltitanium (1,1-dimethyl-N-(1-methylethyl)-1-((1,2,3,3a,7a-η)-2-ethyl-3-(1-pyrrolidinyl)-1H-inden-1-yl)silanaminato(2-)-N)dimethyl titanium (1,1-dimethyl-N-(1-methylethyl)-1-((1,2,3,3a,7a-η)-2-ethyl-6-methyl-3-(1-pyrrolidinyl)-1H-inden-1-yl)silanaminato(2-)-N)dimethyltitanium (1,1-dimethyl-N-(1-methylethyl)-1-((1,2,3,3a,7a-η)-4-methyl-3-(1-pyrrolidinyl)-1H-inden-1-yl)silanaminato(2-)-N)dimethyltitanium (1,1-dimethyl-N-(1-methylethyl)-1-((1,2,3,3a,7a-η)-5-ethyl-3-(1-pyrrolidinyl)-1H-inden-1-yl)silanaminato(2-)-N)dimethyltitanium (1,1-dimethyl-N-(1-methylethyl)-1-((1,2,3,3a,7a-η)-6-(1-methylethyl)-3-(1-pyrrolidinyl)-1H-inden-1-yl)silanaminato(2-)-N)dimethyltitanium (1,1-dimethyl-N-(1-methylethyl)-1-((1,2,3,3a,7a-η)-5-ethyl-6-methyl-3-(1-pyrrolidinyl)-1H-inden-1-yl)silanaminato(2-)-N)dimethyltitanium (1,1-dimethyl-N-(1-methylethyl)-1-((1,2,3,3a,7a-η)-5-butyl-3-(1-pyrrolidinyl)-1H-inden-1-yl)silanaminato(2-)-N)dimethyltitanium (1,1-dimethyl-N-(1-methylethyl)-1-((1,2,3,3a,7a-η)-5-(1,1-dimethylethyl)-3-(1-pyrrolidinyl)-1H-inden-1-yl)silanaminato(2-)-N)dimethyltitanium (1,1-dimethyl-N-(1-methylethyl)-1-((1,2,3,3a,7a-η)-5-phenyl-3-(1-pyrrolidinyl)-1H-inden-1-yl)silanaminato(2-)-N)dimethyltitanium (1,1-dimethyl-N-(phenylmethyl)-1-((1,2,3,3a,7a-η))-3-(1-pyrrolidinyl)-1H-inden-1-yl)silanaminato(2-)-N)dimethyltitanium (1,1-dimethyl-N-(phenylmethyl)-1-((1,2,3,3a,7a-η)-2-methyl-3-(1-pyrrolidinyl)-1H-inden-1-yl)silanaminato(2-)-N)dimethyltitanium (1,1-dimethyl-N-(phenylmethyl)-1-((1,2,3,3a,7a-η)-2-ethyl-3-(1-pyrrolidinyl)-1H-inden-1-yl)silanaminato(2-)-N)dimethyltitanium (1,1-dimethyl-N-(phenylmethyl)-1-((1,2,3,3a,7a-η)-2-ethyl-6-methyl-3-(1-pyrrolidinyl)-1H-inden-1-yl)silanaminato(2-)-N)dimethyltitanium (1,1-dimethyl-N-(phenylmethyl)-1-((1,2,3,3a,7a-η)-4-methyl-3-(1-pyrrolidinyl)-1H-inden-1-yl)silanaminato(2-)-N)dimethyltitanium (1,1-dimethyl-N-(phenylmethyl)-1-((1,2,3,3a,7a-η)-5-ethyl-3-(1-pyrrolidinyl)-1H-inden-1-yl)silanaminato(2-)-N)dimethyltitanium (1,1-dimethyl-N-(phenylmethyl)-1-((1,2,3,3a,7a-η)-6-(1-methylethyl)-3-(1-pyrrolidinyl)-1H-inden-1-yl)silanaminato(2-)-N)dimethyltitanium (1,1-dimethyl-N-(phenylmethyl)-1-((1,2,3,3a,7a-η)-5-ethyl-6-methyl-3-(-1-pyrrolidinyl)-1H-inden-1-yl)silanaminato(2-)-N)dimethyltitanium (1,1-dimethyl-N-(phenylmethyl)-1-((1,2,3,3a,7a-η)-5-butyl-3-(1-pyrrolidinyl)-1H-inden-1-yl)silanaminato(2-)-N)dimethyltitanium (1,1-dimethyl-N-(phenylmethyl)-1-((1,2,3,3a,7a-η)-5-(1,1-dimethylethyl)-3-(1-pyrrolidinyl)-1H-inden-1-yl)silanaminato(2-)-N)dimethyltitanium (1,1-dimethyl-N-(phenylmethyl)-1-((1,2,3,3a,7a-η)-5-phenyl-3-(1-pyrrolidinyl)-1H-inden-1-yl)silanaminato(2-)-N)dimethyltitanium (N-(1,1-dimethylethyl)-1,1-dimethyl-1-((1,2,3,3a,7a-η)-3-(1-pyrrolidinyl)-1H-inden-1-yl)silanaminato(2-)-N)dimethyltitanium (N-methyl-1,1-dimethyl-1-((1,2,3,3a,7a-η)-3-(1-pyrrolidinyl)-1H-inden-1-yl)silanaminato(2-)-N)dimethyltitanium (N-ethyl-1,1-dimethyl-1-((1,2,3,3a,7a-η)-3-(1-pyrrolidinyl)-1H-inden-1-yl)silanaminato(2-)-N)dimethyltitanium (N-cyclohexyl-1,1-dimethyl-1-((1,2,3,3a,7a-η)-3-(1-pyrrolidinyl)-1H-inden-1-yl)silanaminato(2-)-N)dimethyltitanium (1,1-dimethyl-N-phenyl-1-((1,2,3,3a,7a-η)-3-(1-pyrrolidinyl)-1H-inden-1-yl)silanaminato(2-)-N)dimethyltitanium (1,1-dimethyl-N-(methylphenyl)-1-((1,2,3,3a,7a-η)-3-(1-pyrrolidinyl)-1H-inden-1-yl)silanaminato(2-)-N)di methyltitanium (N-cyclododecyl-1,1-dimethyl-1-((1,2,3,3a,7a-η)-3-(1-pyrrolidinyl)-1H-inden-1-yl)silanaminato(2-)-N)dimethyltitanium (N-1,1-dimethyl-N-(1-methylethyl)-1-((1,2,3,3a,7a-η)-3-(1-pyrrolidinyl)-1H-inden-1-yl)silanaminato(2-)-N)dimethyltitanium (N-butyl-1,1-dimethyl-1-((1,2,3,3a,7a-η)-3-(1-pyrrolidinyl)-1H-inden-1-yl)silanaminato(2-)-N)dimethyltitanium (1,1-dimethyl-N-propyl-1-((1,2,3,3a,7a-η)-3-(1-pyrrolidinyl)-1H-inden-1-yl)silanaminato(2-)-N)dimethyltitanium (N-(1,1-dimethylethyl)-1,1-dimethyl-1-((1,2,3,3a,7a-η)-3-(1-pyrrolidinyl)-1H-inden-1-yl)silanaminato(2-)-N)((1,2,3,4-η)-1,3-pentadiene)titanium (N-methyl-1,1-dimethyl-1-((1,2,3,3a,7a-η)-3-(1-pyrrolidinyl)-1H-inden-1-yl)silanaminato(2-)-N)((1,2,3,4-η)-1,3-pentadiene)titanium (N-ethyl-1,1-dimethyl-1-((1,2,3,3a,7a-η)-3-(1-pyrrolidinyl)-1H-inden-1-yl)silanaminato(2-)-N)((1,2,3,4-η)-1,3-pentadiene)titanium (N-cyclohexyl-1,1-dimethyl-1-((1,2,3,3a,7a-η)-3-(1-pyrrolidinyl)-1H-inden-1-yl)silanaminato(2-)-N)((1,2,3,4-η)-1,3-pentadiene)titanium (1,1-dimethyl-N-phenyl-1-((1,2,3,3a,7a-η)-3-(1-pyrrolidinyl)-1H-inden-1-yl)silanaminato(2-)-N)((1,2,3,4-η)-1,3-pentadiene)titanium (1,1-dimethyl-N-(methylphenyl)-1-((1,2,3,3a,7a-η)-3-(1-pyrrolidinyl)-1H-inden-1-yl)silanaminato(2-)-N)((1,2,3,4-η)-1,3-pentadiene)titanium (N-cyclododecyl-1,1-dimethyl-1-((1,2,3,3a,7a-η)-3-(1-pyrrolidinyl)-1H-inden-1-yl)silanaminato(2-)-N)((1,2,3,4-η)-1,3-pentadiene)titanium (N-1,1-dimethyl-N-(1-methylethyl)-1-((1,2,3,3a,7a-η)-3-(1-pyrrolidinyl)-1H-inden-1-yl)silanaminato(2-)-N)((1,2,3,4-η)-1,3-pentadiene)titanium (N-butyl-1,1-dimethyl-1-((1,2,3,3a,7a-η)-3-(1-pyrrolidinyl)-1H-inden-1-yl)silanaminato(2-)-N)((1,2,3,4-η)-1,3-pentadiene)titanium (1,1-dimethyl-N-propyl-1-((1,2,3,3a,7a-η)-3-(1-pyrrolidinyl)-1H-inden-1-yl)silanaminato(2-)-N)((1,2,3,4-η)-1,3-pentadiene)titanium ((2-(dimethylamino)phenyl)methyl)(N-(1,1-dimethylethyl)-1,1-dimethyl-1-((1,2,3,3a,7a-η)-3-(1-pyrrolidinyl)-1H-inden-1-yl)silanaminato(2-)-N)titanium ((2-(dimethylamino)phenyl)methyl)(N-methyl-1,1-dimethyl-1-((1,2,3,3a,7a-η)-3-(1-pyrrolidinyl)-1H-inden-1-yl)silanaminato(2-)-N)titanium ((2-(dimethylamino)phenyl)methyl)(N-ethyl-1,1-dimethyl-1-((1,2,3,3a,7a-η)-3-(1-pyrrolidinyl)-1H-inden-1-yl)silanaminato(2-)-N)titanium ((2-(dimethylamino)phenyl)methyl)(N-cyclohexyl-1,1-dimethyl-1-((1,2,3,3a,7a-η)-3-(1-pyrrolidinyl)-1H-inden-1-yl)silanaminato(2-)-N)titanium ((2-(dimethylamino)phenyl)methyl)(1,1-dimethyl-N-phenyl-1-((1,2,3,3a,7a-η)-3-(1-pyrrolidinyl)-1H-inden-1-yl)silanaminato(2-)-N)titanium ((2-(dimethylamino)phenyl)methyl)(1,1-dimethyl-N-(methylphenyl)-1-((1,2,3,3a,7a-η)-3-(1-pyrrolidinyl)-1H-inden-1-yl)silanaminato(2-)-N)titanium ((2-(dimethylamino)phenyl)methyl)(N-cyclododecyl-1,1-dimethyl-1-((1,2,3,3a,7a-η)-3-(1-pyrrolidinyl)-1H-inden-1-yl)silanaminato(2-)-N)dimethyltitanium ((2-(dimethylamino)phenyl)methyl)(N-1,1-dimethyl-N-(1-methylethyl)-1-((1,2,3,3a,7a-η)-3-(1-pyrrolidinyl)-1H-inden-1-yl)silanaminato(2-)-N)titanium ((2-(dimethylamino)phenyl)methyl)(N-butyl-1,1-dimethyl-1-((1,2,3,3a,7a-η)-3-(1-pyrrolidinyl)-1H-inden-1-yl)silanaminato(2-)-N)titanium ((2-(dimethylamino)phenyl)methyl)(1,1-dimethyl-N-propyl-1-((1,2,3,3a,7a-η)-3-(1-pyrrolidinyl)-1H-inden-1-yl)silanaminato(2-)-N)titanium (N-(1,1-dimethylethyl)-1,1-dimethyl-1-((1,2,3,3a,7a-η)-3-(1-pyrrolidinyl)-1H-inden-1-yl)silanaminato(2-)-N)dimethyltitanium (N-(1,1-dimethylethyl)-1,1-dimethyl-1-((1,2,3,3a,7a-η)-3-(1-piperidinyl)-1H-inden-1-yl)silanaminato(2-)-N)dimethyltitanium (N-(1,1-dimethylethyl)-1,1-dimethyl-1-((1,2,3,3a,7a-η)-3-(hexahydro-1H-azepin-1-yl)-1H-inden-1-yl)silanaminato(2-)-N)dimethyltitanium (N-(1,1-dimethylethyl)-1,1-dimethyl-1-((1,2,3,3a,7a-η)-3-(hexahydro-1(2H)-azocinyl)-1H-inden-1-yl)silanaminato(2-)-N)dimethyltitanium (N-(1,1-dimethylethyl)-1,1-dimethyl-1-((1,2,3,3a,7a-η)-3-(octahydro-1H-azonin-1-yl)dimethyltitanium (N-(1,1-dimethylethyl)-1,1-dimethyl-1-((1,2,3,3a,7a-η)-3-(octahydro-1(2H)-azecinyl)-1H-inden-1-yl)silanaminato(2-)-N)dimethyltitanium (N-(1,1-dimethylethyl)-1,1-dimethyl-1-((1,2,3,3a,7a-η)-3-(dimethylamino)-1H-inden-1-yl)silanaminato(2-)-N)dimethyltitanium (N-(1,1-dimethylethyl)-1,1-dimethyl-1-((1,2,3,3a,7a-η)-3-(diethylamino)-1H-inden-1-yl)silanaminato(2-)-N)dimethyltitanium (N-(1,1-dimethylethyl)-1,1-dimethyl-1-((1,2,3,3a,7a-η)-3-(dipropylamino)-1H-inden-1-yl)silanaminato(2-)-N)dimethyltitanium (N-(1,1-dimethylethyl)-1,1-dimethyl-1-((1,2,3,3a,7a-η)-3-(dibutylamino)-1H-inden-1-yl)silanaminato(2-)-N)dimethyltitanium (N-(1,1-dimethylethyl)-1,1-dimethyl-1-((1,2,3,3a,7a-η)-3-(ethylmethylamino)-1H-inden-1-yl)silanaminato(2-)-N)dimethyltitanium (N-(1,1-dimethylethyl)-1,1-dimethyl-1-((1,2,3,3a,7a-η)-3-(methylphenylamino)-1H-inden-1-yl)silanaminato(2-)-N)dimethyltitanium (N-(1,1-dimethylethyl)-1,1-dimethyl-1(1,2,3,3a,7a-η)-3-(methyl(phenylmethyl)amino)-1H-inden-1-yl)silanaminato(2-)-N)dimethyltitanium (N-(1,1-dimethylethyl)-1,1-dimethyl-1-((1,2,3,3a,7a-η)-3-((,1-dimethylethyl)methylamino)-1H-inden-1-yl)silanaminato(2-)-N)dimethyltitanium (N-(1,1-dimethylethyl)-1,1-dimethyl-1-((1,2,3,3a,7a-η)-3-(methyl(1-methylethyl)amino)-1H-inden-1-yl)silanaminato(2-)-N)dimethyltitanium (N-(1,1-dimethylethyl)-1,1-dimethyl-1-((1,2,3,3a,7a-η)-3-(diphenylphosphino)-1H-inden-1-yl)silanaminato(2-)-N)dimethyltitanium (N-(1,1-dimethylethyl)-1,1-dimethyl-1-((1,2,3,3a,7a-η)-3-(dimethylphosphino)-1H-inden-1-yl)silanaminato(2-)-N)dimethyltitanium (N-(1,1-dimethylethyl)-1,1-dimethyl-1-((1,2,3,3a,7a-η)-3-(methylphenylphosphino)-1H-inden-1-yl)silanaminato(2-)-N)dimethyltitanium (N-(1,1-dimethylethyl)-1,1-dimethyl-1-((1,2,3,3a,7a-η)-3-(diethylphosphino)-1H-inden-1-yl)silanaminato(2-)-N)dimethyltitanium (N-(1,1-dimethylethyl)-1,1-dimethyl-1-((1,2,3,3a,7a-η)-3-(bis(1-methylethyl)phosphino)-1H-inden-1-yl)silanaminato(2-)-N)dimethyltitanium (N-(1,1-dimethylethyl)-1,1-dimethyl-1-((1,2,3,3a,7a-η)-3-methoxy-1H-inden-1-yl)silanaminato(2-)-N)dimethyltitanium (N-(1,1-dimethylethyl)-1,1-dimethyl-1-((1,2,3,3a,7a-η)-3-ethoxy-1H-inden-1-yl)silanaminato(2-)-N)dimethyltitanium (N-(1,1-dimethylethyl)-1,1-dimethyl-1-((1,2,3,3a,7a-η)-3-propoxy-1H-inden-1-yl)silanaminato(2-)-N)dimethyltitanium (N-(1,1-dimethylethyl)-1,1-dimethyl-1-((1,2,3,3a,7a-η)-3-butoxy-1H-inden-1-yl)silanaminato(2-)-N)dimethyltitanium (N-(1,1-dimethylethyl)-1,1-dimethyl-1-((1,2,3,3a,7a-η)-3-((1,1-dimethylethyl)oxy)-1H-inden-1-yl)silanaminato(2-)-N)dimethyltitanium (N-(1,1-dimethylethyl)-1,1-dimethyl-1-((1,2,3,3a,7a-η)-3-(trimethylsiloxy)-1H-inden-1-yl)silanaminato(2-)-N)dimethyltitanium (N-(1,1-dimethylethyl)-1,1-dimethyl-1-((1,2,3,3a,7a-η)-3-(((1,1-dimethylethyl)dimethylsilyl)oxy)-1H-inden--yl)silanaminato(2-)-N)dimethyltitanium (N-(1,1-dimethylethyl)-1,1-dimethyl-1-((1,2,3,3a,7a-η)-3-(1-methylethoxy)-1H-inden-1-yl)silanaminato(2-)-N)dimethyltitanium (N-(1,1-dimethylethyl)-1,1-dimethyl-1-((1,2,3,3a,7a-η)-3-phenoxy-1H-inden-1-yl)silanaminato(2-)-N)dimethyltitanium N-(1,1-dimethylethyl)-1,1-dimethyl-1-((1,2,3,3a,7a-η)-3-(phenylthio)-1i1-inden-1-yl)silanaminato(2-)-N)dimethyltitanium (N-(1,1-dimethylethyl)-1,1-dimethyl-1-((1,2,3,3a,7a-η)-3-(methylthio)-1H-inden-1-yl)silanaminato(2-)-N)dimethyltitanium (N-(1,1-dimethylethyl)-1,1-dimethyl-1-((1,2,3,3a,7a-η)-3-(1-pyrrolidinyl)-1H-inden-1-yl)silanaminato(2-)-N)((1,2,3,4-η)-1,3-pentadiene)titanium (N-(1,1-dimethylethyl)-1,1-dimethyl-1-((1,2,3,3a,7a-η)-3-(1-piperidinyl)-1H-inden-1-yl)silanaminato(2-)-N)((1,2,3,4-η)-1,3-pentadiene)titanium (N-(1,1-dimethylethyl 1)-1,1-dimethyl-1-((1,2,3,3a,7a-η)-3-(hexahydro-1H-azepin-1-yl)-1H-inden-1-yl)silanaminato(2-)-N)((1,2,3,4-7l)-1,3-pentadiene)titanium (N-(1,1-dimethylethyl)-1,1-dimethyl-1-((1,2,3,3a,7a-η)-3-(hexahydro-1(2H)-azocinyl)-1H-inden-1-yl)silanaminato(2-)-N)((1,2,3,4-η)-1,3-pentadiene)titanium (N-(1,1-dimethylethyl)-1,1-dimethyl-1-((1,2,3,3a,7a-η)-3-(octahydro-1H-azonin-1-yl)((1,2,3,4-η)-1,3-pentadiene)titanium (N-(1,1-dimethylethyl)-1,1-dimethyl-1-((1,2,3,3a,7a-η)-3-(octahydro-1(2H)-azecinyl)-1H-inden-1-yl)silanaminato(2-)-N)((1,2,3,4-η)-1,3-pentadiene)titanium (N-(1,1-dimethylethyl)-1,1-dimethyl-1-((1,2,3,3a,7a-η)-3-(dimethylamino)-1H-inden-1-yl)silanaminato(2-)-N)((1,2,3,4-η)-1,3-pentadiene)titanium (N-(1,1-dimethylethyl)-1,1-dimethyl-1-((1,2,3,3a,7a-η)-3-(diethylamino)-1H-inden-1-yl)silanaminato(2-)-N)((1,2,3,4-η)-1,3-pentadiene)titanium (N-(1,1-dimethylethyl)-1,1-dimethyl-1-((1,2,3,3a,7a-η)-3-(dipropylamino)-1H-inden-1-yl)silanaminato(2-)-N)((1,2,3,4-η)-1,3-pentadiene)titanium (N-(1,1-dimethylethyl)-1,1-dimethyl-1-((1,2,3,3a,7a-η)-3-(dibutylamino)-1H-inden-1-yl)silanaminato(2-)-N)((1,2,3,4-η)-1,3-pentadiene)titanium (N-(1,1-dimethylethyl)-1,1-dimethyl-1-((1,2,3,3a,7a-η)-3-(ethylmethylamino)-1H-inden-1-yl)silanaminato(2-)-N)((1,2,3,4-η)-1,3-pentadiene)titanium (N-(1,1-dimethylethyl)-1,1-dimethyl-1-((1,2,3,3a,7a-η)-3-(methylphenylamino)-1H-inden-1-yl)silanaminato(2-)-N)((1,2,3,4-η)-1,3-pentadiene)titanium (N-(1,1-dimethylethyl)-1,1-dimethyl-1-((1,2,3,3a,7a-η)-3-(methyl(phenylmethyl)amino)-1H-inden-1-yl)silanaminato(2-)-N)((1,2,3,4-η)-1,3-pentadiene)titanium (N-(1,1-dimethylethyl)-1,1-dimethyl-1-((1,2,3,3a,7a-η)-3-
((1,1-dimethylethyl)methylamino)-1H-inden-1-yl)
silanaminato(2-)-N)((1,2,3,4-η)-1,3-pentadiene)titanium (N-(1,1-dimethylethyl)-1,1-dimethyl-1-((1,2,3,3a,7a-η)-3-
(methyl(1-methylethyl)amino)-1H-inden-1-yl)
silanaminato(2-)-N)((1,2,3,4-η)-1,3-pentadiene)titanium (N-(1,1-dimethylethyl)-1,1-dimethyl-1-((1,2,3,3a,7a-η)-3-
(diphenylphosphino)-1H-inden-1-yl)silanaminato(2-)-N)
((1,2,3,4-η)-1,3-pentadiene)titanium (N-(1,1-dimethylethyl)-1,1-dimethyl-1-(1,2,3,3a,7a-η)-3-
(dimethylphosphino)-1H-inden-1-yl)silanaminato(2-)-N)
((1,2,3,4-η)-1,3-pentadiene)titanium (N-(1,1-dimethylethyl)-1,1-dimethyl-1-((1,2,3,3a,7a-η)-3-
(methylphenylphosphino)-1H-inden-1-yl)silanaminato
(2-)-N)((1,2,3,4-η)-1,3-pentadiene)titanium (N-(1,1-dimethylethyl)-1,1-dimethyl-1-((1,2,3,3a,7a-η)-3-
(diethylphosphino)-1H-inden-1-yl)silanaminato(2-)-N)
((1,2,3,4-η)-1,3-pentadiene)titanium (N-(1,1-dimethylethyl)-1,1-dimethyl-1-((1,2,3,3a,7a-η)-3-
(bis(1-methylethyl)phosphino)-1H-inden-1-yl)
silanaminato(2-)-N)((1,2,3,4-η)-1,3-pentadiene)titanium (N-(1,1-dimethylethyl)-1-dimethyl-1-((1,2,3,3a,7a-η)-3-
methoxy-1H-inden-1-yl)silanaminato(2-)-N)((1,2,3,4-η)-
1,3-pentadiene)titanium (N-(1,1-dimethylethyl)-1,1-dimethyl-1-((1,2,3,3a,7a-η)-3-
ethoxy-1H-inden-1-yl)silanaminato(2-)-N)((1,2,3,4-η)-1,
3-pentadiene)titanium (N-(1,1-dimethylethyl)-1,1-dimethyl-1-((1,2,3,3a,7a-η)-3-
propoxy-1H-inden-1-yl)silanaminato(2-)-N)((1,2,3,4-η)-
1,3-pentadiene)titanium (N-(1,1-dimethylethyl)-1,1-dimethyl-1-((1,2,3,3a,7a-η)-3-
butoxy-1H-inden-1-yl)silanaminato(2-)-N)((1,2,3,4-η)-1,
3-pentadiene)titanium (N-(1,1-dimethylethyl)-1,1-dimethyl-1-((1,2,3,3a,7a-η)-3-
((1,1-dimethylethyl)oxy)-1H-inden-1-yl)silanaminato
(2-)-N)((1,2,3,4-η)-1,3-pentadiene)titanium (N-(1,1-dimethylethyl)-1,1-dimethyl-1-((1,2,3,3a,7a-η)-3-
(trimethylsiloxy)-1H-inden-1-yl)silanaminato(2-)-N)((1,
2,3,4-η)-1,3-pentadiene)titanium (N-(1,1-dimethylethyl)-1,1-dimethyl-1-((1,2,3,3a,7a-.l)-3-
(((1,1-dimethylethyl)dimethylsilyl)oxy)-1H-inden-1-yl)
silanaminato(2-)-N)((1,2,3,4-η)-1,3-pentadiene)titanium (N-(1,1-dimethylethyl)-1,1-dimethyl-1-((1,2,3,3a,7a-η)-3-
(1-methylethoxy)-1H-inden-1-yl)silanaminato(2-)-N)((1,
2,3,4-η)-1,3-pentadiene)titanium (N-(1,1-dimethylethyl)-1,1-dimethyl-1-((1,2,3,3a,7a-η)-3-
phenoxy-1H-inden-1-yl)silanaminato(2-)-N)((1,2,3,4-η)-
1,3-pentadiene)titanium (N-(1,1-dimethylethyl)-1,1-dimethyl-1-((1,2,3,3a,7a-η))-3-
(phenylthio)-1H-inden-1-yl)silanaminato(2-)-N)((1,2,3,
4-η)-1,3-pentadiene)titanium (N-(1,1-dimethylethyl)-1,1-dimethyl-1-((1,2,3,3a,7a-η)-3-
(methylthio)-1H-inden-1-yl)silanaminato(2-)-N)((1,2,3,
4-η)-1,3-pentadiene)titanium ((2-(dimethylamino)phenyl)methyl)(N-(1,1-dimethylethyl)-
1,1-dimethyl-1-((1,2,3,3a,7a-η)-3-(1-pyrrolidinyl)-1H-
inden-1-yl)silanaminato(2-)-N)titanium ((2-(dimethylamino)phenyl)methyl)(N-(1,1-dimethylethyl)-
1,1-dimethyl-1-((1,2,3,3a,7a-η)-3-(1-piperidinyl)-1H-
inden-1-yl)silanaminato(2-)-N)titanium ((2-(dimethylamino)phenyl)methyl)(N-(1,1-dimethylethyl)-
1,1-dimethyl-1-((1,2,3,3a,7a-η)-3-(hexahydro-1H-
azepin-1-yl)-1H-inden-1-yl)silanaminato(2-)-N)titanium ((2-(dimethylamino)phenyl)methyl)(N-(1,1-dimethylethyl)-
1,1-dimethyl-1-((1,2,3,3a,7a-η)-3-(hexahydro-1(2H)-
azocinyl)-1H-inden-1-yl)silanaminato(2-)-N)titanium ((2-(dimethylamino)phenyl)methyl)(N-(1,1-dimethylethyl)-
1,1-dimethyl-1-((1,2,3,3a,7a-η)-3-(octahydro-1H-
azonin-1-yl)-1H-inden-1-yl)titanium ((2-(dimethylamino)phenyl)methyl)(N-(1,1-dimethylethyl)-
1,1-dimethyl-1-((1,2,3,3a,7a-η)-3-(octahydro-(2H)-
azecinyl)-1H-inden-1-yl)silanaminato(2-)-N)titanium ((2-(dimethylamino)phenyl)methyl)(N-(1,1-dimethylethyl)-
1,1-dimethyl-1-((1,2,3,3a,7a-η)-3-(dimethylamino)-1H-
inden-1-yl)silanaminato(2-)-N)dimethyltitanium (N-(1,1-dimethylethyl)-1,1-dimethyl-1-((1,2,3,3a,7a-η)-3-
(diethylamino)-1H-inden-1-yl)silanaminato(2-)-N)
dimethyltitanium (N-(1,1-dimethylethyl)-1,1-dimethyl-1-((1,2,3,3a,7a-η)-3-
(dipropylamino)-1H-inden-1-yl)silanaminato(2-)-N)
dimethyltitanium (N-(1,1-dimethylethyl)-1,1-dimethyl-1-((1,2,3,3a,7a-η)-3-
(dibutylamino)-1H-inden-1-yl)silanaminato(2-)-N)
dimethyltitanium (N-(1,1-dimethylethyl)-1,1-dimethyl-1-((1,2,3,3a,7a-η)-3-
(ethylmethylamino)-1H-inden-1-yl)silanaminato(2-)-N)
dimethyltitanium (N-(1,1-dimethylethyl)-1,1-dimethyl-1-((1,2,3,3a,7a-η)-3-
(methylphenylamino)-1H-inden-1-yl)silanaminato(2-)-
N)dimethyltitanium (N-(1,1-dimethylethyl)-1,1-dimethyl-1-((1,2,3,3a,7a-η)-3-
(methyl(phenylmethyl)amino)-1H-inden-1-yl)
silanaminato(2-)-N)dimethyltitanium (N-(1,1-dimethylethyl)-1,1-dimethyl-1-((1,2,3,3a,7a-η)-3-
((1,1-dimethylethyl)methylamino)-1H-inden-1-yl)
silanaminato(2-)-N)dimethyltitanium (N-(1,1-dimethylethyl)-1,1-dimethyl-1-((1,2,3,3a,7a-η)-3-
(methyl(1-methylethyl)amino)-1H-inden-1-yl)
silanaminato(2-)-N)dimethyltitanium (N-(1,1-dimethylethyl)-1,1-dimethyl-1-((1,2,3,3a,7a-η))-3-
(diphenylphosphino)-1H-inden-1-yl)silanaminato(2-)-N)
dimethyltitanium (N-(1,1-dimethylethyl)-1,1-dimethyl-1-((1,2,3,3a,7a-η)-3-
(dimethylphosphino)-1H-inden-1-yl)silanaminato(2-)-N)
dimethyltitanium (N-(1,1-dimethylethyl)-1,1-dimethyl-1(1,2,3,3a,7a-η)-3-
(methylphenylphosphino)-1H-inden-1-yl)silanaminato
(2-)-N)dimethyltitanium (N-(1,1,-dimethylethyl)-1,1-dimethyl-1-((1,2,3,3a,7a-η)-3-
(diethylphosphino)-1H-inden-1-yl)silanaminato(2-)-N)
dimethyltitanium (N-(1,1-dimethylethyl)-1,1-dimethyl-1-((1,2,3,3a,7a-η)-3-
(bis(1-methylethyl)phosphino)-1H-inden-1-yl)
silanaminato(2-)-N)dimethyltitanium (N-(1,1-dimethylethyl)-1,1-dimethyl-1-((1,2,3,3a,7a-η)-3-
methoxy-1H-inden-1-yl)silanaminato(2-)-N)
dimethyltitanium (N-(1,1-dimethylethyl)-1,1-dimethyl-1-((1,2,3,3a,7a-η)-3-
ethoxy-1H-inden-1-yl)silanaminato(2-)-N)
dimethyltitanium (N-(1,1-dimethylethyl)-1,1-dimethyl-1-((1,2,3,3a,7a-η)-3-
propoxy-1H-inden-1-yl)silanaminato(2-)-N)
dimethyltitanium (N-(1,1-dimethylethyl)-1,1-dimethyl-1-((1,2,3,3a,7a-η)-3-
butoxy-1H-inden-1-yl)silanaminato(2-)-N)
dimethyltitanium (N-(1,1-dimethylethyl)-1,1-dimethyl-1-((1,2,3,3a,7a-η)-3-
((1,1-dimethylethyl)oxy)-1H-inden-1-yl)silanaminato
(2-)-N)dimethyltitanium (N-(1,1-dimethylethyl)-1,1-dimethyl-1-((1,2,3,3a,7a-η)-3-
(trimethylsiloxy)-1H-inden-1-yl)silanaminato(2-)-N)
dimethyltitanium (N-(1,1-dimethylethyl)-1,1-dimethyl-1-((1,2,3,3a,7a-η)-3-
(((1,1-dimethylethyl)dimethylsilyl)oxy)-1H-inden-1-yl)
silanaminato(2-)-N)dimethyltitanium (N-(1,1-dimethylethyl)-1,1-dimethyl-1-((1,2,3,3a,7a-η)-3-
(1-methylethoxy)-1H-inden-1-yl)silanaminato(2-)-N)
dimethyltitanium ((2-(dimethylamino)phenyl)methyl)(N-(1,1-dimethylethyl)-1,1-dimethyl-1-((1,2,3,3a,7a-η)-3-phenoxy-1H-inden-1-yl)silanaminato(2-)-N)titanium ((2-(dimethylamino)phenyl)methyl)(N-(1,1-dimethylethyl)-1,1-dimethyl-1-((1,2,3,3a,7a-η)-3-(phenylthio)-1H-inden-1-yl)silanaminato(2-)-N)titanium ((2-(dimethylamino)phenyl)methyl)(N-(1,1-dimethylethyl)-1,1-dimethyl-1-((1,2,3,3a,7a-η)-3-(methylthio)-1H-inden-1-yl)silanaminato(2-)-N)titanium (N-(1,1-dimethylethyl)-1,1-dimethyl-1-((1,2,3,3a,7a-η)-3-(1-pyrrolidinyl)-1H-inden-1-yl)silanaminato(2-)-N) dimethyltitanium (N-(1-dimethylethyl)-1,1-diphenyl-1-((1,2,3,3a,7a-η)-3-(1-pyrrolidinyl)-1H-inden-1-yl)silanaminato(2-)-N) dimethyl titanium (N-(1,1-dimethylethyl)-1-methyl-1-phenyl-1-((1,2,3,3a,7a-η)-3-(1-pyrrolidinyl)-1H-inden-1-yl)silanaminato(2-)-N) dimethyl titanium (N-(1,1-dimethylethyl)-1,1-bis(1-methylethoxy)-1-((1,2,3,3a,7a-η))-3-(1-pyrrolidinyl)-1H-inden-1-yl)silanaminato(2-)-N)dimethyltitanium (N-(1,1-dimethylethyl)-1,1-diethyl-1-((1,2,3,3a,7a-η)-3-(1-pyrrolidinyl)-1H-indent-1-yl)silanaminato(2-)-N) dimethyltitanium (N-(1,1-dimethylethyl)-1,1-dimethoxy-1-((1,2,3,3a,7a-η)-3-(1-pyrrolidinyl)-1H-inden-1-yl)silanaminato(2-)-N) dimethyltitanium (N-(1,1-dimethylethyl)-1-ethoxy-1-methyl-1-((1,2,3,3a,7a-η)-3-(1-pyrrolidinyl)-1H-inden-1-yl)silanaminato(2-)-N) dimethyltitanium (N-(1,1-dimethylethyl)-1,1-dimethyl-1-((1,2,3,3a,7a-η)-3-(1-pyrrolidinyl)-1H-inden-1-yl)silanaminato(2-)-N)((1,2,3,4-η)-1,3-pentadiene)titanium (N-(1,1-dimethylethyl)-1,1-diphenyl-1-((1,2,3,3a,7a-η)-3-(1-pyrrolidinyl)-1H-inden-1-yl)silanaminato(2-)-N)((1,2,3,4r)-1,3-pentadiene)titanium (N-(1,1-dimethylethyl)-1-methyl-1-phenyl-1-((1,2,3,3a,7a-η)-3-(1-pyrrolidinyl)-1H-inden-1-yl)silanaminato(2-)-N)((1,2,3,4-η)-1,3-pentadiene)titanium (N-(1,1-dimethylethyl)-1,1-bis(1-methylethoxy)-1-((1,2,3,3a,7a-η)-3-(1-pyrrolidinyl)-1H-inden-1-yl)silanaminato(2-)-N)((1,2,3,4-η)-1,3-pentadiene)titanium (N-(1,1-dimethylethyl)-1,1-diethyl-1-((1,2,3,3a,7a-η)-3-(1-pyrrolidinyl)-1H-inden-1-yl)silanaminato(2-)-N)((1,2,3,4)-1,3-pentadiene)titanium (N-(1,1-dimethylethyl)-1,1-dimethoxy-1-((1,2,3,3a,7a-η)-3-(1-pyrrolidinyl)-1H-inden-1-yl)silanaminato(2-N)((1,2,3,4-η)-1,3-pentadiene)titanium (N-(1,1-dimethylethyl)-1-ethoxy-1-methyl-1-((1,2,3,3a,7a-η)-3-(1-pyrrolidinyl)-1H-inden-1-yl)silanaminato(2-)-N)((1,2,3,4-η)-1,3-pentadiene)titanium ((2-(dimethylamino)phenyl)methyl)(N-(1,1-dimethylethyl)-1,1-dimethyl-1-((1,2,3,3a,7a-η)-3-(1-pyrrolidinyl)-1H-inden-1-yl)silanaminato(2-)-N)titanium ((2-(dimethylamino)phenyl)methyl)(N-(1,1-dimethylethyl)-1,1-diphenyl-1-((1,2,3,3a,7a-η)-3-(1-pyrrolidinyl)-1H-inden-1-yl)silanaminato(2-)-N)titanium ((2-(dimethylamino)phenyl)methyl)(N-(1,1-dimethylethyl)-1-methyl-1-phenyl-1-((1,2,3,3a,7a-η)-3-(1-pyrrolidinyl)-1H-inden-1-yl)silanaminato(2-)-N)titanium ((2-(dimethylamino)phenyl)methyl)(N-(1,1-dimethylethyl)-1,1-bis(1-methylethoxy)-1-((1,2,3,3a,7a-η)-3-(1-pyrrolidinyl)-1H-inden-1-yl)silanaminato(2-)-N)titanium ((2-(dimethylamino)phenyl)methyl)(N-(1,1-dimethylethyl)-1,1-diethyl-1-((1,2,3,3a,7a-η)-3-(1-pyrrolidinyl)-1H-inden-1-yl)silanaminato(2-)-N)titanium ((2-(dimethylamino)phenyl)methyl)(N-(1,1-dimethylethyl)-1,1-dimethoxy-1-((1,2,3,3a,7a-η)-3-pyrrolidinyl)-1H-inden-1-yl)silanaminato(2-)-N)titanium ((2-(dimethylamino)phenyl)methyl)(N-(1,1-dimethylethyl)-1-ethoxy-1-methyl-1-((1,2,3,3a,7a-η)-3-(1-pyrrolidinyl)-1H-inden-1-yl)silanaminato(2-)-N)titanium (1,1'-(η⁴-1,3-butadiene-1,4-diyl)bis(benzene))(N-(1,1-dimethylethyl)-1,1-dimethyl-1-((1,2,3,3a,7a-η)-3-(1-pyrrolidinyl)-1H-inden-1-yl)silanaminato(2-)-N)titanium (N-(1,1-dimethylethyl)-1,1-dimethyl-1-((1,2,3,3a,7a-η)-3-(1-pyrrolidinyl)-1H-inden-1-yl)silanaminato(2-)-N)((1,2,3,4-η)-2,4-hexadiene)titanium ((2-(dimethylamino)methyl)phenyl)(N-(1,1-dimethylethyl)-1,1-dimethyl-1-((1,2,3,3a,7a-η)-3-(1-pyrrolidinyl)-1H-inden-1-yl)silanaminato(2-)-N)titanium dichloro(N-(1,1-dimethylethyl)-1,1-dimethyl-1-((1,2,3,3a,7a-η)-3-(1-pyrrolidinyl)-1H-inden-1-yl)silanaminato(2-)-N)titanium (N-(1,1-dimethylethyl)-1,1-dimethyl-1-((1,2,3,3a,7a-η)-3-(1-pyrrolidinyl)-1H-inden-1-yl)silanaminato(2-)-N)bis(phenylmethyl)titanium (N-(1,1-dimethylethyl)-1,1-dimethyl-1-((1,2,3,3a,7a-η)-3-(1-pyrrolidinyl)-1H-inden-1-yl)silanaminato(2-)-N)bis(phenylmethyl)bis((trimethylsilyl)methyl)titanium (N-(1,1-dimethylethyl)-1,1-dimethyl-1-((1,2,3,3a,7a-η)-3-(1-pyrrolidinyl)-1H-inden-1-yl)silanaminato(2-)-N)bis(phenylmethyl)bis(2,2-dimethylpropyl)titanium (1,1'-(η⁴-1,3-butadiene-1,4-diyl)bis(benzene))(N-cyclohexyl-1,1-dimethyl-1-((1,2,3,3a,7a-η)-3-(1-pyrrolidinyl)-1H-inden-1-yl)silanaminato(2-)-N)titanium (N-cyclohexyl-1,1-dimethyl-1-((1,2,3,3a,7a-η)-3-(1-pyrrolidinyl)-1H-inden-1-yl)silanaminato(2-)-N)((1,2,3,4-η)-2,4-hexadiene)titanium ((2-(dimethylamino)methyl)phenyl)(N-cyclohexyl-1,1-dimethyl-1-((1,2,3,3a,7a-η)-3-(1-pyrrolidinyl)-1H-inden-1-yl)silanaminato(2-)-N)titanium dichloro(N-cyclohexyl-1,1-dimethyl-1-((1,2,3,3a,7a-η)-3-(1-pyrrolidinyl)-1H-inden-1-yl)silanaminato(2-)-N)titanium (N-cyclohexyl-1,1-dimethyl-1-((1,2,3,3a,7a-η)-3-(1-pyrrolidinyl)-1H-inden-1-yl)silanaminato(2-)-N)bis(phenylmethyl)titanium (N-cyclohexyl-1,1-dimethyl-1-((1,2,3,3a,7a-η)-3-(1-pyrrolidinyl)-1H-inden-1-yl)silanaminato(2-)-N)bis(phenylmethyl)bis((trimethylsilyl)methyl)titanium (N-cyclohexyl-1,1-dimethyl-1-((1,2,3,3a,7a-η)-3-(1-pyrrolidinyl)-1H-inden-1-yl)silanaminato(2-)-N)bis(phenylmethyl)bis(2,2-dimethylpropyl)titanium (1,1'-(η⁴-1,3-butadiene-1,4-diyl)bis(benzene))(N-cyclododecyl-1,1-dimethyl-1-((1,2,3,3a,7a-η)-3-(1-pyrrolidinyl)-1H-inden-1-yl)silanaminato(2-)-N)titanium (N-cyclododecyl-1,1-dimethyl-1-((1,2,3,3a,7a-η)-3-(1-pyrrolidinyl)-1H-inden-1-yl)silanaminato(2-)-N)((1,2,3,4-η)-2,4-hexadiene)titanium ((2-(dimethylamino)methyl)phenyl)(N-cyclododecyl-1,1-dimethyl-1-((1,2,3,3a,7a-η)-3-(1-pyrrolidinyl)-1H-inden-1-yl)silanaminato(2-)-N)titanium dichloro(N-cyclododecyl-1,1-dimethyl-1-((1,2,3,3a,7a-η)-3-(1-pyrrolidinyl)-1H-inden-1-yl)silanaminato(2-)-N)titanium (N-cyclododecyl-1,1-dimethyl-1-((1,2,3,3a,7a-η)-3-(1-pyrrolidinyl)-1H-inden-1-yl)silanaminato(2-)-N)bis(phenylmethyl)titanium (N-cyclododecyl-1,1-dimethyl-1-((1,2,3,3a,7a-η)-3-(1-pyrrolidinyl)-1H-inden-1-yl)silanaminato(2-)-N)bis(phenylmethyl)bis((trimethylsilyl)methyl)titanium (N-cyclododecyl-1,1-dimethyl-1-((1,2,3,3a,7a-η)-3-(1-pyrrolidinyl)-1H-inden-1-yl)silanaminato(2-)-N)bis(phenylmethyl)bis(2,2-dimethylpropyltitanium (1,1'-(4-1,3-butadiene-1,4-diyl)bis(benzene))(N-methyl-1,1-dimethyl-1-((1,2,3,3a,7a-η)-3-(1-pyrrolidinyl)-1H-inden-1-yl)silanaminato(2-)-N)titanium (N-methyl-1,1-dimethyl-1-((1,2,3,3a,7a-η))-3-(1-pyrrolidinyl)-1H-inden-1-yl)silanaminato(2-)-N)((1,2,3,4t)-2,4-hexadiene)titanium ((2-(dimethylamino)methyl)phenyl)(N-methyl-1,1-dimethyl-1-((1,2,3,3a,7a-η)-3-(1-pyrrolidinyl)-1H-inden-1-yl)silanaminato(2-)-N)titanium dichloro(N-methyl-1,1-dimethyl-1-((1,2,3,3a,7a-η)-3-(1-pyrrolidinyl)-1H-inden-1-yl)silanaminato(2-)-N)titanium (N-methyl-1,1-dimethyl-1-((1,2,3,3a,7a-η)-3-(1-pyrrolidinyl)-1H-inden-1-yl)silanaminato(2-)-N)bis(phenylmethyl)titanium (N-methyl-1,1-dimethyl-1-((1,2,3,3a,7a-η)-3-(1-pyrrolidinyl)-1H-inden-1-yl)silanaminato(2-)-N)bis(phenylmethyl)bis((trimethylsilyl)methyl)titanium (N-methyl-1,1-dimethyl-1-((1,3,3a,7a-η)-3-(1-pyrrolidinyl)-1H-inden-1-yl)silanaminato(2-)-N)bis(phenylmethyl)bis(2,2-dimethylpropyl)titanium (1,1'-(η$^4$-1,3-butadiene-1,4-diyl)bis(benzene))(1,1-dimethyl-N-(phenylmethyl)-1-((1,2,3,3a,7a-η)-3-(1-pyrrolidinyl)-1H-inden-1-yl)silanaminato(2-)-N)titanium (1,1-dimethyl-N-(phenylmethyl)-1-((1,2,3,3a,7a-η)-3-(1-pyrrolidinyl)-1H-inden-1-yl)silanaminato(2-)-N)((1,2,3,4-η)-2,4-hexadiene)titanium ((2-(dimethylamino)methyl)phenyl)(1,1-dimethyl-N-(phenylmethyl)-1-((1,2,3,3a,7a-η)-3-(1-pyrrolidinyl)-1H-inden-1-yl)silanaminato(2-)-N)titanium dichloro(1,1-dimethyl-N-(phenylmethyl)-1-((1,2,3,3a,7a-,)-3-(1-pyrrolidinyl)-1H-inden-1-yl)silanaminato(2-)-N)titanium (1,1-dimethyl-N-(phenylmethyl)-1-((1,2,3,3a,7a-η)-3-(1-pyrrolidinyl)-1H-inden-1-yl)silanaminato(2-)-N)bis(phenylmethyl)titanium (1,1-dimethyl-N-(phenylmethyl)-1-((1,2,3,3a,7a-η)-3-(1-pyrrolidinyl)-1H-inden-1-yl)silanaminato(2-)-N)bis(phenylmethyl)bis((trimethylsilyl)methyl)titanium (1,1-dimethyl-N-(phenylmethyl)-1-((1,2,3,3a,7a-η)-3-(1-pyrrolidinyl)-1H-inden-1-yl)silanaminato(2-)-N)bis(phenylmethyl)bis(2,2-dimethylpropyl)titanium (1,1'-(η$^4$-1,3-butadiene-1,4-diyl)bis(benzene))(1-((1,2,3,3a,7a-η)-3-(dimethylamino)-1H-inden-1-yl)-N-(1,1-dimethylethyl)-1,1-dimethylsilanaminato(2-)-N)titanium (1-((1,2,3,3a,7a-η)-3-(dimethylamino)-1H-inden-1-yl)-N-(1,1-dimethylethyl)-1,1-dimethylsilanaminato(2-)-N) 1,2,3,4-η)-2,4-hexadiene)titanium ((2-(dimethylamino)methyl)phenyl)(1-((1,2,3,3a,7a-η)-3-(dimethylamino)-1H-inden-1-yl)-N-(1,1-dimethylethyl)-1,1-dimethylsilanaminato(2-)-N)titanium dichloro(1-((1,2,3,3a,7a-η)-3-(dimethylamino)-1H-inden-1-yl)-N-(1,1-dimethylethyl)-1,1-dimethylsilanaminato(2-)-N)titanium (1-((1,2,3,3a,7a-η)-3-(dimethylamino)-1H-inden-1-yl)-N-(1,1-dimethylethyl)-1,1-dimethylsilanaminato(2-)-N)bis(phenylmethyl)titanium (1-((1,2,3,3a,7a-η)-3-(dimethylamino)-1H-inden-1-yl)-N-(1,1-dimethylethyl)-1,1-dimethylsilanaminato(2-)-N)bis(phenylmethyl)bis((trimethylsilyl)methyl)titanium (1-((1,2,3,3a,7a-η)-3-(dimethylamino)-1H-inden-1-yl)-N-(1,1-dimethylethyl)-1,1-dimethylsilanaminato(2-)-N)bis(phenylmethyl)bis(2,2-dimethylpropyl)titanium (1,1'-(η$^4$-1,3-butadiene-1,4-diyl)bis(benzene))(N-(1,1-dimethylethyl)-1,1-dimethyl-1-((1,2,3,3a,7a-η)-3-(1-piperidinyl)-1H-inden-1-yl)silanaminato(2-)-N)titanium (N-(1,1-dimethylethyl)-1,1-dimethyl-1-((1,2,3,3a,7a-η)-3-(1-piperidinyl)-1H-inden-1-yl)silanaminato(2-)-N)((1,2,3,4-η)-2,4-hexadiene)titanium ((2-(dimethylamino)methyl)phenyl)(N-(1,1-dimethylethyl)-1,1-dimethyl1-1-((1,2,3,3a,7a-η)-3-(1-piperidinyl)-1H-inden-1-yl)silanaminato(2-)-N)titanium dichloro(N-(1,1-dimethylethyl)-1,1-dimethyl-1-((,2,3,3a,7a-η)-3-(1-piperidinyl)-1H-inden-1-yl)silanaminato(2-)-N)titanium (N-(1,1-methylethyl)-1,1-dimethyl-1-((1,2,3,3a,7a-η)-3-(1-piperidinyl)-1H-inden-1-yl)silanaminato(2-)-N)bis(phenylmethyl)titanium (N-(1,1-dimethylethyl)-1,1-dimethyl-1-((1,2,3,3a,7a-η)-3-(1-piperidinyl)-1H-inden-1-yl)silanaminato(2-)-N)bis(phenylmethyl)bis((trimethylsilyl)methyl)titanium (N-(1,1-dimethylethyl)-1,1-dimethyl-1-((1,2,3,3a,7a-η)-3-(1-piperidinyl)-1H-inden-1-yl)silanaminato(2-)-N)bis(phenylmethyl)bis(2,2-dimethylpropyl)titanium (1,1'-(η$^4$-1,3-butadiene-1,4-diyl)bis(benzene))(N-(1,1-dimethylethyl)-1,1-dimethyl-1-((1,2,3,3a,7a-η)-3-(hexahydro-1H-azepin-1-yl)-1H-inden-1-yl)silanaminato(2-)-N)titanium (N-(1,1-dimethylethyl)-1,1-dimethyl-1-((1,2,3,3a,7a-,)-3-(hexahydro-1H-azepin-1-yl)-1H-inden-1-yl)silanaminato(2-)-N)((2,3,4-η)-2,4-hexadiene)titanium ((2-(dimethylamino)methyl)phenyl)(N-(1,1-dimethylethyl)-1,1-dimethyl-1-((1,2,3,3a,7a-η)-3-(hexahydro-1H-azepin-1-yl)-1H-inden-1-yl)silanaminato(2-)-N)titanium dichloro(N-(1,1-dimethylethyl)-1,1-dimethyl-1-((1,2,3,3a,7a-η)-3-(hexahydro-1H-azepin-1-yl)-1H-inden-1-yl)silanaminato(2-)-N)titanium (N-(1,1-dimethylethyl)-1,1-dimethyl-1-((11,23,3a,7a-η)-3-(hexahydro-1H-azepin-1-yl)-1H-inden-1-yl)silanaminato(2-)-N)bis(phenylmethyl)titanium (N-(1,1-dimethylethyl)-1,1-dimethyl-1-((1,2,3,3a,7a-η)-3-(hexahydro-1H-azepin-1-yl)-1H-inden-1-yl)silanaminato(2-)-N)bis(phenylmethyl)bis((trimethylsilyl)methyl)titanium (N-(1,1-dimethylethyl)-1,1-dimethyl-1-((1,2,3,3a,7a-η)-3-(hexahydro-1H-azepin-1-yl)-1H-inden-1-yl)silanaminato(2-)-N)bis(phenylmethyl)bis(2,2-dimethylpropyl)titanium (1,1'-(η$^4$-1,3-butadiene-1,4-diyl)bis(benzene))(N-(1,1-dimethylethyl)-1,1-dimethyl-1-((1,2,3,3a,7a-η)-3-methoxy-1H-inden-1-yl)silanaminato(2-)-N)titanium (N-(1,1-dimethylethyl)-1,1-dimethyl-1-((1,2,3,3a,7a-η)-3-methoxy-1H-inden-1-yl)silanaminato(2-)-N)((1,2,3,4-η)-2,4-hexadiene)titanium ((2-(dimethylamino)methyl)phenyl)(N-(1,1-dimethylethyl)-1,1-dimethyl-1-((1,2,3,3a,7a-η)-3-methoxy-1H-inden-1-yl)silanaminato(2-)-N)titanium dichloro(N-(1,1-dimethylethyl)-1,1-dimethyl-1-((1,2,3,3a,7a-η)-3-methoxy-1H-inden-1-yl)silanaminato(2-)-N)titanium (N-(1,1-dimethylethyl)-1,1-dimethyl-1-((1,2,3,3a,7a-η)-3-methoxy-1H-inden-1-yl)silanaminato(2-)-N)bis(phenylmethyl)titanium (N-(1,1-dimethylethyl)-1,1-dimethyl-1-((1,2,3,3a,7a-η)-3-methoxy-1H-inden-1-yl)silanaminato(2-)-N)bis(phenylmethyl)bis((trimethylsilyl)methyl)titanium (N-(1,1-dimethylethyl)-1,1-dimethyl-1-((1,2,3,3a,7a-η)-3-methoxy-1H-inden-1-yl)silanaminato(2-)-N)bis(phenylmethyl)bis(2,2-dimethylpropyl)titanium (1,1'-(η$^4$-1,3-butadiene-1,4-diyl)bis(benzene))(N-(1,1-dimethylethyl)-1,1-dimethyl-1-((1,2,3,3a,7a-η)-3-ethoxy-1H-inden-1-yl)silanaminato(2-)-N)titanium (N-(1,1-dimethylethyl)-1,1-dimethyl-1-((1,2,3,3a,7a-η)-3-ethoxy-1H-inden-1-yl)silanaminato(2-)-N)((1,2,3,4-η)-2,4-hexadiene)titanium ((2-(dimethylamino)methyl)phenyl)(N-(1,1-dimethylethyl)-1,1-dimethyl-1-((1,2,3,3a,7a-η)-3-ethoxy-1H-inden-1-yl)silanaminato(2-)-N)titanium dichloro(N-(1,1-dimethylethyl)-1,1-dimethyl-1-((1,2,3,3a,7a-η)-3-ethoxy-1H-inden-1-yl)silanaminato(2-)-N)titanium (N-(1,1-dimethylethyl)-1,1-dimethyl-1-((1,2,3,3a,7a-η)-3-ethoxy-1H-inden-1-yl)silanaminato(2-)-N)bis(phenylmethyl)titanium (N-(1,1-dimethylethyl)-1,1-dimethyl-1-((1,2,3,3a,7a-η-3-ethoxy-1H-inden-1-yl)silanaminato(2-)-N)bis(phenylmethyl)bis((trimethylsilyl)methyl)titanium (N-(1,1-dimethylethyl)-1,1-dimethyl-1-((1,2,3,3a,7a-η)-3-ethoxy-1H-inden-1-yl)silanaminato(2-)-N)bis(phenylmethyl)bis(2,2-dimethylpropyl)titanium (1,1-(η$^4$-1,3-butadiene-1,4-diyl)bis(benzene))(N-(1,1-dimethylethyl)-1,1-dimethyl-1-((1,2,3,3a,7a-η)-3-((1,1-dimethylethyl)oxy)-1H-inden-1-yl)silanaminato(2-)-N)titanium (N-(1,1-dimethylethyl)-1,1-dimethyl-1-((1,2,3,3a,7a-η)-3-((1,1-dimethylethyl)oxy)-1H-inden-1-yl)silanaminato(2-)-N)((1,2,3,4-η)-2,4-hexadiene)titanium ((2-(dimethylamino)methyl)phenyl)(N-(1,1-dimethylethyl)-1,1-dimethyl-1-((1,2,3,3a,7a-η)-3-((1,1-dimethylethyl)oxy)-1H-inden-1-yl)silanaminato(2-)-N)titanium dichloro(N-(1,1-dimethylethyl)-1,1-dimethyl-1-((1,2,3,3a,7a-η)-3-((1,1,1-dimethylethyl)oxy)-1H-inden-1-yl)silanaminato(2-)-N)titanium (N-(1,1-dimethylethyl)-1,1-dimethyl-1-((1,2,3,3a,7a-η)-3-((1,1-dimethylethyl)oxy)-1H-inden-1-yl)silanaminato(2-)-N)bis(phenylmethyl)titanium (N-(1-dimethylethyl)-1,1-dimethyl-1-((1,2,3,3a,7a-η)-3-((1,1-dimethylethyl)oxy)-1H-inden-1-yl)silanaminato(2-)-N)bis(phenylmethyl)bis((trimethylsilyl)methyl)titanium (N-(1,1-dimethylethyl)-1,1-dimethyl-1-((1,2,3,3a,7a-η)-3-((1,1-dimethylethyl)oxy)-1H-inden-1-yl)silanaminato(2-)-N)bis(phenylmethyl)bis(2,2-dimethylpropyl)titanium (1,1-(η$^4$-1,3-butadiene-1,4-diyl)bis(benzene))(N-(1,1-dimethylethyl)-1,1-dimethyl-1-((1,2,3,3a,7a-η)-3-(((1,1-dimethylethyl)dimethylsilyl)oxy)-1H-inden-1-yl)silanaminato(2-)-N)titanium (N-1,1-dimethylethyl)-1,1-dimethyl)-1-((1,2,3,3a,7a-η)-3-(((1,1-dimethylethyl)dimethylsilyl)oxy)-1H-inden-1-yl)silanaminato(2-)-N)((1,2,3,4r7)-2,4-hexadiene)titanium ((2-(dimethylamino)methyl)phenyl)(N-(1,1-dimethylethyl)-1,1-dimethyl-1-((1,2,3,3a,7a-η)-3-(((1,1-dimethylethyl)dimethylsilyl)oxy)-1H-inden-1-yl)silanaminato(2-)-N)titanium dichloro(N-(1,1-dimethylethyl)-1,1-dimethyl-1-((1,2,3,3a,7a-η)-3-(((1,1-dimethylethyl)dimethylsilyl)oxy)-1H-inden-1-yl)silanaminato(2-)-N)titanium (N-(1,1-dimethylethyl)-1,1-dimethyl-1-((,2,3,3a,7a-η)-3-(((1,1-dimethylethyl)dimethylsilyl)oxy)-1H-inden-1-yl)silanaminato(2-)-N)bis(phenylmethyl)titanium (N-(1,1-dimethylethyl)-1,1-dimethyl-1-((1,2,3,3a,7a-η)-3-(((1,1-dimethylethyl)dimethylsilyl)oxy)-1H-inden-1-yl)silanaminato(2-)-N)bis(phenyl methyl)bis((trimethylsilyl)methyl)titanium (N-(1,1-dimethylethyl)-1,1-dimethyl-1-((1,2,3,3a,7a-η)-3-(((1,1-dimethylethyl)dimethylsilyl)oxy)-1H-inden-1-yl)silanaminato(2-)-N)bis(phenylmethyl)bis(2,2-dimethylpropyl)titanium (N-(1,1-dimethylethyl)-1-(((1,2,3,3a,7a-η)-3-(1-pyrrolidinyl)-1H-inden-1-yl)dimethylsilyl)methanaminato(2-)-N)dimethyltitanium (N-(1,1-dimethylethyl)-1,1-dimethyl-1-(((1,2,3,3a,7a-η)-3-(1-pyrrolidinyl)-1H-inden-1-yl)methyl)silanaminato-(2-)-N-)dimethyltitanium (N-(1,1-dimethylethyl)-2-((1,2,3,3a,7a-η)-3-(1-pyrrolidinyl)-1H-inden-1-yl)-ethanaminato(2-)-N)dimethyltitanium (N-(1,1-dimethylethyl)-2-((1,2,3,3a,7a-η)-3-(1-pyrrolidinyl)-1H-inden-1-yl)-tetramethylethanaminato(2-)-N)dimethyltitanium (N-(1,1-dimethylethyl)-2-((1,2,3,3a,7a-η)-3-(1-pyrrolidinyl)-1H-inden-1-yl)-1,1,2,2-tetramethyldisilanaminato(2-)-N)dimethyltitanium (N-(1,1-dimethylethyl)-3-(1,2,3,3a,7a-η)-3-(1-pyrrolidinyl)-1H-inden-1-yl)-propanaminato(2-)-N)dimethyltitanium (N-(1,1-dimethylethyl)-1-((1,2,3,3a,7a-η)-3-(1-pyrrolidinyl)-1H-inden-1-yl)-methanaminato(2-)-N)dimethyltitanium (N-(1,1-dimethylethyl)-1-((1,2,3,3a,7a-η)-3-(1-pyrrolidinyl)-1H-inden-1-yl)-dimethylmethanaminato(2-)-N)dimethyltitanium (N-(1,1-dimethylethyl)-1,1-dimethyl-1-((1,2,3,3a,7a-η)-3-methoxy-1H-inden-1-yl)-germanaminato(2-)-N)dimethyltitanium ((2-(dimethylamino)phenyl)methyl)(N-(1,1-dimethylethyl)-1-(((1,2,3,3a,7a-η)-3-(1-pyrrolidinyl)-1H-inden-1-yl)dimethylsilyl)methanaminato(2-)-N)((1,2,3,4-η)-1,3-pentadiene)titanium ((2-(dimethylamino)phenyl)methyl)(N-(1,1 11 methylethyl)-1,1-dimethyl-1-(((1,2,3,3a,7a-η)-3-(1-pyrrolidinyl)-1H-inden-1-yl)methyl)silanaminato-(2-)-N-)((1,2,3,4-)-1,3-pentadiene)titanium ((2-(dimethylamino)phenyl)methyl)(N-(1,1-methylethyl)-2-((1,2,3,3a,7a-η)-3-(1-pyrrolidinyl)-1H-inden-1-yl)-ethanaminato(2-)-N)((1,2,3,4-η)-1,3-pentadiene)titanium ((2-(dimethylamino)phenyl)methyl)(N-(1,1-dimethylethyl)-2-((1,2,3,3a,7a-η)-3-(1-pyrrolidinyl)-1H-inden-1-yl)-tetramethylethanaminato(2-)-N)((1,2,3,4-η)-1,3-pentadiene)titanium ((2-(dimethylamino)phenyl)methyl)(N-(1,1-dimethylethyl)-2-((1,2,3,3a,7a-η)-3-(1-pyrrolidinyl)-1H-inden-1-yl)-1,1,2,2-tetramethyldisilanaminato(2-)-N)((1,2,3,4-η)-1,3-pentadiene)titanium ((2-(dimethylamino)phenyl)methyl)(N-(1,1-dimethylethyl)-3-((1,2,3,3a,7a-η)-3-(1-pyrrolidinyl)-1H-inden-1-yl)-propanaminato(2-)-N)((1,2,3,4-η)-1,3-pentadiene)titanium ((2-(dimethylamino)phenyl)methyl)(N-(1,1-dimethylethyl)-1-((1,2,3,3a,7a-η)-3-(1-pyrrolidinyl)-1H-inden-1-yl)-methanaminato(2-)-N)((1,2,3,4-η)-1,3-pentadiene)titanium ((2-(dimethylamino)phenyl)methyl)(N-(1,1-dimethylethyl)-1-((1,2,3,3a,7a-η)-3-(1-pyrrolidinyl)-1H-inden-1-yl)-dimethylmethanaminato(2-)-N)((1,2,3,4-η)-1,3-pentadiene)titanium ((2-(dimethylamino)phenyl)methyl)(N-(1,1-dimethylethyl)-1,1-dimethyl-1-((1,2,3,3a,7a-η)-3-methoxy-1H-inden-1-yl)-germanaminato(2-)-N)((1,2,3,4-η)-1,3-pentadiene)titanium (N-(1,1-dimethylethyl)-1-(((1,2,3,3a,7a-η)-3-(1-pyrrolidinyl)-1H-inden-1-yl)dimethylsilyl)methanaminato(2-)-N)titanium (N-(1,1-dimethylethyl)-1,1-dimethyl-1-(((1,2,3,3a,7a-η))-3-(1-pyrrolidinyl)-1H-inden-1-yl)methyl)silanaminato-(2-)-N-)titanium (N-(1,1-dimethylethyl)-2-((1,2,3,3a,7a-η)-3-(1-pyrrolidinyl)-1H-inden-1-yl)-ethanaminato(2-)-N)titanium (N-(1,1-dimethylethyl)-2-((1,2,3,3a,7a-η)-3-(1-pyrrolidinyl)-1H-inden-1-yl)-tetramethylethanaminato(2-)-N)titanium (N-(1,1-dimethylethyl)-2-((1,2,3,3a,7a-η)-3-(1-pyrrolidinyl)-1H-inden-1-yl)-1,1,2,2-tetramethyldisilanaminato(2-)-N)titanium (N-(1,1-dimethylethyl)-3-((1,2,3,3a,7a-η)-3-(1-pyrrolidinyl)-1H-inden-1-yl)-propanaminato(2-)-N)titanium (N-(1,1-dimethylethyl)-1-((1,2,3,3a-η)-3(1-pyrrolidinyl)-1H-inden-1-yl)-methanaminato(2-)-N)titanium (N-(1,1-dimethylethyl)-1-((1,2,3,3a,7a-η)-3-(1-pyrrolidinyl)-1H-inden-1-yl)-dimethylmethanaminato(2-)-N)titanium (N-(1,1-dimethylethyl)-1,1-dimethyl-1-((1,2,3,3a,7a-η)-3-methoxy-1H-inden-1-yl)-germanaminato(2-)-N)titanium (N-(1-dimethylethyl)-1-(((1,2,3,3a,7a-η)-3-methoxy-1H-inden-1-yl)dimethylsilyl)methanaminato(2-)-N)dimethyltitanium (N-(1,1-dimethylethyl)-1,1-dimethyl-1-(((1,2,3,3a,7a-η)-3-methoxy-1H-inden-1-yl)methyl)silanaminato-(2-)-N-)dimethyl titanium (N-(1,1-dimethylethyl)-2-((1,2,3,3a,7a-η)-3-methoxy-1H-inden-1-yl)-ethanaminato(2-)-N)dimethyltitanium (N-(1,1-dimethylethyl)-2-((1,2,3,3a,7a-η)-3-methoxy-1H-inden-1-yl)-tetramethylethanaminato(2-)-N)dimethyltitanium (N-(1,1-dimethylethyl)-2-((1,2,3,3a,7a-η)-3-methoxy-1H-inden-1-yl)-1,2,2-tetramethyldisilanaminato(2-)-N)dimethyltitanium (N-(1,1-dimethylethyl)-3-((1,2,3,3a,7a-η)-3-methoxy-1H-inden-1-yl)-propanaminato(2-)-N)dimethyltitanium (N-(1,1-dimethylethyl)-1-((1,2,3,3a,7a-η)-3-methoxy-1H-inden-1-yl)-methanaminato(2-)-N)dimethyltitanium (N-(1,1-dimethylethyl)-1-((1,2,3,3a,7a-η)-3-methoxy-1H-inden-1-yl)-dimethylmethanaminato(2-)-N)dimethyltitanium (N-(1,1-dimethylethyl)-1,1-dimethyl-1-((1,2,3,3a,7a-η)-3-methoxy-1H-inden-1-yl)-germanaminato(2-)-N)dimethyltitanium (N-(1,1-dimethylethyl)-1-(((1,1,2,3a,7a-η)-3-(((1,1-dimethylethyl)dimethylsilyl)oxy)-1H-inden-1-yl)dimethylsilyl)methanaminato(2-)-N)dimethyltitanium (N-(1,1-dimethylethyl)-1,1-dimethyl-1-(((1,2,3,3a,7a-η)-3-(((1,1-dimethylethyl)dimethylsilyl)oxy)-1H-inden-1-yl)methyl)silanaminato-(2-)-N-)dimethyltitanium (N-(1,1-dimethylethyl)-2-((1,2,3,3a,7a-η)-3-(((1,1-dimethylethyl)dimethylsilyl)oxy)-1H-inden-1-yl)-ethanaminato(2-)-N)dimethyltitanium (N-(1,1-dimethylethyl)-2-((1,2,3,3a,7a-η)-3-(((1,1-dimethylethyl)dimethylsilyl)oxy)-1H-inden-1-yl)-tetramethylethanaminato(2-)-N)dimethyltitanium (N-(1,1-dimethylethyl)-2-((1,2,3,3a,7a-η)-3-(((1,1-dimethylethyl)dimethylsilyl)oxy)-1H-inden-1-yl)-1,2,2-tetramethyldisilanaminato(2)-N)dimethyltitanium (N-(1,1-dimethylethyl)-3-((1,2,3,3a,7a-η)-3-(((1,1-dimethylethyl)dimethylsilyl)oxy)-1H-inden-1-yl)-propanaminato(2-)-N)dimethyltitanium (N-(1,1-dimethylethyl)-1-((1,2,3,3a,7a-η)-3-(((1,1-dimethylethyl)dimethylsilyl)oxy)-1H-inden-1-yl)-methanaminato(2-)-N)dimethyltitanium (N-(1,1-dimethylethyl)-1-((1,2,3,3a,7a-η)-3-(((1,1-dimethylethyl)dimethylsilyl)oxy)-1H-inden-1-yl)-dimethylmethanaminato(2-)-N)dimethyltitanium (N-(1,1-dimethylethyl)-1,1-dimethyl-1-((1,2,3,3a,7a-η)-3-(((1,1-dimethylethyl)dimethylsilyl)oxy)-1H-inden-1-yl)-germanaminato(2-)-N)dimethyltitanium (N-(1,1-dimethylethyl)-1-(((1,2,3,3a,7a-η)-3-(1-piperidinyl)-1H-inden-1-yl)dimethylsilyl)methanaminato(2-)-N)dimethyltitanium (N-(1,1-dimethylethyl)-1,1-dimethyl-1-(((1,2,3,3a,7a-η)-3-(1-piperidinyl)-1H-inden-1-yl)methyl)silanaminato-(2-)-N-)dimethyltitanium (N-(1,1-dimethylethyl)-2-((1,2,3,3a,7a-η)-3-(1-piperidinyl)-1H-inden-1-yl)-ethanaminato(2-)-N)dimethyltitanium (N-(1,1-dimethylethyl)-2-((1,2,3,3a,7a-η)-3-(1-piperidinyl)-1H-inden-1-yl)-tetramethylethanaminato(2-)-N)dimethyltitanium (N-(1,1-dimethylethyl)-2-((1,2,3,3a,7a-η)-3-(1-piperidinyl)-1H-inden-1-yl)-1,1,2,2-tetramethyldisilanaminato(2-)-N)dimethyltitanium (N-(1,1-dimethylethyl)-3-((1,2,3,3a,7a-η)-3-(1-piperidinyl)-1H-inden-1-yl)-propanaminato(2-)-N)dimethyltitanium (N-(1,1-dimethylethyl)-1-((1,2,3,3a,7a-η)-3-(1-piperidinyl)-1H-inden-1-yl)-methanaminato(2-)-N)dimethyltitanium (N-(1,1-dimethylethyl)-1-((1,2,3,3a,7a-η)-3-(1-piperidinyl)-1H-inden-1-yl)-dimethylmethanaminato(2-)-N)dimethyltitanium (N-(1,1-dimethylethyl)-1,1-dimethyl-1-((1,2,3,3a,7a-η)-3-(1-piperidinyl)-1H-inden-1-yl)-germanaminato(2-)-N)dimethyltitanium (N-(1,1-dimethylethyl)-1-(((1,2,3,3a,7a-η)-3-(ethylmethylamino)-1H-inden-1-)dimethylsilyl)methanaminato(2-)-N)dimethyltitanium (N-(1,1-dimethylethyl)-1,1-dimethyl-1-(((1,2,3,3a,7a-η)-3-(ethylmethylamino)-1H-inden-1-yl)methyl)silanaminato-(2-)-N-)dimethyltitanium (N-(1,1-dimethylethyl)-2-((1,2,3,3a,7a-η)-3-(ethylmethylamino)-1H-inden-1-yl)-ethanaminato(2-)-N)dimethyltitanium (N-(1,1-dimethylethyl)-2-((1,2,3,3a,7a-η)-3-(ethylmethylamino)-1H-inden-1-yl)-tetramethylethanaminato(2-)-N)dimethyltitanium (N-(1,1-dimethylethyl)-2-((1,2,3,3a,7a-η)-3-(ethylmethylamino)-1H-inden-1-yl)-1,1,2,2-tetramethyldisilanaminato(2-)-N)dimethyltitanium (N-(1,1-dimethylethyl)-3-((1,2,3,3a,7a-η)-3-(ethylmethylamino)-1H-inden-1-yl)-propanaminato(2-)-N)dimethyltitanium (N-(1,1-dimethylethyl)-1-((1,2,3,3a,7a-η)-3-(ethylmethylamino)-1H-inden-1-yl)-methanaminato(2-)-N)di methyltitanium (N-(1,1-dimethylethyl)-1-((1,2,3,3a,7a-η)-3-(ethylmethylamino)-1H-inden-1-yl)-di methylmethanaminato(2-)-N)dimethyltitanium (N-(1,1-dimethylethyl)-1,1-dimethyl-1-((1,2,3,3a,7a-η)-3-(ethylmethylamino)-1H-inden-1-yl)-germanaminato(2-)-N)dimethyltitanium (N-cyclohexyl-1-(((1,2,3,3a,7a-η)-3-(1-pyrrolidinyl)-1H-inden-1-yl)dimethylsilyl)methanaminato(2-)-N)dimethyltitanium (N-cyclohexyl-1,1-dimethyl-1-(((1,2,3,3a,7a-η)-3-(1-pyrrolidinyl)-1H-inden-1-yl)methyl)silanaminato-(2-)-N-)dimethyltitanium (N-cyclohexyl-2-((1,2,3,3a,7a-η)-3-(1-pyrrolidinyl)-1H-inden-1-yl)-ethanaminato(2-)-N)dimethyltitanium (N-cyclohexyl-2-((1,2,3,3a,7a-η)-3-(1-pyrrolidinyl)-1H-inden-1-yl)-tetramethylethanaminato(2-)-N)dimethyltitanium (N-cyclohexyl-2-((1,2,3,3a,7a-η)-3-(1-pyrrolidinyl)-1H-inden-1-yl)-1,1,2,2-tetramethyldisilanaminato(2-)-N)dimethyltitanium (N-cyclohexyl-3-((1,2,3,3a,7a-η)-3-(1-pyrrolidinyl)-1H-inden-1-yl)-propanaminato(2-)-N)dimethyltitanium (N-cyclohexyl-1-((1,2,3,3a,7a-η)-3-(1-pyrrolidinyl)-1H-inden-1-yl)-methanaminato(2-)-N)dimethyltitanium (N-cyclohexyl-1-((1,2,3,3a,7a-η)-3-(1-pyrrolidinyl)-1H-inden-1-yl)-dimethylmethanaminato(2-)-N)dimethyltitanium (N-cyclohexyl-1,1-dimethyl-1-((1,2,3,3a,7a-η)-3-(1-pyrrolidinyl)-1H-inden-1-yl)-germanaminato(2-)-N)dimethyltitanium (N-ethyl-1-(((1,2,3,3a,7a-η)-3-(1-pyrrolidinyl)-1H-inden-1-yl)dimethylsilyl)methanaminato(2-)-N)dimethyltitanium (N-ethyl-1,1-dimethyl-1-(((1,2,3,3a,7a-η)-3-(1-pyrrolidinyl)-1H-inden-1-yl)methyl)silanaminato-(2-)-N-)dimethyltitanium (N-ethyl-2-((1,2,3,3a,7a-η)-3-(1-pyrrolidinyl)-1H-inden-1-yl)-ethanaminato(2-)-N)dimethyltitanium (N-ethyl-2-((1,2,3,3a,7a-η)-3-(1-pyrrolidinyl)-1H-inden-1-yl)-tetramethylethanaminato(2-)-N)dimethyltitanium (N-ethyl-2-((1,2,3,3a,7a-η)-3-(1-pyrrolidinyl)-1H-inden-1-yl)-1,1,2,2-tetramethyldisilanaminato(2-)-N)dimethyltitanium (N-ethyl-3-((1,2,3,3a,7a-η)-3-(1-pyrrolidinyl)-1H-inden-1-yl)-propanaminato(2-)-N)dimethyltitanium (N-ethyl-1-((1,2,3,3a,7a-η)-3-(1-pyrrolidinyl)-1H-inden-1-yl)-methanaminato(2-)-N)dimethyltitanium (N-ethyl-1-((1,2,3,3a,7a-η)-3-(1-pyrrolidinyl)-1H-inden-1-yl)-dimethylmethanaminato(2-)-N)dimethyltitanium (N-ethyl-1,1-dimethyl-1-((1,2,3,3a,7a-η)-3-(1-pyrrolidinyl)-1H-inden-1-yl)-germanaminato(2-)-N)dimethyltitanium (N-(1,1-dimethylethyl)-1-(((,2,3,3a,7a-η)-2-methyl-3-(1-pyrrolidinyl)-1H-inden-1-yl)dimethylsilyl)methanaminato(2-)-N)dimethyltitanium (N-(1,1-dimethylethyl)-1,1-dimethyl-1-(((1,2,3,3a,7a-η)-2-methyl-3-(1-pyrrolidinyl)-H-inden-1-yl)methyl)silanaminato-(2-)-N-)dimethyltitanium (N-(1,1-dimethylethyl)-2-((1,2,3,3a,7a-η)-2-methyl-3-(1-pyrrolidinyl)-1H-inden-1-yl)-ethanaminato(2-)-N)dimethyltitanium (N-(1,1-dimethylethyl)-2-((1,2,3,3a,7a-η)-2-methyl-3-(1-pyrrolidinyl)-1H-inden-1-yl)-tetramethylethanaminato(2-)-N)dimethyltitanium (N-(1,1-dimethylethyl)-2-((1,2,3,3a,7a-η)-2-methyl-3-(1-pyrrolidinyl)-1H-inden-1-yl)-1,1,2,2-tetramethyldisilanaminato(2-)-N)dimethyltitanium (N-(1,1-dimethylethyl)-3-((1,2,3,3a,7a-η)-2-methyl-3-(1-pyrrolidinyl)-1H-inden-1-yl)-propanaminato(2-)-N)dimethyltitanium (N-(1,1-dimethylethyl)-1-((1,2,3,3a,7a-η)-2-methyl-3-(1-pyrrolidinyl)-1H-inden-1-yl)-methanaminato(2-)-N)dimethyltitanium (N-(1,1-dimethylethyl)-1-((1,2,3,3a,7a-η))-2-methyl-3-(1-pyrrolidinyl)-1H-inden-1-yl)-dimethylmethanaminato(2-)-N)dimethyltitanium (N-(1,1-dimethylethyl)-1,1-dimethyl-1-((1,2,3,3a,7a-η))-2-methyl-3-(1-pyrrolidinyl)-1H-inden-1-yl)-germanaminato(2-)-N)dimethyltitanium (1,1'-(η$^4$-1,3-butadiene-1,4-diyl)bis(benzene))(N-(1,1-dimethylethyl)-1,1-dimethyl-1-((1,2,3,4,5-η)-3-(1-pyrrolidinyl)-2,4-cyclopentadien-1-yl)silanaminato(2-)-N)titanium (N-(1,1-dimethylethyl)-1,1-dimethyl-1-((1,2,3,4,5-η)-3-(1-pyrrolidinyl)-2,4-cyclopentadien-1-yl)silanaminato(2-)-N)((1,2,3,4-η)-2,4-hexadiene)titanium (N-(1,1-dimethylethyl)-1,1-dimethyl-1-((1,2,3,4.5-l)-3-(1-pyrrolidinyl)-2,4-cyclopentadien-1-yl)silanaminato(2-)-N)((1,2,3,4-η)-1,3-pentadiene)titanium ((2-(dimethylamino)methyl)phenyl)(N-(1,1-dimethylethyl)-1,1-dimethyl-1-((1,2,3,4,5-η)-3-(1-pyrrolidinyl)-2,4-cyclopentadien-1-yl)silanaminato(2-)-N)titanium dichloro(N-(1,1-dimethylethyl)-1,1-dimethyl-1-((1,2,3,4,5-η)-3-(1-pyrrolidinyl)-2,4-cyclopentadien-1-yl)silanaminato(2-)-N)titanium (N-(1,1-dimethylethyl)-1,1-dimethyl-1-((1,2,3,4,5-η)-3-(1-pyrrolidinyl)-2,4-cyclopentadien-1-yl)silanaminato(2-)-N)dimethyltitanium (N-(1,1-dimethylethyl)-1,1-dimethyl-1-((1,2,3,4,5-η)-3-(1-pyrrolidinyl)-2,4-cyclopentadien-1-yl)silanaminato(2-)-N)bis(phenylmethyl)titanium (N-(1,1-dimethylethyl)-1,1-dimethyl-1-((1,2,3,4,5-η)-3-(1-pyrrolidinyl)-2,4-cyclopentadien-1-yl)silanaminato(2-)-N)bis(phenylmethyl)bis((trimethylsilyl)methyl)titanium (N-(1,1-dimethylethyl)-1,1-dimethyl-1-((1,2,3,4,5-η)-3-(1-pyrrolidinyl)-2,4-cyclopentadien-1-yl)silanaminato(2-)-N)bis(phenylmethyl)bis(2,2-dimethylpropyl)titanium (1,1-dimethyl-N-(phenylmethyl)-1-((1,2,3,4,5-η)-3-(1-pyrrolidinyl)-2,4-cyclopentadien-1-yl)silanaminato(2-)-N)((1,2,3,4-η)-1,3-pentadiene)titanium ((2-(dimethylamino)methyl)phenyl)(1,1-dimethyl-N-(phenylmethyl)-1-((1,2,3,4,5-η)-3-(1-pyrrolidinyl)-2,4cyclopentadien-1-yl)silanaminato(2-)-N)titanium dichloro(1,1-dimethyl-N-(phenylmethyl)-1-((1,2,3,4,5-η)-3-(1-pyrrolidinyl)-2,4-cyclopentadien-1-yl)silanaminato(2-)-N)titanium (1,1-dimethyl-N-(phenylmethyl)-1-((1 2,3,4,5-η)-3-(1-pyrrolidinyl)-2,4-cyclopentadien-1-yl)silanaminato(2-)-N)dimethyltitanium (1,1-dimethyl-N-phenyl-1-((1,2,3,4,5-η)-3-(1-pyrrolidinyl)-2,4-cyclopentadien-1-yl)silanaminato(2-)-N)dimethyltitanium (1,1-dimethyl-1-((1,2,3,4,5η)-3-(1-pyrrolidinyl)-2,4-cyclopentadien-1-yl)-N-((tricyclo(3.3.1.1.3,7)dec-1-yl))silanaminato(2-)-N)dimethyltitanium (1,1-dimethyl-N-cyclododecyl-1-((1,2,3,4,5-η)-3-(1-pyrrolidinyl)-2,4-cyclopentadien-1-yl)silanaminato(2-)-N)dimethyltitanium (1,1-dimethyl-N-(phenylmethyl)-1-((1,2,3,4,5-η)-3-(1-pyrrolidinyl)-2,4-cyclopentadien-1-yl)silanaminato(2-)-N)bis(phenylmethyl)titanium (1,1'-(η$^4$-1,3-butadiene-1,4-diyl)bis(benzene))(1,1-dimethyl-N-(1-methylethyl)-1-((1,2,3,4,5-η)-3-(1-pyrrolidinyl)-2,4-cyclopentadien-1-yl)silanaminato(2-)-N)titanium (1,1-dimethyl-N-(1-methylethyl)-1-((1,2,3,4,5-η)-3-(1-pyrrolidinyl)-2,4-cyclopentadien-1-yl)silanaminato(2-)-N)((1,2,3,4-η)-2,4-hexadiene)titanium (1,1-dimethyl-N-(1-methylethyl)-1-((1,2,3,4,5-η)-3-(1-pyrrolidinyl)-2,4-cyclopentadien-1-yl)silanaminato(2-)-N)((1,2,3,4-η)-1,3-pentadiene)titanium ((2-(dimethylamino)methyl)phenyl)(1,1-dimethyl-N-(1-methylethyl)-1-((1,2,3,4,5-η)-3-(1-pyrrolidinyl)-2,4-cyclopentadien-1-yl)silanaminato(2-)-N)titanium dichloro(1,1-dimethyl-N-(1-methylethyl)-1-((1,2,3,4,5-η)-3-(1-pyrrolidinyl)-2,4-cyclopentadien-1-yl)silanaminato(2-)-N)titanium (1,1-dimethyl-N-(1-methylethyl)-1-((1,2,3,4,5 -)-3-(1-pyrrolidinyl)-2,4-cyclopentadien-1-yl)silanaminato(2-)-N)dimethyltitanium (1,1'-(η$^4$-1,3-butadiene-1,4-diyl)bis(benzene))(N-(1,1-dimethylethyl)-1,1-dimethyl-1-((1,2,3,4, 5-η)-3-(1-pyrrolidinyl)-2,4-cyclopentadien-1-yl)silanaminato(2-)N)titanium (N-ethyl-1,1-dimethyl-1-((1,2,3,4,5-η)-3-(1-pyrrolidinyl)-2,4-cyclopentadien-1-yl)silanaminato(2-)-N)((1,2,3,4-η)-2,4-hexadiene)titanium (N-ethyl-1,1-dimethyl-1-((1,2,3,4,5-η)-3-(1-pyrrolidinyl)-2,4-cyclopentadien-1-yl)silanaminato(2-)-N)((1,2,3,4-η)-1,3-pentadiene)titanium ((2-(dimethylamino)methyl)phenyl)(N-ethyl-1-dimethyl-1-((1,2,3,4,5-η)-3-(1-pyrrolidinyl)-2,4-cyclopentadien-1-yl)silanaminato(2-)-N)titanium dichloro(N-ethyl-1,1-dimethyl-1-((1,2,3,4,5-η)-3-(1-pyrrolidinyl)-2,4-cyclopentadien-1-yl)silanaminato(2-)-N)titanium (N-ethyl-1,1-dimethyl-1-((1,2,3,4,5-η)-3-(1-pyrrolidinyl)-2,4-cyclopentadien-1-yl)silanaminato(2-)-N)dimethyltitanium (1,1'-(η⁴-1,3-butadiene-1,4-diyl)bis(benzene))(N-(1,1-dimethylethyl)-1,1-dimethyl-1-((1,2,3,4,5-η)-3-(1-piperidinyl)-2,4-cyclopentadien-1-yl)silanaminato(2-)-N)titanium (N-(1,1-dimethylethyl)-1,1-dimethyl-1-((1,2,3,4,5-η)-3-(1-piperidinyl)-2,4-cyclopentadien-1-yl)silanaminato(2-)-N)((1,2,3,4-η)-2,4-hexadiene)titanium (N-(1,1-dimethylethyl)-1,1-dimethyl-1-((1,2,3,4,5-η)-3-(1-piperidinyl)-2,4-cyclopentadien-1-yl)silanaminato(2-)-N)((1,2,3,4-η)-1,3-pentadiene)titanium ((2-(dimethylamino)methyl)phenyl)(N-(1,1-dimethylethyl)-1,1-dimethyl-1-((1,2,3,4,5-η)-3-(1-piperidinyl)-2,4-cyclopentadien-1-yl)silanaminato(2-)-N)titanium dichloro(N-(1,1-dimethylethyl)-1,1-dimethyl-1-((1,2,3,4,5-η)-3-(1-piperidinyl)-2,4-cyclopentadien-1-yl)silanaminato(2-)-N)titanium (N-(1,1-dimethylethyl)-1,1-dimethyl-1-((1,2,3,4,5-η)-3-(1-piperidinyl)-2,4-cyclopentadien-1-yl)silanaminato(2-)-N)dimethyltitanium (1,1'-(η⁴-1,3-butadiene-1,4-diyl)bis(benzene))(N--(1,1-dimethylethyl)-1,1-dimethyl-1-((1,2,3,4,5-η)-3-(1-piperidinyl)-2,4-cyclopentadien-1-yl)silanaminato(2-)-N)titanium (N-(1,1-dimethylethyl)-1,1-dimethyl-1-((1,2,3,4,5-η)-3-(methylphenylamino)-2,4-cyclopentadien-1-yl)silanaminato(2-)-N)((1,2,3,4-η)-2,4-hexadiene)titanium (N-(1,1-dimethylethyl)-1,1-dimethyl-1-((1,2,3,4,5-η)-3-(methylphenylamino)-2,4-cyclopentadien-1-yl)silanaminato(2-)-N)((1,2,3,4-η)-1,3-pentadiene)titanium ((2-(dimethylamino)methyl)phenyl)(N-(1,1-dimethylethyl)-1,1-dimethyl-1-((1,2,3,4,5-η)-3-(methylphenylamino)-2,4-cyclopentadien-1-yl)silanaminato(2-)-N)titanium dichloro(N-(1,1-dimethylethyl)-1,1-methyl-1-((1,2,3,4,5-η)-3-(methylphenylamino)-2,4-cyclopentadien-1-yl)silanaminato(2-)-N)titanium (N-(1,1-dimethylethyl)-1,1-dimethyl-1-((1,2,3,4,5-η)-3-(methylphenylamino)-2,4-cyclopentadien-1-yl)silanaminato(2-)-N)dimethyltitanium (N-(1,1-dimethylethyl)-1,1-dimethyl-1-((1,2,3,4,5-η)-3-(methylphenylamino)-2,4cyclopentadien-1-yl)silanaminato(2-)-N)bis(phenylmethyl)titanium (N-(1,1-dimethylethyl)-1,1-dimethyl-1-((1,2,3,4,5-η)-3-(methylphenylamino)-2,4-cyclopentadien-1-yl)silanaminato(2-)-N)bis(phenylmethyl)bis((trimethylsilyl)methyl)titanium (N-(1,1-dimethylethyl)-1,1-dimethyl-1-((1,2,3,4,5-η)-3-(methylphenylamino)-2,4-cyclopentadien-1-yl)silanaminato(2-)-N)bis(phenylmethyl)bis(2,2-dimethylpropyl)titanium (1,1'-(η⁴-1,3-butadiene-1,4-diyl)bis(benzene))(1-((1,2,3,4,5-η)-3-(dimethylamino)-2,4-cyclopentadien-1-yl)-N-(1,1-dimethylethyl)-1,1-dimethylsilanaminato(2-)-N)titanium (1-((1,2,3,4,5-η)-3-(dimethylamino)-2,4-cyclopentadien-1-yl)-N-(1,1-dimethylethyl)-1,1-dimethylsilanaminato(2-)-N)((1,2,3,4-η)-2,4-hexadiene)titanium (1-((1,2,3,4,5-η)-3-(dimethylamino)-2,4-cyclopentadien-1-yl)-N-(1,1-dimethylethyl)-1,1-dimethylsilanaminato(2-)-N)((1,2,3,4-7)-1,3-pentadiene)titanium ((2-(dimethylamino)methyl)phenyl)(1-((1,2,3,4,5-η)-3-(dimethylamino)-2,4-cyclopentadien-1-yl)-N-(1,1-dimethylethyl)-1,1-dimethylsilanaminato(2-)-N)titanium dichloro(1-((1,2,3,4,5-η)-3-(dimethylamino)-2,4-cyclopentadien-1-yl)-N-(1,1-dimethylethyl)-1,1-dimethylsilanaminato(2-)-N)titanium (1-((1,2,3,4,5-η)-3-(dimethylamino)-2,4-cyclopentadien-1-yl)-N-(1,1-dimethylethyl)-1,1-dimethylsilanaminato(2-)-N)dimethyltitanium (1,1'-(η⁴-1,3-butadiene-1,4-diyl)bis(benzene))(N-(1,1-dimethylethyl)-1-((1,2,3,4,5-η)-3-(ethylmethylamino)-2,4-cyclopentadien-1-yl)-1,1-dimethylsilanaminato(2-)-N)titanium (N-(1,1-dimethylethyl)-1-((1,2,3,4,5-η)-3-(ethylmethylamino)-2,4-cyclopentadien-1-yl)-1,1-dimethylsilanaminato(2-)-N)((1,2,3,4-η)-2,4-hexadiene)titanium (N-(1,1-dimethylethyl)-1-((1,2,3,4,5-η)-3-(ethylmethylamino)-2,4-cyclopentadien-1-yl)-1,1-dimethylsilanaminato(2-)-N)((1,2,3,4-η)-1,3-pentadiene)titanium ((2-(dimethylamino)methyl)phenyl)(N-(1,1-dimethylethyl)-1-((1,2,3,4,5-η)-3-(ethylmethylamino)-2,4-cyclopentadien-1-yl)-1,1-di methylsilanaminato(2-)-N)titanium dichloro(N-(1,1-dimethylethyl)-1-((1,2,3,4,5-η)-3-(ethylmethylamino)-2,4-cyclopentadien-1-yl)-1,1-dimethylsilanaminato(2-)-N)titanium (N-(1,1-dimethylethyl)-1-((1,2,3,4,5-η)-3-(ethylmethylamino)-2,4-cyclopentadien-1-yl)-1,1-dimethylsilanaminato(2-)-N)dimethyltitanium (N-(1,1-dimethylethyl)-1-((1,2,3,4,5-η)-3-(ethylmethylamino)-2,4-cyclopentadien-1-yl)-1,1-dimethylsilanaminato(2-)-N)bis(phenylmethyl)titanium (N-(1,1-dimethylethyl)-1-((1,2,3,4,5-η)-3-(ethylmethylamino)-2,4-cyclopentadien-1-yl)-1,1-di methylsilanaminato(2-)-N)bis(phenylmethyl)bis((trimethylsilyl)methyl)titanium (N-(1,1-dimethylethyl)-1-((1,2,3,4,5-η)-3-(ethylmethylamino)-2,4-cyclopentadien-1-yl)-1,1-dimethylsilanaminato(2-)-N)bis(phenylmethyl)bis(2,2-dimethylpropyl)titanium (1,1'-(η⁴-1,3-butadiene-1,4-diyl)bis(benzene))(N-(1,1-dimethylethyl)-1,1-dimethyl-1-((1,2,3,4,5-η)-3-methoxy-2,4-cyclopentadien-1-yl)silanaminato(2-)-N)titanium (N-(1,1-dimethylethyl)-1,1-dimethyl-1-((1,2,3,4,5-η)-3-methoxy-2,4-cyclopentadien-1-yl)silanaminato(2-)-N)((1,2,3,4-η)-2,4-hexadiene)titanium (N-(1,1-dimethylethyl)-1,1-dimethyl-1-((1,2,3,4,5-η)-3-methoxy-2,4-cyclopentadien-1-yl)silanaminato(2-)-N)((1,2,3,4-η)-1,3-pentadiene)titanium ((2-(dimethylamino)methyl)phenyl)(N-(1,1-dimethylethyl)-1,1-dimethyl-1-((1,2,3,4,5-η)-3-methoxy-2,4-cyclopentadien-1-yl)silanaminato(2-)-N)titanium dichloro(N-(1,1-dimethylethyl)-1,1-dimethyl-1-((1,2,3,4,5-η)-3-methoxy-2,4-cyclopentadien-1-yl)silanaminato(2-)-N)titanium (N-(1,1-dimethylethyl)-1,1-dimethyl-1-((1,2,3,4,5-η)-3-methoxy-2,4-cyclopentadien-1-yl)silanaminato(2-)-N)dimethyltitanium (N-(1,1-dimethylethyl)-1,1-dimethyl-1-((1,2,3,4,5-η)-3-methoxy-2,4-cyclopentadien-1-yl)silanaminato(2-)-N)bis(phenylmethyl)titanium (1,1'-(η⁴-1,3-butadiene-1,4-diyl)bis(benzene))(N-(1,1-dimethylethyl)-1,1-dimethyl-1-((1,2,3,4,5-η)-3-((1,-dimethylethyl)oxy)-2,4-cyclopentadien-1-yl)silanaminato(2-)-N)titanium (N-(1,1-dimethylethyl)-1,1-dimethyl-1-((1,2,3,4,5-η)-3-((1,1-dimethylethyl)oxy)-2,4-cyclopentadien-1-yl)silanaminato(2-)-N)((1,2,3,4-η)-2,4-hexadiene)titanium (N-(1,1-dimethylethyl)-1,1-dimethyl-1-((1,2,3,4,5-η)-3-((1,1-dimethylethyl)oxy)-2,4-cyclopentadien-1-yl)silanaminato(2-)-N)((1,2,3,4-η)-1,3-pentadiene)titanium ((2-(dimethylamino)methyl)phenyl)(N-(1,1-dimethylethyl)-1,1-dimethyl-1-((1,2,3,4,5-η)-3-((1,1-dimethylethyl)oxy)-2,4-cyclopentadien-1-yl)silanaminato(2-)-N)titanium dichloro(N-(1,1-dimethylethyl)-1,1-dimethyl-1-((1,2,3,4,5-η)-3-((1,1-dimethylethyl)oxy)-2,4-cyclopentadien-1-yl)silanaminato(2-)-N)titanium (N-(1,1-dimethylethyl)-1,1-dimethyl-1-((1,2,3,4,5-η)-3-((1,1-dimethylethyl)oxy)-2,4-cyclopentadien-1-yl)silanaminato(2-)-N)dimethyltitanium (N-(1,1-dimethylethyl)-1,1-dimethyl-1-((1,2,3,4,5-η)-3-(hexahydro-1H-azepin-1-yl)-2,4-cyclopentadien-1-yl)silanaminato(2-)-N)dimethyltitanium (N-(1,1-dimethylethyl)-1,1-dimethyl-1-((1,2,3,4,5-η)-3-(hexahydro-1(2H)-azocinyl)-2,4cyclopentadien-1-yl)silanaminato(2-)-N)dimethyltitanium (N-(1,1-dimethylethyl)-1,1-dimethyl-1-((1,2,3,4,5-η)-3-(octahydro-1H-azonin-1-yl)-2,4-cyclopentadien-1-yl)silanaminato(2-)-N)dimethyltitanium (N-(1,1-dimethylethyl)-1,1-dimethyl-1-((1,2,3,4,5-η)-3-(octahydro-1(2H)-azecinyl)-2,4-cyclopentadien-1-yl)silanaminato(2-)-N)dimethyltitanium (N-(1,1-dimethylethyl)-1,1-dimethyl-1-((1,2,3,4,5-η)-3-(methyl(phenylmethyl)amino)-2,4-cyclopentadien-1-yl)silanaminato(2-)-N)dimethyltitanium (N-(1,1-dimethylethyl)-1,1-dimethyl-1-((1,2,3,4,5-η)-3-((1,1-dimethylethyl)methylamino)-2,4-cyclopentadien-1-yl)silanaminato(2-)-N)dimethyltitanium (N-(1,1-dimethylethyl)-1,1-dimethyl-1-((1,2,3,4,5-η)-3-(methyl1,1-methylethyl)amino)-2,4-cyclopentadien-1-yl)silanaminato(2-)-N)dimethyltitanium (N-(1,1-dimethylethyl)-1,1-dimethyl-1-((1,2,3,4,5-η)-3-(methylphenylamino)-2,4-cyclopentadien-1-yl)silanaminato(2-)-N)dimethyltitanium (N-(1,1-dimethylethyl)-1,1-dimethyl-1-((1,2,3,4,5-η)-3-(dimethylphosphino)-2,4-cyclopentadien-1-yl)silanaminato(2-)-N)dimethyltitanium (N-(1,1-dimethylethyl)-1,1-dimethyl-1-((1,2,3,4,5-yl)-3-(diphenylphosphino)-2,4-cyclopentadien-1-yl)silanaminato(2-)-N)dimethyltitanium (N-(1,1-dimethylethyl)-1,1-dimethyl-1-((1,2,3,4,5-η)-3-(methylphenylphosphino)-2,4cyclopentadien-1-yl)silanaminato(2-)-N)dimethyltitanium (N-(1,1-dimethylethyl)-1,1-dimethyl-1-((1,2,3,4,5-η)-3-ethoxy-2,4-cyclopentadien-1-yl)silanaminato(2-)-N)dimethyltitanium (N-(1,1-dimethylethyl)-1,1-dimethyl-1-((1,2,3,4,5-η)-3-propoxy-2,4-cyclopentadien-1-yl)silanaminato(2-)-N)dimethyltitanium (N-(1,1-dimethylethyl)-1,1-dimethyl-1-((1,2,3,4,5-η))-3-(1-methylethoxy)-2,4-cyclopentadien-1-yl)silanaminato(2-)-N)dimethyltitanium (N-(1,1-dimethylethyl)-1,1-dimethyl-1-((1,2,3,4,5-η)-3-(phenoxy)-2,4-cyclopentadien-1-yl)silanaminato(2-)-N)dimethyltitanium (N-(1,1-dimethylethyl)-1,1-dimethyl-1-((1,2,3,4,5-η))-3-(phenylthio)-2,4-cyclopentadien-1-yl)silanaminato(2-)-N)dimethyltitanium (N-(1,1-dimethylethyl)-1,1-dimethyl-1-((1,2,3,4,5-η)-3-(methylthio)-2,4-cyclopentadien-1-yl)silanaminato(2-)-N)dimethyltitanium (1,1'-(η$^4$-1,3-butadiene-1,4-diyl)bis(benzene))(N-(1,1-dimethylethyl)-1,1-dimethyl-1-((1,2,3,4,5-η)-2-methyl-3-(1-pyrrolidinyl)-2,4-cyclopentadien-1-yl)silanaminato(2-)-N)titanium (N-(1,1-dimethylethyl)-1,1-dimethyl-1-((1,2,3,4,5-η)-2-methyl-3-(1-pyrrolidinyl)-2,4-cyclopentadien-1-yl)silanaminato(2-)-N)((1,2,3,4-η)-2,4-hexadiene)titanium (N-(1,1-dimethylethyl)-1,1-dimethyl-1-((1,2,3,4,5-η)-2-methyl-3-(1-pyrrolidinyl)-2,4-cyclopentadien-1-yl)silanaminato(2-)-N)((1,2,3,4-η)-1,3-pentadiene)titanium ((2-(dimethylamino)methyl)phenyl)(N-(1,1-dimethylethyl)-1,1-dimethyl-1-((1,2,3,4,5-η)-2-methyl-3-(1-pyrrolidinyl)-2,4cyclopentadien-1-yl)silanaminato(2-)-N)titanium dichloro(N-(1,1-dimethylethyl)-1,1-dimethyl-1-((1,2,3,4,5-η)-2-methyl-3-(1-pyrrolidinyl)-2,4-cyclopentadien-1-yl)silanaminato(2-)-N)titanium (N-(1,1-dimethylethyl)-1,1-dimethyl-1-((1,2,3,4,5-η)-2-methyl-3-(1-pyrrolidinyl)-2,4-cyclopentadien-1-yl)silanaminato(2-)-N)dimethyltitanium (1,1'-(η$^4$-1,3-butadiene-1,4-diyl)bis(benzene))(N-(1,1-dimethylethyl)-1,1-dimethyl-1-((1,2,3,4,5-η)-2-propyl-3-(1-pyrrolidinyl)-2,4-cyclopentadien-1-yl)silanaminato(2-)-N)titanium (N-(1,1-dimethylethyl)-1,1-dimethyl-1-((1,2,3,4,5-η)-2-propyl-3-(1-pyrrolidinyl)-2,4-cyclopentadien-1-yl)silanaminato(2-)-N)((1,2,3,4-η)-2,4-hexadiene)titanium (N-(1,1-dimethylethyl)-1,1-dimethyl-1-((1,2,3,4,5-η)-2-propyl-3-(1-pyrrolidinyl)-2,4-cyclopentadien-1-η)silanaminato(2-)-N)((1,2,3,4-η)-1,3-pentadiene)titanium ((2-(dimethylamino)methyl)phenyl)(N-(1,1-dimethylethyl)-1,1-dimethyl-1-((1,2,3,4,5-η)-2-propyl-3-(1-pyrrolidinyl)-2,4-cyclopentadien-1-yl)silanaminato(2-)-N)titanium dichloro(N-(1,1-dimethylethyl)-1,1-dimethyl-1-((1,2,3,4,5-η)-2-propyl-3-(1-pyrrolidinyl)-2,4-cyclopentadien-1-yl)silanaminato(2-)-N)titanium (N-(1,1-dimethylethyl)-1,1-dimethyl-1-((1,2,3,4,5-η)-2-propyl-3-(1-pyrrolidinyl)-2,4-cyclopentadien-1-yl)silanaminato(2-)-N)dimethyltitanium (1,1'-(η$^4$-1,3-butadiene-1,4-diyl)bis(benzene))(N-(1,1-dimethylethyl)-1,1-dimethyl-1-((1,2,3,4,5-η)-2-methyl-4-ethyl-3-(1-pyrrolidinyl)-2,4-cyclopentadien-1-yl)silanaminato(2-)-N)titanium (N-(1,1-dimethylethyl)-1,1-dimethyl-1-((1,2,3,4,5-η)-2-methyl-4-ethyl-3-(1-pyrrolidinyl)-2,4cyclopentadien-1-yl)silanaminato(2-)-N)((1,2,3,4-)-2,4-hexadiene)titanium (N-(1,1-dimethylethyl)-1,1-dimethyl-1-((1,2,3,4,5-η)-2-methyl-4-ethyl-3-(1-pyrrolidinyl)-2,4-cyclopentadien-1-yl)silanaminato(2-)-N)((1,2,3,4-η)-1,3-pentadiene)titanium ((2-(dimethylamino)methyl)phenyl)(N-(1,1-dimethylethyl)-1,1-dimethyl-1-((1,2,3,4,5-η)-2-methyl-4-ethyl-3-(1-pyrrolidinyl)-2,4-cyclopentadien-1-yl)silanaminato(2-)-N)titanium dichloro(N-(1,1-dimethylethyl)-1,1-dimethyl-1-((1,2,3,4,5-η)-2-methyl-4-ethyl-3-(1-pyrrolidinyl)-2,4-cyclopentadien-1-yl)silanaminato(2-)-N)titanium (N-(1,1-dimethylethyl)-1,1-dimethyl-1-((1,2,3,4,5-η)-2-methyl-4-ethyl-3-(1-pyrrolidinyl)-2,4-cyclopentadien-1-yl)silanaminato(2-)-N)dimethyltitanium (1,1'-(η$^4$-1,3-butadiene-1,4-diyl)bis(benzene))(N-(1,1-dimethylethyl)-1,1-dimethyl-1-((1,2,3,4,5-η)-3-(1-methylethyl)-4-(1-pyrrolidinyl)-2,4-cyclopentadiene-1-yl)silanaminato(2-)-N)titanium (N-(1,1-dimethylethyl)-1,1-dimethyl-1-((1,2,3,4,5-η)-3-(1-methylethyl)4-(1-pyrrolidinyl)-2,4-cyclopentadien-1-yl)silanaminato(2-)-N)((t,2,3,4-η)-2,4-hexadiene)titanium (N-(1,1-dimethylethyl)-1,1-dimethyl-1-((1,2,3,4,5-η)-3-(1-methylethyl)4-(1-pyrrolidinyl)-2,4-cyclopentadien-1-yl)silanaminato(2-)-N)((1,2,3,4-η)-1,3-pentadiene)titanium ((2-(dimethylamino)methyl)phenyl)(N-(1,1-dimethylethyl)-1,1-dimethyl-1-((1,2,3,4,5-η)-3-(1-methylethyl)-4-(1-pyrrolidinyl)-2,4-cyclopentadien-1-yl)silanaminato(2-)-N)titanium dichloro(N-(1,1-dimethylethyl)-1,1-dimethyl-1-((1,2,3,4,5-η)-3-(1-methylethyl)4-(1-pyrrolidinyl)-2,4-cyclopentadien-1-yl)silanaminato(2-)-N)titanium (N-(1,1-dimethylethyl)-1,1-dimethyl-1-((1,2,3,4,5-η)-3-(1-methylethyl)-4-(1-pyrrolidinyl)-2,4-cyclopentadien-1-yl)silanaminato(2-)-N)dimethyltitanium (1,1'-(η$^4$-1,3-butadiene-1,4-diyl)bis(benzene))(N-(1,1-dimethylethyl)-1,1-dimethyl-1-((1,2,3,4,5-η)-2,4,5-trimethyl-(1-pyrrolidinyl)-2,4-cyclopentadien-1-yl)silanaminato(2-)-N)titanium (N-(1,1-dimethylethyl)-1,1-dimethyl-1-((1,2,3,4,5-η)-2,4,5-trimethyl-(1-pyrrolidinyl)-2,4cyclopentadien-1-yl)silanaminato(2-)-N)((1,2,3,4-η)-2,4-hexadiene)titanium (N-(1,1-dimethylethyl)-1,1-dimethyl-1-((1,2,3,4,5-η)-2,4,5-trimethyl-(1-pyrrolidinyl)-2,4-cyclopentadien-1-yl)silanaminato(2-)-N)((1,2,3,4-η)-1,3-pentadiene)titanium ((2-(dimethylamino)methyl)phenyl)(N-(1,1-dimethylethyl)-1,1-dimethyl-1-((1,2,3,4,5-η)-2,4,5-trimethyl-(1-pyrrolidinyl)-2,4-cyclopentadien-1-yl)silanaminato(2-)-N)titanium dichloro(N-(1,1-dimethylethyl)-1,1-dimethyl-1-((1,2,3,4,5-η)-2,4,5-trimethyl-(1-pyrrolidinyl)-2,4-cyclopentadien-1-yl)silanaminato(2-)-N)titanium (N-(1,1-dimethylethyl)-1,1-dimethyl-1-((1,2,3,4,5-η)-2,4,5-trimethyl-(1-pyrrolidinyl)-2,4-cyclopentadien-1-yl)silanaminato(2-)-N)dimethyltitanium (N-(1,1-dimethylethyl)-1-methyl-1-phenyl-1-((1,2,3,4,5-η)-3-(1-pyrrolidinyl)-2,4-cyclopentadien-1-yl)silanaminato(2-)-N)dimethyltitanium (N-(1,1-dimethylethyl)-1,1-diphenyl-1-((1,2,3,4,5-η)-3-(1-pyrrolidinyl)-2,4-cyclopentadien-1-yl)silanaminato(2-)-N)dimethyltitanium (N-(1,1-dimethylethyl)-1,1-bis(1-methylethoxy)-1-((1,2,3,4,5-η1)-3-(1-pyrrolidinyl)-2,4-cyclopentadien-1-yl)silanaminato(2-)-N)dimethyltitanium (N-(1,1-dimethylethyl)-1-ethoxy-1-methyl-1-((1,2,3,4,5-η)-3-(1-pyrrolidinyl)-2,4-cyclopentadien-1-yl)silanaminato(2-)-N)dimethyltitanium (N-(1,1-dimethylethyl)-1,1-dimethoxy-1-((1,2,3,4,5-η)-3-(1-pyrrolidinyl)-2,4-cyclopentadien-1-yl)silanaminato(2-)-N)dimethyltitanium (N-(1,1-dimethylethyl)-2-((1,2,3,4,5-η)-3-(1-pyrrolidinyl)-2,4-cyclopentadien-1-yl)ethanaminato(2-)-N)dimethyltitanium (N-(1,1-dimethylethyl)-2-((1,2,3,4,5-η)-3-(1-pyrrolidinyl)-2,4-cyclopentadien-1-yl)-1,1,2,2-tetramethylethanaminato(2-)-N)dimethyltitanium (N-(1,1-dimethylethyl)-2-((1,2,3,4,5-η)-3-(1-pyrrolidinyl)-2,4-cyclopentadien-1-yl)-1,1,2,2-tetramethyldisilanaminato(2-)-N)dimethyltitanium (N-(1,1-dimethylethyl)-3-((1,2,3,4,5-η)-3-(1-pyrrolidinyl)-2,4-cyclopentadien-1-yl)-propanaminato(2-)-N)dimethyltitanium (N-(1,1-dimethylethyl)-2-((1,2,3,4,5-η)-3-(1-pyrrolidinyl)-2,4-cyclopentadien-1-yl)methylaminato(2-)-N)dimethyltitanium (N-(1,1-dimethylethyl)-2-((1,2,3,4,5-η)-3-(1-pyrrolidinyl)-2,4-cyclopentadien-1-yl)-1,1-dimethylmethanaminato(2-)-N)dimethyltitanium (N-(1,1-dimethylethyl)-2-((1,2,3,4,5-η)-3-(1-pyrrolidinyl)-2,4-cyclopentadien-1-yl)-1,1-dimethylgermanaminato(2-)-N)dimethyltitanium (N-(1,1-dimethylethyl)-1,1-dimethyl-1-((1,2,3,3a,7a-η)4,5,6,7-tetrahydro-3-(1-pyrrolidinyl)-2,4-cyclopentadien-1-yl)silanaminato(2-)-N)dimethyltitanium (N-(1,1-dimethylethyl)-1,1-dimethyl-1-((1,2,3,3a,7a-η)4,5,6,7-tetrahydro-3-(methyl(1-methylethyl)amino)-2,4-cyclopentadien-1-yl)silanaminato(2-)-N)dimethyltitanium (N-(1,1-dimethylethyl)-1,1-dimethyl-1(1,2,3,3a,7a-η)4,5,6,7-tetrahydro-2-methyl-3-(1-pyrrolidinyl)-2,4-cyclopentadien-1-yl)silanaminato(2-)-N)dimethyltitanium (N-(1,1-dimethylethyl)-1,1-dimethyl-1-((1,2,3,3a,7a-η)-4,5,6,7-tetrahydro-2,4,5-trimethyl-3-(1-pyrrolidinyl)-2,4-cyclopentadien-1-yl silanaminato(2-)-N)dimethyltitanium (N-cyclohexyl-1,1-dimethyl-1-((1,2,3,3a,7a-η)-4,5,6,7-tetrahydro-3-(1-pyrrolidinyl)-2,4-cyclopentadien-1-yl)silanaminato(2-)-N)dimethyltitanium (N-methyl-1,1-dimethyl-1-((1,2,3,3a,7a-η)-4,5,6,7-tetrahydro-3-(1-pyrrolidinyl)-2,4-cyclopentadien-1-yl)silanaminato(2-)-N)dimethyltitanium dichloro(N-(1,1-dimethylethyl)-1,1-dimethyl-1-((1,2,3,3a,7a-η)4,5,6,7-tetrahydro-3-(1-pyrrolidinyl)-2,4-cyclopentadien-1-yl)silanaminato(2-)-N)titanium (N-(1,1-dimethylethyl)-1,1-dimethyl-1-((1,2,3,3a,7a-η)4,5,6,7-tetrahydro-3-(1-pyrrolidinyl)-2,4-cyclopentadien-1-yl)silanaminato(2-)-N)((1,2,3,4-η)-1,3-pentadiene)titanium ((2-(dimethylamino)methyl)phenyl)(N-(1,1-dimethylethyl)-1,1-dimethyl-1-((1,2,3,3a,7a-η)-4,5,6,7-tetrahydro-3-(1-pyrrolidinyl)-2,4-cyclopentadien-1-yl)silanaminato(2-)-N)titanium (N-(1,1-dimethylethyl)-1,1-dimethoxy-1-((1,2,3,3a,7a-η)4,5,6,7-tetrahydro-3-(1-pyrrolidinyl)-2,4-cyclopentadien-1-yl)silanaminato(2-)-N)dimethyltitanium (1-((1,2,3,3a,6a-η)-3-(dimethylamino)-1,4,5,6-tetrahydro-1-pentalenyl)-N-(1,1-dimethylethyl))-1,1-dimethylsilanaminato(2-)-N)dimethyltitanium (1-((1,2,3,3a,6a-η)-3-(dimethylamino)-1,4,5,6-tetrahydro-1-pentalenyl)-N-(1,1-dimethylethyl))-1,1-dimethylsilanaminato(2-)-N)((1,2,3,4-η)-1,3-pentadiene)titanium ((2-(dimethylamino)methyl)phenyl)(1-((1,2,3,3a,6a-η)-3-(dimethylamino)-1,4,5,6-tetrahydro-1-pentalenyl)-(N-1,1-dimethylethyl))-1,1-dimethylsilanaminato(2-)-N)titanium (1-((1,2,3,3a,6a-η)-3-(dimethylamino)-1,4,5,6-tetrahydro-1-pentalenyl)-N-(1,1-dimethylethyl))-1,1-dimethoxysilanaminato(2-)-N)dimethyltitanium (1-((1,2,3,3a,6a-η)-3-(diethylamino)-1,4,5,6-tetrahydro-1-pentalenyl)-N-(1,1-dimethylethyl))-1,1-dimethylsilanaminato(2-)-N)dimethyltitanium (N-cyclohexyl-(1-((1,2,3,3a,6a-η)-3-(dimethylamino)-1,4,5,6-tetrahydro-1-pentalenyl))-1,1-dimethylsilanaminato(2-)-N)dimethyltitanium (1-((1,2,3,3a,6a-η)-3-(dimethylamino)-2methyl 1,4,5,6-tetrahydro-1-pentalenyl)-N-(1,1-dimethylethyl))-1,1-dimethylsilanaminato(2-)-N)dimethyltitanium (1-((1,2,3,3a,6a-η)-3-(dimethylamino)-4-methyl-1,4,5,6-tetrahydro-1-pentalenyl)-N-(1,1-dimethylethyl))-1,1-dimethylsilanaminato(2-)-N)dimethyltitanium (1-((1,2,3,3a,6a-η)-3-(dimethylamino)-4,5,6-trimethyl-1,4,5,6-tetrahydro-1-pentalenyl)-N-(1,1-dimethylethyl))-1,1-dimethylsilanaminato(2-)-N)dimethyltitanium (1-((1,2,3,3a,6a-7 )4-ethyl-3-(dimethylamino)-1,4,5,6tetrahydro-1-pentalenyl)-N-(1,1-dimethylethyl))-1,1-dimethylsilanaminato(2-)-N)dimethyltitanium The complexes can be prepared by use of well known synthetic techniques. Optionally a reducing agent can be employed to produce the lower oxidation state complexes. Such a process is disclosed in U.S. Ser. No. 8/241,523, filed May 13, 1994, published as WO 95/00526, the teachings of which are hereby incorporated by reference. The reactions are conducted in a suitable noninterfering solvent at a temperature from −100 to 300° C., preferably from −78 to 100° C., most preferably from 0 to 50° C. By the term "reducing agent" herein is meant a metal or compound which, under reducing conditions causes the metal M, to be reduced from a higher to a lower oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are sodium naphthalenide, potassium graphite, lithium alkyls, lithium or potassium alkadienyls, and Grignard reagents. Most preferred reducing agents are the alkali metals or alkaline earth metals, especially lithium and magnesium metal.

Suitable reaction media for the formation of the complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, and tetrahydrofuran. Mixtures of the foregoing are also suitable.

One synthesis of heteroatom-substituted cyclopentadienyl systems, which are useful as precursors to constrained geometry catalyst systems (CGC), is depicted in Scheme 1, below, where:

a.) excess amine, benzene, reflux 24 hr (—$H_2O$); b.) excess amine (8 eq), $TiCl_4$ (1 eq) in $CH_2Cl_2$, 0° C., then add ketone and warm to 25° C.; c) 1.05 eq n-BuLi/hexane at 25° C.; d.) 1.0–1.5 eq Cl-silane/THF at 25° C.; e.) 2.05 eq n-BuLi/hexane at 25° C.

R, R', R", R''', R"" independently selected in each case are H (except on the nitrogen bound directly to the cyclopentadienyl ring), alkyl, cycloalkyl, aryl, alkaryl, aralkyl, and are not limited only to these groups.

Scheme 1

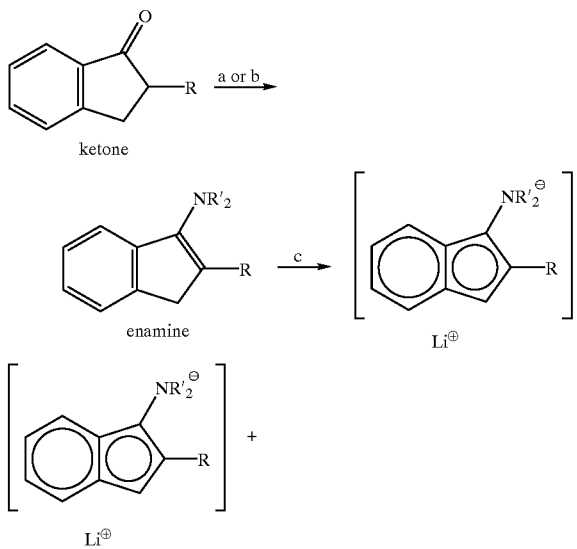

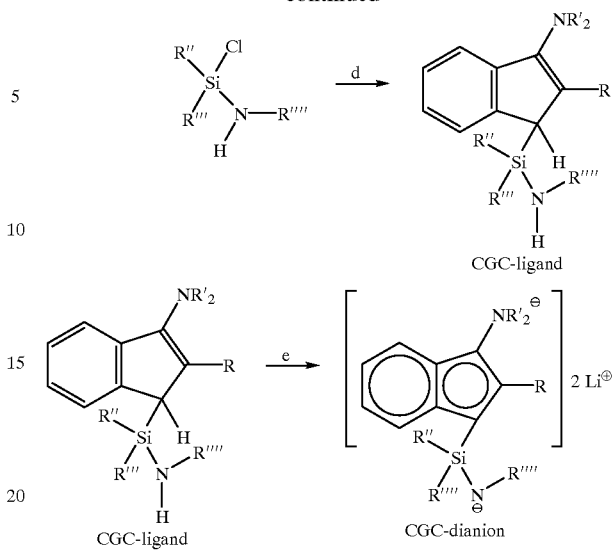

The heteroatom-containing substituent has a nitrogen in the 3-position of the indenyl system. 1-Indanone is a convenient starting material for conversion to the corresponding enamine, although formation of the latter is not restricted to the use of this compound. Enamines of indanone are typically formed by methods known in the art, including condensation of secondary amines with the ketone (W. E. Noland, V. Kameswaran J. Org. Chem. 1981, 46, 1940–1944). The corresponding water by-product may be azeotropically removed using a benzene or toluene solvent under reflux conditions and optionally an acid catalyst such as p-toluene sulfonic acid (O. Cervinka in The Chemistry of Enamines Part 1, Ch. 9; Z. Rappoport, Ed.; Wiley Interscience, New York, 1994, 468–500). With more sterically-hindered ketones, such as 2-methyl-1-indanone, or more volatile amines, such as dimethyl amine, it may be preferable to employ stronger dehydrating reagents such as titanium chloroamides (generated in situ from titanium tetrachloride and the condensation amine) (R. Carlson, A. Nilsson Acta Chemica Scandinavica B 38, 1984, 49–53). These two methods have been employed to produce enamines substituted in the 2- and 3-positions of the indene (the 1-position is typically bonded to a silicon or other linking moiety in subsequent compounds). Another method for the preparation of enamines involves electrophilic amination of carbanions such as lithium indenide (E. Erdik; M, Ay Chem. Rev., 1989, 89, 1947–1980).

For subsequent formation of highly pure CGC-ligands, enamines prepared by these routes must be highly pure and free of ketone, Aldol by-products and higher weight reaction tars which typically accompany product formation. None of the aforementioned routes uniformly provides a product which can be used without some sort of further purification. We have found that chromatographic purification using flash-grade silica gel or alumina rapidly promotes hydrolysis of the enamine to free amine and ketone, an unfortunate consequence. Although these compounds are highly water and air sensitive, enamines of this nature may be purified by careful fractional distillation, or occasionally, recrystallization. In particular, rapid distillation of indanone enamines is required to prevent thermal polymerization in the still at elevated temperature. Expedient conversion of pure enamine to its corresponding anionic salt is required to obtain a highly pure CGC-ligand, since enamines may also be photochemically sensitive.

1-indanone is also a preferred starting material for CGC-ligands substituted with oxygen in the 3-position. In particular, enol ethers in this position can be made by dehydration of the appropriate hemiketal which is formed in situ from indanone and alcohol in the presence of an acidic catalyst (L. A. Paquette; A. Varadarajan; E. Bey *J. Am. Chem. Soc.* 1984, 106, 6702–6708). Enol ethers of indanones, like the enamine analogues, are also susceptible to hydrolysis and are very oxygen sensitive. Once purified, they are best expediently converted to their corresponding anionic salts, which is shown in Scheme 2, below, where:

a.) alcohol, benzene, reflux 24 hr (—$H_2O$); b.) 1.05 eq n-BuLi/hexane at 25° C.; c.) 1.0–1.5 eq Cl-silane/THF at 25° C.; d.) 2.05 eq n-BuLi/hexane at 25° C.; and R, R', R'', R''', R'''' independently selected in each case are H (except on oxygen), alkyl, cycloalkyl, aryl, alkaryl, aralkyl, and are not limited only to these groups.

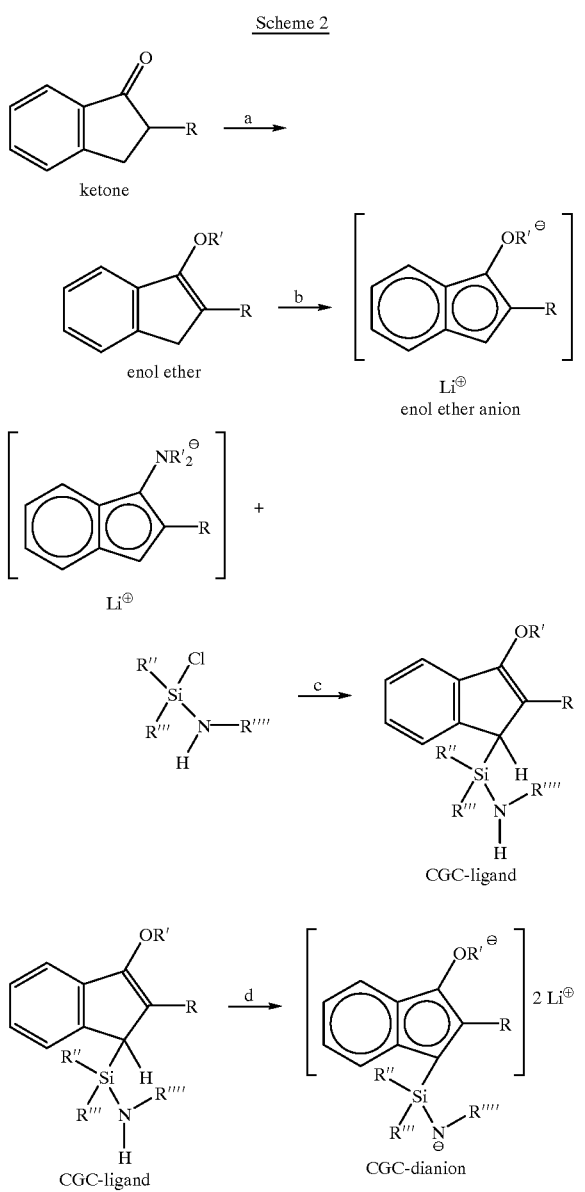

Scheme 2

Once highly purified, conversion of the enamine to its corresponding anionic salt may be accomplished by reaction with an appropriate base of suitable strength in an appropriate noninterfering solvent Under appropriate, anaerobic, anhydrous conditions, the often solid anionic salt may be filtered, washed and dried in nearly quantitative yield. Likewise, enol ethers of 1-indanone can be deprotonated to the corresponding anionic salt.

The formation of constrained geometry ligands (CGC-ligand) based upon heteroatom-substituted indenes is based upon the anion alkylation method described by Nickias and coworkers (Nickias, Peter N.; Devore, David D.; Wilson, David R., PCT Int. Appl., WO 93/08199 A1 930429. CAN 119:160577; Carpenetti, Donald W.; Kloppenburg, Lioba; Kupec, Justin T., Petersen, Jeffrey L. *Organometallics* 1996, 15(6), 1572–81) in which a cyclopentadienyl anion is reacted with electrophiles such as halogenated secondary alkylamines or halogenated secondary silylamines to give the corresponding cyclopentadienyl alkylamine or cyclopentadienyl silylamine. Under halogenated secondary alkylamines or halogenated secondary silylamines are included for example (t-butyl)(chlorodimethylsilyl)amine, (t-butyl)(chlorodimethylsilylmethyl)amine, (t-butyl)(bromomethyldimethylsilyl)amine, (t-butyl)(2-chloroethyl)amine, (chlorodimethylsilyl)(phenyl)amine, (adamantyl)(chlorodiphenylsilyl)amine, (chlorodimethylsilyl)(cyclohexyl)amine, (benzyl)(chlorodimethylsilyl)amine and (t-butyl)(chloromethylphenylsilyl)amine. For example, dropwise addition of the lithio derivative of the anionic salt in THF to a molar excess of (t-butyl)(chlorodimethylsilyl)amine in THF followed by standard removal of lithium chloride and excess electrophile often provides highly pure ligand which may be subsequently used without further purification. This so-called CGC-ligand may be converted to its insoluble dianionic salt by reaction of the free base with two equivalents of a base of suitable strength in an appropriate noninterfering solvent.

By appropriate noninterfering solvent in the context of the present invention is meant a solvent that doesn't interfere with the formation of, or react deleteriously with, the desired product. Such solvents suitable for the preparation of the anionic salts and dianionic salts of the invention include, but are not limited to aliphatic and aromatic hydrocarbons, particularly straight and branched chain hydrocarbons such as butane, pentane, hexane, heptane, octane, decane, including their branched isomers and mixtures thereof; cyclic and alicyclic hydrocarbons such as cyclohexane, cycloheptane. methylcyclohexane, methylcycloheptane and mixtures thereof; aromatic and hydrocarbyl-substituted aromatic compounds such as benzene, toluene, xylene, ethylbenzene, diethylbenzene and mixtures thereof; ethers and cyclic ethers, particularly $C_{1-6}$ dialkyl ethers, such as diethyl ether, dibutyl ether and methyl-t-butyl ether, $C_{1-6}$ dialkyl ether derivatives of (poly)alkylene glycols, such as dimethoxyethane, and dioxane and THF and mixtures thereof. Mixtures of the foregoing are also suitable.

Bases of suitable strength for the preparation of the dianionic salts of the invention include hydrocarbyl salts of Group 1 and Group 2 metals, especially alkyl or aryl salts of lithium or magnesium, such as methyllithium, ethyllithium, n-butyllithium, s-butyllithium, t-butyllithium, phenyllithium, methyl magnesium chloride, ethyl magnesium bromide, i-propyl magnesium chloride, dibutylmagnesium, (butyl)(ethyl)magnesium, dihexylmagnesium; Group 1 or Group 2 metals, such as lithium, sodium, potassium and magnesium; Group 1, Group 2 or Group 13 metal hydrides, such as lithium hydride, sodium hydride, potassium hydride or lithium aluminum hydride; Group 1 or Group 2 metal amide complexes, such as lithium diisopropylamide, lithium dimethylamide, lithium hexamethyldisilazane, sodamide and magnesium diisopropylamide.

Bases of suitable strength for the preparation of the anionic salts of the invention include the foregoing as well as Group 1 or Group 2 metal alkoxide complexes, such as sodium ethoxide, sodium t-butoxide, potassium butoxide and potassium amylate.

Another potential synthetic approach to the formation of free base ligand involves reacting the indenyl anionic salt with an excess of bis-electrophile, for example, dichlorodimethylsilane in a polar, aprotic solvent such as THF. Unexpectedly, we have found that this approach is inferior to the aforementioned technique for many 3-heteroatom-substituted ligand systems in that a large portion of ansa-ligand (bis alkylation adduct) is often formed, despite the use of excess electrophile, as shown in Scheme 3, below.

Scheme 3

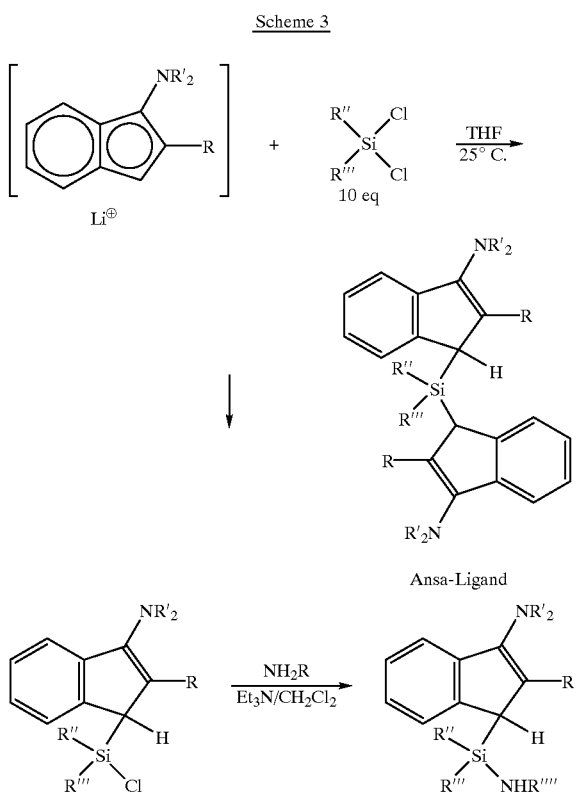

Ansa-Ligand

The synthetic feasibility of either approach is dependent upon steric and electronic consideration of the substituent groups (R groups) and requires experimental evaluation in each case.

The metallation of the dianionic salt may be accomplished by methods cited in this art as well. Reaction of the dianionic salt in THF with $TiCl_3$ $(THF)_3$, followed by oxidation with methylene chloride or lead dichloride is a well established procedure (J. Okuda, S. Verch, T. P. Spaniol, R. Sturmer Chem. Ber., 1996, 129, 1429–1431, D. D. Devore EP 514, 828) which affords the titanium (IV) dichloride complex. The dichloride may he silylated or hydrocarbylated by ligand exchange with an appropriate silylating or hydrocarbylating agent, such as methyllithium, methyl magnesium chloride, benzyl potassium, allyl lithium, trimethylsilylmethyl lithium, neopentyl magnesium bromide and phenyllithium. A more complete list of appropriate silylating or hydrocarbylating agents is given below.

A general method for producing the titanium(II) diene complex from the corresponding titanium(IV) dichloride has been described by Devore and coworkers (D. D. Devore, F. J. Timmers, D. L. Hasha, R. K. Rosen, T. J. Marks, P. A. Deck, C. L. Stern, Organometallics. 1995, 14, 3132–3134; D. D. Devore, F. J. Timmers, J. C. Stevens, R. D. Mussell, L. H. Crawford, D. R. Wilson, U.S. Pat. No. 5,556,928). Thus, treatment of the dichloride with n-butyl lithium in the presence of an appropriate diene produces the analogous titanium (II) diene complex for heteroatom-substituted systems.

The formation of the CGC metal (III) complexes according to the invention can be accomplished by any of several synthesis methods, among which are the following: The reaction under anaerobic and anhydrous conditions of the dianionic salts with trivalent metal salts, such as Group 4 metal (III) halide or alkoxide complexes, can be carried out, optionally followed by silylation or hydrocarbylation with suitable silylating or hydrocarbylating agents, to form the corresponding CGC metal (III) halide, alkoxide, silyl or hydrocarbyl complexes of the invention.

A further synthesis method involves reducing an appropriate CGC metal (IV) dihalide or dialkoxide complex, or, preceded by monosilylation or monohydrocarbylation, the corresponding CGC (IV) silyl or hydrocarbyl monohalide or monoalkoxide complex with a suitable reducing agent to the corresponding CGC metal (Ill) halide, alkoxide, silyl or hydrocarbyl complex.

Found to be particularly suitable in the synthesis of the CGC metal (III) complexes according to the present invention are the methods described by Wilson (D. R. Wilson U.S. Pat. No. 5,504,224, 1996) which is incorporated herein by reference. For example, cyclopentadienyl ligands can be displaced by the dianionic salts and/or by the (stabilizing) hydrocarbylating agents from cyclopentadienyl-containing Group 4 metal complexes in the +3 oxidation state to give the CGC metal (III) complexes of the invention.

Suitable reducing agents for reducing the oxidation state of the metals of the CGC metal (IV) complexes from +4 to +3 have been described above and especially include zinc, aluminum and magnesium.

Suitable silylating and hydrocarbylating agents for the CGC metal (III) complexes and the CGC metal (IV) complexes of the invention include alkyl, such as methyl, ethyl, propyl, butyl, neopentyl and hexyl; aryl, such as phenyl, naphthyl and biphenyl; aralkyl, such as benzyl, tolylmethyl, diphenylmethyl; alkaryl, such as tolyl and xylyl; allyl; silyl- or alkyl-substituted allyl, such as methylallyl, trimethylsilylallyl, dimethylallyl and trimethylallyl; trialkylsilyl, such as trimethylsilyl and triethylsilyl; trialkylsilylalkyl, such as trimethylsilylmethyl; pentadienyl; alkyl- or silyl-substituted pentadienyl, such as methylpentadienyl, dimethylpentadienyl, trimethylsilylpentadienyl, bis(trimethylsilyl)pentadienyl, cyclohexadienyl and dimethylcyclohexadienyl; dialkylaminoalkaryl, such as o-(N,N-dimethylaminomethyl) phenyl; and dialkylaminoaralkyl, such as o-(N,N-dimethylamino)benzyl; salts of Group 1, 2 or 13 metals, preferably the salts of lithium, sodium, potassium, magnesium and aluminum. Preferred silylating and hydrocarbylating agents include trimethylaluminum, methyllithium, methyl magnesium chloride, neopentyllithium, trimethylsilylmethyl magnesium chloride and phenyllithium. Stabilizing group-containing hydrocarbylating agents are also included, especially the stabilizing group-containing hydrocarbylating agents and salts of the stabilizing group-containing hydrocarbyl groups described in U.S. Pat. No. 5,504,224, whose salts include, for example, benzyl potassium, 2-(N,N-dimethylamino)benzyllithium, allyllithium and dimethylpentadienyl potassium. The stabilizing groups are further described in U.S. Ser. No. 8003, filed Jan. 21, 1993 (corresponding to WO 93/19104), incorporated herein by reference.

Preferred halides or alkoxides of the metal (III) halide or alkoxide complexes and the CGC metal (III) halide or alkoxide complexes include fluoride, chloride, bromide, iodide, methoxide, ethoxide, i-propoxide, n-propoxide, butoxide. Preferred metal (III) halide or alkoxide complexes include titanium (III) chloride, titanium (III) ethoxide, titanium (III) bromide, titanium (III) isopropoxide, titanium (III) (dichloro)(isopropoxide), as well as Lewis base complexes of the foregoing, especially ether complexes thereof, particularly diethyl ether, tetrahydrofuran and ethylene glycol dimethyl ether complexes thereof. Preferred cyclopentadienyl-containing Group 4 metal complexes in the +3 oxidation state include triscyclopentadienyl titanium, biscyclopentadienyl titanium chloride, biscyclopentadienyl titanium bromide, biscyclopentadienyl titanium isopropoxide, cyclopentadienyl titanium dichloride, cyclopentadienyl titanium diphenoxide, cyclopentadienyl titanium dimethoxide and bis((trimethylsilyl)(t-butyl)cyclopentadienyl)zirconium chloride.

The ligands of this invention are 3-heteroatom substituted cyclopentadienyl-containing ligands where the ligand is in the form of:

(A) a free base with 2 protons capable of being deprotonated;
(B) a dilithium salt;
(C) a magnesium salt; or
(D) a mono or disilylated dianion.

Within the scope of this invention is the use of a ligand of this invention for synthesis to produce a metal complex of this invention, for synthesis to produce a metal complex comprising a metal from one of Groups 3 to 13 of the Periodic Table of the Elements, the lanthanides or actinides, and from 1 to 4 of the ligands.

The ligands of this invention may be used in various forms, including salts, with various groups attached at the Z position in syntheses leading to metal complexes in which the metal is from Groups 3–16 of periodic table or the lanthanides, and in which from one to four of these ligands, alone or in combination with other ligands, are present in the metal complex. The methods of synthesis may be similar or analogous to those discussed herein for the Group 4 metal complexes of this invention, as well as various other synthetic procedures known in the art. The metal complexes are useful as catalysts in various reactions, including olefin polymerization reactions.

Obviously, naming of these metal complexes, as well as the neutral ligands and various intermediates is complicated and challenging, and the rules in various systems for these names are evolving. Therefore, reference to the structural representations is recommended. Generally, with attachment of the bridge of a constrained geometry complex or of a bridged bis-Cp complex in the 1-position, the heteroatom then is in the 3-position. The structural representations herein should not be given a strictly literal interpretation with regard to bond orders, bond lengths or strengths. For example, the X-ray data show that the N—Cp bonds of some complexes are shorter than would be expected for a single bond, which indicates at least some double bond character in the N—Cp bond.

If the ligands are used in complexes with only $\eta^5$ attachment, where there is no bridge, the heteroatom in those cases may be named as being in the 1-position.

Within the scope of the above discussion relating to ligands, preferred ligands of this invention correspond to the formula:

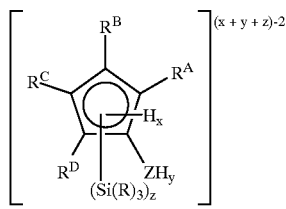

where x is 0 or 1, y is 0 or 1, z is 0 or 1, x+y is 0 or 1, x+z is 0 or 1, and the other symbols are as previously defined, where the dotted circle within the Cp ring implies the various possibilities for double bond character, partial double bond character or aromatic character as appropriate, depending upon the values for x, y, and z.

The complexes are rendered catalytically active by combination with an activating cocatalyst or by use of an activating technique. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C_{1-45}$ hydrocarbyl substituted Group 13 compounds, especially tri(hydrocarbyl)aluminum- or tri (hydrocarbyl)boron compounds and halogenated (including perhalogenated) derivatives thereof, having from 1 to 15 carbons in each hydrocarbyl or halogenated hydrocarbyl group, more especially perfluorinated tri(aryl)boron compounds, and most especially tris(o-nonafluorobiphenyl) borane, tris(pentafluorophenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium- salts of compatible, noncoordinating anions, or ferrocenium salts of compatible, noncoordinating anions; bulk electrolysis (explained in more detail hereinafter); and combinations of the foregoing activating cocatalysts and techniques. The foregoing activating cocatalysts and activating techniques have been previously taught with respect to different metal complexes in the following references: EP-A-277,003, U.S. Pat. Nos. 5,153,157, 5,064,802, EP-A-468,651 (equivalent to U.S. Ser. No. 07/547,718), EP-A-520,732 (equivalent to U.S. Ser. No. 07/876,268), and EP-A-520,732 (equivalent to U.S. Ser. No. 07/884,966 filed May 1, 1992), the teachings of which are hereby incorporated by reference.

Combinations of neutral Lewis acids, especially the combination of a trialkyl aluminum compound having from 1 to 4 carbons in each alkyl group and a halogenated tri (hydrocarbyl)boron compound having from 1 to 20 carbons in each hydrocarbyl group, especially tris (pentafluorophenyl)borane, tris(o-nonafluorobiphenyl) borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. A benefit according to the present invention is the discovery that the most efficient catalyst activation using such a combination of tris(pentafluorophenyl)borane/ alumoxane mixture occurs at reduced levels of alumoxane. Preferred molar ratios of Group 4 metal complex:tris (pentafluorophenyl)borane:alumoxane are from 1:1:1 to 1:5:5, more preferably from 1:1:1.5 to 1:5:3. The surprising efficient use of lower levels of alumoxane with the present invention allows for the production of olefin polymers with high catalytic efficiencies using less of the expensive alumoxane cocatalyst. Additionally, polymers with lower levels of aluminum residue, and hence greater clarity, are obtained.

Suitable ion forming compounds useful as cocatalysts in one embodiment of the present invention comprise a cation which is a Bronsted acid capable of donating a proton, and a compatible, noncoordinating anion, A. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitrites. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

$$(L^*-H)_d^+(A)^{d-}$$

wherein:

L* is a neutral Lewis base;

(L*—H)+ is a Bronsted acid;

$(A)^{d-}$ is a noncoordinating, compatible anion having a charge of d−, and d is an integer from 1 to 3.

More preferably $(A)^{d-}$ corresponds to the formula: $[M'Q_4]^-$;

wherein:

M' is boron or aluminum in the +3 formal oxidation state; and

Q independently each occurrence is selected from hydride, dialkylamido, halide, hydrocarbyl, hydrocarbyloxide, halosubstituted-hydrocarbyl, halosubstituted hydrocarbyloxy, and halo- substituted silylhydrocarbyl radicals (including perhalogenated hydrocarbyl- perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433, the teachings of which are herein incorporated by reference.

In a more preferred embodiment, d is one, that is, the counter ion has a single negative charge and is A⁻. Activating cocatalysts comprising boron which are particularly useful in the preparation of catalysts of this invention may be represented by the following general formula:

$$(L^*-H)^+(BQ_4)^-;$$

wherein:

L* is as previously defined;

B is boron in a formal oxidation state of 3; and

Q is a hydrocarbyl-, hydrocarbyloxy-, fluorinated hydrocarbyl-, fluorinated hydrocarbyloxy-, or fluorinated silylhydrocarbyl-group of up to 20 nonhydrogen atoms, with the proviso that in not more than one occasion is Q hydrocarbyl.

Most preferably, Q is each occurrence a fluorinated aryl group, especially, a pentafluorophenyl group.

Illustrative, but not limiting, examples of ion forming compounds comprising proton donatable cations which may be used as activating cocatalysts in the preparation of the catalysts of this invention are tri-substituted ammonium salts such as:
trimethylammonium tetraphenylborate,
methyldioctadecylammonium tetraphenylborate,
triethylammonium tetraphenylborate,
tripropylammonium tetraphenylborate,
tri(n-butyl)ammonium tetraphenylborate,
methyltetradecyloctadecylammonium tetraphenylborate,
N,N-dimethylanilinium tetraphenylborate,
N,N-diethylanilinium tetraphenylborate,
N,N-dimethyl(2,4,6-trimethylanilinium)tetraphenylborate,
trimethylammonium tetrakis(penta-fluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-diethylanilinium tetrakis(pentafluorophenyl)borate,
N,N-dimethyl(2,4,6-trimethylanilinium)tetrakis(pentafluorophenyl)borate,
trimethylammonium tetrakis(2,3,4,6-tetrafluorophenyl)borate,
triethylammonium tetrakis(2,3,4,6-tetrafluorophenyl)borate,
tripropylammonium tetrakis(2,3,4,6-tetrafluorophenyl)borate,
tri(n-butyl)ammonium tetrakis(2,3,4,6-tetrafluorophenyl)borate,
dimethyl(t-butyl)ammonium tetrakis(2,3,4,6-tetrafluorophenyl)borate,
N,N-dimethylanilinium tetrakis(2,3,4,6-tetrafluorophenyl)borate,
N,N-diethylanilinium tetrakis(2,3,4,6-tetrafluorophenyl)borate, and
N,N-dimethyl-(2,4,6-trimethylanilinium)tetrakis-(2,3,4,6-tetrafluorophenyl)borate.

Dialkyl ammonium salts such as:
di-(i-propyl)ammonium tetrakis(pentafluorophenyl)borate, and
dicyclohexylammonium tetrakis(pentafluorophenyl)borate.

Tri-substituted phosphonium salts such as:
triphenylphosphonium tetrakis(pentafluorophenyl)borate,
tri(o-tolyl)phosphonium tetrakis(pentafluorophenyl)borate, and
tri(2,6-dimethylphenyl)phosphonium tetrakis(pentafluorophenyl)borate.

Preferred are tetrakis(pentafluorophenyl)borate salts of long chain alkyl mono- and disubstituted ammonium complexes, especially $C_{14}$–$C_{20}$ alkyl ammonium complexes, especially methyldi(octadecyl)ammonium tetrakis(pentafluorophenyl)borate and methyldi(tetradecyl)ammonium tetrakis(pentafluorophenyl)borate.

An especially preferred group of activating cocatalysts is tris(pentafluorophenyl)borane, N—$R_3$,N—$R_4$ anilinium tetrakis(pentafluorophenyl)borate where $R_3$ and $R_4$ independently each occurrence are substituted or unsubstituted saturated hydrocarbyl groups having from 1 to 8 carbon atoms, $(R_1R_2NHCH_3)^+(C_6H_4OH)B(C_6F_5)_3^{31}$, or $(R_1R_2NHCH_3)^+B(C_6F_5)_4^-$, where $R_1$ and $R_2$ independently each occurrence are substituted or unsubstituted saturated hydrocarbyl groups having from 12 to 30 carbon atoms.

Another suitable ion forming, activating cocatalyst comprises a salt of a cationic oxidizing agent and a noncoordinating, compatible anion represented by the formula:

$$(Ox^{e+})_d(A^{d-})_e.$$

wherein:

$Ox^{e+}$ is a cationic oxidizing agent having a charge of e+;

e is an integer from 1 to 3; and $A^{d-}$ and d are as previously defined.

Examples of cationic oxidizing agents include: ferrocenium, hydrocarbyl-substituted ferrocenium, $Ag^+$ or $Pb^{+2}$. Preferred embodiments of $A^{d-}$ are those anions previously defined with respect to the Bronsted acid containing activating cocatalysts, especially tetrakis(pentafluorophenyl)borate.

Another suitable ion forming, activating cocatalyst comprises a compound which is a salt of a carbenium ion and a noncoordinating, compatible anion represented by the formula:

$$©^+A^-$$

wherein:

$©^+$ is a $C_{1-20}$ carbenium ion; and $A^{31}$ is as previously defined. A preferred carbenium ion is the trityl cation, i.e. triphenylmethylium.

A further suitable ion forming, activating cocatalyst comprises a compound which is a salt of a silylium ion and a noncoordinating, compatible anion represented by the formula:

$$R_3Si(X')_q^+A^-$$

wherein:

R is $C_{1-10}$ hydrocarbyl, and X', q and $A^-$ are as previously defined.

Preferred silylium salt activating cocatalysts are trimethylsilylium tetrakispentafluorophenylborate, triethylsilylium tetrakispentafluorophenylborate and ether substituted adducts thereof. Silylium salts have been previously generically disclosed in J. Chem Soc. Chem. Comm., 1993, 383–384, as well as Lambert, J. B., et al., Organometallics, 1994, 13, 2430–2443. The use of the above silylium salts as activating cocatalysts for addition polymerization catalysts is claimed in United States Patent Application entitled, "Silylium Cationic Polymerization Activators For Metallocene Complexes", filed in the names of David Neithamer, David Devore, Robert LaPointe and Robert Mussell on Sep. 12, 1994.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433, the teachings of which are herein incorporated by reference.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0 to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), dimethoxyethane (DME), and mixtures thereof.

The electrolysis may be conducted in a standard electrolytic cell containing an anode and cathode (also referred to as the working electrode and counter electrode respectively). Suitable materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may he determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and a compatible, noncoordinating anion, A–. Preferred supporting electrolytes are salts corresponding to the formula $G^+A^-$; wherein:

$G^+$ is a cation which is nonreactive towards the starting and resulting complex, and $A^-$ is as previously defined.

Examples of cations, $G^+$, include tetrahydrocarbyl substituted ammonium or phosphonium cations having up to 40 nonhydrogen atoms. Preferred cations are the tetra(n-butylammonium)- and tetraethylammonium-cations.

During activation of the complexes of the present invention by bulk electrolysis the cation of the supporting electrolyte passes to the counter electrode and $A^-$ migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoroaryl) borates having from 1 to 10 carbons in each hydrocarbyl or perfluoroaryl group, especially tetra (n-butylammonium)tetrakis(pentafluorophenyl) borate.

A further recently discovered electrochemical technique for generation of activating cocatalysts is the electrolysis of a disilane compound in the presence of a source of a noncoordinating compatible anion. This technique is more fully disclosed and claimed in the previously mentioned United States Patent application entitled, "Silylium Cationic Polymerization Activators For Metallocene Complexes", filed on Sep. 12, 1994.

The foregoing electrochemical activating technique and activating cocatalysts may also be used in combination. An especially preferred combination is a mixture of a tri (hydrocarbyl)aluminum or tri(hydrocarbyl)borane compound having from 1 to 4 carbons in each hydrocarbyl group with an oligomeric or polymeric alumoxane compound.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris (pentafluorophenyl)borane, where used as an activating cocatalyst, is employed in a molar ratio to the metal complex of form 0.5:1 to 10:1, more preferably from 1:1 to 6:1, most preferably from 1:1 to 5:1. The remaining activating cocatalysts are generally employed in approximately equimolar quantity with the metal complex.

The process may be used to polymerize ethylenically unsaturated monomers having from 2 to 20 carbon atoms either alone or in combination. Preferred monomers include monovinylidene aromatic monomers, especially styrene, 4-vinylcyclohexene, vinylcyclohexane, norbrnadiene and $C_{2-10}$ aliphatic ($\alpha$-olefins, especially ethylene, propylene, isobutylene, 1-butene, 1-pentene, 1-hexene, 3-methyl-1-pentene, 4-methyl- 1-pentene, 1-heptene, and 1-octene, $C_{4-40}$ dienes, and mixtures thereof. Most preferred monomers are ethylene, propylene, 1-butene, 1-hexene, 1-octene and mixtures of ethylene, propylene and a nonconjugated diene, especially ethylidenenorbornene.

In general, the polymerization may be accomplished at conditions well known in the prior art for Ziegler-Natta or Kaminsky-Sinn type polymerization reactions, that is, temperatures from 0–250° C., preferably 30 to 200° C. and pressures from atmospheric to 10,000 atmospheres. Suspension, solution, slurry, gas phase, bulk, solid state powder polymerization or other process condition may be employed if desired. A support, especially silica, alumina, or a polymer (especially poly(tetrafluoroethylene) or a polyolefin) may be employed, and desirably is employed when the catalysts are used in a gas phase or slurry polymerization process. The support is preferably employed in an amount to provide a weight ratio of catalyst (based on metal):support from 1:100,000 to 1:10, more preferably from 1:50,000 to 1:20, and most preferably from 1:10,000 to 1:30. One such polymerization process comprises: contacting, optionally in a solvent, one or more $\alpha$-olefins with a catalyst according to the present invention, in one or more continuous stirred tank or tubular reactors, connected in series or parallel, or in the absence of solvent, optionally in a fluidized bed gas phase reactor, and recovering the resulting polymer. Condensed monomer or solvent may be added to the gas phase reactor as is well known in the art.

In most polymerization reactions the molar ratio of catalyst:polymerizable compounds employed is from $10^{-12}$:1 to $10^{-1}$:1, more preferably from $10^{-9}$:1 to $10^{-5}$:1.

Suitable solvents for polymerization are inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and the like and aromatic and alkyl-substituted aromatic compounds such as benzene, toluene, xylene, ethylbenzene and the like. Suitable solvents also include liquid olefins which may act as monomers or comonomers including ethylene, propylene, butadiene, 1-butene, cyclopentene, 1-hexene, 1-heptene, 4-vinylcyclohexene, vinylcyclohexane, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), and the like. Mixtures of the foregoing are also suitable.

The catalyst systems may be utilized in combination with at least one additional homogeneous or heterogeneous polymerization catalyst in separate reactors connected in series or in parallel to prepare polymer blends having desirable properties. An example of such a process is disclosed in WO 94/00500, equivalent to U.S. Ser. No. 07/904,770, as well as U.S. Ser. No. 08/10958, filed Jan. 29, 1993, the teachings or which are hereby incorporated by reference herein.

Utilizing the catalyst systems of the present invention copolymers having high comonomer incorporation and correspondingly low density, yet having a low melt index may be readily prepared. That is, high molecular weight polymers are readily attained by use of the present catalysts even at elevated reactor temperatures. This result is highly desirable because the molecular weight of $\alpha$-olefin copolymers can be readily reduced by the use of hydrogen or similar chain transfer agent, however increasing the molecular weight of $\alpha$-olefin copolymers is usually only attainable by reducing the polymerization temperature of the reactor. Disadvantageously, operation of a polymerization reactor at reduced temperatures significantly increases the cost of operation since heat must be removed from the reactor to maintain the reduced reaction temperature, while at the same time heat must be added to the reactor effluent to vaporize the solvent. In addition, productivity is increased due to improved polymer solubility, decreased solution viscosity, and a higher polymer concentration. Utilizing the present catalysts, $\alpha$-olefin homopolymers and copolymers having densities from 0.85 g/cm$^3$ to 0.96 g/cm$^3$, and melt flow rates from 0.001 to 10.0 dg/min are readily attained in a high temperature process.

The catalyst systems of the present invention are particularly advantageous for the production of ethylene homopolymers and ethylene/$\alpha$-olefin copolymers having high levels of long chain branching. The use of the catalyst systems of the present invention in continuous polymerization processes, especially continuous, solution polymerization processes, allows for elevated reactor temperatures which favor the formation of vinyl terminated polymer chains that may be incorporated into a growing polymer, thereby giving a long chain branch. The use of the present catalysts system advantageously allows for the economical production of ethylene/$\alpha$-olefin copolymers having processability similar to high pressure, free radical produced low density polyethylene.

In another aspect of the processes of this invention, a preferred process is a high temperature solution polymerization process for the polymerization of olefins comprising contacting one or more $C_{2-20}$ $\alpha$-olefins under polymerization conditions with a catalyst system of this invention at a temperature from about 100° C. to about 250° C. More preferred as a temperature range for this process is a temperature from about 120° C. to about 200° C., and even more preferred is temperature from about 150° C. to about 200° C.

The present catalysts system may be advantageously employed to prepare olefin polymers having improved processing properties by polymerizing ethylene alone or ethylene/α-olefin mixtures with low levels of a "H" branch inducing diene, such as norbornadiene, 1,7-octadiene, or 1,9-decadiene. The unique combination of elevated reactor temperatures, high molecular weight (or low melt indices) at high reactor temperatures and high comonomer reactivity advantageously allows for the economical production of polymers having excellent physical properties and processability. Preferably such polymers comprise a $C_{3-20}$ (α-olefin, including ethylene, and a "H"-branching comonomer. Preferably, such polymers are produced in a solution process, most preferably a continuous solution process. Alternatively, such polymers may be produced in a gas phase process or a slurry process.

As previously mentioned, the present catalyst system is particularly useful in the preparation of EP and EPDM copolymers in high yield and productivity. The process employed may be either a solution or slurry process both of which are previously known in the art. Kaminsky, *J. Poly. Sci.*, Vol. 23, pp. 2151–64 (1985) reported the use of a soluble bis(cyclopentadienyl) zirconium dimethyl-alumoxane catalyst system for solution polymerization of EP and EPDM elastomers. U.S. Pat. No. 5,229,478 disclosed a slurry polymerization process utilizing similar bis (cyclopentadienyl) zirconium based catalyst systems.

In general terms, it is desirable to produce such EP and EPDM elastomers under conditions of increased reactivity of the diene monomer component. The reason for this was explained in the above-identified '478 patent in the following manner, which still remains true despite the advances attained in such reference. A major factor affecting production costs and hence the utility of an EPDM is the diene monomer cost. The diene is a more expensive monomer material than ethylene or propylene. Further, the reactivity of diene monomers with previously known metallocene catalysts is lower than that of ethylene and propylene. Consequently, to achieve the requisite degree of diene incorporation to produce an EPDM with an acceptably fast cure rate, it has been necessary to use a diene monomer concentration which, expressed as a percentage of the total concentration of monomers present, is in substantial excess compared to the percentage of diene desired to be incorporated into the final EPDM product. Since substantial amounts of unreacted diene monomer must be recovered from the polymerization reactor effluent for recycle the cost of production is increased unnecessarily.

Further adding to the cost of producing an EPDM is the fact that, generally, the exposure of an olefin polymerization catalyst to a diene, especially the high concentrations of diene monomer required to produce the requisite level of diene incorporation in the final EPDM product, often reduces the rate or activity at which the catalyst will cause polymerization of ethylene and propylene monomers to proceed. Correspondingly, lower throughputs and longer reaction times have been required, compared to the production of an ethylene-propylene copolymer elastomer or other α-olefin copolymer elastomer.

The present catalyst system advantageously allows for increased diene reactivity thereby preparing EPDM polymers in high yield and productivity. Additionally, the catalyst system of the present invention achieves the economical production of EPDM polymers with diene contents of up to 20 weight percent or higher, which polymers possess highly desirable fast cure rates.

The nonconjugated diene monomer can be a straight chain, branched chain or cyclic hydrocarbon diene having from about 6 to about 15 carbon atoms. Examples of suitable nonconjugated dienes are straight chain acyclic dienes such as 1,4-hexadiene and 1,6-octadiene; branched chain acyclic dienes such as 5-methyl-1,4-hexadiene, 3,7-dimethyl-1,6-octadiene; 3,7-dimethyl-1,7-octadiene and mixed isomers of dihydromyricene and dihydroocinene; single ring alicyclic dienes such as 1,3-cyclopentadiene; 1,4-cyclohexadiene; 1,5-cyclooctadiene and 1,5-cyclododecadiene: and multi-ring alicyclic fused and bridged ring dienes such as tetrahydroindene, methyl tetrahydroindene, dicyclopentadiene; bicyclo-(2,2,1)-hepta-2, 5-diene; alkenyl, alkylidene, cycloalkenyl and cycloalkylidene norbornenes such as 5-methylene-2-norbornene (MNB); 5-propenyl-2-norbornene, 5-isopropylidene-2-norbornene, 5-(4-cyclopentenyl)-2-norbornene, 5-cyclohexylidene-2-norbornene, 5-vinyl-2-norbornene and norbornadiene.

Of the dienes typically used to prepare EPDMs, the particularly preferred dienes are 1,4-hexadiene (HD), 5-ethylidene-2-norbornene (ENB), 5-vinylidene-2-norbornene (VNB), 5-methylene-2-norbornene (MNB), and dicyclopentadiene (DCPD). The especially preferred dienes are 5-ethylidene-2-norbornene (ENB) and 1,4-hexadiene (HD).

The preferred EPDM elastomers may contain about 20 up to about 90 weight percent ethylene, more preferably about 30 to 85 weight percent ethylene, most preferably about 35 to about 80 weight percent ethylene.

The alpha-olefins suitable for use in the preparation of elastomers with ethylene and dienes are preferably $C_{3-16}$ alpha-olefins. Illustrative nonlimiting examples of such alpha-olefins are propylene, 1-butene, 1-pentene, 1-hexene, 4-methyl-1-pentene, 1-heptene, 1-octene, 1-decene, and 1-dodecene. The alpha-olefin is generally incorporated into the EPDM polymer at about 10 to about 80 weight percent, more preferably at about 20 to about 65 weight percent. The nonconjugated dienes are generally incorporated into the EPDM at about 0.5 to about 20 weight percent, more, preferably at about 1 to about 15 weight percent, and most preferably at 3 to about 12 weight percent. If desired, more than one diene may be incorporated simultaneously, for example HD and ENB, with total diene incorporation within the limits specified above.

The catalyst system may be prepared as a homogeneous catalyst by addition of the requisite components to a solvent in which polymerization will be carried out by solution polymerization procedures. The catalyst system may also be prepared and employed as a heterogeneous catalyst by adsorbing the requisite components on a catalyst support material such as silica gel, alumina or other suitable inorganic support material. When prepared in heterogeneous or supported form, it is preferred to use silica as the support material. Inorganic support materials, such as, for example, silica, may be treated with aluminum alkyls or other chemical pacification agents to reduce surface hydroxyl content of the support. The heterogeneous form of the catalyst system may be employed in a gas phase or slurry polymerization. As a practical limitation, slurry polymerization takes place in liquid diluents under conditions in which the polymer product is substantially insoluble. Preferably, the diluent for slurry polymerization is one or more hydrocarbons with less than 5 carbon atoms. If desired, saturated hydrocarbons such as ethane, propane or butane may be used in whole or part as the diluent. Likewise the α-olefin monomer or a mixture of different α-olefin monomers may be used in whole or part as the diluent. Most preferably the diluent comprises in at least major part the α-olefin monomer or monomers to be polymerized.

The catalyst system of this invention may comprise an aluminum organometallic component which comprises an alumoxane, an aluminum alkyl or a combination thereof. This component may be present in a nonactivating amount and function primarily as a scavenger, or it may interact with the cocatalyst component to enhance the activity of the catalyst component, or it may do both.

It is understood with suitable functionality on the catalyst or cocatalyst of the catalyst system can be covalently or ionically attached to the support material of the support component, which comprises a support material which is a polymer, an inorganic oxide, a metal halide, or a mixture thereof.

Preferred supports for use in the present invention include highly porous silicas, aluminas, aluminosilicates, and mixtures thereof. The most preferred support material is silica. The support material may be in granular, agglomerated, pelletized, or any other physical form. Suitable materials include, but are not limited to, silicas available from Grace Davison (division of W.R. Grace & Co.) under the designations SD 3216.30, Davison Syloid 245, Davison 948 and Davison 952, and from Crossfield under the designation ES70, and from Degussa AG under the designation Aerosil 812; and aluminas available from Akzo Chemicals Inc. under the designation Ketzen Grade B.

Supports suitable for the present invention preferably have a surface area as determined by nitrogen porosimetry using the B.E.T. method from 10 to about 1000 m$^2$/g. and preferably from about 100 to 600 m$^2$/g. The pore volume of the support, as determined by nitrogen adsorption, advantageously is between 0.1 and 3 cm$^3$/g, preferably from about 0.2 to 2 cm$^3$/g. The average particle size depends upon the process employed, but typically is from 0.5 to 500 μm, preferably from 1 to 100 μm.

Both silica and alumina are known to inherently possess small quantities of hydroxyl functionality. When used as a support herein, these materials are preferably subjected to a heat treatment and/or chemical treatment to reduce the hydroxyl content thereof. Typical heat treatments are carried out at a temperature from 30° C. to 1000° C. (preferably 250° C. to 800° C. for 5 hours or greater) for a duration of 10 minutes to 50 hours in an inert atmosphere or under reduced pressure. Typical chemical treatments include contacting with Lewis acid alkylating agents such as trihydrocarbyl aluminum compounds, trihydrocarbylchlorosilane compounds, trihydrocarbyl alkoxysilane compounds or similar agents. Residual hydroxyl groups are then removed via chemical treatment.

The support may be functionalized with a silane or chlorosilane functionalizing agent to attach thereto pendant silane —(Si—R)=, or chlorosilane —(Si—Cl)= functionality, wherein R is a C$_{1-10}$ hydrocarbyl group. Suitable functionalizing agents are compounds that react with surface hydroxyl groups of the support or react with the silicon or aluminum of the matrix. Examples of suitable functionalizing agents include phenylsilane, hexamethyldisilazane diphenylsilane, methylphenylsilane, dimethylsilane, dimethylsilane, dichlorosilane, and dichlorodimethylsilane. Techniques for forming such functionalized silica or alumina compounds were previously disclosed in U.S. Pat. Nos. 3,687,920 and 3,879,368, the teachings of which are herein incorporated by reference.

The support may also be treated with an aluminum component selected from an alumoxane or an aluminum compound of the formula AlR$^1_x$'R$^2$y', wherein R$^1$ independently each occurrence is hydride or R, R$^2$ is hydride, R or OR, x' is 2 or 3, y' is 0 or 1 and the sum of x' and y' is 3. Examples of suitable R$^1$ and R$^2$ groups include methyl, methoxy, ethyl, ethoxy, propyl (all isomers), propoxy (all isomers), butyl (all isomers), butoxy (all isomers), phenyl, phenoxy, benzyl, and benzyloxy. Preferably, the aluminum component is selected from the group consisting of aluminoxanes and tri(C$_{1-4}$ hydrocarbyl)aluminum compounds. Most preferred aluminum components are aluminoxanes, trimethylaluminum, triethyl aluminum, tri-isobutyl aluminum, and mixtures thereof.

Alumoxanes (also referred to as aluminoxanes) are oligomeric or polymeric aluminum oxy compounds containing chains of alternating aluminum and oxygen atoms, whereby the aluminum carries a substituent, preferably an alkyl group. The structure of alumoxane is believed to be represented by the following general formulae (—Al(R)—O)$_{m'}$, for a cyclic alumoxane, and R$_2$Al—O(—Al(R)—O)$_{m'}$—AlR$_2$, for a linear compound, wherein R is as previously defined, and m' is an integer ranging from 1 to about 50, preferably at least about 4. Alumoxanes are typically the reaction products of water and an aluminum alkyl, which in addition to an alkyl group may contain halide or alkoxide groups. Reacting several different aluminum alkyl compounds, such as for example trimethyl aluminum and tri-isobutyl aluminum, with water yields so-called modified or mixed alumoxanes. Preferred alumoxanes are methylalumoxane and methylalumoxane modified with minor amounts of C$_{2-4}$ alkyl groups, especially isobutyl. Alumoxanes generally contain minor to substantial amounts of starting aluminum alkyl compound.

Particular techniques for the preparation of alumoxane type compounds by contacting an aluminum alkyl compound with an inorganic salt containing water of crystallization are disclosed in U.S. Pat. No. 4,542,119. In a particular preferred embodiment an aluminum alkyl compound is contacted with a regeneratable water-containing substance such as hydrated alumina, silica or other substance. This is disclosed in EP-A-338,044. Thus the alumoxane may be incorporated into the support by reaction of a hydrated alumina or silica material, which has optionally been functionalized with silane, siloxane, hydrocarbyloxysilane, or chlorosilane groups, with a tri(C$_{1-10}$ alkyl)aluminum compound according to known techniques. For the teachings contained therein the foregoing patents and publications, or there corresponding equivalent United States applications, are hereby incorporated by reference.

The treatment of the support material in order to also include optional alumoxane or trialkylaluminum loadings involves contacting the same before, after or simultaneously with addition of the complex or activated catalyst hereunder with the alumoxane or trialkylaluminum compound, especially triethylaluminum or triisobutylaluminum. Optionally the mixture can also be heated under an inert atmosphere for a period and at a temperature sufficient to fix the alumoxane, trialkylaluminum compound, complex or catalyst system to the support. Optionally, the treated support component containing alumoxane or the trialkylaluminum compound may be subjected to one or more wash steps to remove alumoxane or trialkylaluminum not fixed to the support.

Besides contacting the support with alumoxane the alumoxane may be generated in situ by contacting an unhydrolyzed silica or alumina or a moistened silica or alumina with a trialkyl aluminum compound optionally in the presence of an inert diluent. Such a process is well known in the art, having been disclosed in EP-A-250,600; U.S. Pat. Nos. 4,912,075; and 5,008,228; the teachings of which, or of the corresponding U.S. application, are hereby incorporated by reference. Suitable aliphatic hydrocarbon diluents include pentane, isopentane, hexane, heptane, octane, isooctane, nonane, isononane, decane, cyclohexane, methylcyclohexane and combinations of two or more of such diluents. Suitable aromatic hydrocarbon diluents are benzene, toluene, xylene, and other alkyl or halogen substituted aromatic compounds. Most preferably, the diluent is an aromatic hydrocarbon, especially toluene. After preparation in the foregoing manner the residual hydroxyl content thereof is desirably reduced to a level less than 1.0 meq of OH per gram of support by any of the previously disclosed techniques.

The cocatalysts of the invention may also be used in combination with a tri(hydrocarbyl)aluminum compound having from 1 to 10 carbons in each hydrocarbyl group, an oligomeric or polymeric alumoxane compound, a di(hydrocarbyl)(hydrocarbyloxy)aluminum compound having from 1 to 10 carbons in each hydrocarbyl or hydrocarbyloxy group, or a mixture of the foregoing compounds, if desired. These aluminum compounds are usefully employed for their beneficial ability to scavenge impurities such as oxygen, water, and aldehydes from the polymerization mixture. Preferred aluminum compounds include $C_{2-6}$ trialkyl aluminum compounds, especially those wherein the alkyl groups are ethyl, propyl, isopropyl, n-butyl, isobutyl, pentyl, neopentyl, or isopentyl, and methylalumoxane, modified methylalumoxane and diisobutylalumoxane. The molar ratio of aluminum compound to metal complex is preferably from 1:10,000 to 1000:1, more preferably from 1:5000 to 100: 1, most preferably from 1:100 to 100:1.

In contrast, solution polymerization takes place under conditions in which the diluent acts as a solvent for the respective components of the reaction, particularly the EP or EPDM polymer. Preferred solvents include mineral oils and the various hydrocarbons which are liquid at reaction temperatures. Illustrative examples of useful solvents include alkanes such as pentane, isopentane, hexane, heptane, octane and nonane, as well as mixtures of alkanes including kerosene and Isopar E™, available from Exxon Chemicals Inc.; cycloalkanes such as cyclopentane and cyclohexane; and aromatics such as benzene, toluene, xylenes, ethylbenzene and diethylbenzene.

At all times, the individual ingredients as well as the recovered catalyst components must be protected from oxygen and moisture. Therefore, the catalyst components and catalysts must be prepared and recovered in an oxygen and moisture free atmosphere. Preferably, therefore, the reactions are performed in the presence of a dry, inert gas such as, for example, nitrogen.

Ethylene is added to the reaction vessel in an amount to maintain a differential pressure in excess of the combined vapor pressure of the α-olefin and diene monomers. The ethylene content of the polymer is determined by the ratio of ethylene differential pressure to the total reactor pressure. Generally the polymerization process is carried out with a differential pressure of ethylene of from about 10 to about 1000 psi (70 to 7000 kPa), most preferably from about 40 to about 400 psi (30 to 300 kPa). The polymerization is generally conducted at a temperature of from 25 to 200° C., preferably from 75 to 170° C., and most preferably from greater than 95 to 140° C.

The polymerization may be carried out as a batchwise or a continuous polymerization process. A continuous process is preferred, in which event catalyst, ethylene, α-olefin, and optionally solvent and diene are continuously supplied to the reaction zone and polymer product continuously removed therefrom. Within the scope of the terms "continuous" and "continuously" as used in this context are those processes in which there are intermittent additions of reactants and removal of products at small regular intervals, so that, over time, the overall process is continuous.

Without limiting in any way the scope of the invention, one means for carrying out such a polymerization process is as follows: In a stirred-tank reactor propylene monomer is introduced continuously together with solvent, diene monomer and ethylene monomer. The reactor contains a liquid phase composed substantially of ethylene, propylene and diene monomers together with any solvent or additional diluent. If desired, a small amount of a "H"-branch inducing diene such as norbornadiene, 1,7-octadiene or 1,9-decadiene may also be added. Catalyst and cocatalyst are continuously introduced in the reactor liquid phase. The reactor temperature and pressure may be controlled by adjusting the solvent/monomer ratio, the catalyst addition rate, as well as by cooling or heating coils, jackets or both. The polymerization rate is controlled by the rate of catalyst addition. The ethylene content of the polymer product is determined by the ratio of ethylene to propylene in the reactor, which is controlled by manipulating the respective feed rates of these components to the reactor. The polymer product molecular weight is controlled, optionally, by controlling other polymerization variables such as the temperature, monomer concentration, or by a stream of hydrogen introduced to the reactor, as is well known in the art. The reactor effluent is contacted with a catalyst kill agent such as water. The polymer solution is optionally heated, and the polymer product is recovered by flashing off gaseous ethylene and propylene as well as residual solvent or diluent at reduced pressure, and, if necessary, conducting further devolatilization in equipment such as a devolatilizing extruder. In a continuous process the mean residence time of the catalyst and polymer in the reactor generally is from about 5 minutes to 8 hours, and preferably from 10 minutes to 6 hours.

In a preferred manner of operation, the polymerization is conducted in a continuous solution polymerization system comprising two reactors connected in series or parallel. In one reactor a relatively high molecular weight product (Mw from 300,000 to 600,000, more preferably 400,000 to 500,000) is formed while in the second reactor a product of a relatively low molecular weight (Mw 50,000 to 300,000) is formed. The final product is a blend of the two reactor effluents which are combined prior to devolatilization to result in a uniform blend of the two polymer products. Such a dual reactor process allows for the preparation of products having improved properties. In a preferred embodiment the reactors are connected in series, that is effluent from the first reactor is charged to the second reactor and fresh monomer, solvent and hydrogen is added to the second reactor. Reactor conditions are adjusted such that the weight ratio of polymer produced in the first reactor to that produced in the second reactor is from 20:80 to 80:20. In addition the temperature of the second reactor is controlled to produce the lower molecular weight product. This system beneficially allow for production of EPDM products having a large range of Mooney viscosities as well as excellent strength and processability. Preferably the Mooney viscosity (ASTM D1646-94, ML1+4 @ 125° C.) of the resulting product is adjusted to fall in the range from 1 to 200, preferably from 5 to 150 and most preferably from 10 to 110.

The process of the present invention can be employed to advantage in the gas phase copolymerization of olefins. Gas phase processes for the polymerization of olefins, especially the homopolymerization and copolymerization of ethylene and propylene, and the copolymerization of ethylene with higher α-olefins such as, for example, 1-butene, 1-hexene, 4-methyl-1-pentene are well known in the art. Such processes are used commercially on a large scale for the manufacture of high density polyethylene (HDPE), medium density polyethylene (MDPE), linear low density polyethylene (LLDPE) and polypropylene.

The gas phase process employed can be, for example, of the type which employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported or suspended above a perforated plate, the fluidization grid, by a flow of fluidization gas.

The gas employed to fluidize the bed comprises the monomer or monomers to be polymerized, and also serves as a heat exchange medium to remove the heat of reaction from the bed. The hot gases emerge from the top of the reactor, normally via a tranquilization zone, also known as a velocity reduction zone, having a wider diameter than the fluidized bed and wherein fine particles entrained in the gas stream have an opportunity to gravitate back into the bed. It can also be advantageous to use a cyclone to remove ultra-fine particles from the hot gas stream. The gas is then normally recycled to the bed by means of a blower or compressor and one or more heat exchangers to strip the gas of the heat of polymerization.

A preferred method of cooling of the bed, in addition to the cooling provided by the cooled recycle gas, is to feed a volatile liquid to the bed to provide an evaporative cooling effect, often referred to as operation in the condensing mode. The volatile liquid employed in this case can be, for example, a volatile inert liquid, for example a saturated hydrocarbon having about 3 to about 8, preferably 4 to 6, carbon atoms. In the case that the monomer or comonomer itself is a volatile liquid, or can be condensed to provide such a liquid, this can suitably be fed to the bed to provide an evaporative cooling effect. Examples of olefin monomers which can be employed in this manner are olefins containing about three to about eight, preferably three to six carbon atoms. The volatile liquid evaporates in the hot fluidized bed to form gas which mixes with the fluidizing gas. If the volatile liquid is a monomer or comonomer, it will undergo some polymerization in the bed. The evaporated liquid then emerges from the reactor as part of the hot recycle gas, and enters the compression/heat exchange part of the recycle loop. The recycle gas is cooled in the heat exchanger and, if the temperature to which the gas is cooled is below the dew point, liquid will precipitate from the gas. This liquid is desirably recycled continuously to the fluidized bed. It is possible to recycle the precipitated liquid to the bed as liquid droplets carried in the recycle gas stream. This type of process is described, for example in EP 89691; U.S. Pat. No. 4,543,399; WO 94/25495 and U.S. Pat. No. 5,352,749, which are hereby incorporated by reference. A particularly preferred method of recycling the liquid to the bed is to separate the liquid from the recycle gas stream and to reinject this liquid directly into the bed, preferably using a method which generates fine droplets of the liquid within the bed. This type of process is described in BP Chemicals' WO 94/28032, which is hereby incorporated by reference.

The polymerization reaction occurring in the gas fluidized bed is catalyzed by the continuous or semi-continuous addition of catalyst. Such catalyst can be supported on an inorganic or organic support material as described above. The catalyst can also be subjected to a prepolymerization step, for example, by polymerizing a small quantity of olefin monomer in a liquid inert diluent, to provide a catalyst composite comprising catalyst particles embedded in olefin polymer particles.

The polymer is produced directly in the fluidized bed by catalyzed copolymerization of the monomer and one or more comonomers on the fluidized particles of catalyst, supported catalyst or prepolymer within the bed. Start-up of the polymerization reaction is achieved using a bed of preformed polymer particles, which are preferably similar to the target polyolefin, and conditioning the bed by drying with inert gas or nitrogen prior to introducing the catalyst, the monomers and any other gases which it is desired to have in the recycle gas stream, such as a diluent gas, hydrogen chain transfer agent, or an inert condensable gas when operating in gas phase condensing mode. The produced polymer is discharged continuously or discontinuously from the fluidized bed as desired.

The gas phase processes suitable for the practice of this invention are preferably continuous processes which provide for the continuous supply of reactants to the reaction zone of the reactor and the removal of products from the reaction zone of the reactor, thereby providing a steady-state environment on the macro scale in the reaction zone of the reactor.

Typically, the fluidized bed of the gas phase process is operated at temperatures greater than 50° C., preferably from about 60° C. to about 100° C., more preferably from about 70° C. to about 110° C.

Typically the molar ratio of comonomer to monomer used in the polymerization depends upon the desired density for the composition being produced and is about 0.5 or less. Desirably, when producing materials with a density range of from about 0.91 to about 0.93 the comonomer to monomer ratio is less than 0.2, preferably less than 0.05, even more preferably less than 0.02, and may even be less than 0.01. Typically, the ratio of hydrogen to monomer is less than about 0.5, preferably less than 0.2, more preferably less than 0.05, even more preferably less than 0.02 and may even be less than 0.01.

The above-described ranges of process variables are appropriate for the gas phase process of this invention and may be suitable for other processes adaptable to the practice of this invention.

A number of patents and patent applications describe gas phase processes which are adaptable for use in the process of this invention, particularly, U.S. Pat. Nos. 4,588,790; 4,543,399; 5,352,749; 5,436,304; 5,405,922; 5,462,999; 5,461,123; 5,453,471; 5,032,562; 5,028,670; 5,473,028; 5,106,804; and EP applications 659,773; 692,500; and PCT Applications WO 94/29032, WO 94/25497, WO 94/25495, WO 94/28032; WO 95/13305; WO 94/26793; and WO 95/07942 all of which are hereby incorporated herein by reference.

The catalysts, whether or not supported in any of the foregoing methods, may be used to polymerize ethylenically and/or acetylenically unsaturated monomers having from 2 to 100,000 carbon atoms either alone or in combination. Preferred monomers include the $C_{2-20}$ α-olefins especially ethylene, propylene, isobutylene, 1-butene, 1-pentene, 1-hexene, 3-methyl-1-pentene, 4-methyl-1-pentene, 1-octene, 1-decene, long chain macromolecular α-olefins, and mixtures thereof. Other preferred monomers include styrene, $C_{1-4}$ alkyl substituted styrene, tetrafluoroethylene, vinylbenzocyclobutane, ethylidenenorbornene, 1,4-hexadiene, 1,7-octadiene, vinylcyclohexane, 4-vinylcyclohexene, divinylbenzene, and mixtures thereof with ethylene. Long chain macromolecular α-olefins are vinyl terminated polymeric remnants formed in situ during continuous solution polymerization reactions. Under suitable processing conditions such long chain macromolecular units are readily polymerized into the polymer product along with ethylene and other short chain olefin monomers to give small quantities of long chain branching in the resulting polymer.

The catalysts may also be utilized in combination with at least one additional homogeneous or heterogeneous polymerization catalyst in the same or in separate reactors connected in series or in parallel to prepare polymer blends having desirable properties. An example of such a process is disclosed in WO 94/00500, equivalent to U.S. Ser. No. 07/904,770, as well as U.S. Ser. No. 08/10958, filed Jan. 29, 1993, the teachings or which are hereby incorporated by reference herein.

The highly preferred complexes of this invention have a nitrogen heteroatom bond to the 3-position of the cyclopentadienyl group. When used in an olefin polymerization catalyst system with tris(pentafluorophenyl)boron as the activating cocatalyst, an unusual blue color is observed. This can be due to the formation of a radical cation in which the titanium is in a formal oxidation state of (III), which may exist in a diamagnetic or paramagnetic form as shown below.

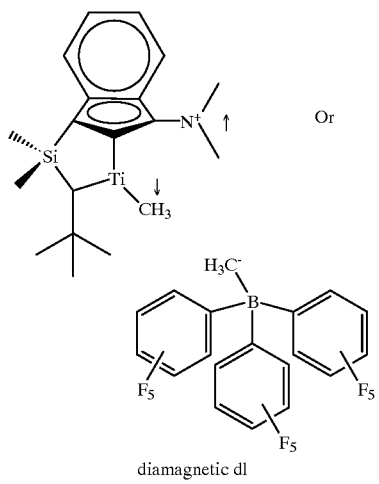

diamagnetic d1

Or

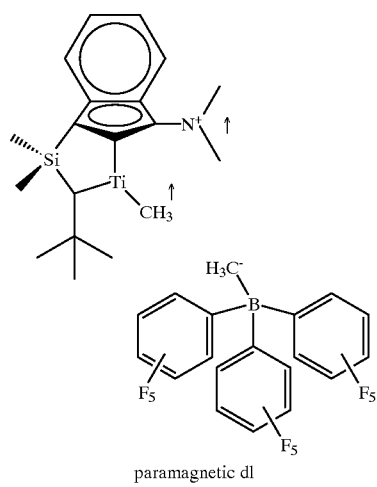

paramagnetic d1

While reserving our right not to be bound by any particular theory of the mechanism by which an olefin polymerization catalyst system comprising this complex would operate, polymerization could occur wherein the aforementioned Ti(III) radical cation is an active participant.

For the preferred polyolefin polymer compositions of this invention, which may be produced by the polymerization processes of this invention using the catalyst systems of this invention, the long chain branch is longer than the short chain branch that results from the incorporation of one or more α-olefin comonomers into the polymer backbone. The empirical effect of the presence of long chain branching in the copolymers of this invention is manifested as enhanced rheological properties which are indicated by higher flow activation energies, and greater $I_{21}/I_2$ than expected from the other structural properties of the compositions.

Further, highly preferred polyolefin copolymer compositions of this invention have reverse molecular architecture, that is, there is a molecular weight maximum which occurs in that 50 percent by weight of the composition which has the highest weight percent comonomer content. Even more preferred are polyolefin copolymer compositions which also have long chain branches along the polymer backbone, especially when produced with a catalyst system of this invention having a single metallocene complex of this invention in a single reactor in a process for the polymerization of an a-olefin monomer with one or more olefin comonomers, more especially when the process is a continuous process Measurement of Comonomer Content vs Log Molecular Weight by GPC/FTIR The comonomer content as a function of molecular weight was measured by coupling a Fourier transform infrared spectrometer (FTIR) to a Waters 150° C. Gel Permeation Chromatograph (GPC). The setting up, calibration and operation of this system together with the method for data treatment has been described previously (L. J. Rose et al, "Characterisation of Polyethylene Copolymers by Coupled GPC/FTIR" in "Characterisation of Copolymers", Rapra Technology, Shawbury UK, 1995, ISBN 1-85957-048-86.) In order to characterize the degree to which the comonomer is concentrated in the high molecular weight part of the polymer, the GPC/FTIR was used to calculate a parameter named comonomer partition factor, $C_{pf}$. $M_n$ and $M_w$ were also determined using standard techniques from the GPC data.

Comonomer Partitioning Factor (GPC-FTIR)

The comonomer partitioning factor $C_{pf}$ is calculated from GPC/FTIR data. It characterizes the ratio of the average comonomer content of the higher molecular weight fractions to the average comonomer content of the lower molecular weight fractions. Higher and lower molecular weight are defined as being above or below the median molecular weight respectively, that is, the molecular weight distribution is divided into two parts of equal weight. $C_{pf}$ is calculated from the following equation:

$$C_{pf} = \frac{\frac{\sum_{i=1}^{n} w_i \cdot c_i}{\sum_{i=1}^{n} w_i}}{\frac{\sum_{j=1}^{m} w_j \cdot c_j}{\sum_{j=1}^{m} w_j}},$$

where: $c_i$ is the mole fraction comonomer content and $w_i$ is the normalized weight fraction as determined by GPC/FTIR for the n FTIR data points above the median molecular weight, $c_j$ is the mole fraction comonomer content and $w_j$ is the normalized weight fraction as determined by GPC/FTIR for the m FTIR data points below the median molecular weight. Only those weight fractions, $w_i$ or $w_j$ which have associated mole fraction comonomer content values are used to calculate $C_{pf}$. For a valid calculation, it is required that n and m are greater than or equal to 3. FTIR data corresponding to molecular weight fractions below 5,000 are not included in the calculation due to the uncertainties present in such data.

For the polyolefin copolymer compositions of this invention, $C_{pf}$ desirably is equal to or greater than 1.10, more desirably is equal to or greater than 1.15, even more desirably is equal to or greater than 1.20, preferably is equal to or greater than 1.30, more preferably is equal to or greater than 1.40. even more preferably is equal to or greater than 1.50, and still more preferably is equal to or greater than 1.60.

ATREF-DV

ATREF-DV has been described in U.S. Pat. No. 4,798,081, which is hereby incorporated by reference, and in "Determination of Short-Chain Branching Distributions of Ethylene copolymers by Automated Analytical Temperature Rising Elution Fractionation" (Auto-ATREF), *J. of Appl Pol Sci*: Applied Polymer Symposium 45, 25–37 (1990). ATREF-DV is a dual detector analytical system that is capable of fractionating semi-crystalline polymers like Linear Low Density Polyethylene (LLDPE) as a function of crystallization temperature while simultaneously estimating the molecular weight of the fractions. With regard to the fractionation, ATREF-DV is analogous to Temperature Rising Elution Fractionation (TREF) analysis that have been published in the open literature over the past 15 years. The primary difference is that this Analytical-TREF (ATREF) technique is done on a small scale and fractions are not actually isolated. Instead, a typical liquid chromatographic (LC) mass detector, such as an infrared single frequency detector, is used to quantify the crystallinity distribution as a function of elution temperature. This distribution can then be transformed to any number of alternative domains such as short branching frequency, comonomer distribution, or possibly density. Thus, this transformed distribution can then be interpreted according to some structural variable like comonomer content, although routine use of ATREF for comparisons of various LLDPE's is often done directly in the elution temperature domain.

To obtain ATREF-DV data, a commercially available viscometer especially adapted for LC analysis, such as a Viskotek™ is coupled with the IR mass detector. Together these two LC detectors can be used to calculate the intrinsic viscosity of the ATREF-DV eluant. The viscosity average molecular weight of a given fraction can then be estimated using appropriate Mark Houwink constants, the corresponding intrinsic viscosity, and suitable coefficients to estimate the fractions concentration (dl/g) as it passes through the detectors. Thus, a typical ATREF-DV report will provide the weight fraction polymer and viscosity average molecular weight as a function of elution temperature. $M_{pf}$ is then calculated using the equation given.

Molecular Weight Partitioning Factor

The molecular weight partitioning factor $M_{pf}$ is calculated from TREF/DV data. It characterizes the ratio of the average molecular weight of the fractions with high comonomer content to the average molecular weight of the fractions with low comonomer content. Higher and lower comonomer content are defined as being below or above the median elution temperature of the TREF concentration plot respectively, that is, the TREF data is divided into two parts of equal weight. $M_{pf}$ is calculated from the following equation:

$$M_{pf} = \frac{\frac{\sum_{i=1}^{n} w_i \cdot M_i}{\sum_{i=1}^{n} w_i}}{\frac{\sum_{j=1}^{m} w_j \cdot M_j}{\sum_{j=1}^{m} w_j}},$$

where: $M_i$ is the viscosity average molecular weight and $w_i$ is the normalized weight fraction as determined by ATREF-DV for the n data points in the fractions below the median elution temperature. $M_j$ is the viscosity average molecular weight and $w_j$ is the normalized weight fraction as determined by ATREF-DV for the m data points in the fractions above the median elution temperature. Only those weight fractions, $w_i$ or $w_j$ which have associated viscosity average molecular weights greater than zero are used to calculate $M_{pf}$. For a valid calculation, it is required that n and m are greater than or equal to 3.

For the polyolefin copolymer compositions of this invention, $M_{pf}$ desirably is equal to or greater than 1.15, more desirably is equal to or greater than 1.30, even more desirably is equal to or greater than 1.40, preferably is equal to or greater than 1.50, more preferably is equal to or greater than 1.60. even more preferably is equal to or greater than 1.70.

EXAMPLES

The skilled artisan will appreciate that the invention disclosed herein may be practiced in the absence of any component which has not been specifically disclosed. The following examples are provided as further illustration of the invention and are not to be construed as limiting. Unless stated to the contrary all parts and percentages are expressed on a weight basis.

$^1$H and $^{13}$C NMR spectra were recorded on a Varian XL (300 MHz) spectrometer. Chemical shifts were determined relative to TMS or through the residual CHCl$_3$ in CDCl$_3$ or the residual C$_6$HD$_5$ in C$_6$D$_6$, relative to TMS. Tetrahydrofuran (THF), diethylether, toluene, and hexane were used following passage through double columns charged with activated alumina and alumina supported mixed metal oxide catalyst (Q-5® catalyst, available from Engelhard Corp.). The compounds n-BuLi, Grignard reagents were all used as purchased from Aldrich Chemical Company. All syntheses were performed under dry nitrogen atmosphere using a combination of glove box and high vacuum techniques.

Example A

Preparation of Lithium 1-N-pyrrolidineindenide

In a 150 ml of hexane 3.5 g of 1-N-pyrrolidineindene (can be made via the route of Noland, et al., JOC, 1981, 46, 1940) (18.8 mmol) was added. To this solution 9.5 ml of nBuLi (2.0 M) was added dropwise over a 20 minute period. The solution was stirred 24 hours with deposition of a light yellow solid. The solid was collected by filtration, washed with hexane, dried in vacuo to give 3.61 g (100 percent yield) of product.

Preparation of (N-t-Butylamino)(dimethyl)1-N-pyrrolidineindenyl) silane

In the drybox in a round flask 100 ml of THF was stirred with 2.16 g of ClSiMe$_2$NHCMe$_3$ (17.3 mmol). To this solution a 50 ml THF solution containing 3.30 g (34.9 mmol) of lithium-1-N-pyrrolidineindenide was added dropwise. The solution was then stirred overnight. The solvent was then removed under reduced pressure, the residue extracted with hexane, filtered, and the solvent again removed under reduced pressure to give 5.13 g of product (95 percent yield).

Preparation of Dilithium (N-t-Butylamino)(dimethyl)(1-N-pyrrolidineindenide)silane In the drybox 5.13 g (16.3 mmol) of (N-t-Butylamino)(dimethyl)(1-N-pyrrolidineindenyl)silane was combined with 100 ml of hexane. To this solution 16.3 ml (32.6 mmol) of nBuLi (2.0 M) was added dropwise. Upon complete addition of the n-BuLi the solution was stirred overnight. The resulting precipitate was collected via filtration, washed with hexane to give 5.32 g (100 percent yield) of a yellow solid.

Preparation of [(N-t-Butylamino)(dimethyl)(1-N-pyrrolidineindenyl)silane]Titanium Dichloride In the drybox 6.05 g (16.3 mmol) of TiCl$_3$(THF)$_3$ was dissolved in 75 ml of THF. To this solution 5.32 g (1.63 mmol) of dilithium (N-t-Butylamino)(dimethyl)(1-N-pyrrolidineindenyl)silane) was added as a solid while stirring. The solution was then stirred for 45 minutes. After this time period. 2.27 D of PbCl$_2$ (8.2 mmol) was added and the solution stirred for 45 minutes. The THF was then removed under reduced pressure. The residue was then extracted with toluene, the solution filtered, and the toluene removed under reduced pressure. The residue was then triturated with hexane and the solution cooled to −20° C. for 3 hours. The blue precipitate was collected via filtration and washed with cold hexane. The solid product was dried under vacuum to yield 5.08 g (72 percent yield) of product.

Preparation of [(N-t-Butylamino)(dimethyl)(1-N-pyrrolidineindenyl)silane)]Titanium Dimethyl In the drybox 0.65 g of (N-t-Butylamino)(dimethyl)(1-N-pyrrolidineindenyl)silane)]titanium dichloride (1.5 mmol) was suspended in 50 ml of Et$_2$O. To this suspension 1.05 ml of MeMgBr (3.0 M) was added dropwise while stirring over a 20 minute period. After the addition of MeMgI was completed, the solution was stirred for 40 minutes. Then the Et$_2$O was removed under reduced pressure and the residue extracted with hexane, the solution filtered, the filtrate evaporated to dryness under reduced pressure to give 0.47 g (80 percent yield) of product.

Polymerizations

A two-liter Parr reactor was charged with 740 g of Isopar-E™ mixed alkanes solvent (available from Exxon Chemicals Inc.) and 118 g of 1-octene comonomer. Hydrogen was added as a molecular weight control agent by differential pressure expansion from a 75 mL addition tank at 25 psi (2070 kPa). The reactor was heated to the polymerization temperature of 140° C. and saturated with ethylene at 500 psig (3.4 MPa). The appropriate amount of catalyst and cocatalyst as 0.005M solutions in toluene were premixed in the drybox. After the desired premix time, the solution was transferred to a catalyst addition tank and injected into the reactor. The polymerization conditions were maintained for 15 minutes with ethylene on demand. The resulting solution was removed from the reactor, and a hindered phenol antioxidant (Irganox™ 1010 from Ciba Geigy Corporation) was added to the resulting solution. Polymers formed were dried in a vacuum oven set at 120° C. for about 20 hours. Results are contained in Table 1.

TABLE

| Catalyst[a] | Cocatalyst[b] | Efficiency[c] | MI[d] |
|---|---|---|---|
| 1 | B(C$_6$F$_5$)$_3$ | 2.3 | 0.04 |
| 2 | B(C$_6$F$_5$)$_3$ | 1.2 | 1.2 | a Catalyst 1-[(N-t-Butylamino)(dimethyl)(1-N-pyrrolidineindenyl)silane)]Titanium Dimethyl;

Catalyst 2-[(N-t-Butylamino)(dimethyl)(tetramethylcyclopentadienyl) silane)]Titanium Dimethyl b Equimolar amounts of catalyst and cocatalyst were premixed together c grams polymer per gram Ti d melt index (dg/min)

General Experimental for Examples 1–79. All experiments involving organometallic compounds were carried out using drybox techniques. Solvents (THF, hexane, toleuene, ether) were purified by passing through alumina and Q5 columns. C$_6$D$_6$ was dried under Na/K alloy and vacuum distilled before use. NMR spectra were measured on a Varian XL-300 (FT 300 MHz, $^1$H; 75 MHz, $^{13}$C). $^1$H NMR and $^{13}C\{^1H\}$ NMR spectra are referenced to the residual solvent peaks and are reported in ppm relative to tetramethylsilane. All J values are given in Hz. Mass spectra (EI) were obtained on the AutoSpecQFDP. Indane, $NaBH_4$, MeMgI, n-BuLi, $Me_2SiCl_2$, NHz-t-Bu, 2-bromoisobutyryl bromide were purchased from Aldrich Chemical Co. All compounds were used as received. 3-methoxy-1H-indene (J.Am.Chem.Soc, 1984, 106, 6702), N-(1H-2-indenyl)-N,N-dimethylamine (Acta Chem Scand. 1973, 27, 4027), 1-(1H-2-indenyl)pyrrolidine (Acta Chem Scand. 1973, 27, 4027), tert-butyl(1H-2-indenyloxy)dimethylsilane (Organometallics. 1996. 15. 2450), were prepared by literature procedures.

Example 1

Preparation of 1,1',4,4'-Tetramethyl-2,3-dihydronapthalene. Benzene (500 mL) and 2,3-dimethyl-2,3-butanediol (50.00 g. 341.9 mmol) were cooled in an ice-bath as $AlCl_3$ (100.30 g, 752.24 mmol) was added slowly as a solid over a 30 minute period of time under a nitrogen flow such that the mixture never exceeded room temperature. The mixture was held at room temperature for 30 minutes and then heated to 50° C. for 1 hour. It is critical that this reaction is closely monitored by GC and is terminated as the reaction is completed. Minor changes in reaction conditions results in varying reaction times. After the reaction period the mixture decanted over crushed ice careful to leave behind a smaller and denser oily phase. The upper phase of the reaction mixture was then transferred to an extraction funnel and washed with 1 M HCl (1×200 mL), saturated $NaHCO_3$ (2×200 mL), and $H_2O$ (1×200 mL). The organic fraction was then dried over $MgSO_4$. The mixture was then filtered and the volatiles removed resulting in the isolation of the desired product as a clear colorless oil (53.10 g, 82.5 percent yield).

$^1H$ NMR $(CDCl_3)\delta1.31$ (s, 12 H), 1.71 (s, 4 H), 7.1–7.4 (m, 4 H).

$^{13}C$ NMR$(CDCl_3)\delta31.67$, 34.19, 35.09, 125.50, 126.45, 144.76.

GC-MS Calculated for $C_{14}H_{20}$ 188.16, found 188.10.

Preparation of 2,3,5,7-Tetrahydro-2,5,5,8,8-pentamethyl-1H-Benz(f)inden-1-one. 1,1',4,4'-Tetramethyl-2,3-dihydronapthalene (30.00 g, 159.3 mmol) and 2-bromoisobutyryl bromide (36.62 g, 159.3 mmol) were stirred in $CH_2Cl_2$ (500 mL) at 0° C. as $AlCl_3$ (48.86 g, 366.4 mmol) was added slowly as a solid under a nitrogen flow over a 30 minute period of time. This mixture was then allowed to stir at room temperature overnight. After the reaction period the mixture was poured onto crushed ice. The organic layer was then separated and washed with 1M HCl (1×200 mL). saturated $NaHCO_3$ (1×200 mL) and $H_2O$ (1'200 mL). The organic fraction was then dried over $MgSO_4$, filtered, and then the volatiles removed resulting in the isolation of a dark crystalline residue. Recrystallization from diethylether (0° C.) resulted in the isolation of the desired product as a white crystalline solid (30.70 g, 75.2 percent yield).

$^1H$ NMR $(CDCl_3)\delta1.2$–1.4 (m, 15H). 1.71 (s, 4 H), 2.6–2.7(m, 2H), 3.34 (dd, $^1J_{HH}$=17.6 Hz, $^3J_{HH}$=8.7 Hz, 1 H), 7.41 (s, 1H), 7.76 (s, 1H).

$^{13}C$ NMR $(CDCl_3)\delta16.50$, 31.98, 32.09, 32.14. 34.58, 34.84. 35.25, 42.30, 121.92, 124.18, 133.85, 144.77, 149.94. 152.94, 209.05.

GC-MS Calculated for $C_{18}H_{24}O$ 256.18, found 256.15.

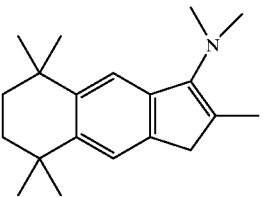

(1)

Preparation of 3-(dimethylamino)-5,6,7,8-tetrahydro-2,5,5,8,8-pentamethyl-1H-benz(f)indene, (1). $TiCl_4$ (6.6 g, 35.0 mmol) was added dropwise to a solution of anhydrous dimethylamine (12.8 g, 290 mmol) in 200 mL of hexane with stirring under nitrogen at −30 to −40° C. Large lumps of solid amide began to form during this process and 2,3,5,7-Tetrahydro-2,5,5,8,8-pentamethyl-1H-Benz(f) inden-1-one, (4.98 g. 19.6 mmol) was added. The reaction was allowed to equilibrate to 25° C. and then was heated to 55° C. with stirring for 10 minutes. Workup of an aliquot revealed no starting material by $^1H$ NMR analysis. The solution was cooled to 10° C. and acetone (approximately 500 mg dried over 4A sieves) was added dropwise to destroy soluble titanium amide complex. Upon addition of the final amount of acetone all color was discharged and $TiO_2$ was formed. The oxide was filtered through dry Celite and the solvent reduced in vacuo to afford product (3.3 g. 11.6 mmol) in 60 percent yield as a clear oil which crystallized on standing overnight: mp=74–75.5° C. from hexane as light yellow prisms.

$^1H$ NMR $(C_6D_6)\delta7.52$ (2, 1H), 7.31 (s, 1H), 3.03 (s, 2H), 2.83 (s, 6H), 1.97 (s, 3H), 1.67 (s, 4H), 1.35 (s, 6H), 1.33 (s, 6H).

$^{13}C\{^1H\}$ NMR $(C_6D_6)\delta142.0$, 142.7, 142.3, 140.3, 139.7, 126.4, 121.7, 117.2, 43.3, 41.4, 36.0, 34.7, 34.6, 32.7, 32.6. 14.6.

CGMS (EI, m/e, percent I) 283 (M+, 35), 268 (M−CH3. 100), 238 (10)

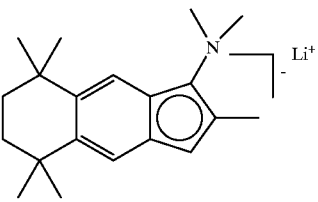

(2)

Preparation of (3-(dimethylamino)-5,6,7,8-tetrahydro-2,5,5,8,8-pentamethyl-1H-benz(f)indenyl)lithium, (2). 3-(dimethylamino)-5,6,7,8-tetrahydro-2,5,5,8,8-pentamethyl-1H-benz(f)indene (2.11 g, 7.46 mmol) was stirred in hexane (75 mL) as n-BuLi (4.10 mL of 2.0 M solution in hexane, 8.20 mmol) was added slowly. This mixture was allowed to stir overnight during which time a pale yellow precipitate formed. After the reaction period the desired product was collected via filtration, washed with hexane, and dried under vacuum resulting in the isolation of a pale yellow solid which was used without further purification or analysis (2.00 g, 93 percent yield).

(3)

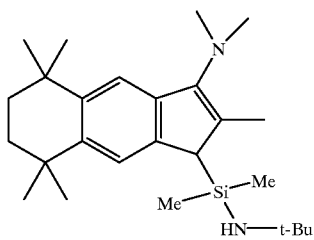

Preparation of 1-(3-(dimethylamino)-5,6,7,8-tetrahydro-2,5,6,7,8-pentamethyl-1H-benz(f)inden-1-yl)-N-(1,1-dimethylethyl)-1,1-dimethylsilanamine, (3). (3-(Dimethylamino)-5,6,7,8-tetrahydro-2,5,5,8,8-pentamethyl-1H-benz(f)indenyl)lithium (1.99 g, 6.87 mmol) in THF (30 mL) was added dropwise to a solution of N-(tert-butyl)-N-(1-chloro-1,1-dimethylsilyl)amine (1.71 g, 10.3 mmol) in THF (50 mL). This mixture was allowed to stir overnight. After the reaction period the volatiles were removed and the residue was extracted and filtered using hexane. Removal of the hexane resulted in the isolation of the desired product as an orange oil (2.793 g, 98 percent).

$^1$H NMR (C$_6$D$_6$)δ0.024 (s, 3H), 0.16 (s, 3H), 1.06 (s, 9H), 1.34 (s, 3H), 1.39 (s, 4H), 1.46 (s, 3H), 1.71 (s, 3H), 2.12 (s, 1H), 2.20 (s, 3H), 2.92 (s, 6H), 3.08 (s, 1H), 7.51 (s, 1H), 7.63 (s, 1H).

$^{13}$C NMR (C$_6$D$_6$)δ0.28, 1.47, 15.48, 32.57, 32.68, 32.75, 33.82, 34.50, 34.56, 35.89, 43.63, 47.57, 49.41, 116.99, 121.76, 132.70, 139.02, 140.98, 141.36, 146.14.

(4)

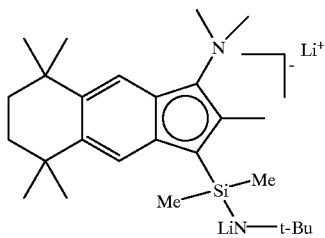

Preparation of (3-(dimethylamino)-1-(((1,1-dimethylethyl)amino)dimethylsilyl)-5,6,7,8-tetrahydro-2,5,6,7,8-pentamethyl-1H-benz(f)indenyl)lithium, lithium salt, (4). 1-(3-(Dimethylamino)-5,6,7,8-tetrahydro-2,5,6,7,8-pentamethyl-1H-benz(f)inden-1-yl)-N-(1,1-dimethylethyl)-1,1-dimethylsilanamine (2.79 g, 6.77 mmol) was stirred in hexane (75 mL) as n-BuLi (16.24 mmol, 6.50 mL of 2.5 M solution in hexane) was added slowly. This mixture was allowed to stir overnight during which time no precipitate formed. The solution was then placed in the freezer (-10° C.) for 4 days during which time pale yellow crystals formed. The solution was decanted away from the crystals which were then dried under vacuum and used without further purification or analysis (1.30 g, 45 percent yield).

(5)

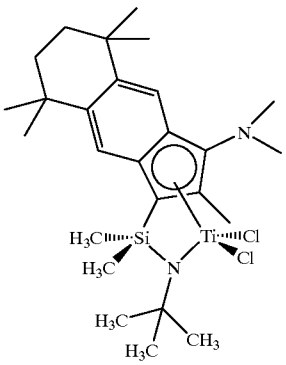

Preparation of dichloro(N-(1,1-dimethylethyl)-1,1-dimethyl-1-(3-(dimethylamino)-5,6,7,8-tetrahydro-2,5,5,8,8-pentamethyl-1H-benz(f)inden-1-yl)silanaminato(2-)-N) titanium, (5). (3-(Dimethylamino)-1-(((1,1-dimethylethyl)amino)dimethylsilyl)-5,6,7,8-tetrahydro-2,5,6,7,8-pentamethyl-1H-benz(f)indenyl)lithium, lithium salt (1.30 g, 2.08 mmol) in THF (30 mL) was added dropwise to a slurry of TiCl$_3$(THF)$_3$ ( 1.14 g, 3.08 mmol) in THF (50 mL). This mixture was allowed to stir for 1 hour. PbCl$_2$ (0.43 g. 1.54 mmol) was then added as a solid and the mixture was allowed to stir for an additional hour. After the reaction period the volatiles were removed and the residue was extracted and filtered using hexane. The hexane solution was concentrated and placed in the freezer (-10° C.) overnight during which time deep purple crystals formed. The solution was then decanted away and the crystals were dried under vacuum (1.23 g, 76 percent yield).

$^1$H NMR (C$_6$D$_6$)δ0.59 (s, 3H), 0.78 (s, 3H), 1.26 (s, 3H), 1.29 (s, 3H), 1.32 (s, 3H), 1.38 (s, 9H), 1.44 (s, 3H), 1.5–1.7 (m, 4H), 2.35 (s, 3H), 2.94 (s, 6H), 7.79 (s, 1H), 7.81 (s, 1H).

$^{13}$C NMR (C$_6$D$_6$)δ5.62, 6.34, 18.34, 32.18, 32.33, 32.59, 32.84, 33.42, 34.94, 35.09, 43.46, 60.83, 92.03, 122.50, 125.80. 131.70, 134.08, 146.10, 147.80, 150.14.

Example 2

(6)

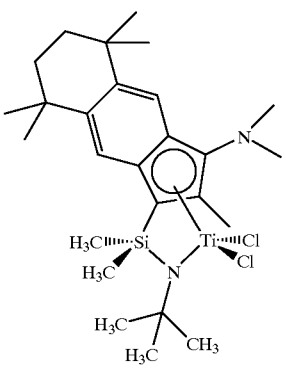

Preparation of ((3-(dimethylamino)-5,6,7,8-tetrahydro-2,5,5,8,8-pentamethyl-1H-benz(f)inden-1-yl)-N-(1,1-dimethylethyl)-1,1-dimethyl silanaminato(2-)-N) dimethyltitanium, (6). Dichloro(N-(1,1-dimethylethyl)-1,1-dimethyl-1-(3-(dimethylamino)-5,6,7,8-tetrahydro-2,5,5,8,8-pentamethyl-1H-benz(f)inden-1-yl)silanaminato(2-)-N) titanium (0.65 g, 1.23 mmol) was stirred in diethylether (50 mL) as MeMgBr (2.70 mmol, 0.90 mL of 3.0 M solution in diethylether) was added slowly. This mixture was then allowed to stir for 2 hours. After the reaction period the volatiles were removed and the residue was extracted and filtered using hexane. Removal of the hexane resulted in the isolation of the desired product as an orange microcrystalline solid (0.44 g, 74 percent yield).

$^1$H NMR (C$_6$D$_6$)δ−0.12 (s, 3H), 0.54 (s, 3H), 0.75 (s, 3H), 0.96 (s, 3H), 1.21 (s, 3H), 1.33 (s, 3H), 1.35 (s, 3H), 1.36 (s, 3H), 1.52 (s, 9H), 1.6–1.7 (m, 4H), 2.11 (s, 3H), 2.92 (s, 6H), 7.65 (s, 1H), 7.93 (s, 1H).

$^{13}$C NMR (C$_6$D$_6$)δ5.92, 6.85, 15.48, 32.58, 32.76, 33.79, 34.51, 34.77, 35.26, 35.45, 44.47, 53.09, 53.97, 57.86, 83.82, 121.46, 124.92, 126.42, 131.45, 133.30, 142.64, 143.25, 144.51.

Example 3

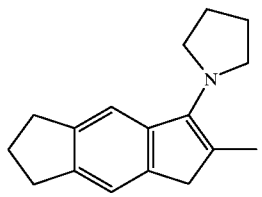

(7)

Preparation of 1-(3,5,6,7-tetrahydro-2-methyl-s-indacen-1-yl)pyrrolidine, (7). 1,2,3,5,6,7-Hexahydro-s-indacen-1-one (7.0 g) was treated with 25 g of pyrrolidine as in Example 1 in 100 mL of dry benzene, except that p-toluenesulfonic acid (15 mg) catalyst was added. GC analysis indicated that only 25 area percent conversion to enamine occurred after 17 hours; white 80 area percent conversion occurred after 64 hours. Distillation of lower boiling ketone afforded two fractions of enamine: ketone ratios (area percent GC) of 75:25 (3.1 g, bp=183–192° C. @ 1 mm) and 85:15 (2.3 g, bp=192–195° C. @ 1 mm). The viscous, dark pot residue was triturated with hexane to give upon solvent removal 650 mg of dark oil which assayed at 91 area percent enamine a&s determined by GC analysis. This material was provided for lithium salt formation:

$^1$H NMR (CDCl$_3$)δ7.26 (s, 1H), 7.18 (s, 1H), 3.45 (m, 4H), 3.21 (s, 2H), 2.91 (m, 4H), 2.15 (s, 3H, 2-Me), 2.05–2.17 (m, 2H), 1.95 (m, 4H).

$^{13}$C{$^1$H} NMR (CDCl$_3$)δ141.3, 140.4, 139.3, 123.2, 121.9, 121.4, 118.4, 118.1, 115.2, 50.9, 41.5, 33.2, 32.6, 26.0, 25.3; CGMS (EI, m/e, percent 1) 239 (M+, 30), 224 (M−CH$_3$, 100), 169 (27), 155 (55).

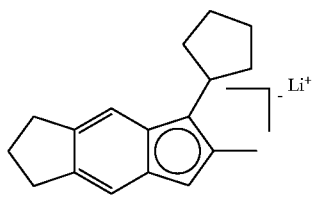

(8)

Preparation of 1,2,3,7-tetrahydro-6-methyl-5-(1-pyrrolidinyl-s-indacenyl)lithium, (8). 1-(3,5,6,7-Tetrahydro-2-methyl-s-indacen-1-yl)pyrrolidine (0.64 g, 2.93 mmol) was stirred in hexane (25 mL) as n-BuLi (3.00 mmol, 1.50 mL of 2.0 M solution in cyclohexane) was added slowly.

This mixture was allowed to stir overnight during which time a precipitate formed. After the reaction period the desired product was isolated as a tan solid following filtration and drying under vacuum and used without further purification or analysis (0.55 g, 84 percent yield).

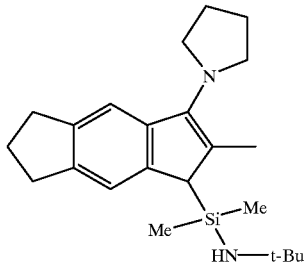

(9)

Preparation of N-(1,1-dimethylethyl)-1,1-dimethyl-1-(1,5,6,7-tetrahydro-2-methyl-3-(1-pyrrolidinyl)-s-indacen-1-yl)silanamine, (9). 1,2,3,7-Tetrahydro-6-methyl-5-(1-pyrrolidinyl-s-indacenyl)lithium (0.55 g. 2.46 mmol) in THF (25 mL) was added dropwise to a solution of N-(tert-butyl)-N-(1-chloro-1,1-dimethylsilyl)amine (1.02 g, 6.13 mmol) in THF (75 mL). This mixture was allowed to stir overnight. After the reaction period the volatiles were removed and the residue was extracted and filtered using hexane. Removal of the hexane resulted in the isolation of the desired product as a green oil (0.84 g, 99 percent).

$^1$H NMR (CDCl$_3$)δ−0.040 (s, 3H), 0.060 (s, 3H), 1.18 (s, 9H), 1.9–2.2 (m, 6H), 2.17 (s, 3H), 2.8–3.0 (m, 4H), 3.16 (s, 1H), 3.2–3.3 (m, 2H), 3.3–3.5 (m, 2H), 7.23 (s, 1H), 7.25 (s, 1H).

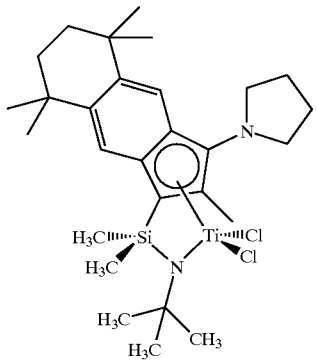

(10)

Preparation of dichloro(N-(1,1-dimethylethyl)-1,1-dimethyl-1-((1,2,3,3a.8a-η)-1,5,6,7-tetrahydro-2-methyl-3-(1-pyrrolidinyl)-s-indacen-1-yl)silanaminato(2-)-N) titanium, (10). N-(1,1-dimethylethyl)-1,1-dimethyl-1-(1,5,6,7-tetrahydro-2-methyl-3-(1-pyrrolidinyl)-s-indacen-1-yl) silanamine (0.84 g. 2.43 mmol) was stirred in hexane (50 mL) as n-BuLi (4.86 mmol, 2.43 mL of 2.0 M solution in cyclohexane) was added slowly. This mixture was allowed to stir overnight during which time little precipitate formed. The volatile, were removed resulting in the isolation of a dark residue. This residue was then dissolved in THF (30 mL) and added dropwise to a slurry of TiCl$_3$ (THF)$_3$ ( 0.90 g, 2.43 mmol) in THF (50 mL). This mixture was allowed to stir for 1 hour. PbCl$_2$ (0.37 g, 1.32 mmol) was then added as a solid and the mixture was allowed to stir for an additional 30 minutes. After the reaction period the volatiles were removed and the residue was extracted and filtered using toluene. Removal of the toluene resulted in the isolation of a black residue. This residue was then slurried in hexane and cooled to 0° C. overnight The mixture was then filtered resulting in the isolation of a black microcrystalline solid. This procedure of slurrying in hexane and then cooling before filtration was repeated and then the black compound was dried under vacuum (0.37 g, 33 percent yield).

$^1$H NMR (CDCl$_3$)δ–0.78 (s, 3H), 0.84 (s, 3H), 1.32 (s, 9H), 1.5–2.2 (m, 8H), 2.59 (s, 3H), 2.8–3.1 (m, 6H), 3.8–4.0 (m, 2H), 4.1–4.3 (m, 2H) 7.42 (s, 1H), 7.74 (s, 1H).

Example 4

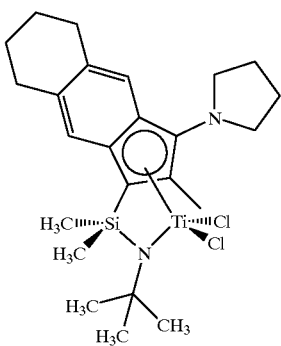
(11)

Preparation of (N-(1,1-dimethylethyl)-1,1-dimethyl-1-((1,2,3,3a,8a-η)-1,5,6,7-tetrahydro-2-methyl-3-(1-pyrrolidinyl)-s-indacen-1-yl)silanaminato(2-)-N) dimethyltitanium, (11). Dichloro(N-(1,1-dimethylethyl)-1,1-dimethyl-1-((1,2,3,3a,8a-η)-1,5,6,7-tetrahydro-2-methyl-3-(1-pyrrolidinyl)-s-indacen-1-yl)silanaminato(2-)-N) titanium(0.37 g, 0.76 mmol) was stirred in diethylether (50 mL) as MeMgBr (1.53 mmoles, 1.02 mL of 3.0 M solution in diethylether) was added slowly. This mixture was then allowed to stir for 1 hour. After the reaction period the volatiles were removed and the residue was extracted and filtered using hexane. Removal of the hexane resulted in the isolation of the desired product as a red solid (0.11 g, 33 percent yield).

$^1$H NMR (CDCl$_3$)δ0.038 (s, 3H), 0.59 (s, 3H), 0.74 (s, 3H), 0.94 (s, 3H), 1.54 (s, 9H), 1.5–1.8 (m, 8H), 2.21 (s, 3H), 2.6–2.9 (m, 6H), 3.2–3.2 (m, 2H), 3.7–3.8 (m, 2H), 7.53 (s, 1H), 7.68 (s, 1H).

Example 5

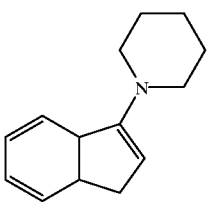
(12)

Preparation of 1-(1H-inden-3-yl)piperidine, (12). According to the general method for titanium catalyzed enamine formation of Example 7, dry piperidine (51.4 g, 600 mmol) was treated with TiCl$_4$ (14.35 g, 75.7 mmol) in 400 mL of CH$_2$Cl$_2$ at 0° C. 1-Indanone (10.0 g, 75.6 mmol) was added at this temperature and the reaction mixture was brought to 25° C. $^1$H NMR analysis of a worked-up aliquot revealed complete conversion to product. Solvent was removed by rotary evaporation and the resulting dark oil and TiO$_2$ residue was triturated with 300 mL of hexane. The solution was filtered through dry Celite and evaporated to afford crude product (20 g dark oil). The product was distilled through a 6" Vigreaux column to afford pure product (11.01 g, 55.1 mmol) in 73 percent yield as a light yellow oil (98 area percent enamine by GC analysis): bp=143° C. @ 1 mm.

$^1$H (CDCl$_3$)δ7.41 (d, 2H, J=7.7 Hz), 7.27 (t. 1H, J=7.5 Hz), 7.18 (d, 1H, J=7.5 Hz), 5.52 (d, 1H, J=2 Hz), 3.30 (d, 2H, J=2 Hz), 3.04 (t, 4H, J=5.2 Hz), 1.74 (m, 4H,), 1.60, (m, 2H).

$^{13}$C{$^1$H}(CDCl$_3$)δ154.0, 144.4, 141.7, 125.6. 124.6, 124.1, 119.8, 108.8, 52.3, 35.8, 26.2, 24.9.

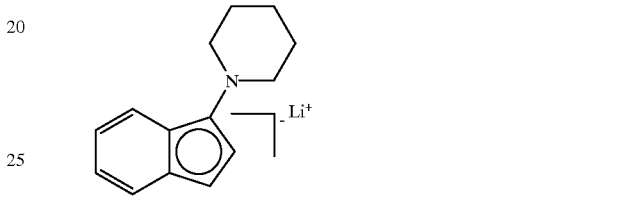
(13)

Preparation of (3-(1-piperidinyl)-1H-indenyl)lithium, (13). 1-(1H-inden-3-yl)piperidine (3.00 g, 15.1 mmol) was dissolved in 75 mL of hexane and 7.1 mL of 2.5 M n-BuLi (1.09 eq) was added dropwise via syringe over a 5 minute period. The solution developed a yellow precipitate upon the addition of the first 0.5 mL of n-BuLi. The resulting slurry was allowed to stir 24 hours. After this time the solid was filtered, washed with 50 mL of hexane and allowed to dry in vacuo overnight to afford the desired anion as a yellow solid (2.96 g, 14.3 mmol) in 95 percent yield.

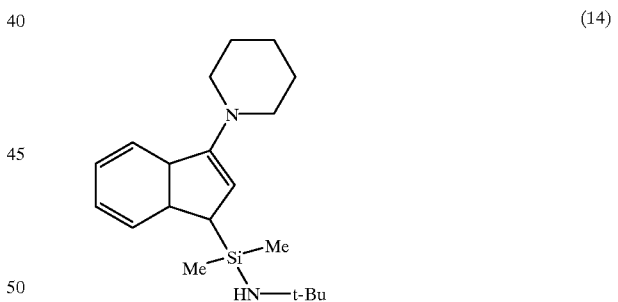
(14)

Preparation of N-(1,1-dimethylethyl)-1,1-dimethyl-1-(3-(1-piperidinyl)-1H-inden-1-yl)silanamine, (14). (3-(1-Piperidinyl)-1H-indenyl)lithium (2.96 g, 14.4 mmol) was dissolved in 40 mL of THF and added dropwise to a solution of N-(tert-butyl)-N-(1-chloro-1,1-dimethylsilyl)amine (3.20 g. 19.3 mmol) in 30 mL of THF over a 45 minute period, with stirring continued for 25 hour. The solution was evaporated in vacuo to give a dark red oil which was dissolved in hexane (100 mL). LiCl was filtered from this solution and the solvent was removed in under vacuum overnight to give N-(tert-butyl)-N-(1,1-dimethyl-1-(3-piperidino-1H-1-indenyl)silyl)amine (4.5 g, 13.7 mmol) as a dark burgundy oil in 95 percent yield.

$^1$H (C$_6$D$_6$)δ7.58 (t, 2H, J=5.7 Hz), 7.27 (t, 1H, J=7.5 Hz), 7.19 (d, 1H, J=7.5 Hz), 5.73 (d, 1H, J=2 Hz), 3.36 (d, 2H,

J=2Hz), 3.01 (m, 4H), 1.63 (p, 4H, J=5.5 Hz), 1.44, (p, 2H, J=5.5 Hz), 1.09 (s, 9H), 0.50 (broad s, 1H), 0.36 (s, 3H), −0.05 (s,3H).

$^{13}C\{^1H\}(C_6D_6)\delta$153.10, 146.1, 141.5, 124.7, 124.1, 123.9, 120.2, 112.2, 49.6, 44.2, 34.1, 26.7, 25.3, 0.4, −0.5.

(15)

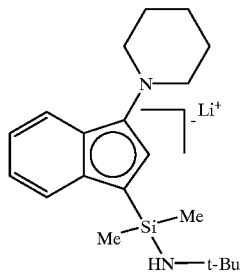

Preparation of (1-(((1,1-dimethylethyl)amino) dimethylsilyl)-3-(1-piperidinyl)-1H-indenyl)lithium, lithium salt, (15). In the drybox 4.73 ; (14.4 mmol) of N-(1,1-dimethylethyl )-1,1-dimethyl-1-(3-(1-piperidinyl)-1H-inden-1-yl )silanamine was dissolved in 65 mL of hexane. To this solution 17.00 mL (34 mmol) of n-BuLi (2 M) was added dropwise. Upon complete addition of the n-BuLi the solution was stirred overnight. The resulting precipitate was collected via filtration, washed with hexane (2×30 mL) and dried under reduced pressure to give 4.70 g of yellow solid. Yield 96 percent.

(16)

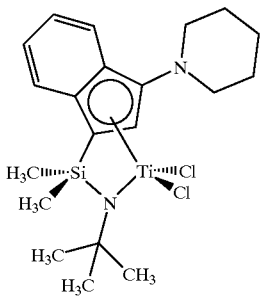

Preparation of dichloro(N-(1,1-dimethylethyl)-1,1-dimethyl-1-((1,2,3,3a,7a-η)-3-(1-piperidinyl)-1H-inden-1-yl)silanaminato(2-)-N)titanium, (16). (1-(((1,1-Dimethylethyl)amino)dimethylsilyl)-3-(1-piperidinyl)-1H-indenyl)lithium, lithium salt (4.70 g, 13.8 mmol) dissolved in 35 mL of THF was added within 2 minutes to a suspension of TiCl₃ (THF)₃ (5.11 g, 13.8 mmol) in 70 mL of THF. After 1 hour of mixing, PbCl₂ (2.50 g, 9.0 mmol) was added as a solid. The reaction mixture was stirred an additional hour. The solvent was then removed under reduced pressure. The residue was extracted with 70 mL of toluene and filtered through a medium size glass frit. Toluene was removed under reduced pressure and the residue was triturated with 30 mL of hexane. The black crystalline solid was collected by filtration, washed with hexane (2×30 mL) and then dried under reduced pressure to give 4.26 g of product as a brown-red solid. Yield 69 percent.

$^1H$ $(C_6D_6)$δ0.48 (s, 3H), 0.64 (s, 3H), 1.31 (m, 6H), 1.38 (s, 9H), 3.18 (m, 2H), 3.58 (m, 2H), 5.92 (s, 1H), 6.98 (t, 1H, $^3J_{H\text{-}H}$=7.54 Hz), 7.09 (t, 1H, $^3J_{H\text{-}H}$=7.5 Hz), 7.52 (d, 1H, $^3J_{H\text{-}H}$=8.5 Hz), 7.63 (d, 1H, $^3J_{H\text{-}H}$=8.7 Hz).

$^{13}C\{^1H\}(C_6D_6)$δ1.35, 4.15, 24.35, 26.14. 32.88, 51.62, 61.46, 92.92, 111.79, 125.08, 128.67, 128.92, 135.42, 151.09.

HRMS (EI, M⁺): calcd 444.1038, found 444.1033.

Example 6

(17)

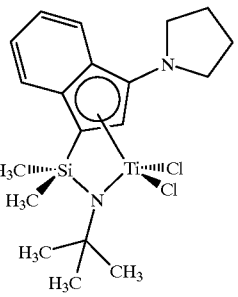

Preparation of (N-(1,1-dimethylethyl)-1,1-dimethyl-1-((1,2,3,3a,7a-η)-3-(1-piperidinyl)-1H-inden-1-yl) silanaminato(2-)-N)dimethyltitanium, (17). In the drybox 0.60 g dichloro(N-(1,1-dimethylethyl)-1,1-dimethyl-1-((1,2,3,3a,7a-η)-3-(1-piperidinyl)-1H-inden-1-yl)silanaminato (2-)-N)titanium (1.35 mmol) was dissolved in 40 mL of Et₂O. To this solution 0.95 mL (2.83 mmol) of MeMgI (3.0 M) was added dropwise with stirring over a 5 minute period. After the addition of MeMgI was completed, the solution was stirred for 60 minutes. Then the Et₂O was removed under reduced pressure and the residue was extracted with hexane (2×30 mL), the solution was filtered and the filtrate was evaporated to dryness under reduced pressure to give 0.40 g (73 percent yield) of red-orange solid.

$^1H$ $(C_6D_6)$δ−0.04 (s, 3H), 0.45 (s, 3H), 0.65 (s, 3H), 0.94 (s, 3H), 1.35 (m, 2H), 1.50 (m, 9H), 1.53 (br s, 4H), 3.14 (m, 2H), 3.3.24 (m, 2H), 5.69 (s, 1H), 6.68 (t, 1H, $^3J_{H\text{-}H}$=7.5 Hz), 7.06 (t, 1H, $^3J_{H\text{-}H}$=7.6 Hz), 7.5 (d, 1H, $^3J_{H\text{-}H}$=8.5 Hz), 7.64 (d, 1H, $^3J_{H\text{-}H}$=8.6 Hz).

$^{13}C\{^1H\}(C_6D_6)$δ2.40, 4.84, 24.94, 26.58, 34.68, 51.97, 52.41, 55.07, 58.31, 85.16, 108.91, 124.60, 125.02, 126.33, 128.18, 133.24, 146.27.

Example 7

(18)

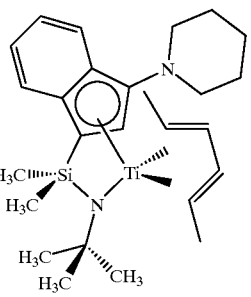

Preparation of (N-(1,1-dimethylethyl )-1,1-dimethyl-1-((1,2,3,3a,7a-η)-3-(1-piperidinyl)-1H-inden-1-yl) silanaminato(2-)-N)((2,3,4.5-η)-2.4-hexadiene)titanium, (18). Dichloro(N-(1,1-dimethylethyl)-1,1-dimethyl-1-((1,2,3,3a,7a-η)-3-(1-piperidinyl)-1 H-inden-1-yl)silanaminato (2-)-N)titanium (0.50 g, 112 mmol) was dissolved in 35 mL of hexane. To this solution 1.28 mL (11.23 mmol) of 2,4-hexadiene was added at once followed by dropwise addition of n-BuMgCl (1.35 mL, 2.69 mmol). The mixture was refluxed for 1.5 hours and then the solvent was removed in vacuum. The black solid residue was dissolved in 15 mL of hexane, filtered and put into the freezer (−27° C.) for three days. The solvent was then decanted and the large, black crystals were washed with 4 mL of cold hexane and dried in under vacuum to give 126 mg (yield 25 percent).

$^1$H (C$_6$D$_6$) δ0.73 (s, 3H), 0.94 (s, 3H), 1.09 (s, 9H), 1.22 (d, 3H, $^3$J$_{H-H}$=5.4 Hz), 1.24 (m, 2H), 1.37 (m, 4H), 1.63 (m, 1H), 1.79 (m, 1H)r 2.1 1 (d, 3H, $^3$JH-H =Hz), 2.51 (m, 2H), 2.87 (m, 2H), 3.23 (dd, 1H, $^2$J$_{H-H}$=13.5. Hz, $^3$J$_{H-H}$=9.6), 4.00 (dd, 1H, $^2$J$_{H-H}$=13.2, Hz, $^3$J$_{H-H}$=9.9), 5.69 (s, 1H), 6.69 (t, 1H, $^3$J$_{H-H}$=9.6 Hz), 6.83 (d, 1H, $^3$J$_{H-H}$=8.4 Hz), 6.94 (t, 1H, $^3$J$_{H-H}$=9.9 Hz), 7.88 (d, 2H, $^3$J$_{H-H}$=9.6 Hz).

$^{13}$C{$^1$H}(C$_6$D$_6$)δ4.11, 6.42, 15.53, 19.75, 24.64, 26.15, 34.98, 52.38, 56.43, 79.37, 80.48, 92.62, 101.21, 110.64, 112.81, 120.76, 121.54, 122.61, 123.40, 128.99, 129.50, 142.65.

Example 8

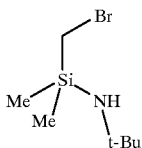

(19)

Preparation of 1-(bromomethyl)-N-(1,1-dimethylethyl)-1,1-dimethylsilanamine, (19). To a stirred solution of 10.00 g (53.32 mmol) of (bromomethyl)chlorodimethylsilane in 200 ml, of diethylether a solution of 7.80 g (106.64 mmol) of t-butyl amine in 10 mL of ether was added. A white solid deposited instantaneously. The reaction mixture was stirred overnight, filtered through a medium frit and the solvent was removed under reduced pressure to give 11.06 g of colorless liquid. Yield 93 percent.

$^1$H (C$_6$D$_6$) δ0.13 (s, 6H), 0.57 (br s, 1H), 0.99 (s, 9H), 2.25 (s, 2H).

$^{13}$C{$^1$H}(C$_6$D$_6$) δ−0.47, 19.75, 33.87. 49.51.

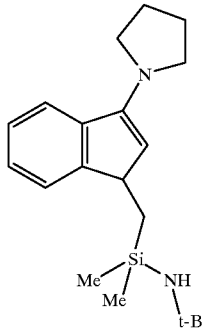

(20)

Preparation of N-(tert-butyl)-N-(1,1-dimethyl-1-((3-tetrahydro-1H-1-pyrrolyl-1H-1-indenyl)methyl)silyl)amine, (20). To a stirred solution of 3.500 g (15.61 mmol) of 1-(bromomethyl)-N-(1,1-dimethylethyl)-1,1-dimethylsilanamine in 30 mL of THF a solution of 2.84 g (14.87 mmol) of 1-(1H-3-indenyl)pyrrolidine, lithium salt in 30 mL of THF was added within 5 minutes. The reaction mixture darkened almost at once. The reaction mixture was stirred overnight and solvent was removed under reduced pressure. The residue was extracted with 50 mL of hexane and filtered. Hexane was removed leaving 4.88 g of red oil. Yield 100 percent.

$^1$H (C$_6$D$_6$) δ0.18 (s, 3H), 0.18 (s, 3H), 0.48 (s, 1H), 0.84 (dd, 1H, $^2$J$_{H-H}$=14.6 Hz, $^3$J$_{H-H}$=10.2 Hz), 1.10 (s, 9H), 1.36 (dd, 1H, $^2$J$_{H-H}$=14.6 Hz, $^3$J$_{H-H}$=4.4 Hz), 1.58 (m, 4H), 3.26 (m, 4H), 3.67 (m, 1H), 5.25 (d, 1H, $^3$J$_{H-H}$=2.4 Hz), 7.20 (m, 2H), 7.38 (d, 1H, $^3$J$_{H-H}$=7.1 Hz), 7.55 (d, 1H, $^3$J$_{H-H}$=6.8 Hz).

$^{13}$C{$^1$H}(C$_6$D$_6$) δ2.97, 3.02, 22.72, 25.62, 34.14, 43.34. 49.59, 50.36, 108.05, 120.94, 123.44. 124.99, 126.04, 141.55. 148.68, 152.43.

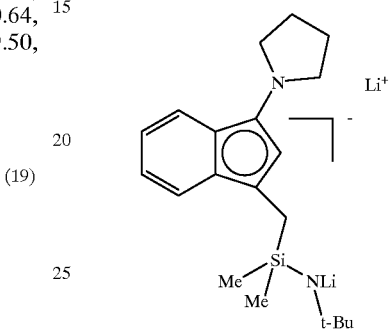

(21)

Preparation of N-(1,1-dimethylethyl)-1,1-dimethyl-1-((3-(1-pyrrolidinyl)-1H-inden-1-yl)methyl)silanamine, dilithium salt, (21). In the drybox 4.88 g (14.86 mmol) of N-(1,1-dimethylethyl)-1,1-dimethyl-1-((3-(1-pyrrolidinyl)-1H-inden-1-yl)methyl)silanamine was combined with 70 mL of hexane. To this solution 23.2 mL (37.2 mmol) of n-BuLi (1.6 M) was added within 2 minutes. Within a short time a yellow precipitate appeared. Upon complete addition of the n-BuLi the solution was stirred overnight. The resulting yellow precipitate was collected via filtration, washed with 80 mL of hexane and dried under reduced pressure to give 5.05 g (100 percent yield) of a yellow solid.

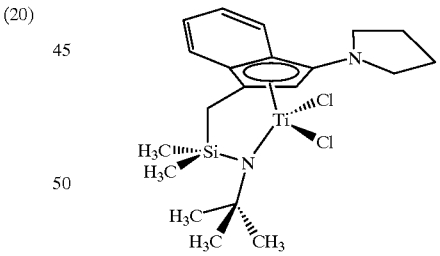

(22)

Preparation of dichloro(N-(1,1-dimethylethyl)-1,1-dimethyl-1-(((1,2,3,3a,7a-η)-3-(1-pyrrolidinyl)-1H-inden-1-yl)methyl)silanaminato-(2-)-N-)titanium, (22). In the drybox 5.50 g (14.85 mmol) of TiCl$_3$(THF)$_3$ was suspended in 80 mL of THF. To this solution 5.05 g (14.85 mmol) of N-(1,1-dimethylethyl)-1,1-dimethyl-1-((3-(1-pyrrolidinyl)-1H-inden-1-yl)methyl)silanamine, dilithium salt dissolved in 50 mL of THF was added within 5 minutes. The solution was then stirred for 1 hour. After this time 2.68 g of PbCl$_2$ (9.65 mmol) was added and the solution was stirred for 60 minutes. The THF was then removed under reduced pressure. The residue was then extracted with 60 mL of toluene, the solution was filtered, and the toluene was removed under reduced pressure. The residue was then triturated with 50 mL of hexane and the precipitate was collected via filtration on the frit, washed with 25 mL of cold hexane and dried under vacuum to give 3.65 g of black solid. Yield 55 percent.

$^1$H (C$_6$D$_6$) δ0.37 (s, 3H), 0.51 (s, 3H), 1.46 (s, 9H), 1.53 (m, 4H), 2.25 (d, $^2$J$_{H-H}$=14.5 Hz), 2, 49 (d, $^2$J$_{H-H}$=14.5 Hz), 3.35 (m, 2H), 3.62 (m, 2H), 5.63 (s, 1H), 7.07 (m, 2H), 7.35 (m, 1H), 7.56 (m, 1H), $^{13}$C{$^1$H}(C$_6$D$_6$) δ6.19, 7.08, 18.93. 25.88, 33.46, 50.42, 61.30, 100.59, 119.33, 120.91, 125.09, 126.07, 126.86, 127.42, 146.10.

Example 9

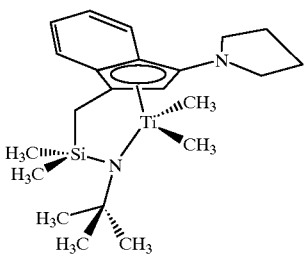
(23)

Preparation of (N-(1,1-dimethylethyl)-1,1-dimethyl-1-(((1,2,3,3a,7a-η)-3-(1-pyrrolidinyl)-1H-inden-1-yl)methyl) silanaminato-(2-)-N-)dimethyl-titanium, (23). In the drybox 0.60 g of dichloro(N-(1,1-dimethylethyl)-1,1-dimethyl-1-(((1,2,3,3a,7a-η) -3-(1-pyrrolidinyl)-1H-inden-1-yl)methyl) silanaminato-(2-)-N-)-titanium (1.35 mmol) was dissolved in 40 mL of Et$_2$O. To this solution 0.945 mL (2.83 mmol) of MeMgI (3.0 M) was added dropwise while stirring over a 5 minute period. The solution changed color from black to dark red. After the addition of MeMgI was completed, the solution was stirred for 1 hour. Then the Et$_2$O was removed under reduced pressure and the residue was extracted with hexane (2×20 mL), the solution was filtered, the filtrate was evaporated to dryness under reduced pressure to give 0.35 g (65 percent yield) of black solid.

$^1$H (C$_6$D$_6$) δ0.23 (s, 3H), 0.38 (s, 3H), 0.40 (s, 3H), 0.82 (s, 3H), 1.54 (m, 6H) 1.60 (s, 9H), 1.99 (d, $^2$J$_{H-H}$=14.5 Hz), 2.22 (d, $^2$J$_{H-H}$=14.5 Hz), 3.33 (m, 4H), 5.32 (s, 1H), 6.91 (m, 2H), 7.22 (m, 1H), 7.64 (m, 1H).

$^{13}$C{$^1$H}(C$_6$D$_6$) δ6.55, 7.23, 17.21, 25.92. 35.21. 50.27, 51.89, 57.02, 58.18, 99.09, 108.85, 116.05, 122.14, 122.92, 123.66, 124.48, 125.53, 138.31.

Example 10

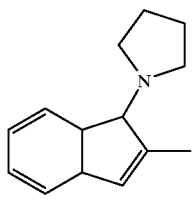
(24)

Preparation of 1-(2-methyl-1H-3-indenyl)pyrrolidine, (24). 2-Methyl-1-indenone (25 g, 171 mmol) was dissolved in 250 mL of anhydrous benzene. To this solution 50 mL of pyrrolidiene was added. The reaction mixture was refluxed using a Dean-Stark trap filled with 4A molecular sieves for 10d. GC analysis showed that conversion was on the order of 70 percent. The solvent was distilled off and the residue was distilled under reduced pressure (1.5 Torr). The first fraction was obtained at 84° C. whereas the desired compound was collected at 126–132° C. The yield of yellow liquid was 16.28 g, 48 percent.

$^1$H (C$_6$D$_6$) δ1.66 (m, 4H), 2.02 (s, 3H) 3.02 (s, 2H), 3.29 (m, 4H), 7.11 (t, 1H, $^3$J$_{H-H}$=7.0 Hz), 7.23 (m, 2H), 7.45 (d, $^2$J$_{H-H}$=7.7 Hz).

$^{13}$C{$^1$H}(C$_6$D$_6$) δ14.68, 25.61, 41.89, 50.92, 119.94, 123.68, 123.86, 124.10, 126.029, 142.61, 143.50, 145.00.

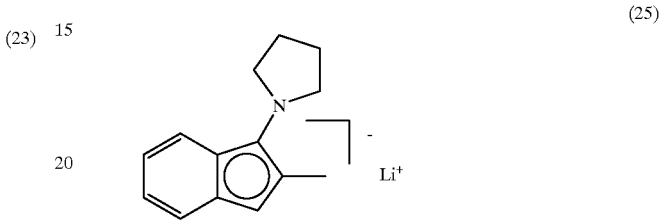
(25)

Preparation of (2-methyl-1-(1-pyrrolidinyl)-1H-indenyl) lithium, (25). 1-(2-Methyl-1H-3-indenyl)pyrrolidine (16.276 g, 81.67 mmol) was stirred in hexane (250 mL) as n-BuLi (98.0 mmol, 49.0 mL of 2.0 M solution in cyclohexane) was added dropwise. This mixture was allowed to stir overnight during which time a precipitate formed. After the reaction period the mixture was filtered. The desired product was isolated as a pale yellow solid following washing with hexane and drying under vacuum and was used without further purification or analysis (14.51 g, 87 percent yield).

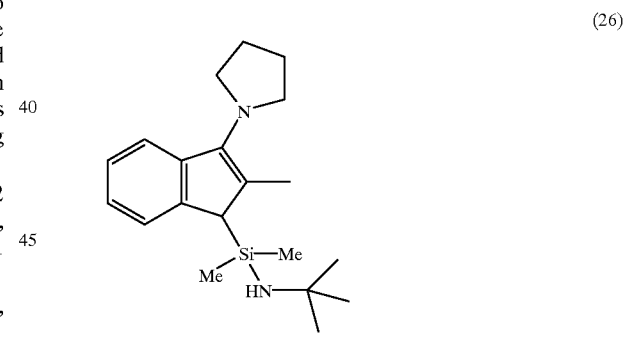
(26)

Preparation of N-(1,1-dimethylethyl)-1,1-dimethyl-1-(2-methyl-3-(1-pyrrolidinyl)-1H-inden-1-yl)silanamine, (26). To a solution of N-(1,1-dimethylethyl)-1-chloro-1,1-dimethyl-silanamine (4.27 g, 25.75 mmol) in 100 mL of THF (2-methyl-1-(1-pyrrolidinyl)-1H-indenyl)lithium (3.52 g, 17.17 mmol) dissolved in 50 mL of THF was added within 3 minutes. The color of the solution became yellow-orange. The reaction mixture was stirred overnight and then the solvent was removed under reduced pressure. The product was extracted with 80 mL of hexane, filtered. Hexane was removed under reduced pressure and the flask was attached to a high-vac line (10$^{-1}$ torr) overnight to remove excess starting material. The yield of product was 5.54 g. 98 percent.

$^1$H (C$_6$D$_6$) δ−0.00 (s, 3H), 0.09 (s, 3H), 0.40 (s, 1H), 1.04 (s, 9H), 1.77 (m, 4H), 2.21 (s, 3H), 3.14 (s, 1H), 3.25 (m, 2H), 3.39 (m, 2H), 7.15 (t, 1H, $^3$J$_{H-H}$=7.3 Hz), 7.23 (t, 1H, $^3J_{H-H}$=7.4 Hz), 7.48 (d, 1H, $^3J_{H-H}$=7.2 Hz), 7.50 (d, 1H, $^3J_{H-H}$=7.1 Hz).

$^{13}C\{^1H\}(C_6D_6)$ δ0.17, 1.07, 15.63, 26.00, 33.81, 48.59, 50.00, 51.23, 119.52, 122.63, 123.86, 124.55, 133.96, 142.73, 143.12, 144.16.

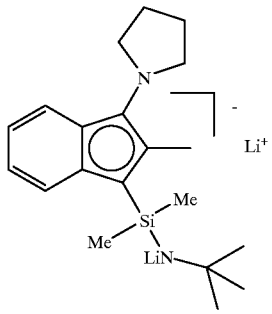

(27)

Preparation of (1-(((1,1-dimethylethyl )amino)dimethylsilyl)methyl)-2-methyl-3-(1-pyrrolidinyl)-1H-indenyl)lithium, lithium salt, (27). In the drybox 5.54 g (16.36 mmol) of N-(1,1-dimethylethyl)-1,1-dimethyl-1-(2-methyl-3-(1-pyrrolidinyl)-1H-inden-1-yl)silanamine was dissolved in 100 mL of hexane. To this solution 16.0 mL (39.8 mmol) of n-BuLi (1.6 M) was added dropwise. Upon complete addition of the n-BuLi the solution was stirred overnight. The resulting precipitate was collected via filtration, washed with 100 mL hexane and dried under reduced pressure to give 4.51 g of yellow solid. Yield 83 percent.

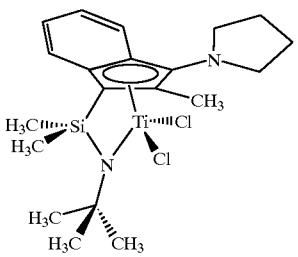

(28)

Preparation of dichloro(N-(1,1-dimethylethyl)-1,1-dimethyl-1-((1,2,3,3a,7a-η)-2-methyl-3-(1-pyrrolidinyl)-1H-inden-1-yl)silanaminato(2-)-N)titanium, (28). In the drybox 4.91 g (13.24 mmol) of TiCl$_3$(THF)$_3$ was suspended in 80 mL of THF. To this solution 4.51 g (13.24 mmol) (1-(((1,1-dimethylethyl)amino)dimethylsilyl)methyl)-2-methyl-3-(1-pyrrolidinyl)-1H-indenyl)lithium, lithium salt dissolved in 30 mL of THF was added within 5 minutes. The solution was then stirred for 55 minutes. After this time 2.39 g of PbCl$_2$ (8.60 mmol) was added and the solution was stirred for 55 minutes. The THF was then removed under reduced pressure. The residue was then extracted with 70 mL of toluene, the solution was filtered, and the toluene was removed under reduced pressure. The residue was then triturated with 40 mL of hexane and the precipitate was collected via filtration, washed with 40 mL of hexane and dried under vacuum to give 3.38 g of black-gray solid. Yield 56 percent.

$^1$H (C$_6$D$_6$) δ0.62 (s, 3H), 0.66 (s, 3H), 1.38 (s, 9H), 1.41 (m, 4H), 2.50 (s, 3H), 3.46 (m, 2H), 3.83 (m, 2H), 6.98 (t, 1H, $^3J_{H-H}$=7.6 Hz), 7.10 (t, 1H, $^3J_{H-H}$=7.5 Hz), 7.65 (t, 1H, $^3J_{H-H}$=8.6 Hz), 7.70 (t, 1H, $^3J_{H-H}$=8.8 Hz).

$^{13}C\{^1H\}(C_6D_6)$ δ6.39, 6.49, 18.95, 25.99. 32.90, 52.36, 60.75, 94.47, 123.90, 126.95, 136.00, 147.75.

Example 11

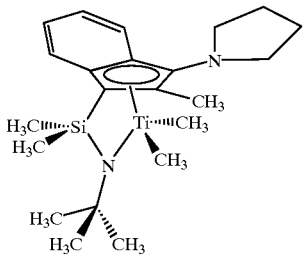

(29)

Preparation of (N-(1,1-dimethylethyl)-1,1-dimethyl-1-((1,2,3,3a,7a-η)-2-methyl-3-(1-pyrrolidinyl)-1H-inden-1-yl)silanaminato(2-)-N )dimethyltitanium, (29). In the drybox 0.65 g (1.42 mmol) of dichloro(N-(1,1-dimethylethyl)-1,1-dimethyl-1-((1,2,3,3a,7a-η)-2-methyl-3-(1-pyrrolidinyl)-1H-inden-1-yl)silanaminato(2-)-N)titanium was dissolved in 40 mL of Et$_2$O. To this solution 1.00 mL (2.98 mmol) of MeMgI (3.0 M) was added dropwise while stirring over a 5 minute period. The solution changed color from black to very dark red. After the addition of MeMgI was completed, the solution was stirred for 1 hour. Et)O was removed under reduced pressure and the residue was extracted with hexane (2×20 mL), the solution was filtered and the filtrate was evaporated to dryness under reduced pressure to give 0.45 g (78 percent yield) of brown-red sticky residue.

$^1$H (C$_6$D$_6$) δ−0.03 (s, 3H), 0.54 (s, 3H), 0.64 (s, 3H), 0.86 (s, 3H) 1.50 (s, 9H), 1.62 (m, 4H), 2.15 (s, 3H), 3.22 (m, 2H), 3.58 (m, 2H), 6.86 (t, 1H, $^3J_{H-H}$=7.6 Hz), 7.06 (t, 1H, $^3J_{H-H}$=7.5 Hz), 7.55 (d, 1H, $^3J_{H-H}$=8.8 Hz), 7.70 (d, 1H, $^3J_{H-H}$=8.6 Hz).

$^{13}C\{^1H\}(C_6D_6)$ δ6.35, 6.99, 16.41, 26.14, 34.47, 52.12, 52.58, 54.81, 57.92. 85.58, 124.36, 124.43, 125.04, 126.83, 127.86, 129.68, 132.79, 141.06.

Example 12

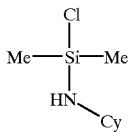

(30)

Preparation of 1-chloro-N-cyclohexyl-1,1-dimethylsilanamine, (30). In the drybox in a 250 mL flask 60.0 mL (490.89 mmol) of dichlorodimethylsilane was stirred in about 80 mL of THF. To this stirring solution 6.00 g (57.08 mmol) of lithium cyclohexylamide was added as a solid slowly and stirred overnight. The THF was removed under vacuum leaving a cloudy solution. Hexane was added to this mixture and the solids were filtered off and washed with hexane. The hexane was then removed from the filtrate under vacuum leaving a clear light yellow product weighing 9.18 g. Yield 84 percent.

$^1$H (C$_6$D$_6$) δ0.28 (s, 6H),)0.82–1.20 (m, 6H), 1.37–1.50 (m, 1H), 1.50–1.60 (m, 2H), 1.8 1 (d, 2H, $^3J_{H-H}$=10.0), 2.64 (m, 1H).

$^{13}C\{^1H\}(C_6D_6)$ δ2.27, 25.65, 25.89, 38.04, 50.67.

(31)

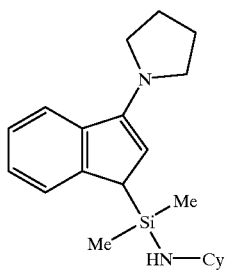

(33)

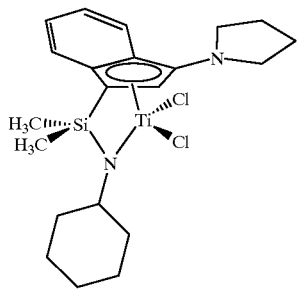

Preparation of N-cyclohexyl-1,1-dimethyl-1-(3-(1-pyrrolidinyl)-1H-inden-1-yl)silanamine, (31). To a solution of 1-chloro-N-cyclohexyl-1,1-dimethylsilanamine (3.61 g, 18.83 mmol) in 150 mL of THF, 1-(1H-3-indenyl) pyrrolidine, lithium salt (3.00 g, 15.69 mmol) dissolved in 50 mL of THF was added within 3 minutes. The color of the solution became deep cherry-red at once. The reaction mixture was stirred overnight and then the solvent was removed under reduced pressure. The product was extracted with 60 mL of hexane and filtered. Hexane was removed under reduced pressure and the flask was attached to a high-vac line ($10^{-4}$ torr) for 4 hours to remove excess starting material. Obtained 5.23 g of product. Yield 98 percent.

$^1$H (C$_6$D$_6$) δ –0.01 (s, 3H), 0.078 (s, 3H), 0.36 (s, 1H), 0.80–1.30 (m, 7H), 1.41–1.92 (m, 8H), 2.52 (m, 1H), 3.27 (m, 4H), 3.396 (s, 1H), 5.384 (s, 1H), 7.252 (m, 2H), 7.586 (d, 1H, $^3J_{H-H}$=7.1 Hz), 7.717 (d, 1H, $^3J_{H-H}$=7.4 Hz).

$^{13}$C{$^1$H}(C$_6$D$_6$) δ –2.539, –1.771, 25.286, 26.021, 26.115, 39.071, 43.603, 50.682, 51.067, 104.480, 120.944, 123.736, 123.797, 124.557, 141.484. 146.923, 149.284.

Preparation of dichloro(N-cyclohexyl-1,1-dimethyl-1-((1,2,3 ,3a,7a-η)-3-(1-pyrrolidinyl)-1H-inden-1-yl) silanaminato(2-)-N)titanium, (33). In the drybox 4.21 g (11.35 mmol) of TiCl$_3$ (THF)$_3$ was suspended in 80 mL of THF. To this solution 4.00 g (11.35 mmol) (1-((cyclohexylamino)dimethylsilyl)-3-(1-pyrrolidinyl)-1H-indenyl)lithium, lithium salt dissolved in 25 mL of THF was added within 5 minutes. The solution was then stirred for 45 minutes. After this time 2.05 g of PbCl$_2$ (7.38 mmol) was added and the solution was stirred for 40 minutes. The THF was then removed under reduced pressure. The residue was then extracted with 70 mL of toluene, the solution was filtered, and the toluene was removed under reduced pressure. The residue was then triturated with 30 mL of hexane and the precipitate was collected via filtration, washed with 30 mL of hexane and dried under vacuum to give 3.79 g of deep purple-black solid. Yield 73 percent.

$^1$H (C$_6$D$_6$) δ 0.53 (s, 3H), 0.62 (s, 3H), 0.93 (m, 3H), 1.18 (m, 2H), 1.39–1.69 (m, 7H), 2.01 (d, 1H, $^3J_{H-H}$=12 Hz), 2.19 (d, 1H, $^3J_{H-H}$=12 Hz), 3.21 (m, 2H), 3.54 (m, 2H), 4.601 (m, 1H), 5.64 (s, 1H), 7.02 (t, 1H, $^3J_{H-H}$=6.9 Hz), 7.08 (t, 1H, $^3J_{H-H}$=6.6 Hz), 7.60 (d, 1H, $^3J_{H-H}$=8.3 Hz), 7.65 (t, 1H, $^3J_{H-H}$=8.5 Hz).

$^{13}$C{$^1$H}(C$_6$D$_6$) δ 1.11, 3.10, 25.67, 26.04, 26.38, 35.90, 50.49, 63.91, 89.43, 106.75, 125.48, 126.40, 126.92, 127.13, 128.67, 136.14, 147.71.

Example 13

(32)

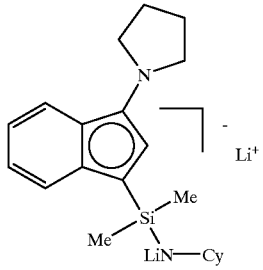

(34)

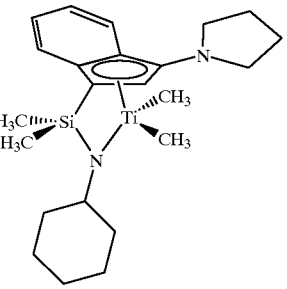

Preparation of (1-((cyclohexylamino)dimethylsilyl)-3-(1-pyrrolidinyl)-1H-indenyl)lithium, lithium salt, (32). In the drybox 5.23 g (15.36 mmol) N-cyclohexyl-1,1-dimethyl-1-(3-(1-pyrrolidinyl)-1H-inden-1-yl)silanamine was dissolved in 100 mL of hexane. To this solution 24 mL (39.39 mmol) of n-BuLi (1.6 M) was added dropwise. Upon complete addition of the n-BuLi the solution was stirred overnight. The resulting precipitate was collected via filtration, washed with 100 mL of hexane and dried under reduced pressure to give 5.11 g of yellow solid. Yield 94 percent.

Preparation of (N-cyclohexyl-1,1-dimethyl-1-((1,2,3,3a,7a-η)-3-(1-pyrrolidinyl)-1H-inden-1-yl)silanaminato(2-)-N)dimethyltitanium, (34). In the drybox 0.70 g of dichloro (N-cyclohexyl-1,1-dimethyl-1-((1,2,3,3a,7a-η)-3-(1-pyrrolidinyl)-1H-inden-1-yl)silanaminato(2-)-N)titanium (1.53 mmol) was dissolved in 40 mL of Et$_2$O. To this solution 1.07 mL (3.21 mmol) of MeMgI (3.0 M) was added dropwise while stirring over a 5 minute period. The solution changed color from black to dark red. After the addition of MeMgI was completed, the solution was stirred for 1 hour. Then the Et$_2$O was removed under reduced pressure and the residue was extracted with hexane (2×20 mL), the solution was filtered and the filtrate was evaporated to dryness under reduced pressure to give 0.50 g (79 percent yield) of red crystalline solid.

$^1$H (C$_6$D$_6$) δ0.04 (s, 3H), 0.47 (s, 3H), 0.63 (s, 3H), 0.72 (s, 3H), 1.10 (m, 1H), 1.32 (m, 5H), 1.54 (m, 5H), 1.73 (m, 2H), 2.04 (d, 1H, $^3J_{H-H}$=6.0 Hz), 2.14 (d, 1H, $^3J_{H-H}$=6.0 Hz), 3.26 (m, 2H), 3.40 (m, 2H), 4.37 (m, 1H), 5.45 (s, 1H), 6.88 (t, 1H, $^3J_{H-H}$=7.6 Hz), 7.02 (t, 1H, $^3J_{H-H}$=7.6 Hz), 7.50 (d, 1H, $^3J_{H-H}$=8.6 Hz), 7.78 (d, 1H, $^3J_{H-H}$=8.7 Hz).

$^{13}$C{$^1$H}(C$_6$D$_6$) δ1.68, 3.70, 25.84, 26.27, 26.82, 38.54, 38.69, 47.97, 50.64, 53.41, 61.15, 81.51, 104.79, 123.69, 124.98, 125, 127.87, 134.16, 142.79.

Example 14

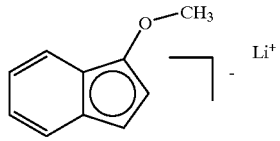
(35)

Preparation of (3-methoxy-1H-indenyl)lithium, (35). 3-Methoxy-1H-indene (9.65 g, 66.04 mmol) was dissolved in 150 mL of hexane. To this solution 50 mL of a 1.6 M solution of n-BuLi was added (80 mmol) within 10 minutes After 20 hours of stirring the off-white solid was collected on a medium-size frit, washed with hexane (3×30 mL) and dried under reduced pressure to give 9.72 g of product. Yield 97 percent.

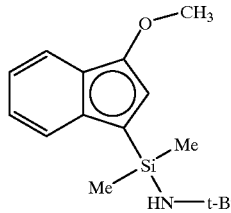
(36)

Preparation of N-(1,1-dimethylethyl)-1-(3-methoxy-1H-inden-1-yl)-1,1-dimethylsilanamine, (36). A solution of (3-methoxy-1H-indenyl)lithium (3.00 g, 19.72 mmol) in 40 mL of THF was added within 30 minutes to a 100 mL THF solution of N-(tert-butyl)-N-(1-chloro-1,1-dimethylsilyl) amine (3.27 g, 19.72 mmol). After the addition was complete the reaction mixture was stirred overnight. The solvent was then removed under reduced pressure. The residue was extracted with hexane and the solution was filtered. The solvent was then removed under reduced pressure leaving 5.20 g of product. Yield 96 percent.

$^1$H (C$_6$D$_6$) δ−0.08 (s, 3H), 0.15 (s, 3H), 1.07 (s, 9H), 3.28 (s, 1H), 5.35 (s, 1H), 7.22 (m, 2H), 7.52 (d, 1H, $^3J_{H-H}$=7.9 Hz), 7.75 (d, 1H, $^3J_{H-H}$=7.9 Hz).

$^{13}$C{$^1$H}(C$_6$D$_6$) δ−0.56, 0.45, 34.08, 42.26, 49.64, 56.41, 100.90, 118.68, 123.62, 124.94, 125.13, 139.24, 144.80, 158.03.

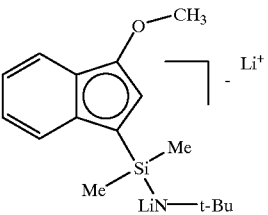
(37)

Preparation of (1-(((1,1-dimethylethyl)amino) dimethylsilyl)-3-methoxy-1H-indenyl)lithium, lithium salt, (37). In the drybox 5.20 g of (18.87 mmol) N-(1,1-dimethylethyl)-1-(3-methoxy-1H-inden-1-yl)-1,1-dimethylsilanamine was combined with 80 mL of hexane. To this solution 23.6 mL (37.75 mmol) of n-BuLi (1.6 M) was added dropwise. Upon complete addition of the n-BuLi the solution was stirred overnight. The resulting precipitate was collected via filtration, washed with 50 mL of hexane and dried under reduced pressure to give 5.00 g of product. Yield 92 percent.

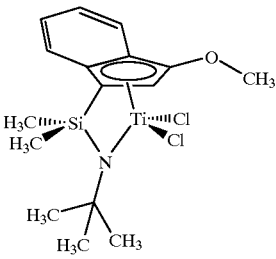
(38)

Preparation of dichloro(N-(1,1-dimethylethyl)-1-((1,2,3,3a,7a-η)-3-methoxy-1H-inden-1-yl)-1,1-dimethylsilanaminato(2-)-N)titanium, (38). (1-(((1,1-Dimethylethyl)amino)dimethylsilyl)-3-methoxy-1H-indenyl)lithium, lithium salt (5.00 g, 17.40 mmol) was dissolved in 30 mL of THF. To this solution TiCl$_3$ (THF)$_3$ (6.44 g, 17.40 mmol) was added as a solid. After 1 hour PbCl$_2$ (2.42 g, 8.70 mmol) was added as a solid. The reaction mixture was then stirred an additional hour. The solvent was removed under reduced pressure. The residue was extracted with 70 mL of toluene and filtered. Toluene was removed under reduced pressure and the residue was triturated with hexane. The solid was collected by filtration, washed with hexane and then dried under reduced pressure. 3.92 g of product was obtained. Yield 57 percent.

$^1$H (C$_6$D$_6$) δ0.41 (s, 3H), 0.58 (s, 3H), 1.33 (s, 9H), 3.71 (s, 3H), 5.70 (s,1H), 7.00 (m, 2H), 7.45 (d, 1H, $^3J_{H-H}$=8.3 Hz), 7.60 (d, 1H, $^3J_{H-H}$=8.3 Hz).

Example 15

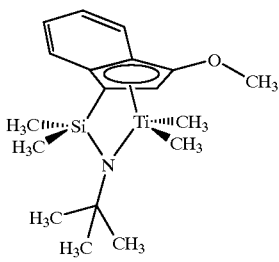
(39)

Preparation of (N-(1,1-dimethylethyl)-1-((1,2,3,3a,7a-η)-3-methoxy-1H-inden-1-yl)-1,1-dimethylsilanaminato(2-)-N)dimethyltitanium, (39). 0.60 g dichloro(N-(1,1-dimethylethyl)-1-((1,2,3,3a,7a-η)-3-methoxy-1H-inden-1-yl)-1,1-dimethylsilanaminato(2-)-N)titanium (1.52 mmol) was suspended in 40 mL of Et$_2$O. To this suspension 1.07 mL of MeMgI (3.0 M) was added dropwise with stirring over a 20 minute period. Upon completion of the addition of the MeMgI the solution was stirred for 40 minutes. After this time the Et$_2$O was removed under reduced pressure and the residue was extracted with hexane, the solution was filtered and the filtrate was evaporated to dryness under reduced pressure to give 0.46 g of product. Yield 86 percent.

$^1$H (C$_6$D$_6$) δ −0.24 (s, 3H), 0.41 (s, 3H), 0.58 (s, 3H), 0.83 (s, 3H), 1.47 (s, 9H), 3.54 (s, 3H), 3.23 (m, 4H), 5.46 (s, 1H), 6.95 (m, 1H), 7.06 (t, 1H), 7.48 (d, 1H, $^3$H$_{H—H}$=8.5 Hz), 7.78 (d, 1H, $^3$J$_{H—H}$=8.5 Hz).

Example 16

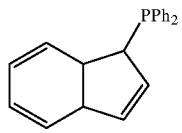
(40)

Preparation of (1H-inden-1-yl)diphenylphosphine, (40). In the drybox lithium indenide (8.00 g, 65.52 mmol) dissolved in 50 mL of THF was added within 15 minutes to a 180 mL ether solution of diphenylchlorophosphine (14.46 g, 65.52 mmol) (diphenylchlorophosphine was distilled before use (97° C. @ 0.4 torr)). After stirring overnight, LiCl was separated by filtration giving a yellow solution. Solvent was removed under vacuum leaving an off-white solid. This solid was triturated with 40 mL of hexane. Hexane was removed by decanting and the solid was dried under reduced pressure to give 16.43 g of off-white solid. Yield 84 percent.

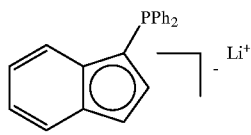
(41)

Preparation of (1-(diphenylphosphino)-1H-indenyl)lithium, (41). (1H-Inden-1-yl)diphenylphosphine (5.00 g, 16.65 mmol) was dissolved in a mixture of 60 mL of ether and 60 mL of hexane. n-BuLi (7.35 mL, 18.31 mmol) was added to the mixture within 10 minutes. After stirring overnight no precipitate appeared. Solvent was removed under reduced pressure leaving a waxy yellow residue. This residue was triturated with 120 mL of hexane for 15 minutes The hexane solution was decanted and the residue was dried under reduced pressure to give 4.45 g of off-white solid. Yield 87 percent.

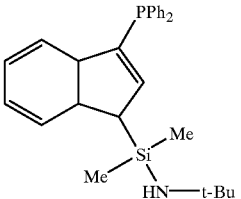
(42)

Preparation of N-(1,1-dimethylethyl )-1-(3-(diphenylphosphino)-1H-inden-1-yl)-1,1-dimethylsilanamine, (42). (1-(Diphenylphosphino)-1H-indenyl)lithium (4.45 g, 14.53 mmol) dissolved in 40 mL of THF was added within 15 minutes to a 100 mL THF solution of N-(tert-butyl)-N-(1-chloro-1,1-dimethylsilyl)amine (3,37 g, 20.34 mmol). After stirring overnight a red solution resulted. Solvent was removed under vacuum to give a red oil. The residue was extracted with 35 mL of hexane and filtered. Hexane was removed leaving 6.12 g of red oil. Yield 98 percent.

$^1$H NMR (C$_6$D$_6$) δ −0.10 (s, 3H), −0.07 (s, 3H), 0.42 (s, 1H), 1.0(s, 9H), 3.59 (m, 1H), 6.56 (m, 1H), 7.0–7.2 (m, 8), 7.54–7.66 (m, 6H).

$^{31}$P{$^1$H } NMR (C$_6$D$_6$): δ24.08.

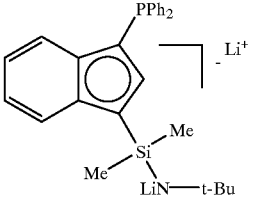
(43)

Preparation of (1-(((1,1-Dimethylethyl)amino)dimethylsilyl)-3-(diphenylphosphino)-1H-indenyl)lithium, lithium salt, (43). N-(1,1-Dimethylethyl)-1-(3-(diphenylphosphino)-1H-inden-1-yl)-1,1-dimethylsilanamine (6.73 g, 15.67 mmol) was stirred in hexane (100 mL) as n-BuLi was added dropwise. This mixture was allowed to stir overnight during which time an off-white precipitate formed. After the reaction period the mixture was filtered. The desired product was isolated as an off-white solid which was washed with hexane and dried under vacuum and used without further purification or analysis (6.04 g, 87 percent yield).

(44)

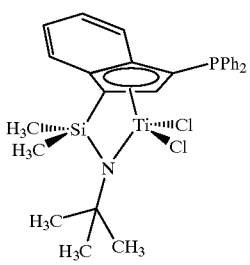

Preparation of dichloro(N-(1,1-dimethylethyl)-1-((1,2,3,3a,7a-η)-3-(diphenylphosphino)-1H-inden-1-yl)-1,1-dimethylsilanaminato(2-)-N)titanium, (44). (1-(((1,1-Dimethylethyl)amino)dimethylsilyl)-3-(diphenylphosphino)-1H-indenyl)lithium, lithium salt (3.00 g, 6.80 mmol) in THF (25 mL) was added dropwise to a slurry of TiCl₃(THF)₃ (2.52 g, 6.80 mmol) in THF (50 mL). This mixture was then allowed to stir for 1 hour. PbCl₂ (0.94 g, 3.40 mmol) was then added as a solid and the mixture was allowed to stir for an additional hour. After the reaction period the volatiles were removed and the residue was extracted and filtered using toluene. Removal of the toluene resulted in the isolation of a dark red oily residue. This residue was dissolved in a hexane/toluene (3/1 v/v) mixture and refiltered. This procedure was repeated resulting in a homogeneous solution which was cooled (−15° C.) overnight resulting in the precipitation of an oily residue which was isolated by decanting away the solution and drying under vacuum (3.13 g, 84 percent yield).

$^1$H NMR (C₆D₆) δ0.18 (s, 3H), 0.54 (s, 3H), 1.28 (s, 9H), 6.48 (s, 1H), 6.8–7.8 (m, 14 H).

$^{31}$P{$^1$H} NMR (C₆D₆) δ−17.49.

Example 17

(45)

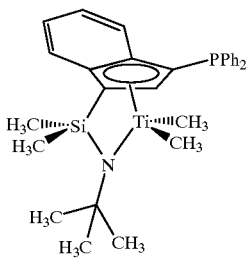

Preparation of (N-(1,1-dimethylethyl)-1-((1,2,3,3a,7a-η)-3-(diphenylphosphino)-1H-inden-1-yl)-1,1-dimethylsilanaminato(2-)-N)dimethyltitanium, (45). Dichloro(N-(1,1-dimethylethyl)-1-((1,2,3,3a,7a-η)-3-(diphenylphosphino)-1H-inden-1-yl)-1,1-dimethylsilanaminato(2-)-N)titanium((0.36 g, 0.660 mmol) was stirred in diethylether (50 mL) as MeMgBr (1.46 mmol, 0.49 mL of 3.0 M solution in diethylether) was added dropwise. This mixture was then allowed to stir for 1 hour. After the reaction period the volatiles were removed and the residue was extracted and filtered using a hexane/toluene (1/1 v/v) mixture. The volatiles were then removed under vacuum and the residue was redissolved and filtered using hexane. Removal of the hexane resulted in the isolation of the desired product as a dark red oil (0.18 g, 53 percent yield).

$^1$H NMR (C₆D₆) δ−0.00 (s, 3H), 0.23 (s, 3H), 0.57 (s, 3H), 1.18 (s, 3H), 1.39 (s, 3H), 6.17 (s, 1H), 6.8–7.8 (m, 14H).

Example 18

(46)

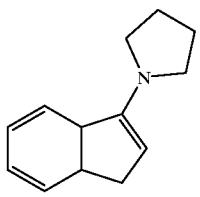

Preparation of 1-(1H-inden-3-yl)pyrrolidine, (46). According to a modification of the procedure of Noland et al (Noland, W. E.; Kaneswaran, V. J. Org. Chem. 1981, 46, 1940–1944.), 1-indanone (25.0 g, 0.189 mol) and 50 mL of pyrrolidine which had been dried over 3A sieves were added to a 500 mL, 3-neck flask equipped with an overhead stirrer, Dean-Stark apparatus and condenser which was maintained under a dry N₂ atmosphere. Benzene (200 mL dried over 4A sieves) was added and the solution was brought to reflux for 30 hours. At the end of this period $^1$H NMR analysis of a reaction aliquot indicated a 93:7 mole percent ratio of desired product to starting material. The bulk of the solvent was removed in vacuo and the crude dark product was distilled (6" Vigreaux column) to give pure enamine as a light yellow oil (24.3 g, 0.132 mol) in 70 percent yield. This compound was both air and water sensitive and was transferred to the dry box upon distillation. Capillary GC analysis indicated a hexane solution of distillate to be of 99 area percent purity: bp=125–127° C. @ 2.0 mm, bp. lit= 118–120° C. @ 1 mm;

$^1$H (C₆D₆) δ7.61 (d, 1H, J=7.4 Hz), 7.39 (d, 1H, J=7.4 Hz), 7.24 (t, 1H, J=7.4 Hz), 7.17 (t, 1H, J=7.4 Hz), 5.07 (s, 1H), 3.41 (m, 4H), 3.31 (s, 2H), 1.94, (m, 4).

$^{13}$C{$^1$H}(C₆D₆) δ6 149.9, 145.1, 141.6, 125.5, 124.2, 123.8, 120.3, 100.6, 50.2, 35.5, 25.2.

(47)

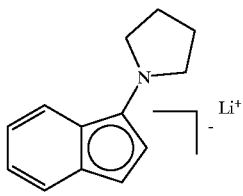

Preparation of(1-(1-pyrrolidinyl)-1H-indenyl)lithium, (47). In the drybox 3.5 g (18.9 mmol) of 1-(1H-inden-3-yl) pyrrolidine was combined with 100 mL of hexane. To this solution 9.5 mL (18.9 mmol) of n-BuLi (2.0 M) was added dropwise. Upon complete addition of the n-BuLi the solution was stirred overnight. The resulting precipitate was collected via filtration, washed with hexane and dried under reduced pressure to give 3.61 g of product. Yield 99 percent.

(48)

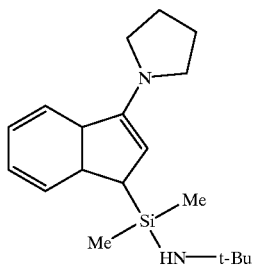

Preparation of N-(1,1-dimethylethyl)-1,1-dimethyl-1-(3-(1-pyrrolidinyl)-1H-inden-1-yl)silanamine, (48). A solution of (1-(1-pyrrolidinyl)-1H-indenyl)lithium (3.30 g, 17.25 mmol) in 40 mL of THF was added within 30 minutes to a 100 mL THF solution N-(tert-butyl)-N-(1-chloro-1,1-dimethylsilyl)amine (2.86 g, 17.25 mmol). After the addition was complete the reaction mixture was stirred overnight. The solvent was then removed under reduced pressure. The residue was extracted with hexane and the solution was filtered. The solvent was then removed under reduced pressure leaving 5.13 g of product. Yield 95 percent.

$^1$H (C$_6$D$_6$) δ0.07 (s, 3H), 0.05 (s, 3H), 1.27 (s, 9H), 2.03 (m, 4H), 3.43 (m, 4H), 5.41 (s, 1H), 7.24 (m, 2H), 7.53 (d, 1H, $^3$J$_{H-H}$=7.7 Hz), 7.70 (d, 1H, $^3$J$_{H-H}$=7.7 Hz).

$^{13}$C{$^1$H}(C$_6$D$_6$) δ2.71, 4.28, 26.19, 34.93, 49.06, 50.68, 54.30, 58.00, 84.15, 104.16, 123.91, 124.50, 125.05, 133.58, 143.95.

(49)

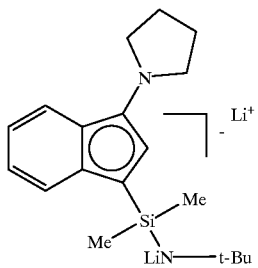

Preparation of (1-(((1,1-dimethylethyl)amino)dimethylsilyl)-3-(1-pyrrolidinyl)-1H-indenyl)lithium, lithium salt, (49). In the drybox 5.13 g (16.3 mmol) of N-(1,1-dimethylethyl)-1,1-dimethyl-1-(3-(1-pyrrolidinyl)-1H-inden-1-yl)silanamine were combined with 80 mL of hexane. To this solution 16.3 mL (32.6 mmol) of n-BuLi (2.0 M) were added dropwise. Upon complete addition of the n-BuLi the solution was stirred overnight. The resulting precipitate was collected via filtration, washed with 50 mL of hexane and dried under reduced pressure to give 5.33 g of product. Yield 100 percent.

(50)

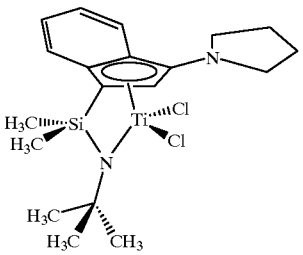

Preparation of dichloro(N-(1,1-dimethylethyl)-1,1-dimethyl-1-((1,2,3,3a,7a-η)-3-(1-pyrrolidinyl)-1H-inden-1-yl)silanaminato(2-)-N)titanium, (50). TiCl$_3$ (THF)$_3$ (6.05 g, 16.32 mmol) was suspended in 30 mL of THF. To this solution (1-(((1,1-dimethylethyl)amino)dimethylsilyl)-3-(1-pyrrolidinyl)-1H-indenyl)lithium, lithium salt (5.33 g, 16.32 mmol) was added as a solid. After 1 hour PbCl$_2$ (2.27 g, 8.16 mmol) was added as a solid. The reaction mixture was then stirred an additional hour. The solvent was removed under reduced pressure. The residue was extracted with 70 mL of toluene and filtered. Toluene was removed under reduced pressure and the residue was triturated with hexane. The solid was collected by filtration, washed with hexane and then dried under reduced pressure. 5.08 g Of product was obtained. Yield 72 percent.

$^1$H (C$_6$D$_6$) δ0.67 (s, 3H), 0.84 (s, 3H), 1.316 (s, 9H), 2.05 (br s, 4H), 3.71 (br s, 2H), 4.01 (br s, 2H) 7.25 (m, 2H), 7.63 (d, 1H), 7.91 (d, 1H).

$^{13}$C{$^1$H}(C$_6$D$_6$) δ1.58, 25.75, 32.97, 50.49, 61.05, 93.11, 106.51, 126.32, 126.89, 127.14, 129.00, 135.82, 149.54.

HRMS (EI, M$^+$): calcd 430.0881, found 430.0881.

Example 19

(51)

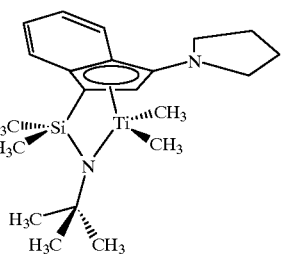

Preparation of (N-(1,1-dimethylethyl)-1,1-dimethyl-1-((1,2,3,3a,7a-η)-3-(-pyrrolidinyl)-1H-inden-1-yl)silanaminato(2-)-N)dimethyltitanium, (51). 0.50 g Of dichloro(N-(1,1-dimethylethyl)-1,1-dimethyl-1-((1,2,3,3a,7a-η)-3-(1-pyrrolidinyl)-1H-inden-1-yl)silanaminato(2-)-N)titanium (1.15 mmol) was suspended in 40 mL of Et$_2$O. To this suspension 0.77 mL of MeMgI (3.0 M) was added dropwise with stirring over a 20 minute period. Upon completion of the addition of the MeMgI the solution was stirred for 40 minutes. After this time the Et$_2$O was removed under reduced pressure and the residue extracted with hexane, the solution filtered, the filtrate evaporated to dryness under reduced pressure to give 0.39 g of product. Yield 86 percent.

$^1$H (C$_6$D$_6$) δ0.10 (s, 3H), 0.50 (s, 3H), 0.65 (s, 3H) 0.75 (s, 3H), 1.53 (s, 9H), 3.23 (m, 4H), 3.23 (m, 4H), 5.43 (s,

1H), 6.95 (t, 1H, $^3J_{H—H}$=7.9 Hz), 7.06 (t, 1H, $^3J_{H—H}$=7.91 Hz), 7.54 (d, 1H, $^3J_{H—H}$=8.5 Hz), 7.63 (d, 1H, $^3J_{H—H}$=8.5 Hz).

$^{13}C\{^1H\}(C_6D_6)$ δ2.62, 2.71, 4.82, 4.90, 26.19, 34.90, 49.06, 50.58, 54.31, 58.00, 84.15. 104.15, 123.91, 124.49, 125.05, 125.63, 133.58. 143.95.

Example 20

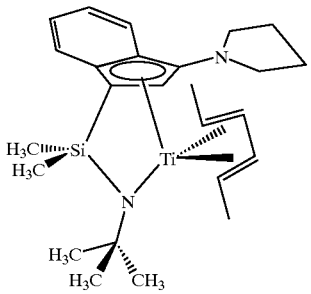

(52)

Preparation of (N-(1,1-dimethylethyl)-1,1-dimethyl-1-((1,2,3,3a,7a-η)-3-(1-pyrrolidinyl )-1H-inden-1-yl)silanaminato(2-)-N)((2,3,4,5-η)-2,4-hexadiene)titanium, (52). In the drybox 0.40 g of dichloro(N-(1,1-dimethylethyl)-1,1-dimethyl-1-((1,2,3,3a,7a-η)-3-(1-pyrrolidinyl)-1H-inden -yl)silanaminato(2-)-N)titanium were combined with 0.76 g of 2,4-hexadiene and suspended in 50 mL of hexane. To this solution 1 15 mL of n-BuLi (1.6M) were added and the solution was refluxed for 2 hours. The solution was then cooled to room temperature, filtered and the solvent was removed under reduced pressure. The residue was then taken up in the minimum amount of hexane and cooled to −20° C. overnight to give 0.16 g of product. Yield 38 percent.

$^1H$ ($C_6D_6$) δ0.77 (s, 3H), 0.96 (s, 3H), 1.14 (s, 9H), 1.32 (m, 7H), 1.61 (m, 1H), 1.81 (m, 1H),2.12 (d, 3H), 2.91 (m, 4H), 3.45(m, 1H), 3.65(m, 1H), 5.30(s, 1H), 6.69 (m, 1H), 6.96 (m, 1H), 7.05 (d, 1H, $^3J_{H—H}$=8.5 Hz), 7.83 (d, 1H $^3J_{H—H}$=8.5 Hz).

$^{13}C\{^1H\}(C_6D_6)$ δ4.22, 6.41, 15.88, 20.84, 25.58, 35.18, 49.66, 55.95, 78.03, 96.87, 109.79, 116.86, 112.86, 119.46, 122.15, 122.63, 122.90, 126.53, 126.92, 127.10, 128.88, 130.11, 130.76, 140.41.

Example 21

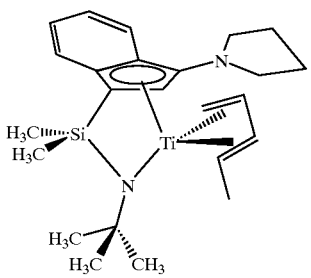

(53)

Preparation of (N-(1,1-dimethylethyl)-1,1-dimethyl-1-((1,2,3,3a,7a-η)-3-(1-pyrrolidinyl)-1H-inden-1-yl) silanaminato(2-)-N)((2,3,4,5-η)-2,4-pentadiene)titanium, (53). In the drybox 0.50 g (1.16 mmol) of dichloro(N-(1,1-dimethylethyl)-1,1-dimethyl-1-((1,2,3,3a,7a-η)-3-(1-pyrrolidinyl)-1H-inden-1-yl)silanaminato-(2-)-N-)titanium were dissolved in 30 mL of hexane. To this solution, 1.14 mL of piperylene (11.6 mmol) was added all at once, followed by dropwise addition of 1.28 mL of n-BuMgCl (2 M in hexanes, 2.55 mmol). The mixture was refluxed for 3 hours and then the solvent was removed in vacuo. The residue was dissolved in 15 mL of pentane, the solution was filtered through a Celite-covered frit, and the solvent was removed under vacuum. The product was obtained as a slightly moist, dark brown solid (0.47 g, 95 percent yield).

$^1H$ ($C_6D_6$) δ8.10 (d, 1H, $^3J_{HH}$=8.4 Hz), 7.82 (d, 1H, $^3J_{HH}$=8.6 Hz), 7.13 (m, 2H), 6.81 (m, 4H), 5.60 (s, 1H), 5.16 (s, 1H), 4.07 (dd, 1H, $^3J_{HH}$=11, 11 Hz). 3.77 (m, 4H), 3.46 (dd, 1H, $^3J_{HH}$=8, 8 Hz), 2.85 (m, 8H), 2.12 (d, 3H, $^3J_{HH}$=1.8–1.4 (m, 4H), 1.38 (d, $^3H$, $^3J_{HH}$=5.4 Hz), 1.29 (m, 8H), 1.17 (s, 9H), 1.15)s, 9H), 1.02 (s, 3H), 0.94 (s, 3H), 0.83 (s, 3H), 0.79 (s, 3H) ppm.

Example 22

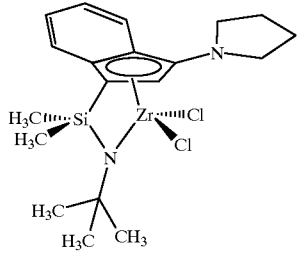

(54)

Preparation of Dichloro(N-(1,1-dimethylethyl )-1,1-dimethyl-1-((1,2,3,3a,7a-η)-3-(1-pyrrolidinyl)-1H-inden-1-yl)silanaminato-(2-)-N-)zirconium, (54). N-(1,1-Dimethylethyl)-1,1-dimethyl-1-(3-(1-pyrrolidinyl)-1H-inden-1-yl)silanamine, dilithium salt (2.41 g, 7.72 mmol) was added slowly as a solid to a slurry of $ZrCl_4$ (1.80 g, 7.72 mmol) in toluene (100 mL). This mixture was then allowed to stir overnight. After the reaction period the mixture was filtered and the volatiles were removed resulting in the isolation of the desired product as a gold microcrystalline solid (1.7386 g, 48.9 percent yield).

$^1H$ NMR ($C_6D_6$) δ0.51 (s, 3H), 0.69 (s, 3H), 1.33 (s, 9H), 1.7–1.7 (m, 4 H), 3.1–3.2 (m, 2H), 3.4–3.5 (m, 2H), 5.59 (s, 1H), 6.9–7.0 (m, 2H), 7.6–7.7)m, 1H), 7.63 (d, 1H $^3J_{HH}$=8.5 Hz).

$^{13}C$ NMR ($C_6D_6$) δ2.28, 4.62, 25.68, 33.28, 50.68, 56.72, 82.15, 103.56, 122.56, 125.49, 125.62, 126.13, 129.28, 133.58, 142.98.

HRMS (EI, M$^+$): calcd 474.0432, found 474.0419

Example 23

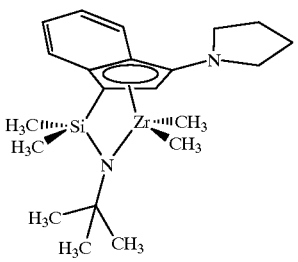

(55)

Preparation of (N-(1,1-dimethylethyl)-1,1-dimethyl-1-((1,2,3,3a,7a-η)-3-(1-pyrrolidinyl)-1H-inden-1-yl)silanaminato(2-)-N-)dimethylzirconium, (55). Dichloro(N-(1,1-dimethylethyl)-1,1-dimethyl-1-((1,2,3,3a,7a-η)-3-(1-pyrrolidinyl)-1H-inden-1-yl)silanaminato-(2-)-N-)zirconium (0.99 g, 2.09 mmol) was stirred in diethylether (50 mL) as MeMgBr (4.60 mmol, 1.53 mL of a 3.0 M solution in diethylether) was added slowly. This mixture was then allowed to stir overnight. After the reaction period the volatiles were removed and the residue was extracted and filtered using hexane. Removal of the hexane resulted in the isolation of the desired product as a red residue (0.72 g, 79 percent yield).

$^1$H NMR ($C_6D_6$) δ −0.58 (s, 3H), 0.22 (s, 1H), 0.51 (s, 3H), 0.69 (s, 3H), 1.37 (s, 9H), 1.0–1.2 (m, 4H), 3.1–3.2 (m, 2H), 3.3–3.4 (m, 2H), 5.60 (s, 1H), 6.88 (t, 1H, $^3J_{HH}$=7.35 Hz), 6.96 (t, 1H, $^3J_{HH}$=6.57 Hz), 7.54 (d, 1H, $^3J_{HH}$=8.49 Hz), 7.68 (d, 1H, $^3J_{HH}$=8.58 Hz).

$^{13}$C NMR ($C_6D_6$) δ3.06, 5.11, 25.72, 34.54, 35.54, 40.32, 50.81, 55.17, 77.82, 103.10, 121.41, 122.96, 125.12, 125.25, 125.78, 132.33, 139.91.

Example 24

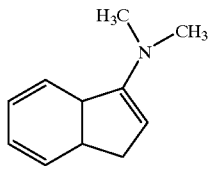

(56)

Preparation of N,N-dimethyl-1H-inden-3-amine, (56). This compound was made by a modification of the general method of Carlson and Nilsson (Carlson, R., Nilsson, A. *Acta Chemica Scand B* 1984, 38, 49–53.). To a 3-neck 500 mL flask equipped with an overhead stirrer, septum and maintained under nitrogen were added 150 mL of dry hexane. The solvent was cooled to −20 to −30° C. while anhydrous dimethylamine (12.6 g, 280 mmol) was purged into the solvent such that no gas escaped through the bubbler. To the cooled, well-stirred solution was added $TiCl_4$ (6.63 g, 35.0 mmol) dropwise such that the pot temperature remained between −30 and −15° C. (caution: a Hershberg stirrer is advisable due to titanium amide formation). The resulting dark brown slurry was stirred for 15 minutes and allowed to come to 0° C. before I-indanone (4.32 g, 32.7 mmol) was added all at once as a solid. The solution was allowed to come to room temperature, and then was heated to 60° C. for 5 minutes whereupon more $TiO_2$ precipitated from the slurry and the solution became clear. The slurry was filtered through a 4 cm pad of oven-dried Celite under a nitrogen stream and the solvent was removed in vacuo to afford title enamine (3.8 g. 23.8 mmol) in 73 percent yield as a dark oil which contained no detectable ketone by NMR analysis. The product assayed at 98 area percent purity by GC analysis.

$^1$H NMR (CDCl$_3$) δ7.49 (d, 1H, J=7.4 Hz), 7.42 (d, 1H, J=7.4 Hz), 7.30 (d, 1H, J=7.4 Hz), 7.21 (d, 1H, J=7.4 Hz), 5.46 (s, 1H), 3.31 (s, 2H), 2.83 (s, 6H).

$^{13}$C{$^1$H} NMR (CDCl$_3$) δ153.8, 144.6, 141.3, 125.6, 124.3, 123.8, 119.9, 107.8, 42.9, 35.6.

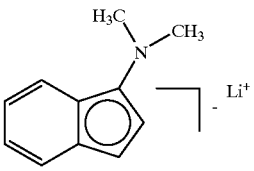

(57)

Preparation of (1-(dimethylamino)-1H-indenyl)lithium, (57). In the drybox 3.8 g (23.9 mmol) of N,N-dimethyl-1H-inden-3-amine was combined with 100 mL of hexane. To this solution 15 mL (23.9 mmol) of n-BuLi (1.6 M) was added dropwise. Upon complete addition of the n-BuLi the solution was stirred overnight. The resulting precipitate was collected via filtration, washed with hexane and dried under reduced pressure to give 3.58 g of product. Yield 91 percent.

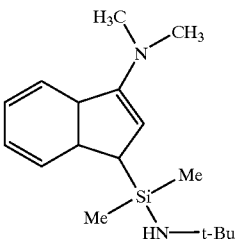

(58)

Preparation of 1-(3-(dimethylamino)-1H-inden-1-yl)-N-(1,1-dimethylethyl)-1,1-dimethylsilanamine, (58). A solution of (1-(dimethylamino)-1H-indenyl)lithium (3.58 g, 21.67 mmol) in 40 mL of THF was added within 30 minutes to a 80 mL THF solution of N-(tert-butyl)-N-(1-chloro-1,1-dimethylsilyl)amine (3.59 g, 21.67 mmol). After the addition was complete the reaction mixture was stirred overnight. The solvent was then removed under reduced pressure. The residue was extracted with hexane and the solution was filtered. The solvent was then removed under reduced pressure leaving 5.92 g of product. Yield 95 percent.

$^1$H ($C_6D_6$) δ−0.05 (s, 3H), 0.03 (s, 3H), 1.06 (s, 9H), 2.68 (s, 6H), 3.40 (s, 1H), 5.63 (s, 1H), 7.24 (m, 2H), 7.56 (d, 1H, $^3J_{H-H}$=7.4 Hz), 7.56 (d, 1H, $^3J_{H-H}$=7.4 Hz).

$^{13}$C{$^1$H}($C_6D_6$) δ−0.46, 0.43, 34.08, 43.33, 44.00, 49.60, 111.20, 120.50, 123.84, 122.63, 123.84, 124.04, 124.75, 141.38, 146.44, 152.92.

Example 25

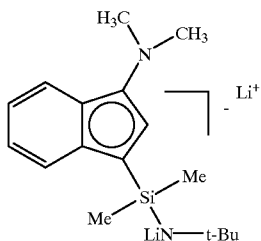
(59)

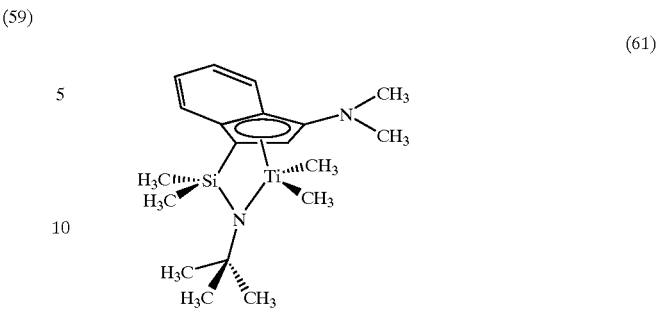
(61)

Preparation of (3-(dimethylamino)-1-(((1,1-dimethylethyl)amino)dimethylsilyl)-1H-indenyl)lithium, lithium salt, (59). In the drybox 5.92 g (20.51 mmol) 1-(3-(dimethylamino)-1H-inden-1-yl)-N-(1,1-dimethylethyl)-1,1-dimethylsilanamine were combined with 80 mL of hexane. To this solution 25.6 mL (41.04 mmol) of n-BuLi (1.6 M) was added dropwise. Upon complete addition of the n-BuLi the solution was stirred overnight. The resulting precipitate was collected via filtration, washed with 50 mL of hexane and dried under reduced pressure to give 5.45 g of material. Yield 88 percent.

Preparation of (1-((1,2,3,3a,7a-η)-3-(dimethylamino)-1H-inden-1-yl)-N-(1,1-dimethylethyl)-1,1-dimethylsilanaminato(2-)-N)dimethyltitanium, (61). 0.60 g Of Dichloro(1-((1,2,3,3a,7a-η)-3-(dimethylamino)-1H-inden-1-yl)-N-(1,1-dimethylethyl)-1,1-dimethylsilanaminato(2-)-N)titanium (1.53 mmol) was suspended in 40 mL of Et$_2$O. To this suspension 1.07 mL of MeMgI (3.0 M) was added dropwise with stirring over a 20 minute period. Upon completion of the addition of the MeMgI the solution was stirred for 40 minutes. After this time the Et$_2$O was removed under reduced pressure and the residue was extracted with hexane, the solution was filtered and the filtrate was evaporated to dryness under reduced pressure to give 0.43 g of product. Yield 80 percent.

$^1$H (C$_6$D$_6$) δ0.03 (s, 3H), 0.44 (s, 3H), 0.63 (s, 3H), 0.85 (s, 3H), 1.49 (s, 9H), 2.78 (s, 6H), 5.56 (s, 1H), 6.85 (t, 1H, $^3J_{H-H}$=7.5 Hz), 7.06 (t, 1H, $^3J_{H-H}$=7.5 Hz), 7.44 (d, 1H, $^3J_{H-H}$=8.5 Hz), 7.63 (d, 1H, $^3J_{H-H}$=8.7 Hz).

Example 26

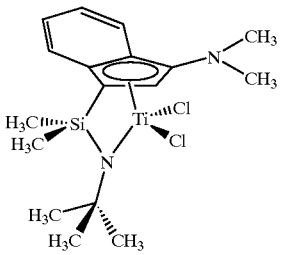
(60)

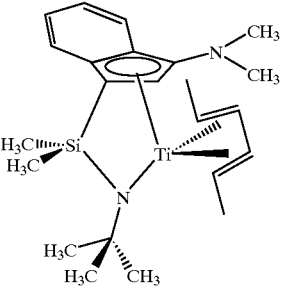
(62)

Preparation of dichloro(1-((1,2,3,3a,7a-η)-3-(dimethylamino)-1H-inden-1-yl)-N-(1,1-dimethylethyl)-1,1-dimethylsilanaminato(2-)-N)titanium, (60). (3-(Dimethylamino)-1-(((1,1-dimethylethyl)amino)dimethylsilyl)-1H-indenyl)lithium, lithium salt (5.45 g, 18.14 mmol) was dissolved in 30 mL of THF. To this solution TiCl$_3$ (THF)$_3$ (6.72 g, 18.14 mmol) was added as a solid. After 1 hour PbCl$_2$ (2.52 g. 9.07 mmol) was added as a solid. The reaction mixture was then stirred an additional hour. The solvent was removed under reduced pressure. The residue was extracted with 70 mL of toluene and filtered. Toluene was removed under reduced pressure and the residue was triturated with hexane. The solid was collected by filtration, washed with hexane and then dried under reduced pressure. 4.00 g Of product was obtained. Yield 56 percent.

$^1$H (C$_6$D$_6$) δ0.48 (s, 3H), 0.61 (s, 3H), 1.06 (s, 9H), 2.82 (s, 3H), 5.74 (s, 1H), 7.00 (m, 2H), 7.14 (t, 2H, $^3J_{H-H}$=7.5 Hz).

$^{13}$C{$^1$H}(C$_6$D$_6$) δ2.43, 4.85, 34.73, 42.79, 50.17, 54.73, 107.25. 124.41, 124.98, 125.09, 137.0, 145.01.

Preparation of (1-((1,2,3,3a,7a-η)-3-(dimethylamino)-1H-inden-1-yl)-N-(1,1-dimethylethyl)-1,1-dimethylsilanaminato(2-)-N)((2,3.4,5-η)-2,4-hexadiene) titanium, (62). To 0.5490 g of dichloro(1-((1,2,3,3a,7a-η)-3-(dimethylamino)-1H-inden-1-yl)-N-(1,1-dimethylethyl)-1,1-dimethylsilanaminato(2-)-N)titanium (1.35 mmol) slurried/dissolved in 50 mL of hexane was added 1.4 mL of 2.4-hexadiene (12.3 mmol), followed by 1.63 mL of BuMgCl (2.0 M in Et$_2$O) (3.26 mmol) along with an additional 3 mL of Et$_2$O. The reaction mixture was refluxed for 1.5 hours, then the reaction mixture was allowed to stir overnight. The solvents were removed under reduced pressure and the residue was extracted with hexane, the solution was filtered and the filtrate was evaporated to dryness under reduced pressure. After adding hexane to dissolve the very dark product, the solution wits stored overnight in a freezer. The supernatant was removed to give 0.0735 g of black crystalline material. The supernatant was concentrated, then cooled in the freezer again to give additional product.

$^1$H (C$_6$D$_6$) δ0.72 (s, 3H), 0.94 (s, 3H), 1.10 (s, 9H), 1.26 (d, 3H, $^3J_{H-H}$=5.3 Hz), 1.60 (m, 1H), 1.78 (m, 1H), 2.10 (d, 3H, $^3J_{H-H}$=5.5 Hz), 2.37 (s, 6H), 3.38 (m, 1H), 3.97 (m, 1H), 5.46 (s, 1H), 6.68 (t, 1H, $^3J_{H-H}$=7.7 Hz), 6.94 (m, 2H), 7.87 (d, 1H, $^3J_{H-H}$=8.5 Hz).

$^{13}$C (C$_6$D$_6$) δ142.9, 130.0, 128.9, 123.2, 122.5, 121.8, 120.1, 112.4, 109.3, 99.0, 92.3, 79.6, 78.6, 56.4, 42.3, 35.0, 20.3, 15.7, 14.4, 6.4, 4.1. High resolution MS: Calcd for C$_{23}$H$_{36}$N$_2$SiTi: 416.2127. Found: 416.2107

Example 27

(63)

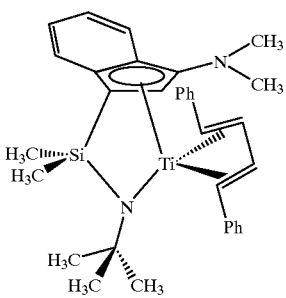

Preparation of (1,1'-(η$^4$-1,3-butadiene 1,4-diyl)bis(benzene))(1-((1,2,3,3a,7a-η)-3-(dimethylamino)-1H-inden-1-yl)-N-(1,1-dimethylethyl)-1,1-dimethylsilanaminato(2-)-N)titanium, (63). In the drybox 0.40 g of dichloro(1-((1,2,3,3a,7a-η)-3-(dimethylamino)-1H-inden-1-yl)-N-(1,1-dimethylethyl)-1,1-dimethylsilanaminato(2-)-N)titanium was combined with 0.21 g of trans-1,4-diphenylbutadiene and suspended in 30 mL of hexane. To this[] solution 1.27 mL of n-BuLi (1.6 M) was added and the solution was refluxed for 2 hours. The solution was then cooled to room temperature, filtered and the solvent was removed under reduced pressure to give 0.23 g of product. Yield 43 percent.

$^1$H (C$_6$D$_6$) δ0.68 (s, 3H), 0.82 (s, 3H), 1.25 (s, 9H), 1.47 (s, 9H), 3.45 (m, 1H), 3.60 (m, 1H), 4.15 (m, 1H) 4.65 (m, 1H), 5.20 (s, 1H), 6.30–7.55 (m, 14H).

Example 28

(64)

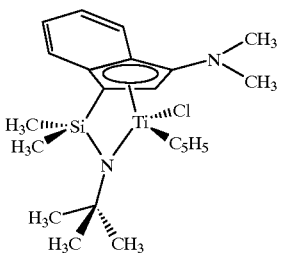

Preparation of chloro(cyclopentadienyl)(1-((1,2,3,3a,7a-η)-3-(dimethylamino)-1H-inden-1-yl)-N-(1,1-dimethylethyl)-1,1-dimethylsilanaminato(2-)-N)titanium, (64). To 0.312 g of dichloro(1-((1,2,3,3a,7a-η)-3-(dimethylamino)-1H-inden-1-yl)-N-(1,1-dimethylethyl)-1,1-dimethylsilanaminato(2-)-N)titanium (0.77 mmol) dissolved in about 35–40 mL of Et$_2$O was slowly added 0.769 mL of NaC$_5$H$_5$ (1.0 M in Et$_2$O) (1.00 mmol). The purple reaction mixture was allowed to stir for a day and a half. The solvents were removed under reduced pressure and the residue was extracted with hexane, the solution was filtered and the filtrate was evaporated to dryness under reduced pressure. After adding hexane to dissolve the very dark product, the very intensely-colored magenta solution was stored overnight in a freezer. After removing the supernatant and drying under reduced pressure the product was obtained as 0.1119 g of crystals. The supernatant was concentrated, then cooled in the freezer to give additional product as microcrystals.

$^1$H (C$_6$D$_6$) δ0.50 (s, 3H), 0.60 (s, 3H), 1.31 (s, 9H), 2.73 (s, 6H), 5.69 (s, 1H), 5.78 (s, 1H), 6.79 (t, 1H, $^3J_{H-H}$=7.4 Hz), 7.15 (m, 2H), 7.33 (d, 1H, $^3J_{H-H}$=8.2 Hz).

$^{13}$C (C$_6$D$_6$) δ170.8, 158.6, 126.6, 124.3, 121.3, 121.1, 115.4, 95.2, 88.4, 61.2, 42.5, 32.9, 3.9, 2.7. High resolution MS: Calcd for C$_{22}$H$_{31}$ ClN$_2$SiTi: 434.14245. Found: 434.1426

Example 29

(65)

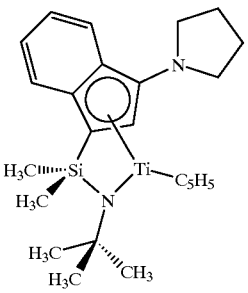

Preparation of cyclopentadienyl(N-(1,1-dimethylethyl)-1,1-dimethyl-1-((1,2,3,3a,7a-η)-3-(1-pyrrolidinyl)-1H-inden-1-yl )silanaminato(2-)-N)titanium, (65). To a well-stirred solution of 0.56 g of tris(cyclopentadienyl)titanium (2.31 mmol) in about 50 mL of THF was slowly added 0.75 g of the dilithium salt of (N-(1,1-dimethylethyl)-1,1-dimethyl-1-(-3-pyrrolidino-1H-inden-1-yl)silanamine (2.31 mmol) as a powder. The yellowish-green (reddish to transmitted light) reaction mixture was allowed to stir overnight. The solvents were removed under reduced pressure and the residue was extracted with about 80 mL of toluene, the solution was filtered to remove a very pale lavender solid from the dark olive-green-brown filtrate. Both product fractions were dried under reduced pressure. The dark toluene-soluble product was extracted with hexane, filtered and the solvent was removed from the deep brown solution to give 0.9113 g of the product as a black-appearing powder (93 percent). Proton NMR showed only broad humps in the 0.8–2.4 ppm region. ESR showed a signal at g=1.98 consistent with a Ti(III) complex. The pale solid collected on the filter was extracted with THF, filtered and the solvent was removed under reduced pressure to give 0.29 g of a pale lavender-pink solid (87 percent, based on LiC$_5$H$_5$). To a solution of 0.20 g of the "LiC$_5$H$_5$" (2.78 mmol) in about 20 mL of THF was added 0.179 g of FeCl$_2$ (1.40 mmol). The solution was stirred for about 4–5 hours. The solvent was removed under reduced pressure. The residue was extracted with toluene, filtered and the solvent was removed under reduced pressure to give 0.22 g of an orange powder which was identified as ferrocene. Yield 85 percent.

$^1$H (C$_6$D$_6$) δ4.00 (s).

$^{13}$C (C$_6$D$_6$) δ68.3. High resolution MS: Calcd for C$_{10}$H$_{10}$Fe: 186.0132. Found: 186.0124

Example 30

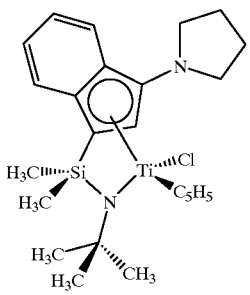

(66)

Preparation of chloro(cyclopentadienyl)(N-(1,1-dimethylethyl)-1,1-dimethyl-1-((1,2,3,3a,7a-η)-3-(1-pyrrolidinyl)-1H-inden-1-yl)silanaminato(2-)-N)titanium, (66). To a solution of 0.0240 g of cyclopentadienyl(N-(1,1-dimethylethyl)-1,1-dimethyl-1-((1,2,3,3a,7a-η)-3-(1-pyrrolidinyl)-1H-inden-1-yl)silanaminato(2-)-N)titanium (0.056 mmol) from above in about 0.5–1 mL of C$_6$D$_6$ in an NMR tube was added 0.048 g of PbCl$_2$ (0.17 mmol). The black solution instantly turned magenta in color. After about 20–30 minutes, the NMR spectra were taken on the crude reaction mixture.

$^1$H (C$_6$D$_6$) δ0.52 (s, 3H), 0.64 (s, 3H), 1.17 (br, 4H), 1.34 (s, 9H), 3.16 (br, 2H), 3.52 (br, 2H), 5.73, (s, 5H), 5.83, (s, 1H), 6.83 (t, 1H, $^3J_{H-H}$=7.4 Hz), 7.2 (m, 2H), 7.37 (d, 1H, $^3J_{H-H}$=8.0 Hz).

$^{13}$C(C$_6$D$_6$) δ167.7, 158.6, 127.3, 127.0, 126.6, 124.1, 121.1, 115.2, 93.6, 88.5, 61.0, 50.7, 32.9, 25.2, 4.0, 2.8. High resolution MS: Calcd for C$_{24}$H$_{33}$ClN$_2$SiTi: 460.1581 Found: 460.1580

Example 31

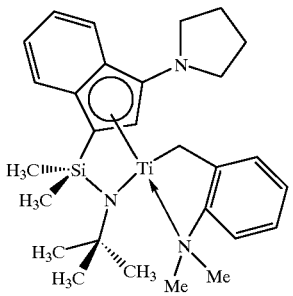

(67)

Preparation of (1-((1,2,3,3a,7a-η)-3-(dimethylamino)-1H-inden-1-yl)-N-(1,1-dimethylethyl)-1,1-dimethylsilanaminato(2-)-N)((2-(dimethylamino-N)phenyl)methyl-C)titanium, (67). To a solution of 0.3390 g of cyclopentadienyl(N-(1,1-dimethylethyl)-1,1-dimethyl-1-((1,2,3,3a,7a-η)-3-(1-pyrrolidinyl)-1H-inden-1-yl)silanaminato(2-)-N)titanium (0.797 mmol) in about 20 mL of Et$_2$O was slowly added 0.1125 g of (2-(N,N-dimethylamino)benzyl)lithium (0.797mmol) as a powder. The reaction mixture was allowed to stir overnight. The solvents were removed under reduced pressure from the deep brownish red solution and the residue was extracted with hexane and the very soluble brown-red solution was filtered from a very dark solid which is much less soluble in hexane. Both product fractions were dried under reduced pressure. Proton NMR spectra of both of the products (in C$_6$D$_6$) showed broad featureless peaks as have been observed for other Ti(III) compounds. After oxidizing the NMR samples with PbCl$_2$ it was determined by $^1$H NMR that the original reaction was incomplete. The solid on the frit was extracted with C$_6$D$_6$ and filtered and combined with the other product fraction. The solvent was removed under reduced pressure and the residue was taken up in about 15 mL of Et$_2$O to which was then added an additional 0.0170 g of (2-(N,N-dimethylamino)benzyl)lithium (total 0.918 mmol) as a powder. After stirring overnight and removing the solvent under reduced pressure, the residue was extracted with hexane, filtered from some solid material and the very dark filtrate was concentrated. The solid collected on the frit was placed in a vial with about 0.075 a of FeCl$_2$ and about 3 mL of THF and let stand overnight. The solvent was removed under reduced pressure and the residue was extracted with C$_6$D$_6$ and filtered into an NMR tube. NMR spectra showed the presence of Cp$_2$Fe and what appears to be a THF complex of an inorganic material. $^1$H (C$_6$D$_6$) δ2.00 (br s), 4.01 (s), 5.06 (br s). $^{13}$C (C$_6$D$_6$) δ72.0, 68.2, 35.1. As the filtrate was concentrated, a very dark solid began to crystallize out, leaving a deep venous blood-red solution. The solid was filtered out, washed with hexane and dried under reduced pressure. Yield of deep reddish-brown product: 0.1718 g. A proton NMR of 0.0399 g of the substance in C$_6$D$_6$ showed broad peaks of indistinct structure. ESR showed a signal at g=1.98 consistent with a Ti(III) complex. Magnetic susceptibility (Evans' method): 1.57 m$_B$.

Example 32

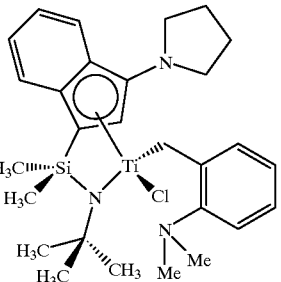

(68)

Preparation of chloro(1-((1,2,3,3a,7a-η)-3-(dimethylamino)-1H-inden-1-yl)-N-(1,1-dimethylethyl)-1,1-dimethylsilanaminato(2-)-N)((2-(dimethylamino)phenyl)methyl)titanium, (68). About 0.070 ? of PbCl$_2$ was added to a solution of 0.0224 g of (1-((1,2,3,3a,7a-η)-3-(dimethylamino)-1H-inden-1-yl)-N-(1,1-dimethylethyl)-1,1-dimethylsilanaminato(2-)-N)((2-(dimethylamino-N)phenyl)methyl-C)titanium (from above) in about ½ to 1 mL of C$_6$D$_6$ in an NMR tube. The reaction mixture was shaken, then let stand overnight. NMR spectra showed the presence of two isomers (approximately in a 1:2 ratio) along with a very small amount of the (chloro)(cyclopentadienyl) complex. $^1$H (C$_6$D$_6$) Unique peaks of one isomer δ0.67 (s, 1H), 0.81 (s, 1H), 1.63 (s, 9H), 2.07, (d, 1H,$^3J_{H-H}$=12.6 Hz), 2.54 (s, 6H), 2.64, (d, 1H, $^3J_{H-H}$=12.6 Hz), 3.17 (m, 2H), 3.57 (m, 2H), 5.53 (s, 1H), 6.35 (s, 1H). Unique peaks of the other isomer δ0.71, (s, 1H), 0.88 (s, 1H), 1.61 (s, 9H), 2.19, (d, 1H, $^3J_{H-H}$=13.5 Hz), 2.21 (m, 2H), 2.53 (s, 6H), 2.76

(m, 2H), 3.32 (d, 1H, $^3J_{H-H}$=13.5 Hz), 5.06 (s, 1H), 7.90 (d, 1H, $^3J_{H-H'}$=7.4 Hz). Common/undifferentiable peaks of both isomers δ1.38 (br, 4H), 6.66 (m), 6.76 (m), 6.87 (m), 7.08 (m), 7.40 (m).

$^{13}$C (C$_6$D$_6$) (both isomers) δ154.2, 153.5, 153.3. 152.9, 147.3, 142.8, 136.0, 133.4, 131.0, 130.0, 128.9, 125.8, 125.7, 125.6, 124.3, 123.4, 123.0, 122.7, 122.3, 122.1, 117.9, 114.3, 105.5, 130.8, 95.2, 95.0, 71.7, 69.6, 62.0, 61.3, 50.0, 49.9, 47.7, 47.4, 34.1, 34.1, 33.0, 31.9, 25.6, 14.4, 4.1, 2.8, 2.2, 1.3.

Example 33

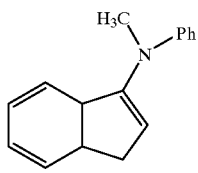
(69)

Preparation of N-methyl-N-phenyl-1H-inden-3-amine, (69). Into a dry flask equipped with a Dean-Stark trap and a reflux condenser were placed 1-indanone (10.0 g, 75.7 mmol). N-methylaniline (15.1 g, 141 mmol) and toluene (200 mL). A catalytic amount of p-toluenesulfonic acid (0.1 g) was added and the mixture was refluxed under N$_2$ for 96 hours. The reaction was cooled and the toluene was removed under reduced pressure before the remaining material was distilled under vacuum. The highest boiling fraction (6.8 g; bp 150–2° C./0.7 mm Hg) was collected as a yellow oil which solidified to a yellow-orange solid on standing. This material was stored in a glove box. Analysis by NMR indicated ca. 10 percent N-methylaniline in the product. However, further distillation on another sample of distilled enamine was not successful in lowering the amount of unwanted amine in the product.

$^{13}$H NMR (d$_8$-PhMe) δ6.78–7.25 (m, 9H); 5.62 (t, 1H); 3.24 (d, 2H); 3.05 (s, 3H).

$^{13}$C {$^1$H} NMR (d$_8$-PhMe) δ149.84, 149.02, 144.30, 141.85, 129.05, 125.82, 124.98, 124.06, 121.79, 121.69, 121.19, 113.66, 42.01, 35.89.

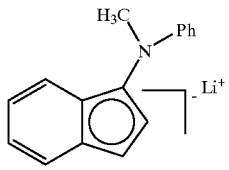
(70)

Preparation of (3-(methylphenylamino)-1H-indenyl) lithium, (70). N-Methyl-N-phenyl-1H-inden-3-amine(6.8g, 30.7 mmol) was dissolved in 100 mL of hexane and 10 12.3 mL of 2.5 M n-BuLi (0.936 eq) was added dropwise via syringe over a 15 minute period. The solution developed a yellow precipitate upon the addition of n-BuLi and the slurry was allowed to stir overnight. After this time the solid was filtered, washed with 50 mL of hexane and allowed to dry in Vacuo overnight to afford the desired anion as a yellow-orange solid (5.83 g, 25.6 mmol) in 89 percent yield based upon the lithio reagent.

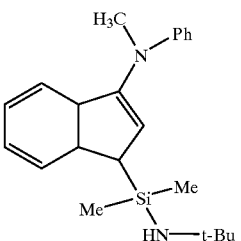
(71)

Preparation of N-(1,1-dimethylethyl)-1,1-dimethyl-1-(3-(methylphenylamino)-1H-inden-1-yl)silanamine, (71). (3-(Methylphenylamino)-1H-indenyl)lithium (3.10 g, 13.64 mmol) was dissolved in 50 mL of THF and added dropwise to a solution of t-butylaminodimethylsilylchloride (2.17 g, 16.35 mmol) in 35 mL. of THF over a 30 minute period, with stirring continued for 25 hours. The solvent was evaporated and the resulting oil was subjected to vacuum for 4 hours. This oil was dissolved in 100 mL of hexane and filtered of from LiCl. Solvent removal in vacuo and overnight vacuum devolatilization provided the product (4.66g, 13.3 mmol) as a dark red oil in 98 percent yield.

$^1$H NMR (C$_6$D$_6$) δ7.56 (d, 1H, J=7.4 Hz), 7.15 (m, 4H), 7.07 (d, 1H, J=7.4 Hz), 7.00 (d, 2H, J=8.0), 6.83 (m, 1H), 6.125 (d, 2H, J=2 Hz), 3.464 (d, 4H, J=2.0 Hz), 3.14 (s, 3H), 1.08 (s, 9H), 1.0 (broad s, 1H N—H), 0.04 (s, 3H), 0.0 (s, 3H).

$^{13}$C{$^1$H} NMR (C$_6$D$_6$) δ149.3, 147.6. 145.7. 141.2, 129.3, 124.8, 124.3, 123.6, 121.4, 120.7, 120.3, 118.8, 68.1, 49.7,44.9, 41.6.34.1, 33.9, 33.6, 25.3,0.54, –0.1.

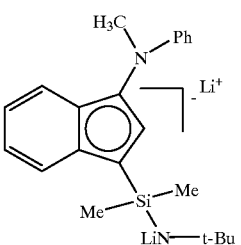
(72)

Preparation of (1-(((1,1-dimethylethyl)amino) dimethylsilyl)-3-(methylphenylamino)-1H-indenyl)lithium, lithium salt. (72). In the drybox 4.47 g (12.3 mmol) N-(1, 1-dimethylethyl)-1,1-dimethyl-1-(3-(methylphenylamino)-1H-inden-1-yl)silanamine was combined with 80 mL of hexane. To this solution 15.9 mL (25.5 mmol) of n-BuLi (1.6 M) was added dropwise. Upon complete addition of the n-BuLi the solution was stirred overnight. The resulting precipitate was collected via by filtration, washed with 50 mL hexane and dried under reduced pressure to give 4.25 g of product. Yield 92 percent.

(73)

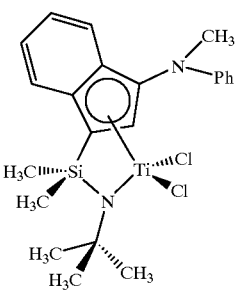

Preparation of dichloro(N-(1,1-dimethylethyl)-1,1-dimethyl-1-((1,2,3,3a,7a-η)-3-(1-methylphenylamino)-1H-inden-1-yl)silanaminato(2-)-N)titanium, (73). (1-(((1,1-Dimethylethyl)amino)dimethylsilyl)-3-(methylphenylamino)-1H-indenyl)lithium, lithium salt (4.25 g, 11.72 mmol) was dissolved in 30 mL of THF. To this solution TiCl$_3$(THF)$_3$ (4.34 g, 11.72 mmol) was added as a solid. After 1 hour PbCl$_2$ (1.63 g. 5.86 mmol) was added as a solid. The reaction mixture was then stirred an additional hour. The solvent was removed under reduced pressure. The residue was extracted with 70 mL of toluene and filtered. Toluene was removed under reduced pressure and the residue was triturated with hexane. The solid was collected by filtration, washed with hexane and then dried under reduced pressure, 1.57 g of product was obtained. Yield 29 percent.

$^1$H (C$_6$D$_6$) δ0.47 (s, 3H), 0.62 (s, 3H), 1.30 (s, 9H), 3.25 (s, 2H), 5.97 (s, 2H), 6.70 (d, 1H, $^3J_{H-H}$=8.1 Hz), 6.80 (m, 3H, $^3J_{H-H}$=7.9 Hz) 7.06 (t, 2H, $^3J_{H-H}$=8.1 Hz), 7.33 (d, 2H, $^3J_{H-H}$=7.9 Hz), 7.58 (d, 1H, $^3J_{H-H}$=7.9 Hz).

$^{13}$C{$^1$H}(C$_6$D$_6$) δ1.44, 3.89, 33.01, 43.21, 61.72, 93.96, 108.97, 125.93, 126.21, 126.33, 127.51, 128.15, 128.51, 135.53, 146.83, 148.49.

Example 34

(74)

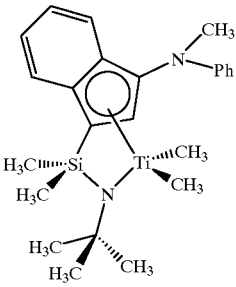

Preparation of (N-(1,1-dimethylethyl 1)-1,1-dimethyl-1-((1,2,3,3a,7a-η)-3-(1-methylphenylamino)-1H-inden-1-yl)silanaminato(2-)-N)dimethyltitanium, (74). 0.40 g of dichloro(N-(1,1-dimethylethyl)-1,1-dimethyl)1-((1,2,3,3a,7a-η)-3-(1-methylphenylamino)-1H-inden-1-yl)silanaminato(2-)-N)titanium (0.80 mmol) was suspended in 40 mL of Et$_2$O. To this suspension 0.57 mL of MeMgI (3.0 M) was added dropwise with stirring over a 20 minute period. Upon completion of the addition of the MeMgI the solution was stirred for 40 minutes. After this time the Et$_2$O was removed under reduced pressure and the residue was extracted with hexane, the solution was filtered and the filtrate was evaporated to dryness under reduced pressure to give 0.35 g of product. Yield 96 percent.

$^1$H (C$_6$D$_6$) δ0.62 (s, 3H), 0.70 (s, 3H), 0.69 (s, 3H), 1.04 (s, 3H), 1.54 (s,9H), 3.29 (s, 3H), 6.04 (s, 1H), 6.88 (m, 2H), 6.96 (t, 1H, $^3J_{H-H}$=7.9 Hz), 7.16 (t, 4H), 7.28 (d, 1H, $^3J_{H-H}$=8.5 Hz) 7.55 (d, 1H, $^3J_{H-H}$=8.5 Hz).

$^{13}${C$^1$H}(C$_6$D$_6$) δ1.58, 4.00, 34.07, 41.48, 52.29, 54.13, 58.24, 83.55, 112.67, 121.05, 121.98, 124.76, 126.24, 129.03, 132.45, 140.91, 148.68.

Example 35

(75)

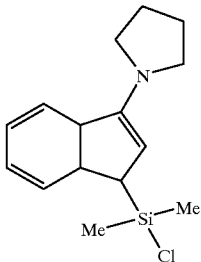

Preparation of 1-(1-(chlorodimethylsilyl)-1H-inden-3-yl)pyrrolidine, (75). A solution of (1-(1-pyrrolidinyl)-1H-indenyl)lithium (2.0) g. 10.46 mmol) in 25 mL of THF was added within 30 minutes to a 50 mL THF solution containing SiMe$_2$Cl$_2$ (8.1 g, 62.76 mmol). After the addition was complete the reaction mixture was stirred overnight. The solvent was then removed under reduced pressure. The residue was extracted with hexane and the solution was filtered. The solvent was then removed under reduced pressure leaving 2.40 g of product. Yield 82 percent.

$^1$H (C$_6$D$_6$) δ0.03 (s, 3H), 0.15 (s, 3H). 1.52 (m, 4H). 3.14 (m, 4H), 3.43 (s, 1H), 5.14 (s, 1H), 7.24 (m, 2H), 7.23 (m,2H). 7.60 (m, 2H).

$^{13}$C{$^1$H}(C$_6$D$_6$) δ–0.75, 0.48, 25.51, 42.72, 50.52, 100.02, 103.77, 121.18, 121.29, 124.30, 124.70, 125.58, 141.29, 144.61, 150.50.

(76)

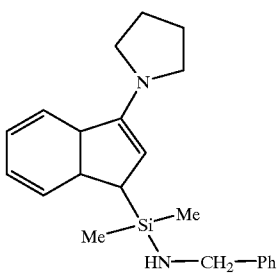

Preparation of 1,1-dimethyl-N-(phenylmethyl)-1-(3-(1-pyrrolidinyl)-1H-inden-1-yl)silanamine, (76). A solution of lithium benzylamide (0.97 g. 8.64 mmol) in 75 mL of THF was added within 30 minutes to a 150 mL THF solution of 1-(1-(chlorodimethylsilyl)-1H-inden-3-yl)pyrrolidine (2.40 g, 8.64 mmol). After the addition was complete the reaction mixture was stirred overnight. The solvent was then removed under reduced pressure. The residue was extracted with hexane and the solution was filtered. The solvent was then removed under reduced pressure leaving 2.99 g of product. Yield 99 percent.

$^1$H (C$_6$D$_6$) δ–0.04 (s, 3H), 0.06 (s, 3H), 1.58 (m, 4H), 3.22 (m, 4H), 3.76 (d, 4H), 5.32 (s, 1H), 7.24 (m, 7H), 7.47 (d, 1H, $^3J_{H-H}$=7.7 Hz). 7.63 (d, 1H, $^3J_{H-H}$=7.7 Hz).

$^{13}$C{$^1$H}(C$_6$D$_6$) δ–2.42, –3.16, 25.47, 43.84, 48.61, 50.91, 104.08, 121.65, 124.64, 126.65, 127.24, 128.46, 141.43, 144.42, 146.68, 148.87.

(77)

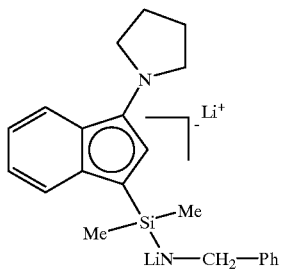

Preparation of (1-(((phenylmethyl)amino)dimethylsilyl)-3-(1-pyrrolidinyl)-1H-indenyl)lithium, lithium salt, (77). In the drybox 2.99 g (8.50 mmol) 1,1-dimethyl-N-(phenylmethyl)-1-(3-(1-pyrrolidinyl)-1H-inden-1-yl)silanamine was combined with 80 mL of hexane. To this solution 11.25 mL (18.0 mmol) of n-BuLi (1.6 M) was added dropwise. Upon complete addition of the n-BuLi the solution was stirred overnight. The resulting precipitate was collected via by filtration, washed with 50 mL of hexane and dried under reduced pressure to give 2.87 g of product. Yield 93 percent.

(78)

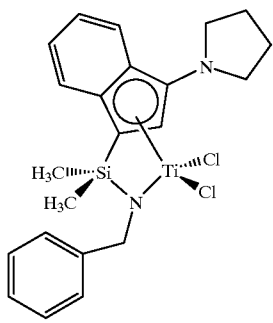

Preparation of dichloro(1,1-dimethyl-N-(phenylmethyl)-1-((1,2,3,3a,7a-η)-3-(1-pyrrolidinyl)-1H-inden-1-yl)silanaminato(2-)-N)titanium, (78). (1-(((Phenylmethyl)amino)dimethylsilyl)-3-(1-pyrrolidinyl)-1H-indenyl)lithium lithium salt (2.87 g, 7.96 mmol) was dissolved in 30 mL of THF. To this solution TiCl$_3$ (THF)$_3$ (2.95 g, 7.96 mmol) was added as a solid. After 1 hour PbCl$_2$ (1.10 g, 3.98 mmol) was added as a solid. The reaction mixture was then stirred an additional hour. The solvent was removed under reduced pressure. The residue was extracted with 70 mL of toluene and filtered. Toluene was removed under reduced pressure and the residue was triturated with hexane. The solid was collected by filtration, washed with hexane and then dried under reduced pressure. 2.30 g Of product was obtained. Yield 62 percent.

$^1$H (C$_6$D$_6$) δ0.17 (s, 3H), 0.27 (s, 3H), 1.48 (m, 4H), 3.19 (m, 2H), 3.50 (m, 2H), 5.25 (AB q, 2H, $^2J_{H-H}$=18.7 Hz) 7.03 (m, 5H), 7.21 (m, 2H), 7.57 (d, 1H, $^3J_{H-H}$=7.9 Hz), 7.61 (d, 1H, $^3J_{H-H}$=7.9 Hz).

Example 36

(79)

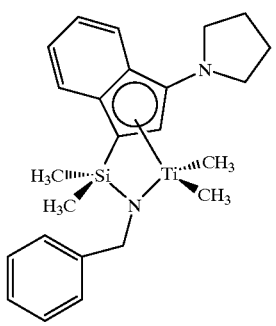

Preparation of (1,1-dimethyl-N-(phenylmethyl)-1-((1,2,3,3a,7a-η)-3-(1-pyrrolidinyl)-1H-inden-1-yl)silanaminato(2-)-N)dimethyltitanium, (79). 0.30 g Of dichloro(1,1-dimethyl-N-(phenylmethyl)-1-((1,2,3,3a,7a-η)-3-(1-pyrrolidinyl)-1H-inden-1-yl)silanaminato(2-)-N)titanium (0.64 mmol) was suspended in 40 mL of Et$_2$O. To this suspension 0.45 mL of MeMgI (3.0 M) was added dropwise with stirring over a 20 minute period. Upon completion of the addition of the MeMgI the solution was stirred for 40 minutes. After this time the Et$_2$O was removed under reduced pressure and the residue was extracted with hexane, the solution was filtered and the filtrate was evaporated to dryness under reduced pressure to give 0.23 g of product. Yield 84 percent.

$^1$H (C$_6$D$_6$) δ0.12 (s, 3H). 0.18 (s, 3H), 0.36 (s, 3H), 0.78 (s, 3H), 1.52 (m, 4H), 3.24 (m, 4H), 5.20 (AB q, 2H, $^2J_{H-H}$=18.0 Hz), 5.48 (s, 1H), 6.88 (t, 1H, $^3J_{H-H}$=9.0 Hz), 7.00 (t, 1H, $^3J_{H-H}$=9.0 Hz), 7.15 (d, 1H, $^3J_{H-H}$=9.0 Hz), 7.19 (t, 1H, $^3J_{H-H}$=9.0 Hz), 7.30 (d, 1H, $^3J_{H-H}$=9.0 Hz), 7.51 (d, 1H, $^3J_{H-H}$=9.0 Hz) 7.78 (d,1H, $^3J_{H-H}$=9.0 Hz).

$^{13}$C{$^1$H}(C$_6$D$_6$) δ–0.63, 1.44, 25.827, 49.57, 50.68, 54.28, 55.29, 105.19, 125.19, 125.21, 126.02, 127.08, 128.64, 128.73, 134.75, 142.57, 143.72, 146.24.

Polymerization data for catalyst systems comprising metal complexes of this invention are presented in Table 2.

TABLE 2

| | Polymerization Data | | |
|---|---|---|---|
| Compound Name[a] | Density[b] | MI[c] | Efficiency[d] |
| [N-(1,1-dimethylethyl)-1,1-dimethyl-1-[(1,2,3,4,5-γ)-2,3,4,5-tetramethyl-2-4-cyclopentadien-1-yl]silanaminato(2-)-N]dimethyl-titanium | 0.895 | 5 | 946,000 |
| (N-(1,1-dimethylethyl)-1,1-dimethyl-1-((1,2,3,3a,7a-γ)-3-(1-pyrrolidinyl)-1H-inden-t-yl)silanaminato-(2-)-N-)dimethyltitanium | 0.907 | <0.04 e | 2,228,000 |

TABLE 2-continued

Polymerization Data

| Compound Name[a] | Density[b] | MI[c] | Efficiency[d] |
|---|---|---|---|
| (1-((1,2,3,3a,7a-γ)-3-(dimethylamino)-1H-inden-1-yl)-N-(1,1-dimethylethyl)-1,1-dimethylsilanaminato(2-)-N) ((2-(dimethylamino-N)phenyl)methyl-C)titanium | 0.910 | 0.22 | 2,960,000 |
| (N-(1,1-dimethylethyl)-1,1-dimethyl-1-((1,2,3,3a,7a-γ)-3-methoxy-1H-inden-1-yl)silanaminato-(2-)-N-)dimethyltitanium | 0.886 | 0.38 | 885,000 |
| (1-((1,2,3,3a,7a-γ)-3-(dimethylamino)-1H-inden-1-yl)-N-(1,1-dimethylethyl)-1,1-dimethylsilanaminato(2-)-N)dimethyltitanium | 0.905 | <0.04 | 1,808,000 |
| (1,1'-(γ[4]-1,3-hutadiene-1,4-diyl)bis(benzene))(1-((1,2,3,3d,7a-γ)-3-(dimethylamino)-1H-inden-1-yl)-N-(1,1-dimethylethyl)-1,1-dimethylsilanaminato(2-)-N)titanium | 0.909 | 0.07 | 1,349,000 |
| (1-((1,2,3,3a,7a-γ)-3-(dimethylamino)-1H-inden-1-yl)-N-(1,1-dimethylethyl)-1,1-dimethylsilanaminato(2-)-N)((2,3,4,5-γ)-2,4-hexadiene)titanium | 0.908 | 0.04 | 5,031,000 |

[a]cocatalyst is $B(C_6F_5)_3$
[b]$g/cm^3$
[c]melt index (g/10 min)
[d]g polymer/g Ti
[e]GPC analysis showed $M_w$ = 246,000 $M_n$ = 116,500, $M_w/M_n$ = 2.11

X-ray structure determination of dichloro(N-(1,1-dimethylethyl)-1,1-dimethyl-1-((1,2,3,3a,7a-η)-3-(1-piperidinyl)-1H-inden-1-yl)silanaminato-(2-)-N-)-titanium.

Data Collection

A dark purple block-shaped crystal of dimensions 0.22× 0.21×0.19 mm was immersed in oil, Paratone N, Exxon, and mounted on a thin glass fiber. The crystal was transferred to a Siemens SMART PLATFORM diffractometer equipped with a graphite monochromatic crystal, a MoKα radiation source (λ=0.71073 Å), a CCD (charge coupled device) area detector which is kept at 5.078 cm from the crystal. The crystal was bathed in a cold nitrogen stream for the duration of data collection (−100° C.). Three sets of 20 frames each were collected covering three perpendicular sectors of space using the ω scan method and with a ten second exposure time. Integration of the frames followed by reflection indexing and least squares refinement produced a crystal orientation matrix and a monclinic lattice.

Data collection was set up to collect a total of 1381 frames in four different runs covering more than one full hemisphere of data. Frame scan parameters are summarized in the following table:

| Run | 2θ | ω | φ | χ | Scan axis | Scan width(°) | Frames (#) | Exposure time (sec) |
|---|---|---|---|---|---|---|---|---|
| 1 | −29 | −26.00 | 0.00 | 54.68 | 2 | −0.3 | 626 | 10 |
| 2 | −29 | −21.00 | 90.00 | 54.68 | 2 | −0.3 | 455 | 10 |
| 3 | −29 | −23.00 | 180.00 | 54.68 | 2 | −0.3 | 250 | 10 |
| 4 | −29 | −26.00 | 0.00 | 54.68 | 2 | −0.3 | 50 | 10 |

The last run (#4) is the remeasurement of the first 50 frames from run number 1. This is done to monitor crystal and diffractometer stability and to correct for any crystal decay.

Diffractometer setup includes a 0.8 mm collimator providing an X-ray beam of 0.8 mm in diameter. Generator power was set at 50 KV and 30 mA. Program SMART[1] was used for diffractometer control, frame scans, indexing, orientation matrix calculations, least squares refinement of cell parameters, crystal faces measurements and the actual data collection. Program ASTRO SMART, SAINT and XPREP programs are part of Siemens crystallographic software package for single crystal data collection, reduction and preparation was used to set up data collection strategy.

Data Preparation

All 1381 crystallographic raw data frames were read by program SAINT and integrated using 3D profiling algorithms. The resulting data were reduced to produce hkl reflections and their intensities and estimated standard deviations. The data were corrected for Lorentz and polarization effects. A total of 16988 reflections were collected representing a range of 2.7 to 3.99 redundancy level and have an $R_{sym}$ value range of 3.3 percent, at the lowest 2θ shell of reflections, to 4.4 percent at the highest 2θ shell of reflections (55°). Crystal decay correction was applied and was less than 1 percent. The unit cell parameters were refined by least squares of the setting angles of 7091 reflections. Unit cell parameters are:

a = 12.2988(3)Å     α = 90°
b = 16.8313(4)Å     β = 106.871(1)°
c = 12.6265(3)Å     γ = 90°
V = 2501.25(10)Å³

Absorption corrections were applied using program SADABS Sheldrick, G. M. (1996). SADABS is a program for the application of absorption corrections based on psi scans according to Blessing, Blessing, R. H. (1995). Acta Cryst. A51, 33–38. Absorption coefficient was 0.617 mm$^{-1}$ and minimum and maximum transmissions were 0.761 and 0.915, respectively.

Data preparation was carried out using program XPREP. The space group was determined to be P2$_1$/n (#14) based on systematic absences. XPREP provided the following crystallographic parameters: 5659 unique reflections (R$_{int}$=3.65 percent) with indices −13≦h≦15, −22≦k<15, −16≦l≦15.

Structure Solution and Refinement

The structure was solved by direct methods in SHELXTL5 Sheldrick, G. M. (1995). SHELXTL5. Crystallographic software package. Siemens Analytical. Inc. Madison, Wis. USA, from which the positions of all of the non-H atoms were obtained. The structure was refined, also in SHELXTL5. using full-matrix least-squares refinement. The non-H atoms were refined with anisotropic thermal parameters and all of the H atoms were located by a Difference Fourier map and refined without any constraints. A toluene molecule was located on a center of inversion occupying the ring center. Thus it is disordered in the methyl group positions occupying para positions with 50 percent site occupation factor for each. In the final cycle of refinement. 4206 observed reflections with I>2σ(I) were used and the resulting R$_1$, wR$_2$ and S (goodness of fit) were 3.59 percent, 8.38 percent and 1.023, respectively. A correction for secondary extinction was applied with x=0.0029(4). The maximum and minimum residual electron density peaks in the final Difference Fourier map were 0.419 and −0.272. respectively. The refinement was carried out using F$^2$ rather than F values. R$_1$ is calculated to provide a reference to the conventional R value but its function is not minimized. Additionally, wR$_2$ is the functions that is minimized and not R$_1$.

FIG. 1 shows the crystal structure of dichloro(N-(1,1-dimethylethyl)-1,1-dimethyl-1-((1,2,3,3a,7a-η)-3-(1-piperidinyl)-1H-inden-1-yl)silanaminato-(2-)-N-)-titanium.

X-ray structure determination of dichloro(N-(1,1-dimethylethyl)-1,1-dimethyl-1-((1,2,3,3a,7a-η)-3-methoxy-1H-inden-1-yl)silanaminato-(2-)-N-)-titanium.

Data Collection

A dark purple block-shaped crystal of dimensions 0.30× 0.21×0.09 mm was immersed in oil, Paratone N, Exxon, and mounted on a thin glass fiber. The crystal was transferred to a Siemens SMART PLATFORM diffractometer equipped with a graphite monochromatic crystal, a MoKα radiation source (λ=0.71073 Å), a CCD (charge coupled device) area detector which is kept at 5.078 cm from the crystal. The crystal was bathed in a cold nitrogen stream for the duration of data collection (−100° C.). Three sets of 20 frames each were collected covering three perpendicular sectors of space using the ω scan method and with a ten second exposure time. Integration of the frames followed by reflection indexing and least squares refinement produced a crystal orientation matrix and a monclinic lattice.

Data collection was set up to collect a total of 1381 frames in four different runs covering more than one full hemisphere of data. Frame scan parameters are summarized in the following table:

| Run | 2θ | ω | φ | χ | Scan axis | Scan width(°) | Frames (#) | Exposure time (sec) |
|---|---|---|---|---|---|---|---|---|
| 1 | −29 | −26.00 | 0.00 | 54.68 | 2 | −0.3 | 626 | 10 |
| 2 | −29 | −21.00 | 90.00 | 54.68 | 2 | −0.3 | 455 | 10 |
| 3 | −29 | −23.00 | 180.00 | 54.68 | 2 | −0.3 | 250 | 10 |
| 4 | −29 | −26.00 | 0.00 | 54.68 | 2 | −0.3 | 50 | 10 |

The last run (#4) is the remeasurement of the first 50 frames from run number 1. This is done to monitor crystal and diffractometer stability and to correct for any crystal decay.

Diffractometer setup includes a 0.8 mm collimator providing an X-ray beam of 0.8 mm in diameter. Generator power was set at 50 KV and 30 mA. Program SMART was used for diffractometer control, frame scans, indexing, orientation matrix calculations. least squares refinement of cell parameters, crystal faces measurements and the actual data collection. Program ASTRO was used to set up data collection strategy.

Data Preparation

All 1381 crystallographic raw data frames were read by program SAINT and integrated using 3D profiling algorithms. The resulting data were reduced to produce hkl reflections and their intensities and estimated standard deviations. The data were corrected for Lorentz and polarization effects. A total of 24545 reflections were collected representing a range of 2.59 to 3.76 redundancy level and have an R$_{sym}$ value range of 4.5 percent, at the lowest 2 θ shell of reflections, to 6.0 percent at the highest 2θ shell of reflections (550). Crystal decay correction was applied and was less than I percent. The unit cell parameters were refined by least squares of the setting angles of 6109 reflections. Unit cell parameters are:

| | |
|---|---|
| a = 23.7620(1)Å | α = 90 ° |
| b = 11.4403(2)Å | β = 108.929(1)° |
| c = 14.3161(2)Å | γ = 90° |
| V = 3681.29(8)Å$^3$ | |

Absorption corrections were applied using program SADABS according to Blessing. Absorption coefficient was 0.821 mm$^{-1}$ and minimum and maximum transmissions were 0.755 and 0.942, respectively.

Data preparation was carried out using program XPREP. The space group was determined to be C2/c (#15) based on systematic absences. XPREP provided the following crystallographic parameters: 4203 unique reflections (R$_{int}$=3.06 percent) with indices −31≦h≦30, −15≦k≦8, −18≦l≦19.

Structure Solution and Refinement

The structure was solved by direct methods in SHELXTL5 from which the positions of all of the non-H atoms were obtained. The structure was refined, also in SHELXTL5. using full-matrix least-squares refinement. The non-H atoms were refined with anisotropic thermal parameters and all of the H atoms were located by a Difference Fourier map and refined without any constraints. In the final cycle of refinement, 3333 observed reflections with I>2σ(I) were used to refine 292 parameters and the resulting $R_1$, $wR_2$ and S (goodness of fit) were 3.00 percent, 6.93 percent and 1.026, respectively. A correction for secondary extinction was applied with x=0.00037(9). The maximum and minimum residual electron density peaks in the final Difference Fourier map were 0.342 and −0.295, respectively. The refinement was carried out using $F^2$ rather than F values. $R_1$ is calculated to provide a reference to the conventional R value but its function is not minimized. Additionally, $wR_2$ is the functions that is minimized and not $R_1$.

Figure 2:
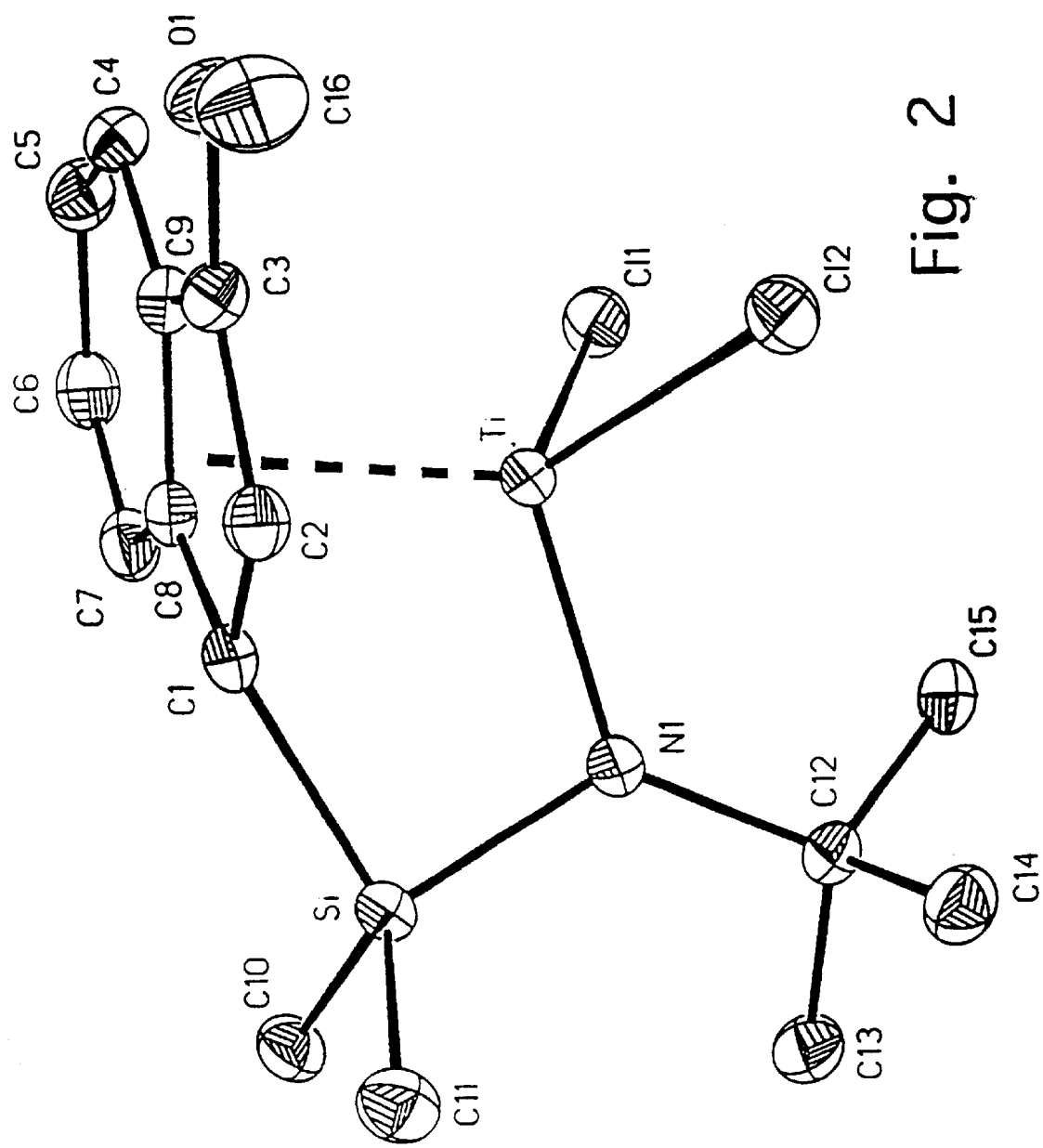
FIG. 2 shows the crystal structure of dichloro(N-(1,1-dimethylethyl)-1,1-dimethyl-1-((1,2,3,3a,7a-η)-3-methoxy-1H-inden-1-yl)silanaminato-(2-)-N-)-titanium.

FIG. 2 shows the crystal structure of dichloro(N-(1,1-dimethylethyl)-1,1-dimethyl-1-((1,2,3,3a,7a-η)-3-methoxy-1H-inden-1-yl)silanaminato-(2-)-N-)-titanium.

X-ray structure determination of [N-(1,1-dimethylethyl)-1,1-dimethyl-1-((1,2,3,3a,7a-η)-3-(1-piperidinyl)-1H-inden-1-yl)silanaminato-(2-)-N][(2,3,4,5η)-2,4-hexadiene)]-titanium.

Data Collection

A dark purple needle shaped crystal of dimensions 0.28× 0.24×0.21 mm was immersed in oil, Paratone N, Exxon, and mounted on a thin glass fiber. The crystal was transferred to a Siemens SMART PLATFORM diffractometer equipped with a graphite monochromatic crystal, a MoKα radiation source (λ=0.71073 Å), a CCD (charge coupled device) area detector which is kept at 4.93 1 cm from the crystal. The crystal was bathed in a cold nitrogen stream for the duration of data collection (−1000 C). Three sets of 20 frames each were collected covering three perpendicular sectors of space using the ω scan method and with a ten second exposure time. Integration of the frames followed by reflection indexing and least squares refinement produced a crystal orientation matrix and a monclinic lattice.

Data collection was set up to collect a total of 1381 frames in four different runs covering more than one full hemisphere of data. Frame scan parameters are summarized in the following table:

Data Preparation

All 1381 crystallographic raw data frames were read by program SAINT and integrated using 3D profiling algorithms. The resulting data were reduced to produce hkl reflections and their intensities and estimated standard deviations The data were corrected for Lorentz and polarization effects. A total of 8673 reflections were collected representing a range of 1.48 to 2.18 redundancy level and have an $R_{sym}$ value range of 2.5 percent, at the lowest 2θ shell of reflections, to 2.6 percent at the highest 2θ shell of reflections (550). Crystal decay correction was applied and was less than 1 percent. The unit cell parameters were refined by least squares of the setting angles of 6908 reflections.

| | |
|---|---|
| a = 9.7153(1)Å | α = 86.327(1)° |
| b = 9.7215(1)Å | β = 89.217(1)° |
| c = 13.3635(1)Å | γ = 82.840(1)° |
| V = 1249.72(2)Å³ | |

Absorption corrections were applied using program SADABS according to Blessing. Absorption coefficient was 0.405 mm$^{-1}$ and minimum and maximum transmissions were 0.805 and 0.928, respectively.

Data preparation was carried out using program XPREP. The space group was determined to be P1 #2 based on systematic absences. XPREP provided the following crystallographic parameters: 5563 unique reflections ($R_{int}$=1.59 percent) with indices−12≦h≦10, −12≦k≦13, −15≦l≦18.

Structure Solution and Refinement

The structure was solved by direct methods in SHELXTL5 from which the positions of all of the non-H atoms were obtained. The structure was refined, also in SHELXTL5, using full-matrix least-squares refinement. The non-H atoms were refined with anisotropic thermal parameters and all of the H atoms were located by a Difference Fourier map and refined without any constraints. In the final cycle of refinement, 4838 observed reflections with I>2σ(I) were used to refine 432 parameters and the resulting $R_1$, $wR_2$ and S (goodness of fit) were 3.13 percent. 7.17 percent and

| Run | 2θ | ω | φ | χ | Scan axis | Scan width(°) | Frames (#) | Exposure time (sec) |
|---|---|---|---|---|---|---|---|---|
| 1 | −29 | −26.00 | 0.00 | 54.68 | 2 | −0.3 | 626 | 10 |
| 2 | −29 | −21.00 | 90.00 | 54.68 | 2 | −0.3 | 455 | 10 |
| 3 | −29 | −23.00 | 180.00 | 54.68 | 2 | −0.3 | 250 | 10 |
| 4 | −29 | −26.00 | 0.00 | 54.68 | 2 | −0.3 | 50 | 10 |

The last run (#4) is the remeasurement of the first 50 frames from run number 1.

This is done to monitor crystal and diffractometer stability and to correct for any crystal decay.

Diffractometer setup includes a 0.8 mm collimator providing an X-ray beam of 0.8 mm in diameter. Generator power was set at 50 KV and 30 mA. Program SMART[1] was used for diffractometer control, frame scans, indexing, orientation matrix calculations least squares refinement of cell parameters, crystal faces measurements and the actual data collection. Program ASTRO was used to set up data collection strategy.

1.023, respectively. A correction for secondary extinction was applied with x=0.0018(7). The maximum and minimum residual electron density peaks in the final Difference Fourier map were 0.324 and −0.368. respectively. The refinement was carried out using $F^2$ rather than F values. $R_1$ is calculated to provide a reference to the conventional R value but its function is not minimized. Additionally, $wR_2$ is the functions that is minimized and not $R_1$.

The linear absorption coefficient, atomic scattering factors and anomalous-dispersion corrections were calculated from values from the International Tables for X-ray Crystallography International Tables for X-ray Crystallography (1974). Vol. IV, p. 55. Birmingham: Kynoch Press. (Present distributor, D. Reidel. Dordrecht.).

Figure 3:
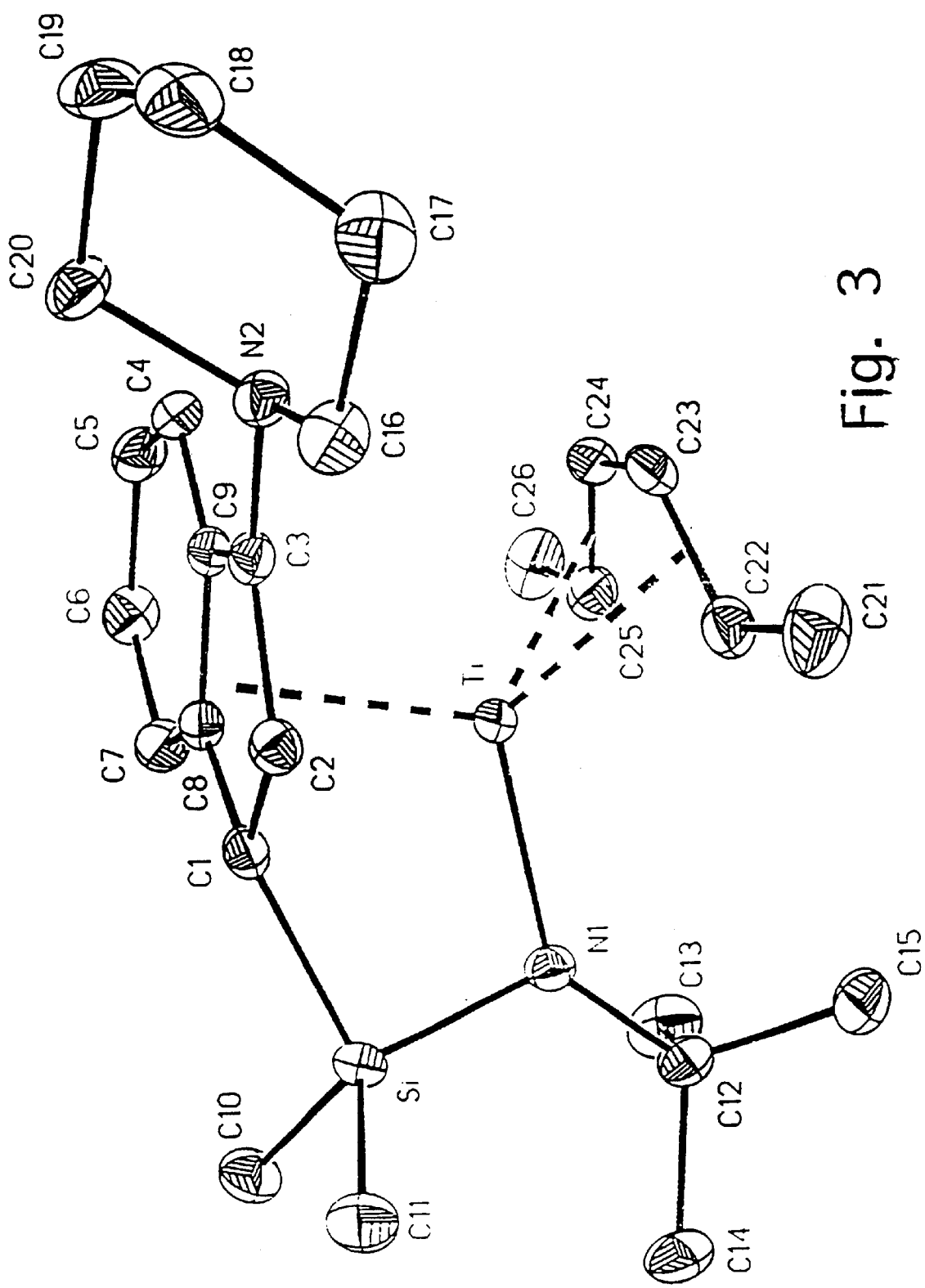
FIG. 3 shows the crystal structure of [N-(1,1-dimethylethyl)-1,1-dimethyl-1((1,2,3a,7a-η)-3-(1-piperidinyl)-1H-inden-1-yl)silanaminato-(2)1-)-N-(2,3,4,5-η)-2,4-hexadiene)]-titanium.

FIG. 3 shows the crystal structure of [N-(1,1-dimethylethyl)-1,1-dimethyl-1-((1,2,3,3a,7a-η)-3-(1-piperidinyl)-1H-inden-1-yl)silanaminato-(2-)-N][(2,3,4,5-η)-2,4-hexadiene)]-titanium.

Relevant functions used for the foregoing structure determinations are given below.

$$R_1 = Â(\|F_o| - |F_c\|)/Â|F_o|$$

$$wR_2 = [Â[w(F_o^2 - F_c^2)^2 / Â[w(F_o^2)^2]]^{1/2}$$

$$R_{int} = Â|F_o^2 - F_o^2|^2 / Â[F_o^2]$$

$$S = [Â[w(F_o^2 - F_c^2)^2]/(n-p)]^{½}$$

where n is the number of reflections and p is the total number of parameters refined $$w = 1/[s^2(F_o^2) + (0.0370 * P)^2 + 0.31 * P],$$

$$p = (F_o^2, 0) + 2 * F_c^2]/3$$

What is claimed is:

1. A metal complex corresponding to the formula:

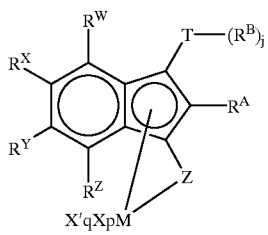

wherein

M is Ti, Zr, or Hf;

j is 1 or 2;

when j is 1, T is O or S, when j is 2, T is N or P;

$R^B$ is independently a group having from 1 to 80 nonhydrogen atoms which is hydrocarbyl, hydrocarbylsilyl, halo-substituted hydrocarbyl, hydrocarbyloxy-substituted hydrocarbyl, hydrocarbylamino-substituted hydrocarbyl, or hydrocarbylsilylhydrocarbyl, each $R^B$ optionally being substituted with one or more groups which are independently hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido, having from 1 to 20 nonhydrogen atoms; or, optionally, two $R^B$ are covalently linked with each other to form one or more fused rings or ring systems;

$R^A$, $R^W$, $R^X$, $R^Y$ and $R^Z$ are independently hydrogen, or a group having from 1 to 80 nonhydrogen atoms which is hydrocarbyl, halo-substituted hydrocarbyl, hydrocarbyloxy-substituted hydrocarbyl, hydrocarbylamino-substituted hydrocarbyl, hydrocarbylsilyl, or hydrocarbylsilylhydrocarbyl, or, optionally, two or more of $R^W$, $R^X$, $R^Y$, $R^Z$, $R^A$ and $R^B$ are covalently linked with each other to form one or more fused rings or ring systems;

Z is a divalent moiety bound to both Cp and M via σ-bonds, where Z comprises boron, or a member of Group 14 of the Periodic Table of the Elements, and also comprises nitrogen, phosphorus, sulfur or oxygen;

X is an anionic or dianionic ligand group having up to 60 atoms exclusive of the class of ligands that are cyclic, delocalized, π-bound ligand groups;

X' independently each occurrence is a neutral Lewis base ligating compound having up to 20 atoms;

p is zero, 1 or 2, and is two less than the formal oxidation state of M, when X is an anionic ligand; when X is a dianionic ligand group, p is 1; and q is zero, 1 or 2.

2. The metal complex of claim 1 wherein M is Ti.

3. The metal complex of claim 2 wherein $R^B$ is hydrocarbyl, hydrocarbylsilyl, hydrocarbyloxy-substituted hydrocarbyl, hydrocarbylamino-substituted hydrocarbyl and T is O or N.

4. The metal complex of claim 3 wherein $R^B$ is hydrocarbyl or hydrocarbylsilyl and T is O or N.

5. The metal complex of claim 4 wherein $R^B$ is hydrocarbyl or hydrocarbylsilyl and T is N.

6. The metal complex of claim 3 wherein the $(R^B)_j$-T group is methoxy, ethoxy, propoxy, methylethyloxy, 1,1-dimethyethyloxy, trimethylsiloxy, 1,1-dimethylethyl (dimethylsilyl)oxy, dimethylamino, diethylamino, methylethylamino, methylphenylamino, dipropylamino, dibutylamino, piperidinyl, morpholinyl, pyrrolidinyl, hexahydro-1H-azepin-1-yl, hexahydro-1(2H)-azocinyl, octahydro-1H-azonin-1-yl or octahydro-1(2H)-azecinyl.

7. The metal complex of claim 6 wherein the $(R^B)_j$-T group is dimethylamino, methylphenylamino, piperidinyl or pyrrolidinyl.

8. The metal complex of claim 1 corresponding to the formula:

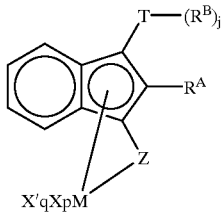

wherein T, M, Z, X, X', $R^A$, $R^B$, j, p, and q are as previously defined in said claim.

9. The metal complex of claim 1 corresponding to the formula:

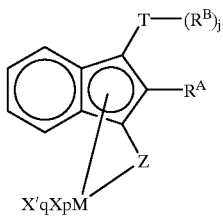

wherein T, M, Z, X, X', $R^B$, j, p, and q are as previously defined in said claim.

10. The metal complex of claim 2 wherein —Z— is —Z*—Y—, and

Y is —O—, —S—, —NR*—, —PR*—;

Z* is SiR*$_2$, CR*$_2$, SiR*$_2$SiR*$_2$, CR*$_2$CR*$_2$, CR*=CR*, CR*$_2$SiR*$_2$, CR*$_2$SiR*$_2$CR*$_2$, SiR*$_2$CR*$_2$SiR*$_2$, CR*$_2$CR*$_2$SiR*$_2$, CR*$_2$CR*$_2$CR*$_2$, GeR*$_2$; and R* is independently is hydrogen, or a member selected from the group consisting of hydrocarbyl, hydrocarbyloxy, silyl, halogenated alkyl, halogenated aryl, and combinations thereof, said R* having up to 20 nonhydrogen atoms, and optionally, two R* groups from Z, when R* is not hydrogen, or an R* group from Z and an R* group from Y form a ring system;

p is 2, q is zero, M is in the +4 formal oxidation state, and X is independently methyl, benzyl, trimethylsilylmethyl, allyl, pyrrolyl or two X groups together are 1,4-butane-diyl, 2-butene-1,4-diyl, 2,3-dimethyl-2-butene-1,4-diyl, 2-methyl-2-butene-1,4-diyl, or xylyldiyl.

11. The metal complex of claim 2 wherein —Z— is —Z*—Y—, and

Y is —O—, —S—, —NR*—, —PR*—;

Z* is $SiR^*_2$, $CR^*_2$, $SiR^*_2SiR^*_2$, $CR^*_2CR^*_2$, $CR^*=CR^*$, $CR^*_2SiR^*_2$, $CR^*_2SiR^*_2CR^*_2$, $SiR^*_2CR^*_2SiR^*_2$, $CR^*_2CR^*_2SiR^*_2$, $CR^*_2CR^*_2CR^*_2$, or $GeR^*_2$; and R* is independently hydrogen, or a member selected from the group consisting of hydrocarbyl, hydrocarbyloxy, silyl, halogenated alkyl, halogenated aryl, and combinations thereof, said R* having up to 20 nonhydrogen atoms, and optionally, two R* groups from Z, when R* is not hydrogen, or an R* group from Z and an R* group from Y form a ring system;

p is 1, q is zero, M is in the +3 formal oxidation state, and X is 2-(N,N-dimethyl)aminobenzyl, 2-(N,N-dimethylaminomethyl)phenyl, allyl, methallyl, trimethylsilylallyl.

12. The metal complex of claim 2 wherein —Z— is —Z*—Y—, and

Y is —O—, —S—, —NR*—, —PR*—;

Z* is $SiR^*_2$, $CR^*_2$, $SiR^*_2SiR^*_2$, $CR^*_2CR^*_2$, $CR^*=CR^*$, $CR^*_2SiR^*_2$, $CR^*_2SiR^*_2CR^*_2$, $SiR^*_2CR^*_2SiR^*_2$, $CR^*_2CR^*_2SiR^*_2$, $CR^*_2CR^*_2CR^*_2$, or $GeR^*_2$; and R* is independently hydrogen, or a member selected from the group consisting of hydrocarbyl, hydrocarbyloxy, silyl, halogenated alkyl, halogenated aryl, and combinations thereof, said R* having up to 20 nonhydrogen atoms, and optionally, two R* groups from Z, when R* is not hydrogen, or an R* group from Z and an R* group from Y form a ring system;

p is 0, q is 1, M is in the +2 formal oxidation state, and X' is 1,4-diphenyl-1,3-butadiene, 1,3-pentadiene or 2,4-hexadiene.

13. The metal complex of any of claims 10–12 wherein R* is a group having a primary or secondary carbon atom bonded to N.

14. The metal complex of claim 13 wherein R* is cyclohexyl or isopropyl.

15. The metal complex of claim 1 which is:

(t-butylamido)(3-(N-perhydropyridinyl)indene-1-yl)(dimethylsilane)titanium dichloride;

(t-butylamido)(3-(N-perhydropyridinyl)indene-1-yl)(dimethylsilane)titanium dimethyl;

(t-butylamido)(2-methyl-3-(N,N-dimethylamino)-4,4,7,7-(tetramethyl)-4,5,6,7-tetrahydroindene-1-yl)(dimethylsilane)titanium dichloride:

(t-butylamido)(2-methyl-3-(N,N-dimethylamino)-4,4,7,7-(tetramethyl)-4,5,6,7-tetrahydroindene-1-yl)(dimethylsilane)titanium dimethyl:

(t-butylamido)(2-methyl-3-(N-pyrrolidinyl)-s-indacen-1-yl)(dimethylsilane)titanium dichloride;

(t-butylamido)(2-methyl-3-(N-pyrrolidinyl)-s-indacen-1-yl)(dimethylsilane)titanium dimethyl;

(t-butylamido)(3-(N-perhydropyridinyl)indene-1-yl)(dimethylsilane)titanium 1,4-hexadiene;

(t-butylamido)(3-(N-pyrrolidinyl)indene-1-yl)(dimethylsilane)titanium dichloride;

(t-butylamido)(3-(N-pyrrolidinyl)indene-1-yl)(dimethylsilane)titanium dimethyl;

(t-butylamido)(3-(N-pyrrolidinyl)indene-1-yl)(dimethylsilane)titanium dichloride;

(t-butylamido)(3-(N-pyrrolidinyl)indene-1-yl)(dimethylsilane)titanium dimethyl;

(t-butylamido)(3-(N-pyrrolidinyl)indene-1-yl)(dimethylsilane)titanium 1,3-pentadiene;

(t-butylamido)(3-(N-pyrrolidinyl)indene-1-yl)(dimethylsilane)titanium 2,4-hexadiene;

(t-butylamido)(3-(N-pyrrolidinyl)indene-1-yl)(dimethylsilane)zirconium dichloride;

(t-butylamido)(3-(N-pyrrolidinyl)indene-1-yl)(dimethylsilane)zirconium dimethyl;

(t-butylamido)(2-methyl-3-(N-pyrrolidinyl)indene-1-yl)(dimethylsilane)titanium dichloride;

(t-butylamido)(2-methyl-3-(N-pyrrolidinyl)indene-1-yl)(dimethylsilane)titanium dimethyl;

(cyclohexylamido)(3-(N-pyrrolidinyl)indene-1-yl)(dimethylsilane)titanium dichloride;

(cyclohexylamido)(3-(N-pyrrolidinyl)indene-1-yl)(dimethylsilane)titanium dimethyl;

(t-butylamido)(3-methoxyindene-1-yl)(dimethylsilane)titanium dichloride;

(t-butylamido)(3-methoxyindene-1-yl)(dimethylsilane)titanium dimethyl;

(t-butylamido)(3-(diphenylphosphino)indene-1-yl)(dimethylsilane)titanium dichloride;

(t-butylamido)(3-(diphenylphosphino)indene-1-yl)(dimethylsilane)titanium dimethyl;

(t-butylamido)(3-(N,N-dimethylamino)indene-1-yl)(dimethylsilane)titanium dichloride;

(t-butylamido)(3-(N,N-dimethylamino)indene-1-yl)(dimethylsilane)titanium dimethyl;

(t-butylamido)(3-(N,N-dimethylamino)indene-1-yl)(dimethylsilane)titanium 2,4-hexadiene;

(t-butylamido)(3-(N,N-dimethylamino)indene-1-yl)(dimethylsilane)titanium 1,4-diphenylbutadiene;

($\eta^5$-cyclopentadienyl)[(t-butylamido)(3-(N,N-dimethylamino)indene-1-yl)(dimethylsilane)]titanium chloride, ($\eta^5$-cyclopentadienyl)[(t-butylamido)(3-(N-pyrrolidinyl)indene-1-yl)(dimethylsilane)]titanium (III)

($\eta^5$-cyclopentadienyl)[(t-butylamido)(3-(N-pyrrolidinyl)indene-1-yl)(dimethylsilane)]titanium chloride (t-butylamido)(3-(N-pyrrolidinyl)indene-1-yl)(dimethylsilane)titanium (III) 2-(N,N-dimethyl)benzyl (t-butylamido)(3-(N-phenyl-N-methylamino)indene-1-yl)(dimethylsilane)titanium dichloride;

(t-butylamido)(3-(N-phenyl-N-methylamino)indene-1-yl)(dimethylsilane)titanium dimethyl;

(benzylamido)(3-(N-pyrrolidinyl)indene-1-yl)(dimethylsilane)titanium dichloride; or (benzylamido)(3-(N-pyrrolidinyl)indene-1-yl)(dimethylsilane)titanium dimethyl.

16. A catalyst system for olefin polymerization prepared from catalyst system components comprising:

(A) a catalyst component comprising a metal complex of claim 1; and (B) a cocatalyst component comprising an activating cocatalyst wherein the molar ratio of (A) to (B) is from 1:10,000 to 100:1.

17. A process for the polymerization of olefins comprising contacting one or more $C_{2-20}$ α-olefins under polymerization conditions with a catalyst system of claim 16.

* * * * *